US007482335B2

(12) United States Patent
Carter et al.

(10) Patent No.: US 7,482,335 B2
(45) Date of Patent: *Jan. 27, 2009

(54) CYCLIC DERIVATIVES AS MODULATORS OF CHEMOKINE RECEPTOR ACTIVITY

(75) Inventors: Percy H. Carter, Princeton, NJ (US); Robert J. Cherney, Newtown, PA (US); Douglas G. Batt, Wilmington, DE (US); John V. Duncia, Newtown, PA (US); Daniel S. Gardner, Furlong, PA (US); Soo S. Ko, Hockessin, DE (US); Anurag S. Srivastava, Belle Mead, NJ (US); Michael G. Yang, Narberth, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/545,415

(22) Filed: Oct. 10, 2006

(65) Prior Publication Data
US 2007/0032526 A1    Feb. 8, 2007

Related U.S. Application Data

(62) Division of application No. 10/923,619, filed on Aug. 19, 2004, now Pat. No. 7,163,937.

(60) Provisional application No. 60/496,947, filed on Aug. 21, 2003.

(51) Int. Cl.
*A61K 31/397* (2006.01)
*A61K 31/5383* (2006.01)
*A61K 31/496* (2006.01)
*A61K 31/454* (2006.01)
*A61K 31/4015* (2006.01)
*C07D 413/12* (2006.01)
*C07D 403/12* (2006.01)
*C07D 401/12* (2006.01)
*C07D 207/277* (2006.01)
*C07D 207/00* (2006.01)
*C07D 205/04* (2006.01)

(52) U.S. Cl. .............. 514/210.18; 514/237.2; 514/254.01; 514/326; 514/422; 544/141; 544/372; 546/208; 548/518; 548/953

(58) Field of Classification Search ........... 548/543, 548/518, 953; 514/210.18, 237.2, 254.01, 514/326, 422; 544/141, 372; 546/208
See application file for complete search history.

(56) References Cited

U.S. PATENT DOCUMENTS

| 6,706,712 | B2 | 3/2004 | Cherney | |
|---|---|---|---|---|
| 7,163,937 | B2* | 1/2007 | Carter et al. | 514/210.18 |
| 2003/0060459 | A1 | 3/2003 | Carter et al. | |
| 2003/0171218 | A1 | 9/2003 | Bojack et al. | |
| 2003/0216434 | A1 | 11/2003 | Cherney | |
| 2004/0006062 | A1 | 1/2004 | Smallheer et al. | |
| 2004/0186143 | A1 | 9/2004 | Carter et al. | |
| 2004/0235835 | A1 | 11/2004 | Carter | |
| 2004/0235836 | A1 | 11/2004 | Cherney | |

FOREIGN PATENT DOCUMENTS

| DE | 812551 | * | 9/1951 |
|---|---|---|---|
| EP | 550924 | | 7/1993 |
| JP | 63083082 | | 4/1988 |
| WO | WO 97/05111 | | 2/1997 |
| WO | WO 97/43257 | | 11/1997 |
| WO | WO 98/01426 | | 1/1998 |
| WO | WO 99/00362 | | 1/1999 |
| WO | WO 99/07678 | | 2/1999 |
| WO | WO 99/37304 | | 7/1999 |
| WO | WO 99/38844 | | 8/1999 |
| WO | WO 99/40914 | | 8/1999 |
| WO | WO 01/10799 | | 2/2001 |
| WO | WO 01/17992 | | 3/2001 |
| WO | WO 01/74783 | | 10/2001 |
| WO | WO 01/74784 | | 10/2001 |
| WO | WO 02/04416 | | 1/2002 |
| WO | WO 02/04416 A2 | * | 1/2002 |
| WO | WO 02/060859 | | 8/2002 |
| WO | WO 02/078679 | | 10/2002 |
| WO | WO 02/102372 | | 12/2002 |
| WO | WO 03/005824 | | 1/2003 |
| WO | WO 2004/022536 | | 3/2004 |
| WO | WO 2004/071460 | | 8/2004 |
| WO | WO 2004/098516 | | 11/2004 |

OTHER PUBLICATIONS

Walton et al. "Search for New Analgesics. Part I. Homologues of Pethidine and Related Compounds" Journal of the Chemical Society, 1945, pp. 315-319.*

(Continued)

*Primary Examiner*—Rei-tsang Shiao
*Assistant Examiner*—Joseph R Kosack
(74) *Attorney, Agent, or Firm*—Terence J. Bogie; Laurelee L. Duncan

(57) ABSTRACT

The present application describes modulators of MCP-1 of formula (I):

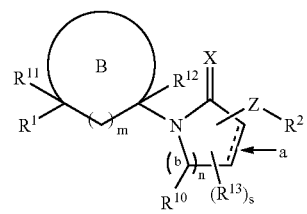

or pharmaceutically acceptable salt forms thereof, useful for the treatment of rheumatoid arthritis, multiple sclerosis, atherosclerosis and asthma.

21 Claims, No Drawings

OTHER PUBLICATIONS

U.S. Appl. No. 10/922,406, filed Aug. 19, 2004, Carter et al.
U.S. Appl. No. 10/922,726, filed Aug. 19, 2004, Carter et al.
U.S. Appl. No. 10/923,538, filed Aug. 19, 2004, Carter et al.
U.S. Appl. No. 10/776,828, filed Feb. 11, 2004, Cherney et al.
Trivedi et al., "Chapter 17, Chemokines: Targets for Novel Therapeutics", Annual Reports in Medicinal Chemistry, vol. 35, pp. 191-200, 2000.

Evans et al., "Synthesis and Dopamine Receptor Modulating Activity of Novel Peptidomimetics of ι-Prolyl-ι-leucyl-glycinamide Featuring α,α-Disubstituted Amino Acids", J. Med. Chem., vol. 42, pp. 1441-1447, 1999.
Costain et al., "Modulatory effects of PLG and its peptidomimetics on haloperidol-induced catalepsy in rats", Peptides, vol. 20, pp. 761-767, 1999.

* cited by examiner

CYCLIC DERIVATIVES AS MODULATORS OF CHEMOKINE RECEPTOR ACTIVITY

CROSS-REFERENCE TO RELATED APPLICATIONS

This application is a divisional of U.S. application Ser. No. 10/923,619 filed Aug. 19, 2004, which was issued as U.S. Pat. No. 7,163,937 on Jan. 16, 2007, which claims priority from provisional application U.S. Ser. No. 60/496,947 filed Aug. 21, 2003, which are incorporated herein by reference in its entirety.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., *J. Immunol.*, 1996, 157, 2759-2763); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1 −/− mice had normal numbers of leukocytes and macrophages, but were unable to recruit monocytes into sites of inflammation after several different types of immune challenge (Bao Lu, et al., *J. Exp. Med.* 1998, 187, 601). Likewise, CCR-2 −/− mice were unable to recruit monocytes or produce interferon-γ when challenged with various exogenous agents; moreover, the leukocytes of CCR-2 null mice did not migrate in response to MCP-1 (Landin Boring, et al., *J. Clin. Invest.* 1997, 100, 2552), thereby demonstrating the specificity of the MCP-1/CCR-2 interaction. Two other groups have independently reported equivalent results with different strains of CCR-2 −/− mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1 −/− and CCR-2 −/− animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

It is known that MCP-1 is upregulated in patients with rheumatoid arthritis (Alisa Koch, et al., *J. Clin. Invest.* 1992, 90, 772-779). Moreover, several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-1pr mouse model of arthritis (Jiang-Hong Gong, et al., *J. Exp. Med.* 1997, 186, 131).

It is known that MCP-1 is upregulated in atherosclerotic lesions, and it has been shown that circulating levels of MCP-1 are reduced through treatment with therapeutic agents, plays a role in disease progression (Abdolreza Rezaie-Majd, et al, *Arterioscler. Thromb. Vasc. Biol.* 2002, 22, 1194-1199). Four key studies have demonstrated the potential therapeutic value of antagonism of the MCP-1/CCR2 interaction in treating atherosclerosis. For example, when MCP-1 −/− mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1 +/+ apoB control mice (Jennifa Gosling, et al., *J. Clin. Invest.* 1999, 103, 773). Likewise, when CCR-2 −/− mice are crossed with apolipoprotein E −/− mice, a significant decrease in the incidence of atherosclerotic lesions was observed (Landin Boring, et al, *Nature* 1998, 394, 894). Finally, when apolipoprotein E −/− mice are administered a gene encoding a peptide antagonist of CCR2, then lesion size is decreased and plaque stability is increased (W. Ni, et al. *Circulation* 2001, 103, 2096-2101).

It is known that MCP-1 is upregulated in human multiple sclerosis, and it has been shown that effective therapy with interferon b-1b reduces MCP-1 expression in peripheral blood mononuclear cells, suggesting that MCP-1 plays a role in disease progression (Carla Iarlori, et al., *J. Neuroimmunol.* 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2 −/− mice are resistant to EAE (Brian T. Fife, et al., *J. Exp. Med.* 2000, 192, 899; Leonid Izikson, et al., *J. Exp. Med.* 2000, 192, 1075).

It is known that MCP-1 is upregulated in patients who develop bronchiolitis obliterans syndrome after lung transplantation (Martine Reynaud-Gaubert, et al., *J. of Heart and Lung Transplant.,* 2002, 21, 721-730; John Belperio et al., *J. Clin. Invest.* 2001, 108, 547-556). In a murine model of bronchiolitis obliterans syndrome, administration of an antibody to MCP-1 led to attenuation of airway obliteration; likewise, CCR2 −/− mice were resistant to airway obliteration in this same model (John Belperio, et al., *J. Clin. Invest.* 2001, 108, 547-556). These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 −/− mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1 −/− mice with induced nephrotoxic serum nephritis showed significantly less tubular damage than their MCP-1 +/+ counterparts (Gregory H. Tesch, et al., *J. Clin. Invest.* 1999, 103, 73).

One study has demonstrated the potential therapeutic value of antagonism of the MCP-1/CCR2 interaction in treating systemic lupus erythematosus. Crossing of MCP-1 −/− mice with MRL-FAS$^{1pr}$ mice—the latter of which have a fatal autoimmune disease that is analogous to human systemic lupus erythematosus—results mice that have less disease and longer survival than the wildtype MRL-FAS$^{1pr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2 −/− mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

One study has demonstrated the potential therapeutic value of antagonism of the MCP-1/CCR2 interaction in treating cancer. When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40).

One study has demonstrated the potential therapeutic value of antagonism of the MCP-1/CCR2 interaction in treating restinosis. Mice deficient in CCR2 showed reductions in the intimal area and in the intima/media ratio (relative to wildtype littermates) after injury of the femoral artery (Merce Roque, et al. *Arterioscler. Thromb. Vasc. Biol.* 2002, 22, 554-559).

Other studies have provided evidence that MCP-1 is overexpressed in various disease states not mentioned above. These reports provide correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR-2 is also the receptor for the chemokines MCP-2, MCP-3, MCP-4, and MCP-5 (Luster, *New Eng. J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

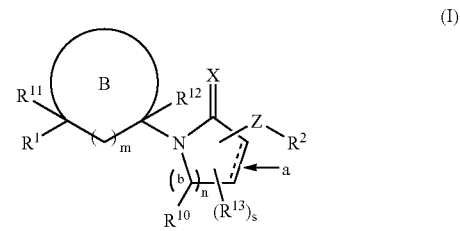

(I)

or stereoisomers or pharmaceutically acceptable salts thereof, wherein B, X, Z, m, n, s, carbon b, bond (a), $R^1$, $R^2$, $R^{10}$, $R^{11}$, $R^{12}$, and $R^{13}$ are defined below, are effective modulators of MCP-1 and chemokine activity.

DETAILED DESCRIPTION OF EMBODIMENTS OF THE PRESENT INVENTION

In one embodiment, the present invention is directed to a compound of formula (I)

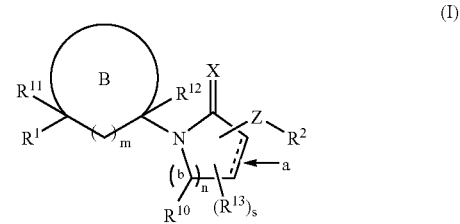

(I)

or a stereoisomer or a pharmaceutically acceptable salt thereof, wherein:

ring B is a cycloalkyl group of 3 to 8 carbon atoms wherein the cycloalkyl group is saturated or partially unsaturated; and being substituted with 1-2 $R^5$;

or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)— and being substituted with 0-2 $R^5$;

X is selected from O or S;

Z is selected from a bond, —NR$^8$C(O)—, —NR$^8$C(S)—, —NR$^8$C(O)NH—, —NR$^8$C(S)NH—, —NR$^8$SO$_2$—, —NR$^8$SO$_2$NH—, —C(O)NR$^8$—, —OC(O)NR$^8$—, —NR$^8$C(O)O—, —CR$^{14}$=CR$^{14}$—, —CR$^{15}$R$^{15}$—, —CR$^{15}$R$^{15}$C(O)—, —C(O)CR$^{15}$R$^{15}$—, —CR$^{15}$R$^{15}$C(=N—OR$^{16}$)—, —O—CR$^{14}$R$^{14}$—, —CR$^{14}$R$^{14}$—O—, —O—, —NR$^9$—, —NR$^9$—CR$^{14}$R$^{14}$—, —CR$^{14}$R$^{14}$—NR$^9$—, —S(O)$_p$—, —S(O)$_p$—, CR$^{14}$R$^{14}$—, —CR$^{14}$R$^{14}$—S(O)$_p$—, and —S(O)$_p$—NR$^9$—;

wherein neither Z nor $R^{13}$ are connected to a carbon atom labeled (b);

bond (a) is a single or double bond;

alternatively, when n is equal to 2, two atoms labeled (b) may join through a double bond;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

with the proviso that if $R^1$ is H, then either
  a) $R^5$ is $(CRR)_rNR^{5a}R^{5a}$, or
  b) ring B is a heterocyclic system containing at least one $N(R^4)$;

and with the further proviso that if $R^5$ is H, then either
  a) $R^1$ is not H, or
  b) ring B is a heterocyclic system containing at least one $N(R^4)$;

with the proviso that $R^1$ is not —$CH_2S(O)_p$—$R^{1a}$, —$CH_2S(O)_2$—$R^{1a}$, —$NHC(O)$—$R^{1a}$, —$NHC(O)NH$—$R^{1a}$, —$NHCH_2$—$R^{1a}$, —$NHSO_2$—$R^{1a}$, —$NHSO_2NH$—$R^{1a}$, when $R^{1a}$ is equal to $C_{6-10}$ aryl group or a 5-10 membered heteroaryl system containing 1-4 heteroatoms selected from N, O, and S;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CHR)_tSR^{4d}$, $(CRR)_tNR^{4a}R^{4a}$, $(CRR)_qC(O)OH$, $(CRR)_rC(O)R^{4b}$, $(CRR)_tC(O)NR^{4a}R^{4a}$, $(CRR)_rOC(O)NR^{4a}R^{4a}$, $(CRR)_rNR^{4a}C(O)OR^{4d}$, $(CRR)_rNR^{4a}C(O)R^{4b}$, $(CRR)_rC(O)OR^{4d}$, $(CRR)_rOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$, $C_{1-6}$ haloalkyl, a $(CRR)_r$—$C_{3-10}$ carbocyclic residue substituted with 0-3 $R^{4e}$, and a $(CRR)_r$-4-10 membered heterocyclic system containing 1-4 heteroatoms selected from N, O, and S, substituted with 0-2 $R^{4e}$;

$R^{4a}$, at each occurrence, is independently selected from H, methyl substituted with 0-1 $R^{4c}$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH2)_r$—$C_{3-10}$ carbocyclic residue substituted with 0-4 $R^{4e}$, and a $(CHR)_r$-4-10 membered heterocyclic system containing 1-4 heteroatoms selected from N, O, and S, substituted with 0-2 $R^{4e}$;

$R^{4b}$, at each occurrence, is selected from H, $C_{1-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-6}$ carbocyclic residue substituted with 0-2 $R^{4e}$, and a $(CHR)_r$-4-10 membered heterocyclic system containing 1-4 heteroatoms selected from N, O, and S, substituted with 0-2 $R^{4e}$;

$R^{4c}$ is independently selected from —$C(O)R^{4b}$, —$C(O)OR^{4d}$, —$C(O)NR^{4f}R^{4f}$, $C(O)OH$, $(CH_2)_rC(O)NHSO_2$—$R^{4h}$, $NHSO_2R^{4h}$, $(CH_2)_r$tetrazolyl, and $(CH_2)_r$phenyl;

$R^{4d}$, at each occurrence, is selected from methyl, $CF_3$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, and a $C_{3-10}$ carbocyclic residue substituted with 0-3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —$C(O)R^{4i}$, —$C(O)OR^{4j}$, —$C(O)NR^{4h}R^{4h}$, —$OC(O)NR^{4h}R^{4h}$, —$NR^{4h}C(O)NR^{4h}R^{4h}$, —$NR^{4h}C(O)OR^{4j}$, $C(O)OH$, $(CH_2)_rC(O)NHSO_2$—$R^{4k}$, $NHSO_2R^{4k}$, $(CH_2)_r$tetrazolyl, and $(CH_2)_r$phenyl;

$R^{4f}$, at each occurrence, is selected from H, $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a $(CH_2)_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a $(CH_2)_r$—$C_{3-6}$ carbocyclic residue;

$R^{4j}$, at each occurrence, is selected from $CF_3$, $C_{1-6}$ alkyl, $C_{3-8}$ alkenyl, $C_{3-8}$ alkynyl, and a $C_{3-10}$ carbocyclic residue;

$R^{4k}$, at each occurrence, is selected from $C_{1-5}$ alkyl, $C_{1-5}$ haloalkyl, and $C_{3-6}$ cycloalkyl, and phenyl;

$R^5$, at each occurrence, is independently selected from H, =O, $C_{1-6}$ alkyl, $C_{2-8}$ alkenyl, $C_{2-8}$ alkynyl, F, Cl, Br, I, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(O)R^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0-3 $R^{5c}$, and a $(CRR)_r$-5-10 membered heterocyclic system containing 1-4 heteroatoms selected from N, O, and S, substituted with 0-3 $R^{5c}$;

$R^{5a}$, at each occurrence, is independently selected from H, methyl substituted with 0-1 $R^{5g}$, $C_{2-6}$ alkyl substituted with 0-3 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-3 $R^{5e}$;

wherein when $R^5$ is $(CRR)_rN(O)R^{5a}R^{5a}$, neither $R^{5a}$ are H;

$R^{5b}$, at each occurrence, is selected from $C_{1-6}$ alkyl substituted with 0-3 $R^{5e}$, $C_{1-6}$ haloalkyl, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, C(O)OH, $(CH_2)_rC(O)NHSO_2$—$R^{5h}$, $NHSO_2R^{5h}$, $(CH_2)_r$tetrazolyl, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)OH$, $(CH_2)_r{}^{C(O)NHSO}{}_2$—$R^{5h}$, $NHSO_2R^{5h}$, a $(CH_2)_r$-5-6 membered heterocyclic system containing 1-4 heteroatoms selected from N, O, and S, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —CN, —C(O)$R^{5b}$, —C(O)O$R^{5d}$, —C(O)NR$^{5f}$R$^{5f}$, —C(O)OH, (CH$_2$)$_r$C(O)NHSO$_2$—R$^{5h}$, and (CH$_2$)$_r$phenyl;

$R^{5h}$, at each occurrence, is selected from C$_{1-5}$ alkyl, C$_{1-5}$ haloalkyl, and C$_{3-6}$ cycloalkyl, and phenyl;

R, at each occurrence, is selected from H, C$_{1-6}$ alkyl substituted with 0-3 R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with 0-3 R$^{5e}$;

$R^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{6a'}$R$^{6a'}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6b}$, (CR'R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O)R$^{6b'}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$R$^{6d'}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$R$^{6b'}$, (CR'R')$_r$S(O)$_2$NR$^{6a}$R$^{6a}$, (CR'R')$_r$NR$^{6f}$S(O)$_p$NR$^{6a}$R$^{6a}$, (CR'R')$_r$NR$^{6f}$S(O)$_2$(CR'R')$_r$R$^{6b}$, (CR'R')$_r$C(O)NHSO$_2$R$^{6b}$, C$_{1-6}$ haloalkyl, C$_{2-8}$ alkenyl substituted with 0-3 R', C$_{2-8}$ alkynyl substituted with 0-3 R', (CR'R')$_r$phenyl substituted with 0-3 R$^{6e}$, and a (CH$_2$)$_r$-5-10 membered heterocyclic system containing 1-4 heteroatoms selected from N, O, and S, substituted with 0-2 R$^{6e}$;

alternatively, two R$^6$ on adjacent atoms on R$^1$ may join to form a cyclic acetal;

$R^{6a}$, at each occurrence, is selected from H, methyl substituted with 0-1 R$^{6g}$, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$—C$_{3-10}$ carbocyclic residue substituted with 0-5 R$^{6e}$, and a (CH$_2$)$_r$-5-10 membered heterocyclic system containing 1-4 heteroatoms selected from N, O, and S, substituted with 0-2 R$^{6e}$;

$R^{6a'}$, at each occurrence, is selected from H, C$_{1-6}$ alkyl and C$_{3-6}$ cycloalkyl;

$R^{6b}$, at each occurrence, is selected from H, C$_{1-6}$ alkyl substituted with 0-3 R$^{6e}$, C$_{1-6}$ haloalkyl, C$_{3-8}$ alkenyl substituted with 0-2 R$^{6e}$, C$_{3-8}$ alkynyl substituted with 0-2 R$^{6e}$, a (CH$_2$)$_r$C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

$R^{6b'}$, at each occurrence, is selected from H, C$_{1-6}$ alkyl and C$_{3-6}$ cycloalkyl;

$R^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, C$_{2-4}$ haloalkyl, a (CH$_2$)$_r$—C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

$R^{6d'}$, at each occurrence, is selected from H, CF$_3$ and C$_{1-6}$ alkyl and C$_{3-6}$ cycloalkyl;

$R^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, C(O)NHR$^{6h}$, C(O)OC$_{1-5}$ alkyl, (CH$_2$)$_r$OH, C(O)OH, (CH$_2$)$_r$C(O)NHSO$_2$—R$^{6h}$, NHSO$_2$R$^{6h}$, (CH$_2$)$_r$tetrazolyl, and (CH$_2$)$_r$phenyl and a (CH$_2$)$_r$-5-6 membered heterocyclic system containing 1-4 heteroatoms selected from N, O, and S;

$R^{6f}$, at each occurrence, is selected from H, C$_{1-5}$ alkyl, and C$_{3-6}$ cycloalkyl, and phenyl;

$R^{6g}$ is independently selected from —C(O)R$^{6b}$, —C(O)OR$^{6d}$, —C(O)NR$^{6f}$R$^{6f}$, (CH$_2$)$_r$OH, C(O)OH, (CH$_2$)$_r$C(O)NHSO$_2$—R$^{6h}$, NHSO$_2$R$^{6h}$, (CH$_2$)$_r$tetrazolyl, and (CH$_2$)$_r$phenyl;

$R^{6h}$, at each occurrence, is selected from C$_{1-5}$ alkyl, C$_{1-5}$ haloalkyl, and C$_{3-6}$ cycloalkyl, and phenyl;

$R^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, (CR'R')$_r$C(O)NHSO$_2$R$^{7b}$, C$_{1-6}$ haloalkyl, C$_{2-8}$ alkenyl substituted with 0-3 R', C$_{2-8}$ alkynyl substituted with 0-3 R', (CR'R')$_r$C$_{3-10}$ carbocycle substituted with 0-3 R$^{7e}$, (CR'R')$_r$phenyl substituted with 0-3 R$^{7e}$, and a (CH$_2$)$_r$-5-6 membered heterocyclic system containing 1-4 heteroatoms selected from N, O, and S, substituted with 0-3 R$^{7e}$;

alternatively, two R$^7$ on adjacent atoms on R$^2$ may join to form a cyclic acetal;

$R^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

$R^{7b}$, at each occurrence, is selected from C$_{1-6}$ alkyl substituted with 0-2 R$^{7e}$, C$_{1-6}$ haloalkyl, C$_{3-8}$ alkenyl substituted with 0-2 R$^{7e}$, C$_{3-8}$ alkynyl substituted with 0-2 R$^{7e}$, a (CH$_2$)$_r$C$_{3-6}$ carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

$R^{7d}$, at each occurrence, is selected from C$_{3-8}$ alkenyl substituted with 0-2 R$^{7e}$, C$_{3-8}$ alkynyl substituted with 0-2 R$^{7e}$, methyl, CF$_3$, C$_{2-4}$ haloalkyl, C$_{2-6}$ alkyl substituted with 0-3 R$^{7e}$, a (CH$_2$)$_r$—C$_{3-10}$ carbocyclic residue substituted with 0-3 R$^{7e}$, and a (CH$_2$)$_r$-5-6 membered heterocyclic system containing 1-4 heteroatoms selected from N, O, and S, substituted with 0-3 R$^{7e}$;

$R^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, OH, SH, C(O)OH, C(O)NHR$^{7h}$, C(O)OC$_{1-5}$ alkyl, (CH$_2$)$_r$SC$_{1-5}$ alkyl, (CH$_2$)$_r$NR$^{7f}$R$^{7f}$, (CH$_2$)$_r$C(O)NHSO$_2$—R$^{7h}$, NHSO$_2$R$^{7h}$, and (CH$_2$)$_r$phenyl, (CH$_2$)$_r$tetrazolyl;

$R^{7f}$, at each occurrence, is selected from H, C$_{1-5}$ alkyl, and C$_{3-6}$ cycloalkyl, and phenyl;

$R^{7g}$ is independently selected from —C(O)R$^{7b}$, —C(O)OR$^{7d}$, —C(O)NR$^{7f}$R$^{7f}$, and (CH$_2$)$_r$phenyl;

$R^{7h}$, at each occurrence, is selected from C$_{1-5}$ alkyl, C$_{1-5}$ haloalkyl, and C$_{3-6}$ cycloalkyl, and phenyl;

R', at each occurrence, is selected from H, C$_{1-6}$ alkyl substituted with 0-3 R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with 0-3 R$^{6e}$;

$R^8$ is selected from H, C$_{1-4}$ alkyl, and C$_{3-4}$ cycloalkyl;

$R^9$ is selected from H, C$_{1-4}$ alkyl, C$_{3-4}$ cycloalkyl, —C(O)H, and —C(O)—C$_{1-4}$ alkyl;

$R^{10}$ is independently selected from H, and $C_{1-4}$alkyl is substituted with 0-1 $R^{10b}$;

$R^{10b}$, at each occurrence, is independently selected from —OH, —SH, $NR^{10c}R^{10c}$, —C(O)$NR^{10c}R^{10c}$, and —NHC(O)$R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_q$OH, $(CHR)_q$SH, $(CHR)_q OR^{11d}$, $(CHR)_q S(O)_p R^{11d}$, $(CHR)_r C(O)R^{11b}$, $(CHR)_r NR^{11a}R^{11a}$, $(CHR)_r C(O)NR^{11a}R^{11a}$, $(CHR)_q C(O)NR^{11a}OR^{11d}$, $(CHR)_q NR^{11a}C(O)R^{11b}$, $(CHR)_q NR^{11a}C(O)OR^{11d}$, $(CHR)_q OC(O)NR^{11a}R^{11a}$, $(CHR)_r C(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, and a $(CH_2)_r$-5-6 membered nonaromatic heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ cycloalkyl substituted with 0-2 $R^{11e}$, and a $(CH_2)_r$-5-6 membered nonaromatic heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ cycloalkyl substituted with 0-3 $R^{11e}$, and a $(CH_2)_r$-5-6 membered nonaromatic heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, and a $(CHR)_r$—$C_{3-6}$ carbocyclic residue substituted with 0-5 $R^{12e}$;

$R^{13}$, at each occurrence, is independently selected from H, and $C_{1-4}$alkyl substituted with 0-1 $R^{13b}$, —OH, —$NH_2$, F, Cl, Br, I, —$OR^{13a}$, —$N(R^{13a})_2$, and $C_{1-4}$ alkyl substituted with 0-3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, $NR^{13}CR^{13c}$, —C(O)$NR^{13c}R^{13c}$, and —NHC(O)$R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$alkyl, OH, $NH_2$, —O—$C_{1-4}$ alkyl, $NR^{15a}R^{15a}$, C(O)$NR^{15a}R^{15a}$, $NR^{15a}C(O)R^{15b}$, $NR^{15a}C(O)OR^{15d}$, OC(O)$NR^{15a}R^{15a}$, and $(CHR)_r C(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently seleced from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

l is selected from 1, 2 and 3;

n is selected from 0, 1, 2, and 3;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

In another embodiment, the present invention provides novel compounds of formula (I):

$$\text{(I)}$$

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)—; ring B being substituted with 1-2 $R^5$; or ring B being substituted with 0-2 $R^5$;

X is selected from O or S;

Z is selected from a bond, —$NR^8C(O)$—, —$NR^8C(S)$—, —$NR^8C(O)NH$—, —$NR^8C(S)NH$—, —$NR^8SO_2$—, —$NR^8SO_2NH$—, —$C(O)NR^8$—, —$OC(O)NR^8$—, —$NR^8C(O)O$—, —$(CR^{15}R^{15})_t$—, —$CR^{14}$=$CR^{14}$—, —$CR^{15}R^{15}C(O)$—, —$C(O)CR^{15}R^{15}$—, $CR^{15}R^{15}C$(=N—$OR^{16}$)—, —O—$CR^{14}R^{14}$—, —$CR^{14}R^{14}$—O—, —O—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$—, —$CR^{14}R^{14}$—$S(O)_p$—, and —$S(O)_p$—$NR^9$—;

wherein neither Z nor $R^{13}$ are connected to a carbon atom labeled (b);

bond (a) is a single or double bond;

alternatively, when n is equal to 2, two atoms labeled (b) may join through a double bond;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

with the proviso that $R^1$ is not —$CH_2S(O)_p$—$R^{1a}$, —$CH_2S(O)_2$—$R^{1a}$, —NHC(O)—$R^{1a}$, —NHC(O)NH—$R^{1a}$, —$NHCH_2$—$R^{1a}$, —$SO_2NH$—$R^{1a}$, —$NHSO_2NH$—$R^{1a}$, when $R^{1a}$ is equal to aryl or heteroaryl; (with the proviso that the compounds of the present invention are not those as defined in U.S. patent application Ser. No. 10/027,644, filed Dec. 20, 2001, U.S. patent application Ser. No. 10/383,391, filed Mar. 7, 2003, U.S. Provisional Patent Application No. 60/446,850, filed Feb. 12, 2003 and U.S. patent application Ser. No. 10/776,828, filed Feb. 11, 2004, and U.S. Provisional Patent Application No. 60/467,003, filed May, 1, 2003 and U.S. patent application Ser. No. 10/837,179, filed Apr. 29, 2004;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^4$ is selected from H, $C_{1-6}$ alkyl, $C_{3-8}$ alkenyl, $C_{3-8}$ alkynyl, $(CRR)_rOH$, $(CRR)_rSH$, $(CRR)_rOR^{4d}$, $(CHR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_rOC(O)NR^{4a}R^{4a}$, $(CRR)_rNR^{4a}C(O)OR^{4d}$, $(CRR)_rNR^{4a}C(O)R^{4b}$, $(CRR)_rC(O)OR^{4d}$, $(CRR)_rOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$, $C_{1-6}$ haloalkyl, a $(CRR)_r$—$C_{3-10}$ carbocyclic residue substituted with 0-3 $R^{4e}$, and a $(CHR)_r$-4-10 membered heterocyclic system containing 1-4 heteroatoms selected from N, O, and S, substituted with 0-2 $R^{4e}$;

$R^{4a}$, at each occurrence, is independently selected from H, methyl substituted with 0-1 $R^{4c}$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-10}$ carbocyclic residue substituted with 0-4 $R^{4e}$, and a $(CHR)_r$-4-10 membered heterocyclic system containing 1-4 heteroatoms selected from N, O, and S, substituted with 0-2 $R^{4e}$;

$R^{4b}$, at each occurrence, is selected from H, $C_{1-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-6}$ carbocyclic residue substituted with 0-2 $R^{4e}$, and a $(CHR)_r$-4-10 membered heterocyclic system containing 1-4 heteroatoms selected from N, O, and S, substituted with 0-2 $R^{4e}$;

$R^{4c}$ is independently selected from —$C(O)R^{4b}$, —$C(O)OR^{4d}$, —$C(O)NR^{4f}R^{4f}$, and $(CH_2)_r$phenyl;

$R^{4d}$, at each occurrence, is selected from methyl, $CF_3$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, and a $C_{3-10}$ carbocyclic residue substituted with 0-3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —$C(O)R^{4i}$, —$C(O)OR^{4j}$, —$C(O)NR^{4h}R^{4h}$, —$OC(O)NR^{4h}R^{4h}$, —$NR^{4h}C(O)NR^{4h}R^{4h}$, —$NR^{4h}C(O)OR^{4j}$, and $(CH_2)_r$phenyl;

$R^{4f}$, at each occurrence, is selected from H, $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a $(CH_2)_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a $(CH_2)_r$—$C_{3-6}$ carbocyclic residue;

$R^{4j}$, at each occurrence, is selected from $CF_3$, $C_{1-6}$ alkyl, $C_{3-8}$ alkenyl, $C_{3-8}$ alkynyl, and a $C_{3-10}$ carbocyclic residue;

$R^5$, at each occurrence, is independently selected from H, =O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(O)R^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0-3 $R^{5c}$, and a $(CRR)_r$-5-10 membered heterocyclic system containing 1-4 heteroatoms selected from N, O, and S, substituted with 0-2 $R^{5c}$;

$R^{5a}$, at each occurrence, is independently selected from H, methyl substituted with 0-1 $R^{5g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-3 $R^{5e}$;

wherein when $R^5$ is $(CRR)_rN(O)R^{5a}R^{5a}$, neither $R^{5a}$ are H;

$R^{5b}$, at each occurrence, is selected from $C_{1-6}$ alkyl substituted with 0-3 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —$C(O)R^{5b}$, —$C(O)OR^{5d}$, —$C(O)NR^{5f}R^{5f}$, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)(CR'R')_rR^{6b}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

$R^{6b}$, at each occurrence, is selected from H, $C_{1-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r C_{3-6}$ carbocyclic residue substituted with 0-3 $R^{6e}$, and a $(CH_2)_r$-5-6 membered heterocyclic system containing 1-4 heteroatoms selected from N, O, and S, substituted with 0-2 $R^{6e}$;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, $C_{2-4}$ haloalkyl, a $(CH_2)_r$—$C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from —$C(O)R^{6b}$, —$C(O)OR^{6d}$, —$C(O)NR^{6f}R^{6f}$, and $(CH_2)_r$phenyl;

$R^7$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $NO_2$, CN, $(CR'R')_r NR^{7a}R^{7a}$, $(CR'R')_r OH$, $(CR'R')_r O(CR'R')_r R^{7d}$, $(CR'R')_r SH$, $(CR'R')_r C(O)H$, $(CR'R')_r S(CR'R')_r R^{7d}$, $(CR'R')_r C(O)OH$, $(CR'R')_r C(O)(CR'R')_r R^{7b}$, $(CR'R')_r C(O)NR^{7a}R^{7a}$, $(CR'R')_r NR^{7f}C(O)(CR'R')_r R^{7b}$, $(CR'R')_r C(O)O(CR'R')_r R^{7d}$, $(CR'R')_r OC(O)(CR'R')_r R^{7b}$, $(CR'R')_r OC(O)NR^{7a}(CR'R')_r R^{7a}$, $(CR'R')_r NR^{7a}C(O)NR^{7a}(CR'R')_r R^{7a}$, $(CR'R')_r NR^{7f}C(O)O(CR'R')_r R^{7d}$, $(CR'R')_r C(=NR^{7f})NR^{7a}R^{7a}$, $(CR'R')_r NHC(=NR^{7f})NR^{7f}R^{7f}$, $(CR'R')_r S(O)_p(CR'R')_r R^{7b}$, $(CR'R')_r S(O)_2 NR^{7a}R^{7a}$, $(CR'R')_r NR^{7a}S(O)_2 NR^{7a}R^{7a}$, $(CR'R')_r NR^{7f}S(O)_2(CR'R')_r R^{7b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{7e}$;

alternatively, two $R^7$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-2 $R^{7e}$;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-4}$ haloalkyl, $C_{2-6}$ alkyl substituted with 0-3 $R^{7e}$, a $(CH_2)_r$—$C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, C(O)OC$_{1-5}$ alkyl, $(CH_2)_r SC_{1-5}$ alkyl, $(CH_2)_r NR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —$C(O)R^{7b}$, —$C(O)OR^{7d}$, —$C(O)NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_r C_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^9$ is selected from H, $C_{1-4}$ alkyl, $C_{3-4}$ cycloalkyl, —C(O)H, and —C(O)—$C_{1-4}$alkyl;

$R^{10}$ is independently selected from H, and $C_{1-4}$alkyl substituted with 0-1 $R^{10b}$;

$R^{10b}$, at each occurrence, is independently selected from —OH, —SH, —$NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_q OH$, $(CHR)_q SH$, $(CHR)_q OR^{11d}$, $(CHR)_q S(O)_p R^{11d}$, $(CHR)_r C(O)R^{11b}$, $(CHR)_r NR^{11a}R^{11a}$, $(CHR)_r C(O)NR^{11a}R^{11a}$, $(CHR)_r C(O)NR^{11a}OR^{11d}$, $(CHR)_q NR^{11a}C(O)R^{11b}$, $(CHR)_q NR^{11a}C(O)OR^{11d}$, $(CHR)_q OC(O)NR^{11a}R^{11a}$, $(CHR)_r C(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, a $(CH_2)_r$—$C_{3-6}$ carbocyclic residue substituted with 0-5 $R^{11e}$, and a $(CH_2)_r$-5-6 membered heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_q OH$, $(CHR)_q SH$, $(CHR)_q OR^{12d}$, $(CHR)_q S(O)_p R^{12d}$, $(CHR)_r C(O)R^{12b}$, $(CHR)_r NR^{12a}R^{12a}$, $(CHR)_r C(O)NR^{12a}R^{12a}$, $(CHR)_r C(O)NR^{12a}OR^{12d}$, $(CHR)_q NR^{12a}C(O)R^{12b}$, $(CHR)_q NR^{12a}C(O)OR^{12d}$, $(CHR)_q OC(O)NR^{12a}R^{12a}$, $(CHR)_r C(O)OR^{12d}$, a $(CHR)_r$—$C_{3-6}$ carbocyclic residue substituted with 0-5 $R^{12e}$, and a $(CHR)_r$-5-10 membered heterocyclic system containing 1-4 heteroatoms selected from N, O, and S, substituted with 0-3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, a $(CH_2)_r$—$C_{3-6}$ carbocyclic residue substituted with 0-5 $R^{12e}$, and a $(CH_2)_r$-5-6 membered heterocyclic system containing 1-4 heteroatoms selected from N, O, and S, substituted with 0-3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{12e}$, and a $(CH_2)_r$-5-6 membered heterocyclic system containing 1-4 heteroatoms selected from N, O, and S, substituted with 0-3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{12e}$, and a $(CH_2)_r$-5-6 membered heterocyclic system containing 1-4 heteroatoms selected from N, O, and S, substituted with 0-3 $R^{12e}$; $R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$alkyl substituted with 0-1 $R^{13b}$, —OH, —$NH_2$, F, Cl, Br, I, —$OR^{13a}$, —$N(R^{13a})_2$, and $C_{1-4}$ alkyl substituted with 0-3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, $NR^{13c}R^{13c}$, —$C(O)NR^{13c}R^{13c}$, and —NHC(O)$R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$alkyl, OH, $NH_2$, —O—$C_{1-4}$ alkyl, $NR^{15a}R^{15a}$, $C(O)NR^{15a}R^{15a}$, $NR^{15a}C(O)R^{15b}$, $NR^{15a}C(O)OR^{15d}$, $OC(O)NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently seleced from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

l is selected from 1, 2 and 3;

n is selected from 0, 1, 2, and 3;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

Thus, in a another embodiment, the present invention provides novel compounds of formula (I):
m is 0.

In another embodiment, the present invention provides novel compounds of formula (I), wherein:
ring B is selected from

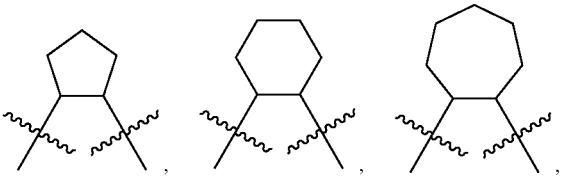

-continued

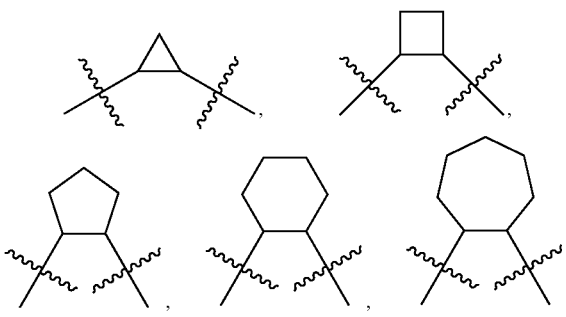

ring B being optionally substituted with 0-1 $R^5$; and
$R^{11}$ and $R^{12}$ are H.

In another embodiment, the present invention provides novel compounds of formula (I), wherein:
ring B is selected from

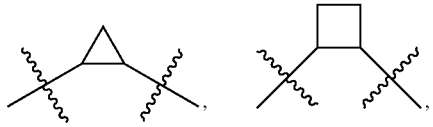

each substituted with 1-2 $R^5$, and

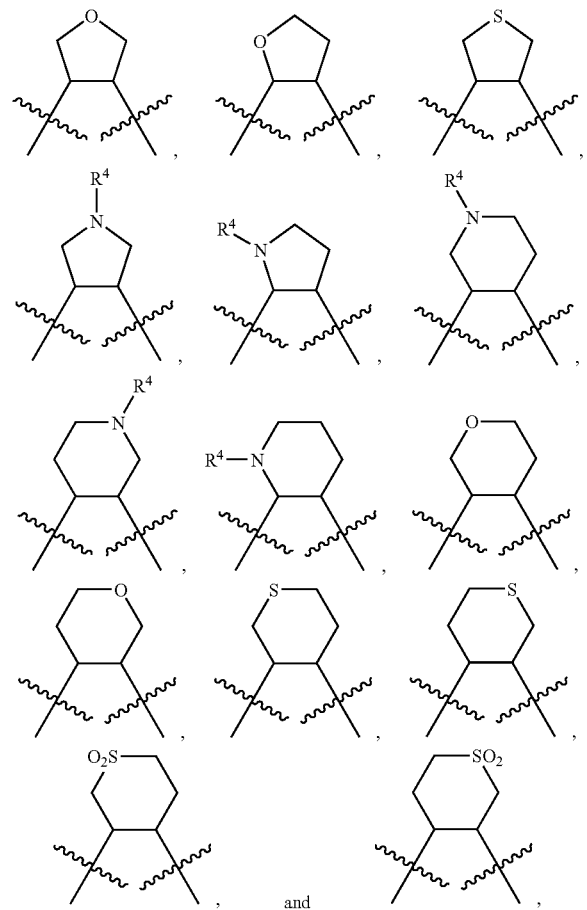

each being substituted with 0-1 $R^5$; and
$R^{11}$ and $R^{12}$ are H.

In another embodiment, the present invention provides novel compounds of formula (I), wherein:

$R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, CRR $(CRR)_r$ $NR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{1-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, and cyclobutyl;

$R^{5b}$, at each occurrence, is selected from $C_{1-6}$ alkyl substituted with 0-2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

In another embodiment, the present invention provides novel compounds of formula (I), wherein:

$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CRR)_tSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_rNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^{4b}$;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{5e}$;

$R^5$, at each occurrence, is independently selected from H, methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl, $(CH_2)_r$phenyl substituted with 0-2 $R^{5e}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

In another embodiment, the present invention provides novel compounds of formula (I), wherein:

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isonicotinyl, isoquinolinyl isothiazolyl, isoxazolinyl, isoxazolyl, oxazolyl, phthalazinyl, picolinyl, pyrazinyl, pyrazolyl, pyridazinyl, pyridyl, pyridinyl, pyrimidinyl, pyrrolyl, quinazolinyl, quinolinyl, thiazolyl, thienyl, triazinyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, pyrrolotrizinyl, quinazolinyl, quinolinyl, thiazolyl, thienyl, and tetrazolyl;

$R^4$ is selected from H, methyl, ethyl, propyl, i-propyl, butyl, i-butyl, allyl, propynyl, $(CRR)_tOH$, $(CRR)_tSH$, $(CRR)_tOR^{4d}$, $(CRR)_tSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C$ (O)R$^{4b}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_r$C(O)OR$^{4b}$, (CRR)$_r$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$;

R$^{4a}$, at each occurrence, is independently selected from H, methyl substituted with 0-1 R$^{4c}$, C$_{2-6}$ alkyl substituted with 0-3 R$^{4e}$ wherein C$_{2-6}$ alkyl is selected from ethyl, propyl, i-propyl, butyl, i-butyl, t-butyl, pentyl and hexyl, and a (CH$_2$)$_r$—C$_{3-6}$ carbocyclic residue substituted with 0-4 R$^{4e}$ wherein the carbocyclic residue is selected from cyclopropyl, cyclohexyl, and phenyl;

R$^{4b}$ is selected from H, methyl, ethyl, propyl, i-propyl, butyl, i-butyl, t-butyl, pentyl, and cyclopropyl;

R$^{4d}$ is selected from methyl, ethyl, propyl, i-propyl, butyl, i-butyl, t-butyl, pentyl, and cyclopropyl; and R$^8$ is selected from H, methyl, ethyl, propyl, i-propyl, and cyclopropyl.

In another embodiment, the present invention provides novel compounds of formula (I), wherein:

R$^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CH$_2$)$_r$NR$^{6a}$R$^{6a'}$, (CH$_2$)$_r$OH, (CH$_2$)$_r$O(CH$_2$)$_r$R$^{6d}$, (CH$_2$)$_r$SH, (CH$_2$)$_r$C(O)H, (CH$_2$)$_r$S(CH$_2$)$_r$R$^{6d}$, (CH$_2$)$_r$C(O)OH, (CH$_2$)$_r$C(O)(CH$_2$)$_r$R$^{6b}$, (CH$_2$)$_r$C(O)NR$^{6a}$R$^{6a}$, (CH$_2$)$_r$NR$^{6f}$C(O)R$^{6b'}$, (CH$_2$)$_r$C(O)O(CH$_2$)$_r$R$^{6d}$, (CH$_2$)$_r$NR$^{6a}$C(O)NR$^{6a'}$R$^{6d'}$, (CH$_2$)$_r$NR$^{6a}$C(S)NR$^{6a}$R$^{6a}$, (CH$_2$)$_r$OC(O)(CH$_2$)$_r$R$^{6b}$, (CH$_2$)$_r$S(O)$_p$(CH$_2$)$_r$R$^{6b}$, (CH$_2$)$_r$S(O)$_2$NR$^{6a}$R$^{6a}$, (CH$_2$)$_r$NR$^{6f}$S(O)$_2$(CH$_2$)$_r$R$^{6b}$, (CH$_2$)$_r$NR$^{6f}$S(O)$_2$NR$^{6a'}$R$^{6a'}$, C$_{1-6}$ haloalkyl, and (CH$_2$)$_r$phenyl substituted with 0-3 R$^{6e}$, and a (CH$_2$)$_r$-5-6 membered heterocyclic system containing 1-2 heteroatoms selected from N, O, and S, substituted with 0-2 R$^{6e}$, wherein the heterocyclic system is selected from aziridinyl, azetidinyl, pyrrolyl, piperidinyl, and morpholinyl;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from H, methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, C(O)NHR$^{6h}$, C(O)OC$_{1-5}$ alkyl, (CH$_2$)$_r$OH, C(O)OH, (CH$_2$)$_r$C(O)NHSO$_2$—R$^{6h}$, NHSO$_2$R$^{6h}$, (CH$_2$)$_r$tetrazolyl, and (CH$_2$)$_r$phenyl and a (CH$_2$)$_r$-5-b 6 membered heterocyclic system containing 1-4 heteroatoms selected from N, O, and S;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CH$_2$)$_r$C$_{3-6}$ cycloalkyl, Cl, Br, I, F, NO$_2$, CN, (CH$_2$)$_r$NR$^{7a}$R$^{7a}$, (CH$_2$)$_r$OH, (CH$_2$)$_r$O(CH$_2$)$_r$R$^{7d}$, (CH$_2$)$_r$SH, (CH$_2$)$_r$C(O)H, (CH$_2$)$_r$S(CH$_2$)$_r$R$^{7d}$, (CH$_2$)$_r$C(O)OH, (CH$_2$)$_r$C(O)(CH$_2$)$_r$R$^{7b}$, (CH$_2$)$_r$C(O)NR$^{7a}$R$^{7a}$, (CH$_2$)$_r$NR$^{7f}$C(O)(CH$_2$)$_r$R$^{7b}$, (CH$_2$)$_r$C(O)O(CH$_2$)$_r$R$^{7d}$, (CH$_2$)$_r$OC(O)(CH$_2$)$_r$R$^{7b}$, (CH$_2$)$_r$OC(O)NR$^{7a}$R$^{7a}$, (CH$_2$)$_r$NR$^{7a}$C(O)NR$^{7a}$R$^{7a}$, (CH$_2$)$_r$NR$^{7a}$C(O)O(CH$_2$)$_r$R$^{7d}$, S(CH$_2$)$_r$S(O)$_p$(CH$_2$)$_r$R$^{7b}$, (CH$_2$)$_r$S(O)$_2$NR$^{7a}$R$^{7a}$, (CH$_2$)$_r$NR$^{7f}$S(O)$_2$(CH$_2$)$_r$R$^{7b}$, C$_{1-6}$ haloalkyl, adamantyl, and (CH$_2$)$_r$phenyl substituted with 0-3 R$^{7e}$ and a (CH$_2$)$_r$-5-6 membered heterocyclic system containing 1-4 heteroatoms selected from N, O, and S, substituted with 0-3 R$^{7e}$, wherein the heterocyclic system is selected from thienyl, pyridinyl, benzothiazolyl, and tetrazolyl;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, CF$_2$CF$_3$, CHF$_2$, CH$_2$F, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, OH, SH, C(O)OH, C(O)NHR$^{7h}$, C(O)OC$_{1-5}$ alkyl, (CH$_2$)$_r$SC$_{1-5}$ alkyl, (CH$_2$)$_r$NR$^{7f}$R$^{7f}$, (CH$_2$)$_r$C(O)NHSO$_2$—R$^{7h}$, NHSO$_2$R$^{7h}$, and (CH$_2$)$_r$phenyl, (CH$_2$)$_r$tetrazolyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel compounds of formula (I), wherein:

R$^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CH$_2$)$_r$NR$^{6a}$R$^{6a}$, (CH$_2$)$_r$OH, (CH$_2$)$_r$OR$^{6d}$, (CH$_2$)$_r$SH, (CH$_2$)$_r$C(O)H, (CH$_2$)$_r$SR$^{6d}$, (CH$_2$)$_r$C(O)OH, (CH$_2$)$_r$C(O)R$^{6b}$, (CH$_2$)$_r$C(O)NR$^{6a}$R$^{6a}$, (CH$_2$)$_r$NR$^{6f}$C(O)R$^{6b}$, (CH$_2$)$_r$C(O)OR$^{6d}$, (CH$_2$)$_r$NR$^{6a}$C(O)NR$^{6a}$R$^{6a}$, (CH$_2$)$_r$NR$^{6a}$C(S)NR$^{6a}$R$^{6a}$, (CH$_2$)$_r$OC(O)R$^{6b}$, (CH$_2$)$_r$S(O)$_p$R$^{6b}$, (CH$_2$)$_r$S(O)$_2$ NR$^{6a}$R$^{6a}$, (CH$_2$)$_r$NR$^{6f}$S(O)$_2$R$^{6b}$, (CH$_2$)$_r$NR$^{6f}$S(O)$_2$NR$^{6a}$R$^{6a}$, C$_{1-6}$ haloalkyl, and (CHR')$_r$phenyl substituted with 0-3 R$^{6e}$;

R$^7$ is selected from methyl, ethyl, propyl, i-propyl, butyl, i-butyl, s-butyl, pentyl, hexyl, Cl, Br, I, F, CN, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, CF$_2$CF$_3$, CHF$_2$, CH$_2$F, OCF$_3$, C(O)R$^{7b}$, C(O)OR$^{7d}$, NR$^{7f}$C(O)NR$^{7a}$R$^{7a}$, NHS(O)$_2$R$^{7b}$,

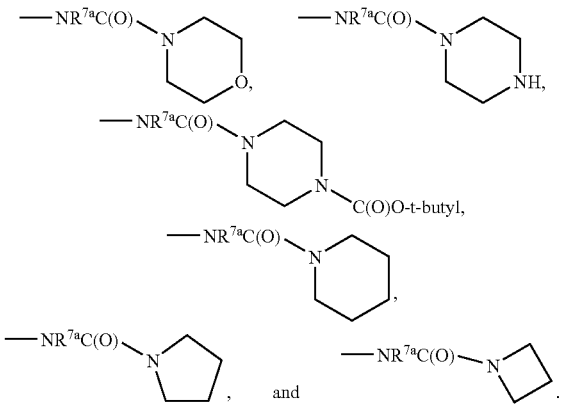

In another embodiment, the present invention provides novel compounds of formula (I), wherein:

ring B is selected from

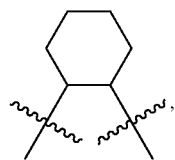

each substituted with 1-2 $R^5$, and

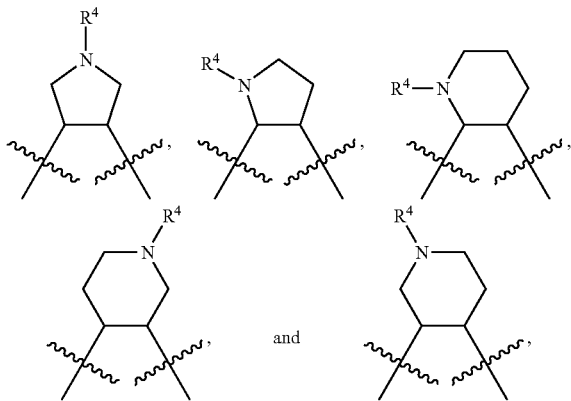

each being substituted with 0-1 $R^5$;

Z is selected from a bond, —$NR^8C(O)$—, —$NR^8$—, —C(O)$NR^8$—, and —NHC(O)NH—;

$R^1$ is selected from H, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$;

$R^2$ is phenyl substituted with 0-2 $R^7$;

$R^4$ is selected from H, methyl, ethyl, propyl, i-propyl, butyl, i-butyl, t-butyl, pentyl, hexyl, and $(CH_2)_rC(O)R^{4b}$;

$R^6$ is selected from methyl, ethyl, propyl, i-propyl, butyl, F, Cl, Br, I, $NO_2$, CN, $(CH_2)_rO(CH_2)_rR^{6d}$, $C(O)R^{6d}$, $SR^{6d}$, $NR^{6a}R^{6a}$, $C(O)NR^{6a}R^{6a}$, $NC(O)R^{6b}$, $OC(O)R^{6b}$, $S(O)_pR^{6b}$, $(CHR')_rS(O)_2NR^{6a}R^{6a}$, and $CF_3$;

$R^{6a}$ is H, methyl, ethyl, propyl, i-propyl, butyl, and phenyl; alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$ is H, methyl, ethyl, propyl, i-propyl or butyl;

$R^{6d}$ is methyl, phenyl, $CF_3$, and $(CH_2)$-phenyl; and r is 0 or 1.

In another embodiment, the present invention provides novel compounds of formula (I), wherein:

$R^7$, at each occurrence, is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rOR^{7d}$, $(CH_2)_rSH$, $(CH_2)_rC(O)H$, $(CH_2)_rSR^{7d}$, $(CH_2)_rC(O)OH$, $(CH_2)_rC(O)R^{7b}$, $(CH_2)_rC(O)NR^{7a}R^{7a}$, $(CH_2)_rNR^{7f}C(O)R^{7b}$, $(CH_2)_rC(O)OR^{7d}$, $(CH_2)_rOC(O)R^{7b}$, $(CH_2)_rOC(O)NR^{7a}R^{7a}$, $(CH_2)_rNR^{7a}C(O)NR^{7a}R^{7a}$, $(CH_2)_rNR^{7f}C(O)OR^{7d}$, $(CH_2)_rS(O)pR^{7b}$, $(CH_2)_rS(O)_2NR^{7a}R^{7a}$, $(CH_2)_rNR^{7a}S(O)_2NR^{7a}R^{7a}$, $(CH_2)_rNR^{7f}S(O)_2R^{7b}$, $C_{1-2}$ haloalkyl, $(CH_2)_r$ adamantyl, $(CH_2)_r$phenyl substituted with 0-3 $R^{7e}$, and a $(CH_2)_r$-5-6 membered heterocyclic system containing 1-4 heteroatoms selected from N, O, and S, substituted with 0-3 $R^{7e}$, wherein the heterocyclic ring is selected from thiophenyl, pyridinyl, benzothiazolyl, and tetrazolyl.

In another embodiment, the present invention provides novel compounds of formula (Ia), wherein:

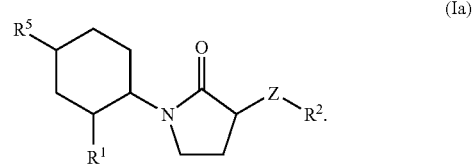

(Ia)

In another embodiment, the present invention provides novel compounds of formula (Ia), wherein:

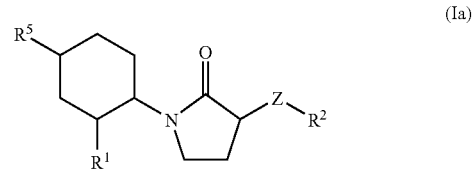

(Ia)

wherein

Z is selected from —NHC(O)—, —NHC(O)NH—, —NH—, $R^1$ is selected from $C_{1-6}$ alkyl substituted from 0-1 $R^6$, —C(O)O—$C_{1-6}$ alkyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl system is selected from from quinazolinyl, triazinyl, pyrimidinyl, picolinyl, isonicotinyl, furanyl, indolyl, pyridinyl, pyrazolyl, pyrazinyl, thiazolyl, thiophenyl, and isoxazolyl;

$R^5$, at each occurrence, is independently selected from methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl.

In another embodiment, the present invention provides novel compounds of formula (I), wherein:

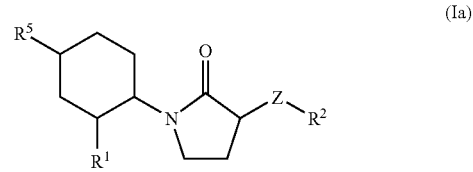

(Ia)

$R^1$ is selected from H, $C_{1-6}$ alkyl substituted with 0-1 $R^6$, —C(O)O—$C_{1-6}$ alkyl; and $R^5$, at each occurrence, is independently selected from F, Cl, Br, I, $(CH_2)_rOH$, $(CH_2)_rOR^{5d}$, $(CH_2)_rNR^{5a}R^{5a}$, and a (CRR)$_r$-5-10 membered heterocyclic system containing 1-4 heteroatoms selected from N, O, and S, substituted with 0-2 R$^{5c}$, wherein the heterocyclic system is selected from pyrrolidinyl, piperidinyl, and morpholinyl.

In another embodiment, the present invention provides novel compounds of formula (I), wherein:

R$^4$ is selected from H, C$_{1-6}$ alkyl, C$_{3-8}$ alkenyl, C$_{3-8}$ alkynyl, (CRR)$_q$OH, (CRR)$_r$SH, (CRR)$_t$OR$^{4d}$, (CRR)$_r$SR$^{4d}$, (CRR)$_t$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_r$NR$^{4a}$C(O)R$^{4b}$, (CRR)$_t$C(O)OR$^{4b}$, (CRR)$_t$OC(O)R$^{4b}$, (CRR)$_r$S(O)$_p$R$^{4b}$, (CRR)$_r$S(O)$_2$NR$^{4a}$R$^{4a}$, (CRR)$_t$NR$^{4a}$S(O)$_2$R$^{4b}$;

R, at each occurrence, is independently selected from H, methyl, ethyl, propyl, allyl, propynyl, (CH$_2$)$_r$C$_{3-6}$ cycloalkyl, and (CH$_2$)$_r$phenyl substituted with R$^{6e}$;

R$^5$, at each occurrence, is independently selected from H, methyl, ethyl, propyl, i-propyl, butyl, i-butyl, allyl, propynyl, (CH$_2$)$_r$OH, (CH$_2$)$_r$OR$^{5d}$, (CH$_2$)$_r$NR$^{5a}$R$^{5a}$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$NR$^{5a}$C(O)R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O)R$^{5b}$, (CH$_2$)$_r$C(O)OR$^{5b}$, (CH$_2$)$_r$OC(O)R$^{5b}$, (CH$_2$)$_r$NR$^{5a}$S(O)$_2$R$^{5b}$, and C$_{1-6}$ haloalkyl;

R$^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

In another embodiment, the present invention provides novel compounds of formula (I), wherein:

R$^1$ is selected from H, R$^6$, C$_{1-6}$ alkyl substituted with 0-3 R$^6$, C$_{2-6}$ alkenyl substituted with 0-3 R$^6$, C$_{2-6}$ alkynyl substituted with 0-3 R$^6$, C$_{6-10}$ aryl group substituted with 0-5 R$^6$, wherein the aryl group is selected from phenyl and napthyl, and a 5-10 membered heteroaryl system containing 1-4 heteroatoms selected from N, O, and S, substituted with 0-3 R$^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

R$^2$ is selected from phenyl substituted with 0-2 R$^7$, and a 5-10 membered heteroaryl system containing 1-4 heteroatoms selected from N, O, and S, substituted with 0-3 R$^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

R$^4$ is selected from H, methyl, ethyl, propyl, i-propyl, butyl, i-butyl, allyl, propynyl, (CRR)$_q$OH, (CRR)$_r$SH, (CRR)$_t$OR$^{4d}$, (CRR)$_r$SR$^{4d}$, (CRR)$_r$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_t$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_r$NR$^{4a}$C(O)R$^{4b}$, (CRR)$_t$C(O)OR$^{4b}$, (CRR)$_t$OC(O)R$^{4b}$, (CRR)$_r$S(O)$_p$R$^{4b}$, (CRR)$_r$S(O)$_2$NR$^{4a}$R$^{4a}$, (CRR)$_t$NR$^{4a}$S(O)$_2$R$^{4b}$;

R$^{4a}$, at each occurrence, is independently selected from H, methyl substituted with 0-1 R$^{4c}$, C$_{2-6}$ alkyl substituted with 0-3 R$^{4e}$ wherein C$_{2-6}$ is selected from ethyl, propyl, i-propyl, butyl, i-butyl, t-butyl, pentyl and hexyl, and a (CH$_2$)$_r$—C$_{3-6}$ carbocyclic residue substituted with 0-4 R$^{4e}$ wherein the carbocyclic residue is selected from cyclopropyl, cyclohexyl, and phenyl;

R$^{4b}$ is selected from H, methyl, ethyl, propyl, i-propyl, butyl, i-butyl, t-butyl, pentyl, and cyclopropyl;

R$^{4d}$ is selected from methyl, ethyl, propyl, i-propyl, butyl, i-butyl, t-butyl, pentyl, and cyclopropyl; and R$^8$ is selected from H, methyl, ethyl, propyl, i-propyl, and cyclopropyl.

In another embodiment, the present invention provides novel compounds of formula (I), wherein:

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CRR)$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$NR$^{6a}$C(O)NR$^{6a}$R$^{6a}$, (CR'R')$_r$NR$^{6a}$C(S)NR$^{6a}$R$^{6a}$, (CR'R')$_r$OC(O)(CR'R')$_r$R$^{6b}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$(CR'R')$_r$R$^{6b}$, (CR'R')$_r$NR$^{6f}$S(O)$_2$NR$^{6a}$R$^{6a}$, C$_{1-6}$ haloalkyl, and (CR'R')$_r$phenyl substituted with 0-3 R$^{6e}$, and a (CH$_2$)$_r$-5-6 membered heterocyclic system containing 1-2 heteroatoms selected from N, O, and S, substituted with 0-2 R$^{6e}$;

R$^{6a}$, at each occurrence, is independently selected from H, methyl, ethyl, propyl, i-propyl, butyl, i-butyl, t-butyl, pentyl, hexyl, cyclopropyl and phenyl;

alternatively, two R$^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

R$^{6b}$, at each occurrence, is selected from methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CRR)$_r$C$_{3-6}$ cycloalkyl, Cl, Br, I, F, NO$_2$, CN, (CRR)$_r$NR$^{7a}$R$^{7a}$, (CRR)$_r$OH, (CRR)$_r$O(CH)$_r$R$^{7d}$, (CRR)$_r$SH, (CRR)$_r$C(O)H, (CRR)$_r$S(CRR)$_r$R$^{7d}$, (CRR)$_r$C(O)OH, (CRR)$_r$C(O)(CRR)$_r$R$^{7b}$, (CRR)$_r$C(O)NR$^{7a}$R$^{7a}$, (CRR)$_r$NR$^{7f}$C(O)(CRR)$_r$R$^{7b}$, (CRR)$_r$C(O)O(CRR)$_r$R$^{7d}$, (CRR)$_r$OC(O)(CRR)$_r$R$^{7b}$, (CRR)$_r$NR$^{7a}$C(O)NR$^{7a}$R$^{7a}$, (CRR)$_r$NR$^{7a}$C(O)O(CRR)$_r$R$^{7d}$, (CRR)$_r$S(O)$_p$(CRR)$_r$R$^{7b}$, (CRR)$_r$S(O)$_2$NR$^{7a}$R$^{7a}$, (CRR)$_r$NR$^{7f}$S(O)$_2$(CRR)$_r$R$^{7b}$, C$_{1-6}$ haloalkyl, and (CRR)$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O)$OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CHR')_rC_{3-6}$ cycloalkyl, Cl, Br, I, F, $NO_2$, CN, $(CHR')_rNR^{6a}R^{6a}$, $(CHR')_rOH$, $(CHR')_rOR^{6d}$, $(CHR')_rSH$, $(CHR')_rC(O)H$, $(CHR')_rSR^{6d}$, $(CHR')_rC(O)OH$, $(CHR')_rC(O)R^{6b}$, $(CHR')_rC(O)NR^{6a}R^{6a}$, $(CHR')_rNR^{6f}C(O)R^{6b}$, $(CHR')_rC(O)OR^{6d}$, $(CHR')_rNR^{6a}C(O)NR^{6a}R^{6a}$, $(CHR')_rNR^{6a}C(S)NR^{6a}R^{6a}$, $(CHR')_rOC(O)R^{6b}$, $(CHR')_rS(O)_pR^{6b}$, $(CHR')_rS(O)_2NR^{6a}R^{6a}$, $(CHR')_rNR^{6f}S(O)_2R^{6b}$, $(CHR')_rNR^{6f}S(O)_2NR^{6a}R^{6a}$, $C_{1-6}$ haloalkyl, and $(CHR')_r$phenyl substituted with 0-3 $R^{6e}$;

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$,

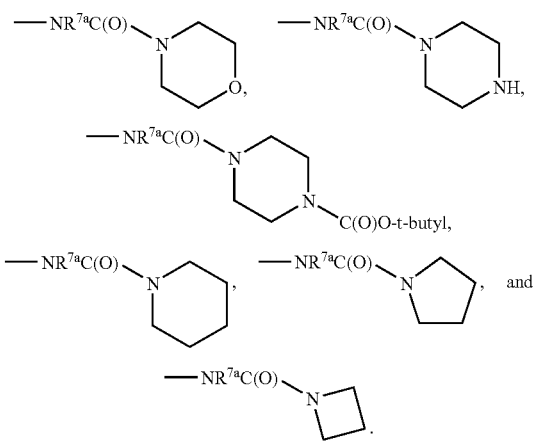

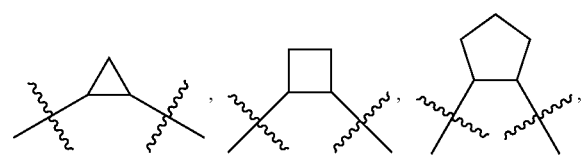

In another embodiment, the present invention provides novel compounds of formula (I), wherein:
ring B is selected from

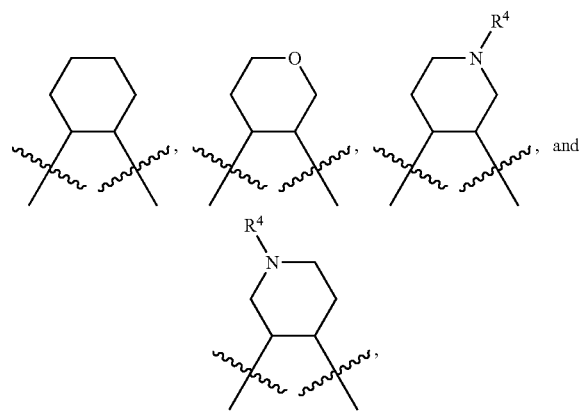

ring B being optionally substituted with 0-1 $R^5$;

Z is selected from a bond, $-NR^8C(O)-$, $-NR^8-$, $-C(O)NR^8-$, and $-NHC(O)NH-$;

$R^1$ is selected from H, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$;

$R^2$ is phenyl substituted with 0-2 $R^7$;

$R^4$ is selected from H, methyl, ethyl, propyl, i-propyl, butyl, i-butyl, t-butyl, pentyl, hexyl, and $(CH_2)_rC(O)R^{4b}$;

$R^6$ is selected from methyl, ethyl, propyl, i-propyl, butyl, F, Cl, Br, I, $NO_2$, CN, $(CH_2)_rO(CH_2)_rR^{6d}$, $C(O)R^{6d}$, $SR^{6d}$, $NR^{6a}R^{6a}$, $C(O)NR^{6a}R^{6a}$, $NC(O)R^{6b}$, $OC(O)R^{6b}$, $S(O)_pR^{6b}$, $(CHR')_rS(O)_2NR^{6a}R^{6a}$, and $CF_3$;

$R^{6a}$ is H, methyl, ethyl, propyl, i-propyl, butyl, and phenyl; alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$ is H, methyl, ethyl, propyl, i-propyl or butyl;

$R^{6d}$ is methyl, phenyl, $CF_3$, and $(CH_2)$-phenyl; and r is 0 or 1.

In another embodiment, the present invention provides novel compounds of formula (I), wherein:
ring B is selected from

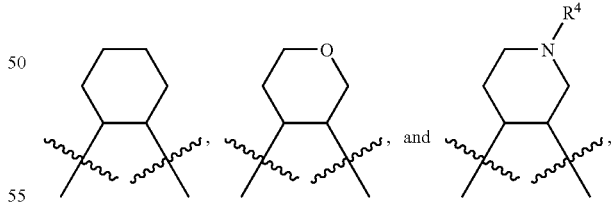

ring B being substituted with 0-1 $R^5$;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, and $NR^{5a}R^{5a}$;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, $-C(O)CF_3$, $C(=N)NH_2$, benzyl, and $-C(O)O$-t-butyl;

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, $NR^{7}C(O)NR^{7a}R^{7a}$, $NHS(O)_2R^{7b}$,

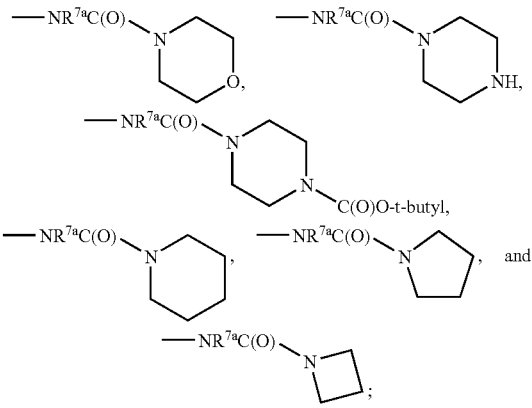

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7b}$ is selected from cyclohexyl and $CF_3$; and
$R^{7d}$ is selected from methyl, ethyl, propyl, i-propyl, butyl, i-butyl, and t-butyl.

In another embodiment, the present invention provides novel compounds of formula (I), wherein:
ring B is selected from

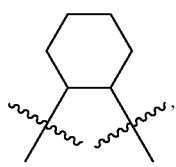

ring B being substituted with 0-1 $R^5$;
$R^5$ is selected from H, OH, $OCH_3$, and $NR^{5a}R^{5a}$;
$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —$C(O)CF_3$, $C(=N)NH_2$, benzyl, and —C(O)O-t-butyl;
$R^7$ is selected from Cl, Br, CN, $NR^{7a}R^{7a}$, $CF_3$, $CF_2CF_3$, $CHF_2$, $CH_2F$, $OCF_3$, $OCF_2CF_3$, $OCHF_2$, and $OCH_2F$; and
$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

In another embodiment, the present invention provides novel compounds of formula (I), wherein:
B is

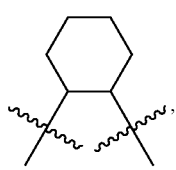

ring B being substituted with 1 $R^5$.

In another embodiment, the present invention provides novel compounds of formula (I), wherein:
$R^5$ is selected from $NR^{5a}R^{5a}$;
$R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl.

In another embodiment, the present invention provides novel compounds of formula (I), wherein:
Z is selected from a bond, —NHC(O)—, —NH—, —C(O)NH—, and —NHC(O)NH—.

In another embodiment, the present invention provides novel compounds of formula (I), wherein:
$R^7$ is selected from Cl, Br, $NR^{7a}R^{7a}$, $NR^{7a}C(O)OR^{7d}$, $NHC(O)NHR^{7a}$, $OCF_3$, and $CF_3$;
$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7d}$ is selected from methyl, ethyl, propyl, i-propyl, butyl, i-butyl, and t-butyl.

In another embodiment, the present invention is directed to a compound of formula (II)

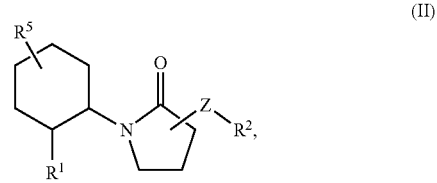

or a stereoisomer or a pharmaceutically acceptable salt thereof, wherein:
Z is selected from —NH—, —NHC(O)—, and —C(O)NH—.

In another embodiment, the present invention is directed to a compound of formula (II-a)

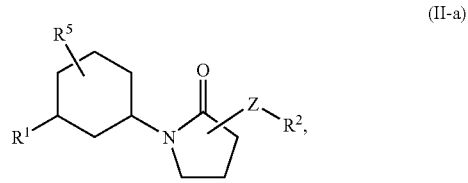

or a stereoisomer or a pharmaceutically acceptable salt thereof, wherein:
Z is selected from —NH—, —NHC(O)—, and —C(O)NH—.

In another embodiment, the present invention is directed to a compound of formula (II-b)

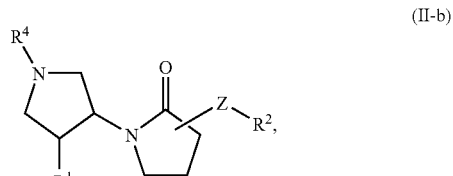

or a stereoisomer or a pharmaceutically acceptable salt thereof, wherein:

Z is selected from —NH—, —NHC(O)—, and —C(O)NH—.

In another embodiment, the present invention provides novel compounds of formula (I), wherein the compound is selected from the compounds of the tables and examples.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of CCR-2 receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for inhibiting CCR2 and CCR5 activity comprising administering to a patient in need thereof a therapeutically effective amount of a compound of Formula (I).

In another embodiment, the present invention is directed to amethod for treating disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from asthma, multiple sclerosis, artherosclerosis, and rheumatoid arthritis.

In another embodiment, the present invention is directed to a method for treating disorders, of Formula (I), wherein said disorders being selected from restinosis, organ transplantation, and cancer.

In another embodiment, the present invention is directed to a method for treating rheumatoid arthritis, comprising administering to a patient in need thereof a therapeutically effective amount of a compound of Formula (I).

In another embodiment, the present invention is directed to amethod for treating multiple sclerosis, comprising administering to a patient in need thereof a therapeutically effective amount of a compound of Formula (I).

In another embodiment, the present invention is directed to amethod for treating atherosclerosis, comprising administering to a patient in need thereof a therapeutically effective amount of a compound of Formula (I).

In another embodiment, the present invention is directed to amethod for treating asthma, comprising administering to a patient in need thereof a therapeutically effective amount of a compound of Formula (I).

In another embodiment, the present invention is directed to amethod for treating restinosis, comprising administering to a patient in need thereof a therapeutically effective amount of a compound of Formula (I).

In another embodiment, the present invention is directed to amethod for treating organ transplantation, comprising administering to a patient in need thereof a therapeutically effective amount of a compound of Formula (I).

In another embodiment, the present invention is directed to amethod for treating cancer, comprising administering to a patient in need thereof a therapeutically effective amount of a compound of Formula (I).

In another embodiment, the present invention is directed to a method for treating inflammatory diseases, comprising administering to a patient in need thereof a therapeutically effective amount of a compound of Formula (I).

In another embodiment, the present invention is directed to a method for treating inflammatory diseases which are at least partially mediated by CCR-2, comprising administering to a patient in need thereof a therapeutically effective amount of a compound of Formula (I).

In another embodiment, the present invention is directed to a method for modulation of CCR2 activity comprising administering to a patient in need thereof a therapeutically effective amount of a compound of Formula (I).

In another embodiment, the present invention is directed to a method for modulation of MIP-1β and RANTES activity that is mediated by the CCR5 receptor comprising administering to a patient in need thereof a therapeutically effective amount of a compound of Formula (I).

In another embodiment, the present invention is directed the use of a compound of Formula (I) in the preparation of a medicament for the treatment of osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a compound of formula (I) for use in therapy.

In another embodiment, ring B is selected from
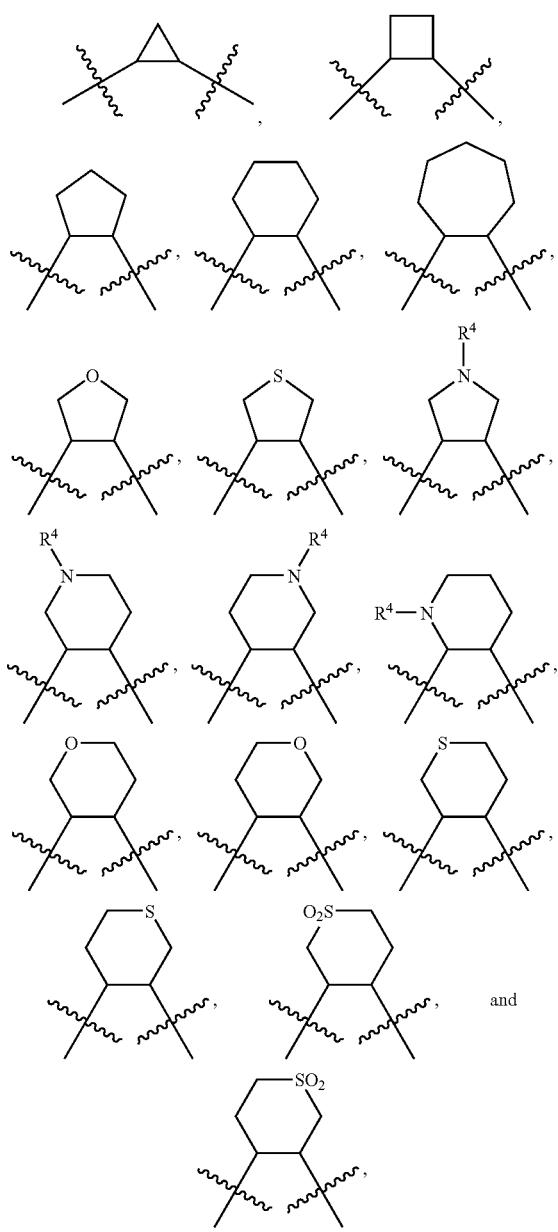
ring B being optionally substituted with 0-1 $R^5$.
In another embodiment, ring B is selected from
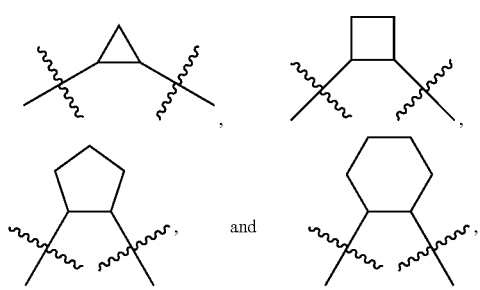
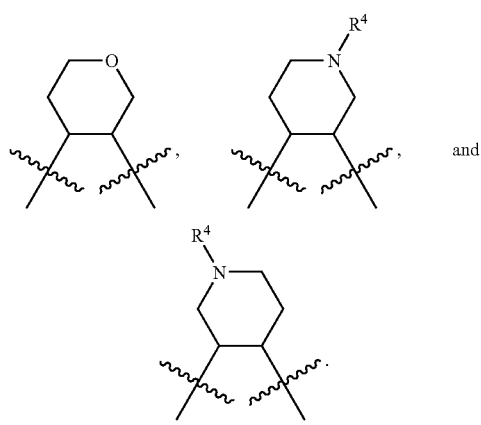
In another embodiment, ring B is selected from
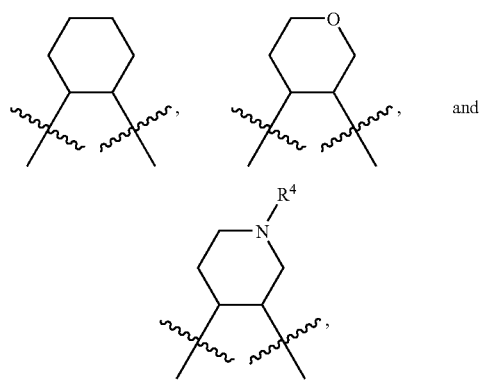
ring B being substituted with 0-1 $R^5$;
In another embodiment, ring B is
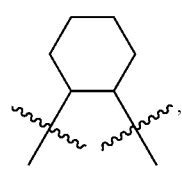
ring B being substituted with 0-1 $R^5$.
In another embodiment, ring B is
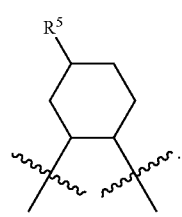

In another embodiment, ring B is selected from

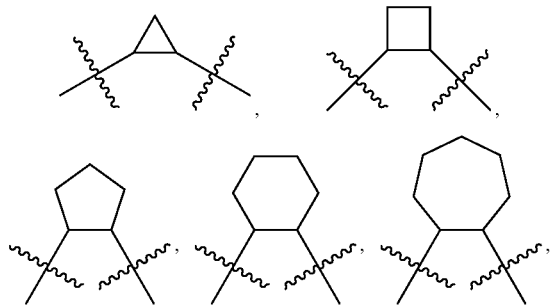

each substituted with 1-2 $R^5$, and

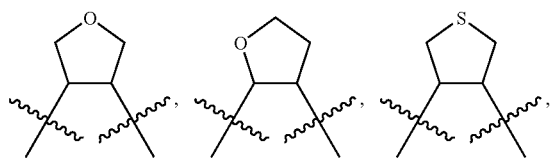

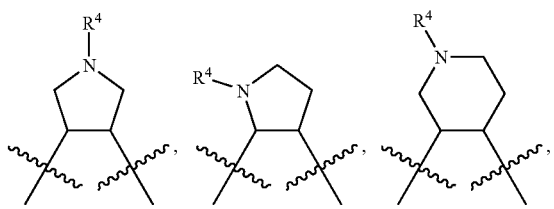

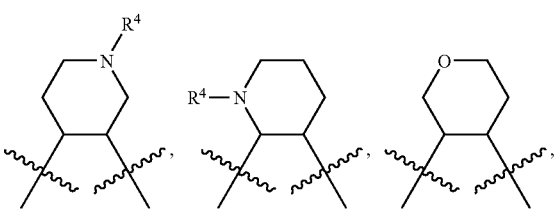

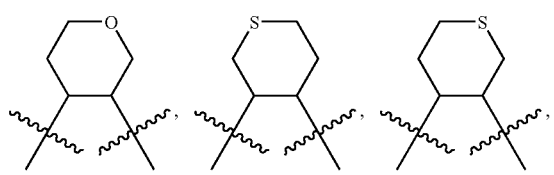

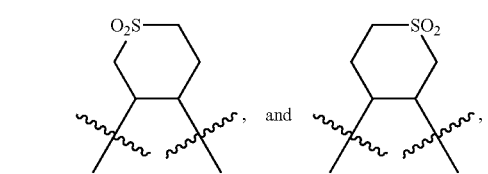

each being substituted with 0-1 $R^5$.

In another embodiment, ing B is selected from each substituted with 1-2 $R^5$, and

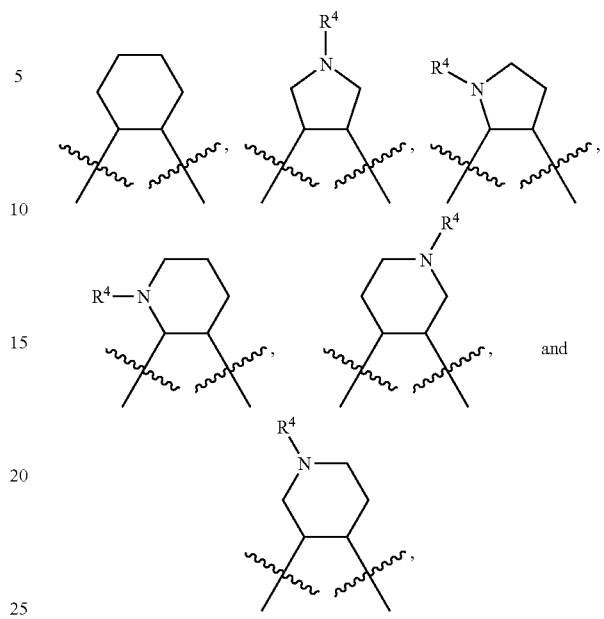

each being substituted with 0-1 $R^5$.

In another embodiment, Z is selected from a bond, —$NR^8C(O)$—, —$NR^8C(O)NH$—, —$C(O)NR^8$—, —$(CR^{15}R^{15})_t$—, —$CR^{15}R^{15}C(O)$—, —$C(O)CR^{15}R^{15}$—, —$O$—$CR^{14}R^{14}$—, —$CR^{14}R^{14}$—$O$—, —$O$—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$—, and —$S(O)_p$—$NR^9$—.

In another embodiment, Z is selected from a bond, —$NR^8C(O)$—, —$NR^8C(O)NH$—, —$NR^9$—, and —$C(O)NR^8$—.

In another embodiment, Z is selected from a bond, —$NR^8C(O)$—, —$C(O)NH$—, and —$NR^9$—.

In another embodiment, Z is —$C(O)NR^8$—.
In another embodiment, Z is —$NR^8C(O)$—.
In another embodiment, Z is —$NR^9$—.

In another embodiment, Z is selected from a bond, and —$NHC(O)$—;

In another embodiment, Z is a bond; and $R^2$ is a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, Z is a —$NR^9$—; and $R^2$ is a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl, triazinyl, picolinyl, isonicotinyl.

In another embodiment, $R^4$ is selected from H, $C_{1-6}$ alkyl, $C_{3-8}$ alkenyl, $C_{3-8}$ alkynyl, $(CRR)_tOH$, $(CHR)_sSH$, $(CRR)_tOR^{4d}$, $(CHR)_sSR^{4d}$, $(CHR)_tNR^{4a}R^{4a}$, $(CHR)_qC(O)$ OH, $(CHR)_tC(O)R^{4b}$, $(CHR)_tC(O)NR^{4a}R^{4a}$, $(CHR)_tNR^{4a}C(O)R^{4b}$, $(CHR)_tOC(O)NR^{4a}R^{4a}$, $(CHR)_tNR^{4a}C(O)OR^{4d}$, $(CHR)_tNR^{4a}C(O)R^{4b}$, $(CHR)_tC(O)OR^{4b}$, $(CHR)_tOC(O)R^{4b}$, $(CHR)_tS(O)_pR^{4b}$, $(CHR)_tS(O)_2NR^{4a}R^{4a}$, $(CHR)_tNR^{4a}S(O)_2R^{4b}$; and R, at each occurrence, is independently selected from H, methyl, ethyl, propyl, allyl, propynyl, $(CH_2)_rC_{3-6}$ cycloalkyl, and $(CH_2)r$phenyl substituted with $R^{6e}$.

In another embodiment, $R^4$ is selected from H, methyl, ethyl, propyl, i-propyl, butyl, i-butyl, allyl, propynyl, $(CRR)_qOH$, $(CRR)_sSH$, $(CRR)_tOR^{4d}$, $(CRR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^4b$.

$R^{4b}$ is selected from H, methyl, ethyl, propyl, i-propyl, butyl, i-butyl, t-butyl, pentyl, and cyclopropyl; and $R^{4d}$ is selected from methyl, ethyl, propyl, i-propyl, butyl, i-butyl, t-butyl, pentyl, and cyclopropyl.

In another embodiment, $R^4$ is selected from H, methyl, ethyl, propyl, i-propyl, butyl, i-butyl, allyl, propynyl, $(CH_2)_rC(O)R^{4b}$.

In another embodiment, $R^4$ is selected from H, $C_{1-6}$ alkyl, $C_{3-8}$ alkenyl, $C_{3-8}$ alkynyl, $(CRR)_tOH$, $(CRR)_sSH$, $(CRR)_tOR^{4d}$, $(CRR)_tSR^{4d}$, $(CRR)_tNR^{4a}R^{4a}$, $(CRR)_qC(O)$ OH, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)OR^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^4b$.

In another embodiment, $R^4$ is selected from H, methyl, ethyl, propyl, i-propyl, butyl, i-butyl, allyl, propynyl, $(CRR)_tOH$, $(CRR)_sSH$, $(CRR)_tOR^{4d}$, $(CRR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^{4b}$;

$R^{4a}$, at each occurrence, is independently selected from H, methyl substituted with 0-1 $R^{4c}$, $C_{2-6}$ alkyl substituted with 0-3 $R^{4e}$ wherein $C_{2-6}$ alkyl is selected from ethyl, propyl, i-propyl, butyl, i-butyl, t-butyl, pentyl and hexyl, and a $(CH_2)_r$—$C_{3-6}$ carbocyclic residue substituted with 0-4 $R^{4e}$ wherein the carbocyclic residue is selected from cyclopropyl, cyclohexyl, and phenyl;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl.

In another embodiment, $R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —$C(O)R^{4i}$, —$C(O)OR^{4j}$, —$C(O)NR^{4h}R^{4h}$, —$OC(O)NR^{4h}R^{4h}$, —$NR^{4h}C(O)NR^{4h}R^{4h}$, —$NR^{4h}C(O)OR^{4j}$, $C(O)OH$, $(CH_2)_rC(O)NHSO_2$—$R^{4k}$, $NHSO_2R^{4k}$, $(CH_2)_r$tetrazolyl, and $(CH_2)_r$phenyl.

In another embodiment, $R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)$ $OR^{5b}$, $(CH_2)_rOC(O)R^{5b}$, $(CH_2)_rNR^{5a}S(O)_2R^{5b}$, and $C_{1-6}$ haloalkyl; and $R^{5a}$, at each occurrence, is independently selected from H, methyl, ethyl, propyl, i-propyl, butyl, i-butyl, pentyl, hexyl, cyclopropyl, and cyclobutyl.

In another embodiment, $R^5$, at each occurrence, is independently selected from H, OH, $OR^{5d}$, $(CH_2)_rNR^{5a}R^{5a}$, $(CH_2)_rNR^{5a}C(O)R^{5b}$, and $(CH_2)_rNR^{5a}C(O)OR^{5d}$.

In another embodiment, $R^5$ is $NR^{5a}R^{5a}$.

In another embodiment, $R^5$, at each occurrence, is independently selected from H, methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)$ $R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl, $(CH_2)_r$phenyl substituted with 0-2 $R^{5e}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl; and $R^{5a}$, at each occurrence, is independently selected from H, methyl, ethyl, propyl, i-propyl, butyl, i-butyl, pentyl, hexyl, cyclopropyl, and cyclobutyl.

In another embodiment, $R^5$, at each occurrence, is independently selected from methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)$ $R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl.

In another embodiment, $R^5$, at each occurrence, is independently selected from F, Cl, Br, I, $(CH_2)_rOH$, $(CH_2)_rOR^{5d}$, $(CH_2)_rNR^{5a}R^{5a}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl.

In another embodiment, $R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)$ OH, $(CH_2)_rC(O)NHSO_2$—$R^{5h}$, $NHSO_2R^{5h}$, a $(CH_2)_r$-5-6 membered heterocyclic system containing 1-4 heteroatoms selected from N, O, and S, and $(CH_2)_r$phenyl.

In another embodiment, $R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_6$-10 aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^1$ is selected from H, $R^6$, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$.

In another embodiment, $R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

with the proviso that $R^1$ is not —CH$_2$S(O)$_2$—$R^{1a}$, —CH$_2$S(O)$_2$—$R^{1a}$, —NHC(O)—$R^{1a}$, —NHC(O)NH—$R^{1a}$, —NHCH$_2$—$R^{1a}$, —SO$_2$NH—$R^{1a}$, —NHSO$_2$NH—$R^{1a}$, when $R^{1a}$ is equal to aryl or heteraryl; (with the proviso that the compounds of the present invention are not those as defined in U.S. patent application Ser. No. 10/027,644, filed Dec. 20, 2001, U.S. patent application Ser. No. 10/383,391, filed Mar. 7, 2003, U.S. Provisional Patent Application No. 60/446,850, filed Feb. 12, 2002, and U.S. Provisional Patent Application No. 60/467,003, filed May, 1, 2003; and $R^5$ is NR$^{5a}$R$^{5a}$.

In another embodiment, $R^1$ is selected from H, $C_{1-6}$ alkyl substituted with 0-1 $R^6$, —C(O)O—$C_{1-6}$ alkyl.

In another embodiment, $R^1$ is selected from H, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$;

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^2$ is selected from phenyl substituted with 0-2 $R^7$.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, Z is a bond and $R^2$ is selected from a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl system is selected from from quinazolinyl, triazinyl, pyrimidinyl, picolinyl, isonicotinyl, furanyl, indolyl, pyridinyl, pyrazolyl, pyrazinyl, thiazolyl, thienyl, thiophenyl, and isoxazolyl.

In another embodiment, $R^6$, at each occurrence, is selected from $C_{1-8}$ alkyl, $C_{2-8}$ alkenyl, $C_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CRR)$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$NR$^{6a}$C(O)NR$^{6a}$R$^{6a}$, (CR'R')$_r$NR$^{6a}$C(S)NR$^{6a}$R$^{6a}$, (CR'R')$_r$OC(O)(CR'R')$_r$R$^{6b}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$(CR'R')$_r$R$^{6b}$, (CR'R')$_r$NR$^{6f}$S(O)$_2$NR$^{6a}$R$^{6a}$, $C_{1-6}$ haloalkyl, and (CR'R')$_r$phenyl substituted with 0-3 $R^{6e}$, and a (CH$_2$)$_r$-5-6 membered heterocyclic system containing 1-2 heteroatoms selected from N, O, and S, substituted with 0-2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, CF$_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

$R^{6f}$, at each occurrence, is selected from H, methyl, ethyl, propyl, i-propyl, butyl, i-butyl, t-butyl, pentyl, hexyl, cyclopropyl, and phenyl.

In another embodiment, $R^6$, at each occurrence, is selected from $C_{1-8}$ alkyl, $C_{2-8}$ alkenyl, $C_{2-8}$ alkynyl, (CHR')$_r$C$_{3-6}$ cycloalkyl, Cl, Br, I, F, NO$_2$, CN, (CHR')$_r$NR$^{6a}$R$^{6a}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b}$, (CHR')$_r$C(O)OR$^{6d}$, (CHR')$_r$NR$^{6a}$C(O)NR$^{6a}$R$^{6a}$, (CHR')$_r$NR$^{6a}$C(S)NR$^{6a}$R$^{6a}$, (CHR')$_r$OC(O)R$^{6b}$, (CHR')$_r$S(O)$_p$R$^{6b}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S(O)$_2$NR$^{6a}$R$^{6a}$, $C_{1-6}$ haloalkyl, and (CHR')$_r$phenyl substituted with 0-3 $R^{6e}$.

In another embodiment, $R^6$ is selected from methyl, ethyl, propyl, i-propyl, butyl, F, Cl, Br, I, NO$_2$, CN, (CH$_2$)$_r$O(CH$_2$)$_r$R$^{6d}$, C(O)R$^{6d}$, SR$^{6d}$, NR$^{6a}$R$^{6a}$, C(O)NR$^{6a}$R$^{6a}$, NC(O)R$^{6b}$, OC(O)R$^{6b}$, S(O)$_p$R$^{6b}$, (CHR')$_r$S(O)$_2$NR$^{6a}$R$^{6a}$, and CF$_3$;

$R^{6a}$ is H, methyl, ethyl, propyl, i-propyl, butyl, and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$ is H, methyl, ethyl, propyl, i-propyl or butyl;

$R^{6d}$ is methyl, phenyl, CF$_3$, and (CH$_2$)-phenyl.

In another embodiment, $R^6$, at each occurrence, is selected from $C_{1-8}$ alkyl, $C_{2-8}$ alkenyl, $C_{2-8}$ alkynyl, (CH$_2$)$_r$C$_{3-6}$ cycloalkyl, Cl, Br, I, F, NO$_2$, CN, (CH$_2$)$_r$NR$^{6a}$R$^{6a}$, (CH$_2$)$_r$OH, (CH$_2$)$_r$OR$^{6d}$, (CH$_2$)$_r$SH, (CH$_2$)$_r$C(O)H, (CH$_2$)$_r$SR$^{6d}$, (CH$_2$)$_r$C(O)OH, (CH$_2$)$_r$C(O)R$^{6b}$, (CH$_2$)$_r$C(O)NR$^{6a}$R$^{6a}$, (CH$_2$)$_r$NR$^{6f}$C(O)R$^{6b}$, (CH$_2$)$_r$C(O)OR$^{6d}$, (CH$_2$)$_r$NR$^{6a}$C(O)NR$^{6a}$R$^{6a}$, (CH$_2$)$_r$NR$^{6a}$C(S)NR$^{6a}$R$^{6a}$, (CH$_2$)$_r$OC(O)R$^{6b}$, (CH$_2$)$_r$S(O)$_p$R$^{6b}$, (CH$_2$)$_r$S(O)$_2$NR$^{6a}$R$^{6a}$, (CH$_2$)$_r$NR$^{6f}$S(O)$_2$R$^{6b}$, (CH$_2$)$_r$NR$^{6f}$S(O)$_2$NR$^{6a}$R$^{6a}$, $C_{1-6}$ haloalkyl, and (CHR')$_r$phenyl substituted with 0-3 $R^{6e}$.

In another embodiment, $R^6$, at each occurrence, is selected from $C_{1-8}$ alkyl, $C_{2-8}$ alkenyl, $C_{2-8}$ alkynyl, (CH$_2$)$_r$C$_{3-6}$ cycloalkyl, Cl, Br, I, F, NO$_2$, CN, (CH$_2$)$_r$NR$^{6a}$R$^{6a}$, (CH$_2$)$_r$OH, (CH$_2$)$_r$O(CH$_2$)$_r$R$^{6d}$, (CH$_2$)$_r$SH, (CH$_2$)$_r$C(O)H, (CH$_2$)$_r$S(CH$_2$)$_r$R$^{6d}$, (CH$_2$)$_r$C(O)OH, (CH$_2$)$_r$C(O)(CH$_2$)$_r$R$^{6b}$, (CH$_2$)$_r$C(O)NR$^{6a}$R$^{6a}$, (CH$_2$)$_r$NR$^{6f}$C(O)(CH$_2$)$_r$R$^{6b}$, (CH$_2$)$_r$C(O)O(CH$_2$)$_r$R$^{6d}$, (CH$_2$)$_r$NR$^{6a}$C(O)NR$^{6a}$R$^{6a}$, (CH$_2$)$_r$NR$^{6a}$C(S)NR$^{6a}$R$^{6a}$, (CH$_2$)$_r$OC(O)(CH$_2$)$_r$R$^{6b}$, (CH$_2$)$_r$S(O)$_p$(CH$_2$)$_r$R$^{6b}$, (CCH$_2$)$_r$S(O)$_2$NR$^{6a}$R$^{6a}$, (CH$_2$)$_r$NR$^{6f}$S(O)$_2$(CH$_2$)$_r$R$^{6b}$, (CH$_2$)$_r$NR$^{6f}$S(O)$_2$NR$^{6a}$R$^{6a}$, C$_{1-6}$ haloalkyl, and (CH$_2$)$_r$phenyl substituted with 0-3 R$^{6e}$, and a (CH$_2$)$_r$-5-6 membered heterocyclic system containing 1-2 heteroatoms selected from N, O, and S, substituted with 0-2 R$^{6e}$, wherein the heterocyclic system is selected from aziridinyl, azetidinyl, pyrrolyl, piperidinyl, and morpholinyl;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from H, methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl.

In another embodiment, R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, C(O)NHR$^{6h}$, C(O)OC$_{1-5}$ alkyl, (CH$_2$)$_r$OH, C(O)OH, (CH$_2$)$_r$C(O)NHSO$_2$—R$^{6h}$, NHSO$_2$R$^{6h}$, (CH$_2$)$_r$tetrazolyl, and (CH$_2$)$_r$phenyl and a (CH$_2$)$_r$-5-6 membered heterocyclic system containing 1-4 heteroatoms selected from N, O, and S.

In another embodiment, R$^7$ is selected from methyl, ethyl, propyl, i-propyl, butyl, i-butyl, s-butyl, t-butyl, pentyl, hexyl, (CH$_2$)$_r$C$_{3-6}$ cycloalkyl, Cl, Br, I, F, NO$_2$, CN, (CH$_2$)$_r$NR$^{7a}$R$^{7a}$, (CH$_2$)$_r$OH, (CH$_2$)$_r$O(CH)$_r$R$^{7d}$, (CH$_2$)$_r$SH, (CH$_2$)$_r$C(O)H, (CH$_2$)$_r$S(CH$_2$)$_r$R$^{7d}$, (CH$_2$)$_r$C(O)OH, (CH$_2$)$_r$C(O)(CH$_2$)$_r$R$^{7b}$, (CH$_2$)$_r$C(O)NR$^{7a}$R$^{7a}$, (CH$_2$)$_r$NR$^{7f}$C(O)(CH$_2$)$_r$R$^{7b}$, (CH$_2$)$_r$NR$^{7a}$C(O)NR$^{7a}$R$^{7a}$, (CH$_2$)$_r$NR$^{7a}$C(O)O(CH$_2$)$_r$R$^{7d}$, (CH$_2$)$_r$S(O)$_p$(CH$_2$)$_r$R$^{7b}$, (CH$_2$)$_r$S(O)$_2$NR$^{7a}$R$^{7a}$, (CH$_2$)$_r$NR$^{7f}$S(O)$_2$(CH$_2$)$_r$R$^{7b}$, C$_{1-6}$ haloalkyl, and (CH$_2$)$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, and cyclopropyl;

R$^{7b}$, at each occurrence, is selected from methyl, ethyl, propyl, i-propyl, butyl, i-butyl, t-butyl, pentyl, hexyl, and cyclopropyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl; and R$^{7f}$, at each occurrence, is selected from H, methyl, ethyl, propyl, i-propyl, butyl, i-butyl, t-butyl, pentyl, hexyl, cyclopropyl, and phenyl.

In another embodiment, R$^7$ is selected from methyl, ethyl, propyl, i-propyl, butyl, i-butyl, s-butyl, t-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)R$^{7b}$, NR$^{7f}$C(O)NHR$^{7a}$, and NHS(O)$_2$R$^{7b}$.

In another embodiment, R$^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)OR$^{7d}$, C(O)R$^{7b}$, NR$^{7f}$C(O)NR$^{7a}$R$^{7a}$, NHS(O)$_2$R$^{7b}$,

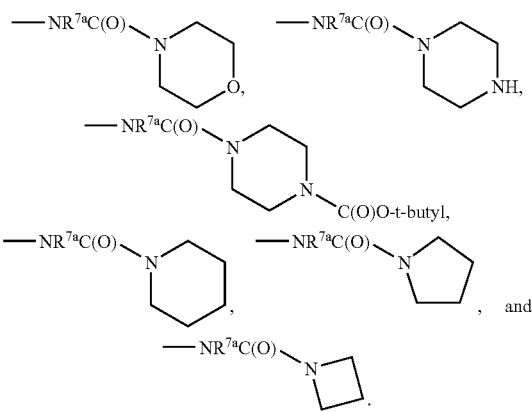

In another embodiment, R$^{7a}$ is selected from H, methyl, ethyl, propyl, i-propyl, butyl, i-butyl, t-butyl, pentyl, neopentyl, cyclopropyl, cyclobutyl, cyclopentyl, and cyclohexyl;

R$^{7b}$ is selected from cyclohexyl and CF$_3$; and

R$^{7d}$ is selected from methyl, ethyl, propyl, i-propyl, butyl, i-butyl, and t-butyl.

In another embodiment, R$^7$ is selected from methyl, ethyl, propyl, i-propyl, butyl, i-butyl, s-butyl, t-butyl, pentyl, hexyl, (CH$_2$)$_r$C$_{3-6}$ cycloalkyl, Cl, Br, I, F, NO$_2$, CN, (CH$_2$)$_r$NR$^{7a}$R$^{7a}$, (CH$_2$)$_r$OH, (CH$_2$)$_r$O(CH$_2$)$_r$R$^{7d}$, (CH$_2$)$_r$SH, (CH$_2$)$_r$C(O)H, (CH$_2$)$_r$S(CH$_2$)$_r$R$^{7d}$, (CH$_2$)$_r$C(O)OH, (CH$_2$)$_r$C(O)(CH$_2$)$_r$R$^{7b}$, (CH$_2$)$_r$C(O)NR$^{7a}$R$^{7a}$, (CH$_2$)$_r$NR$^{7f}$C(O)(CH$_2$)$_r$R$^{7b}$, (CH$_2$)$_r$C(O)O(CH$_2$)$_r$R$^{7d}$, (CH$_2$)$_r$OC(O)(CH$_2$)$_r$R$^{7b}$, (CH$_2$)$_r$OC(O)NR$^{7a}$R$^{7a}$, (CH$_2$)$_r$NR$^{7a}$C(O)NR$^{7a}$R$^{7a}$, (CH$_2$)$_r$NR$^{7a}$C(O)O(CH$_2$)$_r$R$^{7d}$, (CH$_2$)$_r$S(O)$_p$(CH$_2$)$_r$R$^{7b}$, (CH$_2$)$_r$S(O)$_2$NR$^{7a}$R$^{7a}$, (CH$_2$)$_r$NR$^{7f}$S(O)$_2$(CH$_2$)$_r$R$^{7b}$, C$_{1-6}$ haloalkyl, adamantyl, and (CH$_2$)$_r$phenyl substituted with 0-3 R$^{7e}$ and a (CH$_2$)$_r$-5-6 membered heterocyclic system containing 1-4 heteroatoms selected from N, O, and S, substituted with 0-3 R$^{7e}$, wherein the heterocyclic system is selected from thienyl, pyridinyl, benzothiazolyl, and tetrazolyl;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, CF$_2$CF$_3$, CHF$_2$, CH$_2$F, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, OH, SH, C(O)OH, C(O)NHR$^{7h}$, C(O)OC$_{1-5}$ alkyl, (CH$_2$)$_r$SC$_{1-5}$ alkyl, (CH$_2$)$_r$NR$^{7f}$R$^{7f}$, (CH$_2$)$_r$C(O)NHSO$_2$—R$^{7h}$, NHSO$_2$R$^{7h}$, and (CH$_2$)$_r$phenyl, (CH$_2$)$_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl.

In another embodiment, $R^7$, at each occurrence, is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rOR^{7d}$, $(CH_2)_rSH$, $(CH_2)_rC(O)H$, $(CH_2)_rSR^{7d}$, $(CH_2)_rC(O)OH$, $(CH_2)_rC(O)R^{7b}$, $(CH_2)_rC(O)NR^{7a}R^{7a}$, $(CH_2)_rNR^{7f}C(O)R^{7b}$, $(CH_2)_rC(O)OR^{7d}$, $(CH_2)_rOC(O)R^{7b}$, $(CH_2)_rOC(O)NR^{7a}R^{7a}$, $(CH_2)_rNR^{7a}C(O)NR^{7a}R^{7a}$, $(CH_2)_rNR^{7f}C(O)OR^{7d}$, $(CH_2)_rS(O)pR^{7b}$, $(CH_2)_rS(O)_2NR^{7a}R^{7a}$, $(CH_2)_rNR^{7a}S(O)_2NR^{7a}R^{7a}$, $(CH_2)_rNR^{7f}S(O)_2R^{7b}$, $C_{1-2}$ haloalkyl, $(CH_2)_r$ adamantyl, $(CH_2)_r$phenyl substituted with 0-3 $R^{7e}$, and a $(CH_2)_r$-5-6 membered heterocyclic system containing 1-4 heteroatoms selected from N, O, and S, substituted with 0-3 $R^{7e}$, wherein the heterocyclic ring is selected from thiophenyl, pyridinyl, benzothiazolyl, and tetrazolyl.

In another embodiment, $R^8$ is H.

In another embodiment, $R^{11}$ and $R^{12}$ are H.

In another embodiment, ring B is substituted with at least one $R^5$ which is —$NR^{5a}R^{5a}$.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy,* 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced.

When any variable (e.g., $R^{10}$) occurs more than one time in any constituent or formula for a compound, its definition at each occurrence is independent of its definition at every other occurrence. Thus, for example, if a group is shown to be substituted with 0-2 $R^{10}$, then said group may optionally be substituted with up to two $R^{10}$ groups and $R^{10}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,

[3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may optionally include a —C(O)—, carbonyl. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

As used herein, the term "cyclic acetal" or or the phrase when two variables "join to form a cyclic acetal" is intended to mean the substituent —O—CH$_2$—O—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

Chemokine antagonists can be derived from compounds of formula 1.1, as shown in Schemes 1-6; the synthesis of compounds of formula 1.1 is described in Scheme 7 and the accompanying text. Compounds of formula 1.5, which contain a four-membered lactam, are derived from compounds of formula 1.1 as shown in Scheme 1. Deprotection, peptide coupling with the known serine derivative 1.2, and cyclization under Mitsonobu conditions (see G M Salituro and C A Townsend *J. Am. Chem. Soc.* 1990, 112, 760-770) provides the beta-lactam 1.4 from carbamate 1.1. Removal of the Ox protecting group (see G M Salituro and C A Townsend *J. Am. Chem. Soc.* 1990, 112, 760-770) provides a primary amine, which can be conjugated in a variety of ways well known to one skilled in the art (see also Scheme 4 and accompanying text).

Scheme 1

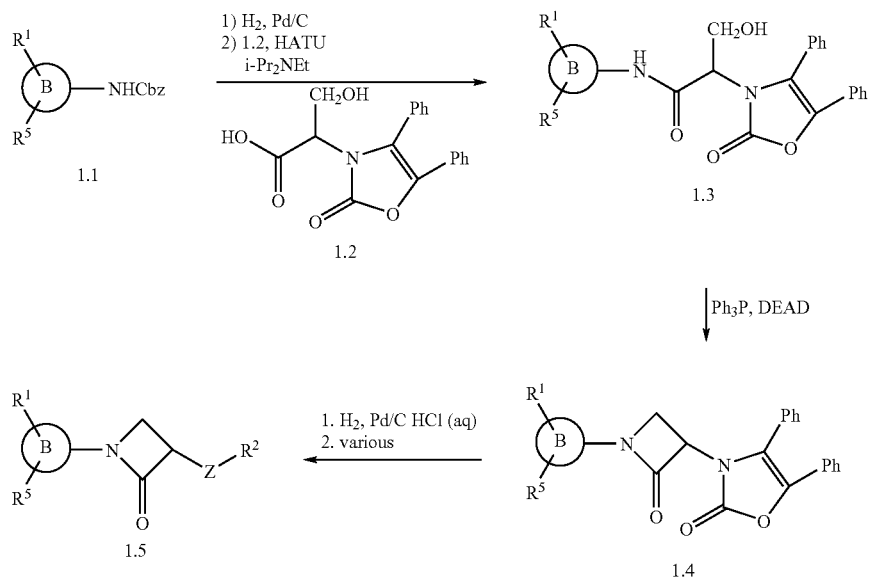

Compounds of formula 2.4, which contain a five-membered lactam, are synthesized as shown in Scheme 2. Acid-mediated Boc removal, peptide coupling with the known methionine derivative 2.1, sulfur alkylation, and intramolecular amide alkylation under basic conditions (NaH may also be used, see Freidinger et al., *J. Org. Chem.* 1982, 47, 104) provides the gamma-lactam 2.3 from carbamate 1.1. Removal of the protecting group provides a primary amine, which can be conjugated in a variety of ways well known to one skilled in the art (see also Scheme 4 and accompanying text).

Compounds of formula 3.4, which contain a six-membered lactam, are synthesized as shown in Scheme 3. Acid-mediated Boc removal, reductive amination with the known glutamic acid derivative 3.1 (X. Zhang, W. Han, WO PCT 0164678, 2001), ester hydrolysis, and intramolecular amide formation provides the delta-lactam 3.3 from carbamate 1.1. Removal of the protecting group provides a primary amine, which can be conjugated in a variety of ways well known to one skilled in the art (see also Scheme 4 and accompanying text).

Scheme 2

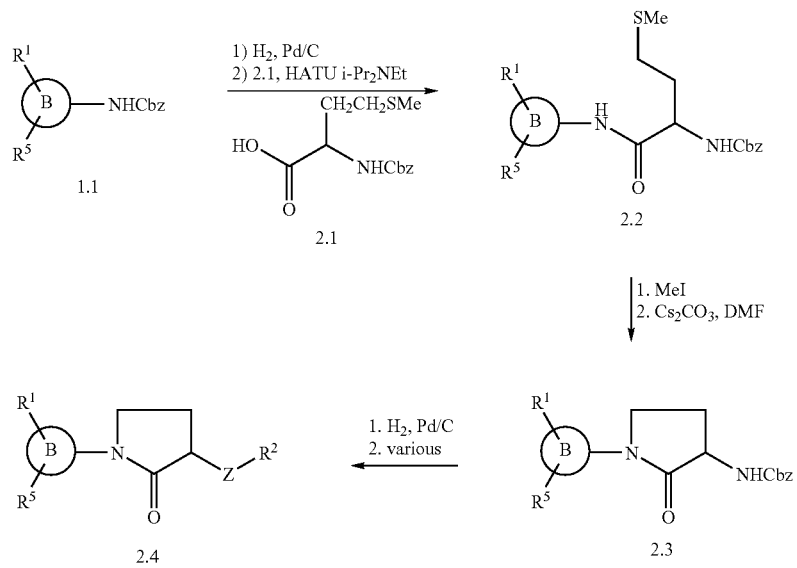

Scheme 3

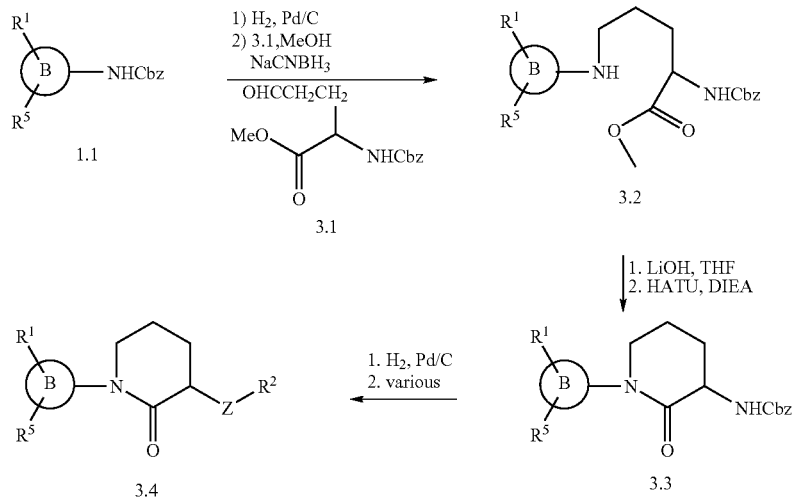

Lactams of formula 4.1 can be made from compounds such as 1.4, 2.3, and 3.3 (deprotection and optional reductive amination to install $R^8$). Variants of 4.1 with $R^{10}$ substituents can be made through syntheses analogous to those shown in Scheme 1-3 simply through substitution of the appropriate $R^{10}$-substituted starting materials. Derivitization of amines of formula 4.1 can be accomplished through a number of conventional methods to form chemokine receptor antagonists; some of these methods are illustrated in Scheme 4. Thus, amide bond formation gives compounds 4.2, reductive amination gives compounds 4.3, and reaction with an isocyanate gives compounds 4.4. Alternatively, amine 4.1 can be arylated (see D. Zim & S. L. Buchwald, *Organic Letters* 2003, 5, 2413 and T. Wang, D. R. Magnia, & L. G. Hamann, ibid, 897, and references cited therein) to give compound 4.5. Alternatively,. amine 4.1 can be arylated with iminoyl chlorides to give 4.6.

Scheme 4

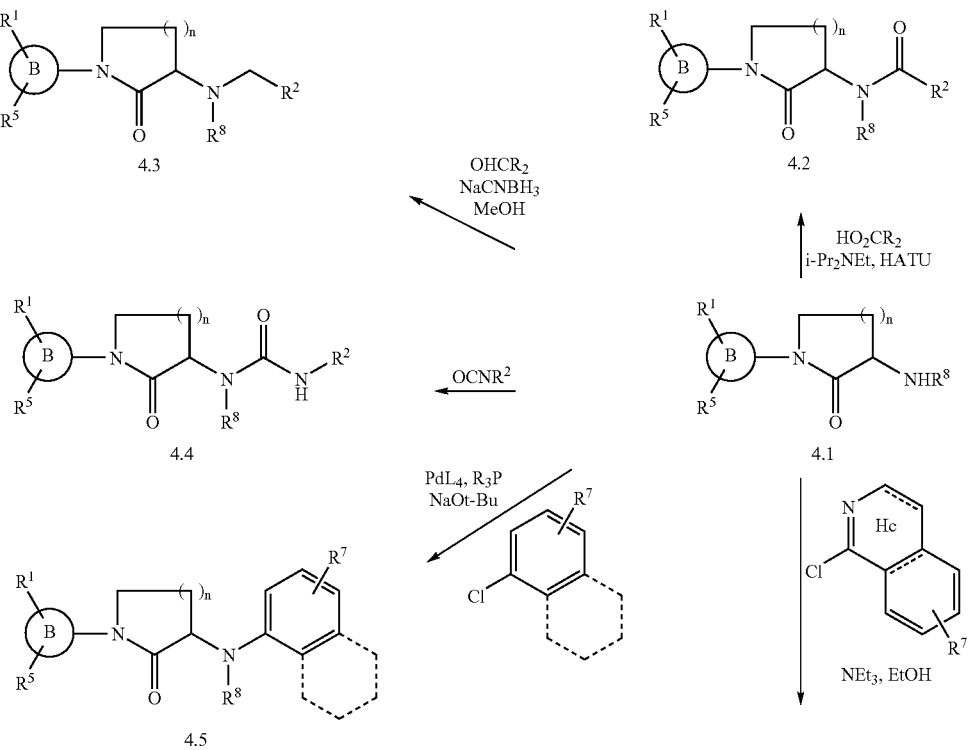

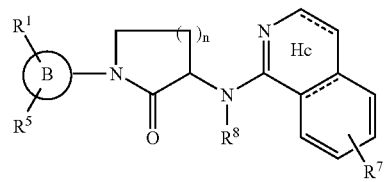

4.6

The combination of the chemistry illustrated in Schemes 1-4 can produce a large number of chemokine receptor antagonists. Conceptually-related antagonists can be produced using the chemistry shown in Scheme 5. Thus, deprotection of 1.1 and reductive amination with aldehyde 5.1 (derived from dimethyl malonate via alkylation and ozonolysis) gives compound 5.2, which can be cyclized to 5.3 with base. Hydrolysis of the methyl ester provides an acid which can be coupled with amines to give compounds of interest with formula 5.4. If $R^2$ is appropriately functionalized, compounds of formula 5.4 can be cyclized to give heterocycles of formula 5.5 (K. Takeuchi et al. *Bioorg. Med. Chem. Lett.* 2000, 2347; G. Nawwar et al. *Collect. Czech. Chem. Commun.* 1995, 2200; T. Hisano et al. *Chem. Pharm. Bull.* 1982, 2996). Other heterocycles (see formula 5.6) can be made from compounds of formula 5.4 through methods well known to one skilled in the art (see T. L. Gilchrist, Heterocyclic Chemistry, Longman Scientific & Technical, 1985).

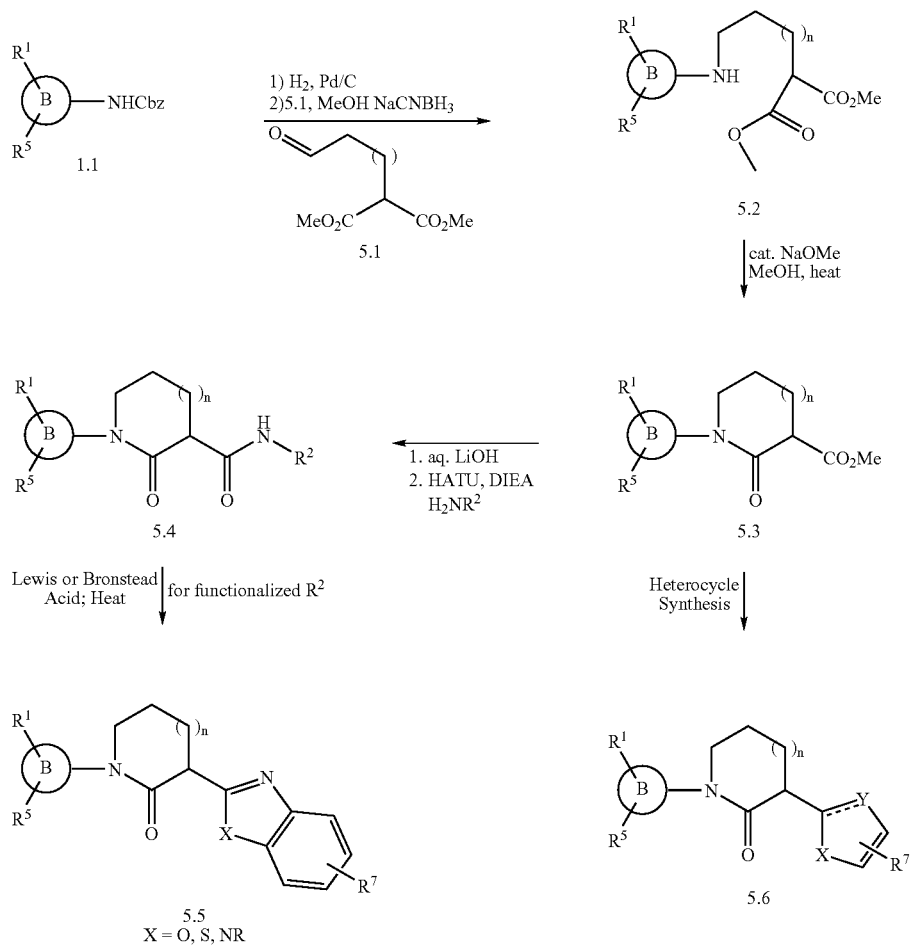

Scheme 5

Other chemistry can produce conceptually related chemokine antagonists. For example, as shown in Scheme 6, compounds of formula 1.1 are readily deprotected and conjugated with compounds of formula 6.1 in methanol via 1,4-addition. The resultant ketone 6.2 may be homologated to 6.3 (isomers are separated via chromatography), which is in turn deprotected and cyclized to give compounds of interest of formula 6.4.

Given the availability of the chemistry described above in Schemes 1-6, all that remains is to describe the synthesis of compounds of formula 1.1. Compounds of formula 1.1 may sometimes be derived in a trivial fashion from manipulation of commercially available cyclic amines (nota bene: although amines of formula 1.1 are shown with Cbz protection, they may synthesized with alternative protecting groups or in unprotected form; only minor adjustments to the chemistry of Schemes 1 and 2 would need be made in this instance). In other instances, they are readily derived from commercially available ketones of general formula 7.1, as shown in Scheme 7. These ketones may be alpha-functionalized (as well documented in the synthetic literature; enantioselective variants of this alkylation are available) to give compounds of formula 7.2. In some instances (El=halide, hydroxyl or azide), these compounds may be elaborated further (through nucleophilic or electrophilic displacement chemistry, making recourse to protecting groups where necessary) to give compounds of formula 7.3, which may be transformed through reductive amination and protection (see note above) to give compounds of formula 7.4 (a variant of 1.1). If $R^1$ is a carbon-connected linker, a convenient method for compound synthesis is shown in the enantioselective transformation of 7.2 (El=$CO_2R$) to 7.6 via enamine 7.5 (C. Cimarelli, et al, *J. Org. Chem.* 1996, 61, 5557 and Y. Hayashi, et al., *J. Am. Chem. Soc.* 1996, 118, 5502). Elaboration to 7.4 (a derivative of formula 1.1) may proceed directly from 7.6 or via initial epimerization to 7.7.

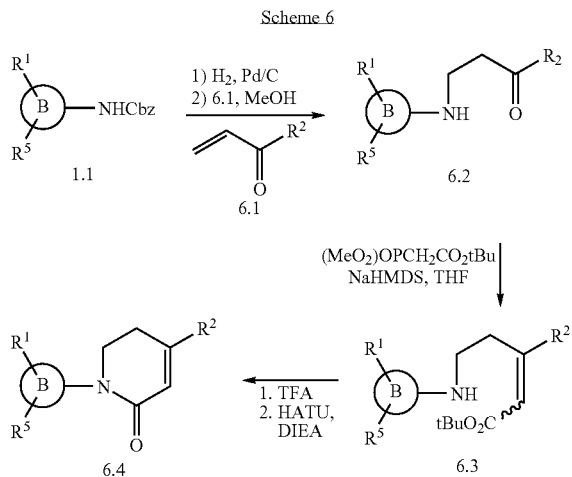

Scheme 6

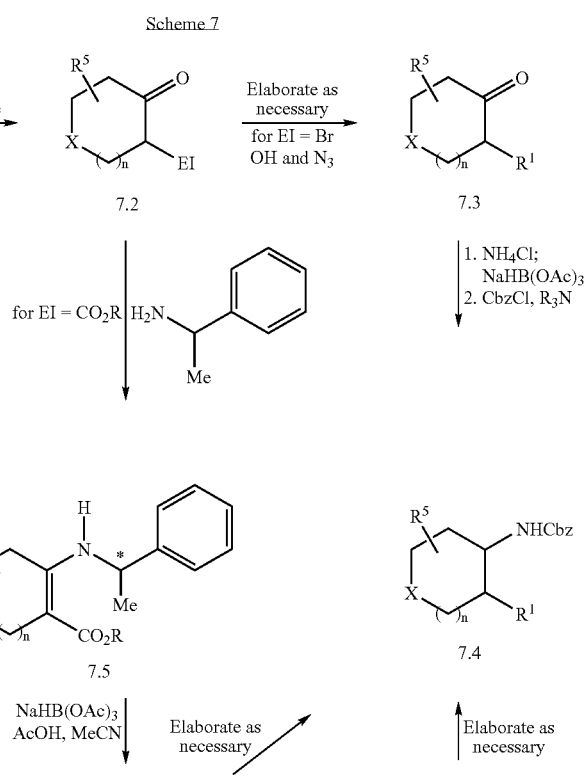

Scheme 7

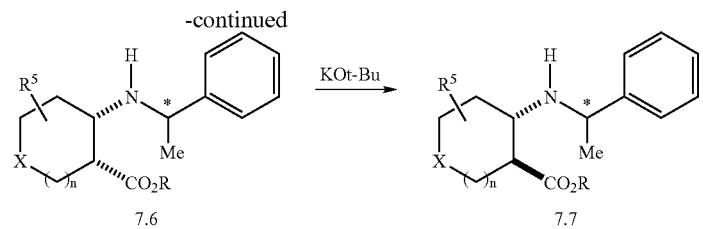

Other methods for the synthesis of 1,2-diaminocarbo- and heterocycles (see R. Cherney WO-PCT 02/060859) and the synthesis of 2-aminocycloalkanecarboxylic acids do exist (reviewed in Ference Fulop, *Chem. Rev.* 2001, 101, 2181; see also J. Duan, et al. WO-01/70673 and Soo S. Ko, et al. WO-02/02525). In particular, 2-aminocycloalkanecarboxylic acids (and their heterocyclic varients) are versatile precursors of compounds of formula 1.1, because the carboxylic acid can be derivatized to a wide variety of $R^1$ groups through addition reactions, amide formation, Wittig extension, reduction and alcohol derivitization, reduction and then reductive amination, Curtius rearrangement, and so forth. In instances where the cycloalkyl group contains a pendant olefin, the carboxylic acid can also serve to relay stereochemical information and allow for further functionalization of the ring, so as to provide for the stereoselective installation of $R^5$. This chemistry has been generally described in the literature (Ference Fulop, *Chem. Rev.* 2001, 101, 2181); specific examples of this strategy are described in the Examples section (vide infra). When these methods are considered along those highlighted in Scheme 7, it is apparent that a large number of compounds of formula 1.1 can be synthesized.

One diastereomer of a compound of Formula I may display superior activity compared with the others. Thus, while not limiting the invention, the following stereochemistries are examples of stereochemistries that are considered to be a part of the present invention.

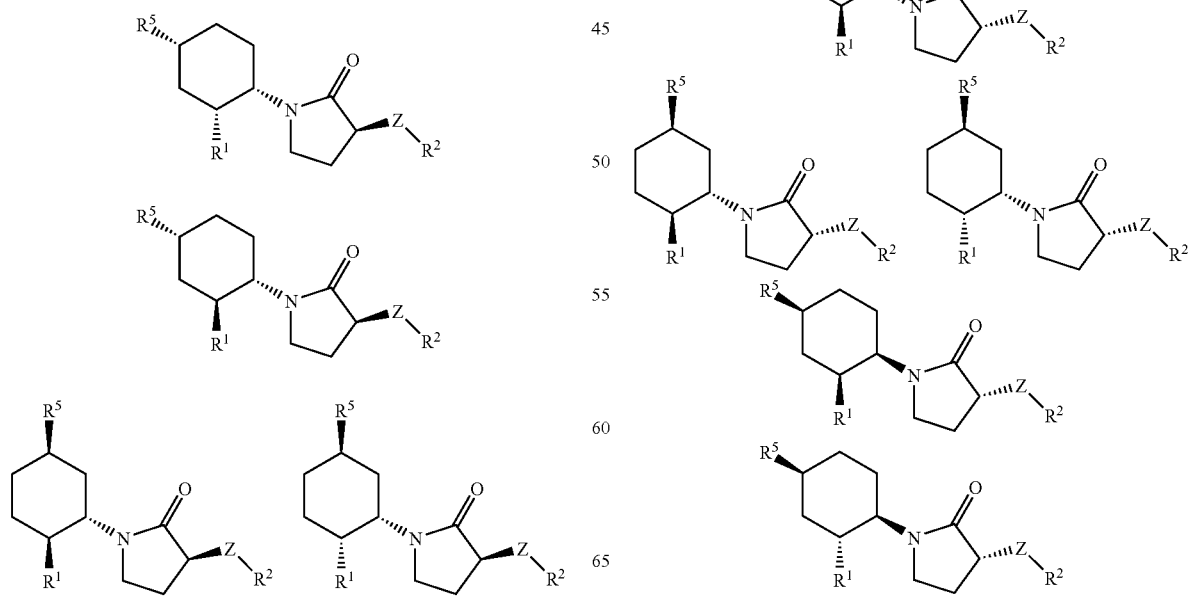

-continued

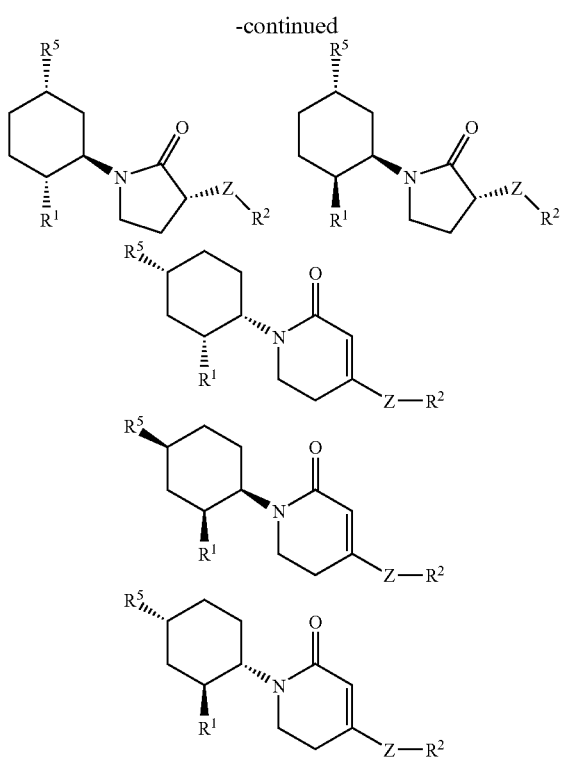

Additional stereoisomers are envisioned based on the schematic shown below. The examples illustrated here are limited to ring B being a cyclohexyl ring. Additional ring systems are possible and therefore additional stereoisomers are envisioned. The compounds of the present invention may also exist in additional stereoisomers which are not shown herein.

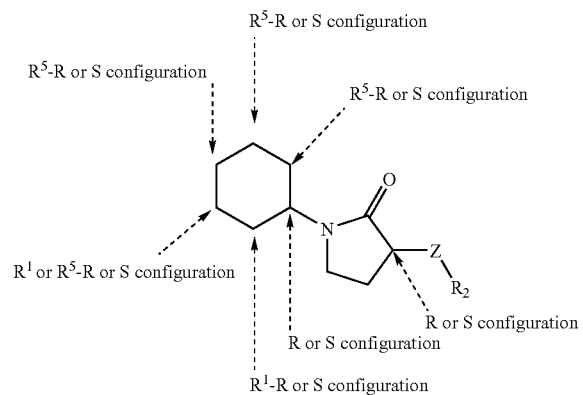

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Copending patent applications, all filed on Aug. 19, 2004, disclose additional chemokine receptor antagonists. These applications are hereby incorporated by reference in their entirety: "N-ALKYLATED DIAMINOPROPANE DERIVATIVES AS MODULATORS OF CHEMOKINE RECEPTOR ACTIVITY", Ser. No. 10/922,406; "LACTAMS OF ALYKLATED ACYCLIC DIAMINE DERIVATIVES AS MODULATORS OF CHEMOKINE RECEPTOR ACTIVITY", Ser. No. 10/922,726; and "SUBSTITUTED CYCLOALKYLAMINE DERIVATIVES AS MODULATORS OF CHEMOKINE RECEPTOR ACTIVITY", Ser. No. 10/923,538.

Other features of the invention will become apparent in the course of the following descriptions of exemplary embodiments that are given for illustration of the invention and are not intended to be limiting thereof.

EXAMPLES

Unless otherwise indicated, it may be assumed that reactions are run under inert atmosphere ($N_2$ or Ar gas). Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1H$" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art. "RP-HPLC" refers to reverse-phase high performance liquid chromatography. Chromatographic methods are not typically specified, given that many different methods will perform equally well; gradient elution using acid-doped MeOH/water or acid-doped acetonitrile/water were typically utilized. Products were often obtained as acid salts after RP-HPLC; if desired, their parent free base can be derived through dissolution in aqueous base and extraction with organic solvents, as will be obvious to one skilled in the art. Chemical names were derived using ChemDraw Ultra, version 8.0.8 (May 2004). When this program failed to provide a name for the exact structure in question, an appropriate name was assigned using the same methodology utilized by the program.

Preparartion of Non-standard Reagents and Synthetic Intermediates Utilized in the Examples Preparation A1

Synthesis of Benzyloxycarbonylamino-7-oxo-6-azabicyclo[3.2.1]octane-6-carboxylic acid tert-butyl ester Preparation A1, Step 1: (1S,2R)-cis-2-Methoxycarbonyl-cyclohex-4-ene-1-carboxylic acid (66.0 g, see Bolm et al. J. Org. Chem. 2000, 65, 6984-6991) was dissolved in dry acetone (815 mL) prior to the addition of triethylamine (43.4 g). This solution was cooled to 0° C. and ethyl chloroformate (46.7 g) was added. The resulting solution was stirred 1 h before $NaN_3$ (35.0 g) was added. The cooling bath was removed, and the reaction was warmed to rt overnight. All solid material was removed by filtration, and the solution was partially concentrated. Water was slowly added and the organic layer was separated. The aqueous layer was extracted with ether. The combined organic layers were washed with water and brine before they were dried, filtered, and concentrated. The resulting oil (66.1 g) was dissolved in benzene (800 mL) and was warmed to a gentle reflux. After 4 h, the solution was cooled back to rt. Benzyl alcohol (37.5 g) and p-TsOH (1.5 g) were added, and the solution was warmed back to a gentle reflux overnight. After cooling to rt, the reaction was washed with NaHCO$_3$ and brine, dried, filtered, and concentrated to give (1R,6S)-6-benzyloxycarbonylamino-cyclohex-3-enecarboxylic acid methyl ester (97.7 g). MS found: (M+H)$^+$=290.2.

Preparation A1, Step 2: A sample of (1R,6S)-6-benzyloxycarbonylamino-cyclohex-3-enecarboxylic acid methyl ester (91.4 g) was dissolved in MeOH (500 mL) prior to the dropwise addition of NaOH (25.3 g) in water (95 mL). After 3 h, the solution was partially concentrated and an Et$_2$O/water mixture was added. The aqueous layer was separated and was acidified (pH~2) with concentrated HCl. The resulting mixture was extracted with EtOAc. The combined organic layers were washed with water and brine before they were dried, filtered, and concentrated to give (1R,6S)-6-benzyloxycarbonylamino-cyclohex-3-enecarboxylic acid (72.7 g). MS found: (M+H)$^+$=276.2.

Preparation A1, Step 3: A sample of (1R,6S)-6-benzyloxycarbonylamino-cyclohex-3-enecarboxylic acid (72 g) was dissolved in CH$_2$Cl$_2$ (750 mL) prior to the addition of CDI (50.9 g). After 2.5 h water was added, and the solution was extracted with CH$_2$Cl$_2$. The combined organic layers were dried, filtered, and concentrated. The resulting material was dissolved in CH$_2$Cl$_2$ and ammonia gas was bubbled through the solution for 1.5 h. After stirring overnight, the majority of the solvent was removed and Et$_2$O was added. The product precipitated as a white solid and was collected to give (1R, 6S)-6-carbamoyl-cyclohex-3-enyl)-carbamic acid benzyl ester (61.5 g). MS found: (M+H)$^+$=275.3.

Preparation A1, Step 4: A sample of (1R,6S)-6-carbamoyl-cyclohex-3-enyl)-carbamic acid benzyl ester (30.7 g) was dissolved in THF (1100 mL) and NMP (220 mL). At –78° C., 2.3M n-BuLi (96.3 mL) was added dropwise. After 2 h, a solution of Boc$_2$O (24.4 g) in THF (40 mL) was added dropwise. This solution was stirred 1.2 h before it was quenched with a saturated NH$_4$Cl solution. Water and Et$_2$O were added. The organic layer was filtered then washed with water, brine, dried, filtered, and concentrated. Flash chromatography of the resulting residue gave (1R,6S)-(6-tert-butoxycarbonylaminocarbonyl-cyclohex-3-enyl)-carbamic acid benzyl ester (29.2 g). MS found: (M+Na)$^+$=397.4.

Preparation A1, Step 5: A sample of (1R,6S)-(6-tert-butoxycarbonyl-aminocarbonyl-cyclohex-3-enyl)-carbamic acid benzyl ester (29.0 g) was dissolved in THF (1290 mL). This was cooled in an ice/brine bath prior to the addition of n-BuLi (1.5 mL, 2.4M). After 30 min, iodine (59.0 g) was added in a single portion. The bath was removed, and the reaction was warmed to rt overnight. The resulting solution was quenched with saturated thiosulfate solution. Water and EtOAc were added. The organic layer was washed with water, brine, dried, filtered, and concentrated. The resulting slurry was diluted with Et$_2$O and (1R,2S,4S,5R)-2-benzyloxycarbonylamino-4-iodo-7-oxo-6-aza-bicyclo[3.2.1]octane-6-carboxylic acid tert-butyl ester (22.8 g) was collected by vacuum filtration. MS found: (M–C$_5$H$_8$O$_2$+H)$^+$=401.1.

Preparation A1, Step 6: A sample of (1R,2S,4S,5R)-2-benzyloxycarbonylamino-4-iodo-7-oxo-6-aza-bicyclo[3.2.1]octane-6-carboxylic acid tert-butyl ester (43.3 g) was dissolved in benzene (580 mL) prior to the addition of Bu$_3$SnH (27.8 g) and AIBN (0.7 g). The resulting mixture was warmed to a gentle reflux for 3 h. After cooling, the solvent was removed and hexane was added. The resulting white solid was collected by vacuum filtration to give the title compound, (1R,2S,5R)-2-Benzyloxycarbonylamino-7-oxo-6-aza-bicyclo[3.2.1]octane-6-carboxylic acid tert-butyl ester (29.5 g). MS found: (M+Na)$^+$=397.4.

Preparation A2

Synthesis Of 7-oxo-6-oxa-bicyclo[3.2.1]oct-2-yl)-carbamic acid benzyl ester

The title compound was prepared using the method of Suga (H. Suga et al., *J. Am. Chem. Soc.* 1994, 116, 11197-98) from the known 1S,2R-cis-2-methoxycarbonyl-cyclohex-4-ene-1-carboxylic acid (see: Bolm et al., *J. Org. Chem.* 2000, 65, 6984-6991).

Preparation A3

Synthesis of (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate Preparation A3, Step 1: (1R,2S,5R)-Tert-butyl 2-benzyloxycarbonylamino-7-oxo-6-aza-bicyclo[3.2.1]octane-6-carboxylate (4.0 g) in MeOH (30 mL) was charged with 10% Pd/C, Degussa (600 mg). The reaction flask was evacuated and then back-filled with hydrogen; this was repeated three more times. The reaction was stirred under 1 atm of H$_2$ for 3 h and then filtered and concentrated to provide (1R,2S,5R)-tert-butyl 2-amino-7-oxo-6-aza-bicyclo[3.2.1]octane-6-carboxylate (2.5 g). MS (ES+)=241.1 (M+H)$^+$.

Preparation A3, Step 2: A solution of (1R,2S,5R)-tert-butyl 2-amino-7-oxo-6-aza-bicyclo[3.2.1]octane-6-carboxylate (2.5 g) was dissolved in DMF (34 mL) and cooled to 0° C. prior to the addition of N-Cbz methionine (5.3 g), 4-methyl morpholine (3.7 g), and BOP (8.3 g). The reaction was stirred for 12 h at RT and then partitioned between EtOAc and 1N HCl solution. The organic phases were combined, washed with saturated NaHCO$_3$ and brine, dried (MgSO$_4$), filtered, and concentrated in vacuo. The residue was purified by flash chromatography to afford (1R,2S,5R)-tert-butyl 2-((S)-2-(benzyloxycarbonylamino)-4-(methylthio)butanamido)-7-oxo-6-aza-bicyclo[3.2.1]octane-6-carboxylate (5.1 g). MS found: (M+H)$^+$=506.2.

Preparation A3, Step 3: (1R,2S,5R)-Tert-butyl 2-((S)-2-(benzyloxycarbonylamino)-4-(methylthio)butanamido)-7-oxo-6-aza-bicyclo[3.2.1]octane-6-carboxylate (5.1 g) was dissolved in iodomethane (40 mL). The resulting solution was stirred at rt for 12 h before being concentrated in vacuo. The residue was dissolved in methylene chloride, and the resulting solution was concentrated; this was repeated to afford the salt. This material was dissolved in DMF (30 mL) and the solution was charged with Cs$_2$CO$_3$ (6.6 g). After 12 h, the reaction was partitioned between EtOAc and brine. The organic phase was dried (MgSO$_4$), filtered, and concentrated. The resulting residue was purified by flash chromatography to afford (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate (2.0 g). MS found: (M+H)$^+$=458.6.

Preparation B1

Synthesis of 2-(3-ethylureido)-5-(trifluoromethyl)Benzoic Acid

Preparation B1, Step 1: N-Boc 2-amino-5-(trifluoromethyl)benzoic acid (S. Takagishi, et al., *Synlett* 1992, 360; 5.1 g, 17 mmol) was dissolved in DMF (42 mL) and the solution was charged with allyl bromide (3.8 mL, 44 mmol) and potassium carbonate (3.4 g, 25 mmol). The slurry was stirred for 14 h at RT, diluted with EtOAc, and washed successively with brine, water, and brine. The organic phase was dried ($Na_2SO_4$), filtered, and concentrated in vacuo to provide the allyl ester as a white solid. This material was dissolved in methylene chloride (30 mL) and TFA (15 mL) and stirred at RT for 2 h before being concentrated in vacuo. The residue was dissolved in methylene chloride and the solution was concentrated in vacuo; this procedure was repeated twice to provide the presumed TFA salt of allyl 2-amino-5-(trifluoromethyl)benzoate. MS found: (free M+H)$^+$=246.29.

Preparation B1, Step 2: The allyl 2-amino-5-(trifluoromethyl)benzoate from step 1 (ca. 15.7 mmol) was dissolved in THF (60 mL) and phosgene (24.9 mL, 47 mmol) was added at 0° C. dropwise. The reaction was stirred for 15 minutes at 0° C. Triethylamine (13.1 mL, 94 mmol) was slowly added and stirring was continued for 2 hours. The reaction was concentrated in vacuo to afford a yellow solid. A portion (2.4 g, ca. 7.7 mmol) of the yellow solid was dissolved in THF (40 mL) and the solution was charged with ethylamine (20 mL of a 2.0 M solution in THF). The reaction was stirred for 14 h at RT and then diluted with EtOAc. The organic phase was washed successively with 1N HCl (2×) and brine (1×) before being dried ($Na_2SO_4$), filtered, and concentrated in vacuo to give allyl 2-(3-ethylureido)-5-(trifluoromethyl)benzoate as a white solid (1.8 g). MS found: (M+Na)$^+$=339.29.

Preparation B1, Step 3: The allyl 2-(3-ethylureido)-5-(trifluoromethyl)benzoate (1.8 g, ca. 5.7 mmol) was dissolved in acetonitrile (50 mL) The solution was charged with pyrrolidine (1.0 mL, 12 mmol) and Ph(PPh$_3$)$_4$ (140 mg, 0.17 mmol) and then stirred for 2 h at RT before being concentrated in vacuo. The residue was diluted with EtOAc and this was washed successively with 1N HCl (2×) and brine (1×) before being dried ($Na_2SO_4$), filtered, and concentrated in vacuo. The residue was triturated with methylene chloride to afford pure 2-(3-ethylureido)-5-(trifluoromethyl)benzoic acid (0.89 g).

$^1$H-NMR (300 MHz, d$_4$-MeOH): δ 8.59 (d, 1H, J=9.6 Hz), 8.26 (d, 1H, J=1.5 Hz), 7.72 (dd, 1H, J=9.2, 1.8 Hz), 3.23 (q, 2H, J=7.3 Hz), 1.17 (t, 3H, J=7.2 Hz).

Preparation B2

Synthesis of 2-(isopropylureido)-5-(trifluoromethyl)benzoic acid

The complete three-step procedure described in Preparation B1 was followed, substituting isopropylamine for ethylamine in Step 2 to provide the title compound. MS found: (M−H)−=289.

Preparation B3

Synthesis of 2-(azetidine-1-carboxamido)-5-(trifluoromethyl)benzoic acid

The complete three-step procedure described in Preparation B1 was followed, substituting azetidine for ethylamine in Step 2 to provide the title compound. MS found: (M−H)−=287.

Preparation B4

Synthesis of 2-(cyclopropylureido)-5-(trifluoromethyl)benzoic acid

The complete three-step procedure described in Preparation B1 was followed, substituting cyclopropylamine for ethylamine in Step 2 to provide the title compound. $^1$H NMR (300 MHz, CD$_3$OD) δ 8.56 (d, J=9.8 Hz, 1H), 8.32 (s, 1H), 7.59 (d, J=9.8 Hz, 1H), 2.62-2.61 (m, 1H), 0.83 (s, 2H), 0.58 (s, 2H); $^{19}$F NMR (282 MHz, CD$_3$OD) δ −61.7.

Preparation B5

Synthesis of 2-(methylsulfonamido)-5-(trifluoromethyl)benzoic acid

Preparation B5, Step 1: To a solution of 4-(trifluoromethyl)benzenamine (10.0 g, 0.0617 mol) in dry methanol (200 ml) was added iodine monochloride (10.49 g, 0.148 mol) in dry MDC (40 ml) at RT slowly. Reaction mixture was stirred at RT over night. The reaction mixture was concentrated, water was added and extracted with ethyl acetate (2×100 ml). The organic layer was washed with water, brine (2×50 ml), dried over $Na_2SO_4$ and concentrated. The crude product was purified by column chromatography using 6% ethyl acetate in pet-ether to get 2-iodo-4-(trifluoromethyl)benzenamine (12.5 g, 70%) as pale yellow liquid. $^1$H NMR (400 MHz, CDCl$_3$) δ 4.42 (bs, 2H), 6.75 (d, 1H), 7.38 (d, 1H), 7.87 (s, 1H).

Preparation B5, Step 2: A mixture of 2-iodo-4-(trifluoromethyl)benzenamine (11.0 g, 0.0382 mol), pyridine (40 ml), methanesulfonylchloride (5.3 g, 0.046 mol) and DMAP (0.46 g, 0.0038 mol) in a 100 ml RB flask was heated slowly to 105° C. and maintained the same temperature for over night. The reaction mixture was concentrated to remove the pyridine. The crude product obtained was purified by column chromatography using 10% ethyl acetate in pet ether as eluent to get N-(2-iodo-4-(trifluoromethyl)phenyl)methanesulfonamide (4.5 g, 32%) as white solid. $^1$H NMR (400 MHz, CDCl$_3$) δ 3.08 (s, 3H), 6.88 (bs, 1H), 7.65 (d, 1H), 7.75 (d, 1H), 8.07 (s, 1H).

Preparation B5, Step 3: To a mixture of N-(2-iodo-4-(trifluoromethyl)phenyl)methanesulfonamide (3.5 g, 9.589 mmol) dry methanol (30 ml) DMF (30 ml) was added palladium(II)acetate (0.07 g, 0.35 mmol), 1,1-bis(diphenylphosphene)ferrocene (0.32 g, 0.577 mmol) and TEA (1.96 g, 19.4 mmol) at RT. To that reaction mixture was purged with carbon monoxide for 30 min at RT. Reaction mixture was slowly heated to 60° C. and maintained at the same temperature for over night under carbon monoxide atm. Water was added and the reaction mixture was extracted with ethyl acetate (3×50 ml). The organic layer was washed with brine, dried ($Na_2SO_4$) and concentrated. The crude product was purified by column chromatography 15% ethyl acetate in pet ether as eluent to get methyl 2-(methylsulfonamido)-5-(trifluoromethyl)benzoate (2.0 g, 70%) as white solid. $^1$H NMR (400 MHz, CDCl$_3$) δ 3.14 (s, 3H), 3.99 (s, 3H), 7.78 (d, 1H), 7.87 (d, 1H), 8.34 (s, 1H), 10.75 (bs, 1H).

Preparation B5, Step 4: To a mixture of methyl 2-(methylsulfonamido)-5-(trifluoromethyl)benzoate (1.0 g, 3.367 mmol) in THF (20 ml) and water (20 ml) was added lithium hydroxide (0.4242 g, 10.10 mmol) and stirred at RT for 6 h. The reaction mixture was acidified with 1.5 N HCl and extracted with ethyl acetate (3×50 ml). The organic layer was washed with water, brine, dried ($Na_2SO_4$) and concentrated. The solid was filtered and dried under vaccum to get 2-(methylsulfonamido)-5-(trifluoromethyl)benzoic acid (0.7 g, 73%) as white solid. $^1$H NMR (400 MHz, CDCl$_3$) δ 3.31 (s, 3H), 7.78 (d, 1H), 7.97 (d, 1H), 8.24 (s, 1H), 11.13 (bs, 1H);

$^{13}$C NMR (100 MHz, CDCl$_3$) δ 40.74, 116.5, 118.3, 122.8 (m), 128.8, 131.6, 144.3, 169.1. MS found: (M–H)$^-$=282.

Preparation B6

Synthesis of 5-(trifluoromethyl)-2-(trifluoromethylsulfonamido)benzoic acid

Preparation B6, Step 1: To a solution of 4-trifluoromethylaniline (5 g, 0.031 mol) in 50 ml of dry benzene was added triethylamine (6.26 g, 8.63 ml, 0.06 mol) at 0° C. Pivaloyl chloride (4.5 g, 0.04 mol) was added slowly and stirred at RT over night. The RM was quenched with water and extracted with ethyl acetate. The organic layer was washed with water, brine and concentrated. To the solid was triturated with pet-ether and filtered to give N-(4-(trifluoromethyl)phenyl)pivalamide (6.7 g) as white solid.

Preparation B6, Step 2: To a solution of N-(4-(trifluoromethyl)phenyl)pivalamide (1 g, 4.08 mmol) in 20 ml of dry THF under nitrogen was added n-butyllithium (0.65 g, 4.1 ml) at 0° C. The reaction mixture was maintained at 0° C. for 3 h and added onto dry ice and stirred at RT over night. The reaction mixture was concentrated and the solid product obtained was dissolved in 25 ml of dry methanol and purged HCl gas for 30 min at 0° C. The mixture was stirred at RT for 2 h and heated at 55° C. over night. The reaction mixture was concentrated, basified with sodium bicarbonate solution and extracted with ethyl acetate. The organic layer was washed with water, brine and concentrated. The crude product was purified by flash chromatography to give methyl 2-amino-5-(trifluoromethyl)benzoate (0.55 g) as white solid.

Preparation B6, Step 3: To a solution of methyl 2-amino-5-(trifluoromethyl)benzoate (0.25 g, 1.141 mmol) and triethylamine (0.115 g, 0.16 ml, 1.14 mmol) in 3 ml of dry dichloromethane was added trifluoromethane sulfonic anhydride (0.64 g, 2.28 mmol) at –78° C. The mixture was maintained below –40° C. for 3 h and stirred at RT for over night. Water was added and extracted with dichloromethane. The organic layer was dried and concentrated. The product was purified by flash chromatography to give 0.3 g (75%) of methyl 5-(trifluoromethyl)-2-(trifluoromethylsulfonamido) benzoate as white solid. MS found: (M+H)$^+$=352.

Preparation B6, Step 4: To a solution of methyl 5-(trifluoromethyl)-2-(trifluoromethylsulfonamido)benzoate (2.7 g, 7.7 mmol) in 55 ml of THF was added lithium hydroxide (0.97 g, 23.1 mmol) in 55 ml of water and stirred at RT over night. The reaction mixture was acidified with 1.5N HCl and extracted with ethyl acetate. The organic layer was washed with water, brine and concentrated to give 5-(trifluoromethyl)-2-(trifluoromethylsulfonamido)benzoic acid (2 g) as white solid. $^1$H NMR (DMSO-d$_6$, 400 MHz) δ 7.77 (m, 2H), 8.18 (s, 1H). MS found: (M–H)$^-$=336.

Preparation B7

Synthesis of 5-isopropyl-2-(trifluoromethylsulfonamido)benzoic acid

The complete four-step procedure described in Preparation B6 was followed, substituting 4-isopropylaniline for 4-trifluoromethylaniline in Step 1 to provide the title compound. $^1$H NMR (DMSO-d$_6$, 400 MHz) δ 1.19 (d, 6H), 2.92 (m, 1H), 7.37 (d, 1H), 7.47 (d, 1H), 7.77 (s, 1H). MS found: (M–H)$^-$=310.

Preparation C1

Synthesis of 2-tert-butylpyrimidine-4-carboxylic acid

Preparation C1, Step 1: A 22% solution of sodium ethoxide in ethanol (53 mL, 165 mmol) was added dropwise to a magnetically stirred suspension of tert-butylcarbamidine hydrochloride (20.0 g, 146 mmol) in ethanol (100 mL). When the addition was complete, the yellow suspension was warmed to 50° C., the heating mantle was removed, and a solution of mucobromic acid (15.7 g, 61 mmol) in ethanol (50 mL) was added dropwise at a rate which did not allow the temperature to exceed 55° C. When this addition was complete, a 22% solution of sodium ethoxide in ethanol (32 mL, 98 mmol) was added dropwise, then the mixture was allowed to cool to room temperature. The suspension was filtered, the solids were rinsed with ethanol (2×20 mL), and the combined filtrates were concentrated in-vacuo. The residue thus obtained was stirred in 2 N aqueous HCl (30 mL). The resulting solids were collected by filtration, rinsed with ice-cold water (2×20 mL), and air dried to yield 12.1 g of 5-Bromo-2-tert-butyl-pyrimidine-4-carboxylic acid as a beige powder. MS (ES+)=259, 261 (M+H)$^+$.

Preparation C1, Step 2: A mixture of 5-Bromo-2-tert-butyl-pyrimidine-4-carboxylic acid (1.65 g, 6.37 mmol) and aqueous sodium hydroxide (1.0 N, 19.1 mL, 19.1 mmol) in methanol (100 ml) was treated with a catalytic amount of 10% palladium on carbon. The mixture was degassed under vacuum/nitrogen, then hydrogenated at 50 psi for 2 hours. The catalyst was removed by filtration, the methanol was removed under vacuum, and the aqueous was acidified by the addition of 1.0 N aqueous hydrochloric acid (40 mL). The resulting suspension was extracted with ethyl acetate (4×50 mL), the combined organic phases were washed with brine, dried over sodium sulfate, and concentrated in-vacuo to yield 1.06 g of 2-tert-butylpyrimidine-4-carboxylic acid as a white powder. MS (ES+)=181 (M+H+).

Preparation C2

Synthesis of 3-tert-Butyl-benzoic acid

Preparation C2, Step 1: A mixture of the commercially available methyl 3-bromo-5-tert-butylbenzoate (700 mg, 2.58 mMol), aqueous NaOH (1 N, 7.75 mL, 7.75 mMol), and Pearlman's catalyst (100 mg) in methanol (20 mL) was hydrogenated at 50 psi for 22 hours. The catalyst was removed by filtration and rinsed with a small amount of methanol. The filtrate was concentrated in-vacuo to remove methanol, and the aqueous mixture was acidified with 1 N HCl (10 mL), then extracted with ethyl acetate (3×20 mL). The combined organic phases were dried over sodium sulfate, then concentrated in-vacuo. Analysis of the resulting material by LC/MS showed that the ester had hydrolyzed to the carboxylic acid, but that the bromide was still present. The material was dissolved in methanol (20 mL), and hydrogenated overnight at 50 psi in the presence of 1 N aqueous NaOH (5.2 mL, 5.2 mMol) and 10% palladium on activated carbon (50 mg). Analysis of the crude reaction mixture by LC/MS showed that the bromine was still present, so Pearlman's catalyst (200 mg) was added, and hydrogenation at 50 psi was continued for 23 hours. MS showed that the reaction was now complete, so the reaction was worked up as described previously in this example to yield 376 mg (81% yield) of white powder as product. MS (AP−)=177 (M−H)

Preparation C3

Synthesis of 6-tert-butylpicolinic acid $HC_1$ salt

Preparation C3, Step 1: 2-tert-butylpyridine (2.00 g, 14.8 mmol, 1 eq.) was dissolved in HOAc (10 mL) and 30% hydrogen peroxide (1.68 mL, 14.8 mmol, 1 eq.) at room temperature then the reaction was refluxed for 20 hours. The reaction was stripped to obtain an amber oil which was dissolved in methylene chloride (10 mL) then dried over sodium sulfate and stripped to obtain 2-tert-butylpyridine-N-oxide (1.60 g) as an amber oil. Yield=71.5%. LCMS detects $(M+H)^+$=152.09.

Preparation C3, Step 2: 2-tert-butylpyridine-N-oxide (1.60 g, 10.6 mmol, 1 eq) was dissolved in methylene chloride (25 mL) at room temperature under nitrogen then trimethylsilyl cyanide (1.79 mL, 13.4 mmol, 1.27 eq.) was added followed by the dropwise addition of dimethylcarbamyl chloride (1.24 mL, 13.4 mmol, 1.27 eq.) over 3 minutes. Stirred for 20 hours. Worked up by adding 10% potassium carbonate (aqueous) (25 mL). Foaming occurred. Stirred 10 minutes then extracted 3 times with methylene chloride (25 mL). The organic layers were combined, dried over sodium sulfate then stripped to give an amber oil. Purified over silica gel in 3:1 hexanes/ethyl acetate. Obtained 6-tert-butylpicolinonitrile (1.08 g) as an amber oil. Yield=59%. LCMS detects $(M+H)^+$=161.14.

Preparation C3, Step 3: 6-tert-butylpicolinonitrile (1.05 g) was dissolved in 6N HCl (aqueous) at room temperature then refluxed for 20 hours. Worked up by stripping 3 times from acetonitrile. Obtained solids. The solids were refluxed in 10 mL of acetonitrile. Solids which didn't dissolve were filtered off. The filtrate was stripped to give 6-tert-butylpicolinic acid HCl salt (680 mg) as a colorless oil. Yield=48%. LCMS detects $(M+H)^+$=180.16.

Preparation C4

Synthesis of 6-(trifluoromethyl)picolinic acid

Preparation C4, Step 1: 2-bromo-6-(trifluoromethyl)pyridine (100 mg, 0.44 mmol, 1 eq.) was dissolved in diethyl ether at room temperature under nitrogen then cooled to −70° C. Added 1.6M n-Butyllithium in hexanes (0.28 mL, 0.44 mmol, 1 eq.) dropwise via an addition funnel. Stirred at −40° C. for 15 minutes then cooled to −70° C. and bubbled in $CO_2$ gas for 10 minutes. Allowed to warm to room temperature. Added water then rinsed 3 times with diethyl ether. The aqueous pH was adjusted to =3 with conc. HCl. Extracted the acidic aqueous layer 3 times with ethyl acetate. The ethyl acetate layers were combined, dried over sodium sulfate and stripped to give 6-(trifluoromethyl)picolinic acid (30 mg) as a white solid. Yield=35%. LCMS detects $(M+H)^+$=192.06.

Preparation C5

Synthesis of 3-(adamant-1-yl)-pyrrole-5-carboxylic acid

Preparation C5, Step 1: Ethyl pyrrole-2-carboxylate (2.09 g, 15 mmol, 1 eq), was added to a mixture of gallium(III) chloride (2.90 g, 16.5 mmol, 1.1 eq) in carbon disulfide (40 mL) and the contents heated at 40° C. for 30 min. Afterwards, 1-chloroadamantane (2.82 g, 16.5 mmol, 1.1 eq), was added thereto and the contents heated for another 40 minutes. The reaction was poured onto a mixture of ice and 1.0 N HCl, and extracted with chloroform. The extracts were washed with saturated sodium bicarbonate, dried ($MgSO_4$) and the solvent stripped to yield a crude solid. Recrystallization from EtOAc yielded 2 crops of ethyl 3-(adamanty-1-yl)-pyrrole-5-carboxylate. $1^{st}$ crop wt.=0.67 grams. $2^{nd}$ crop wt.=1.10 grams. MS found: (M+H)+=274.44 and 274.45, respectively.

Preparation C5, Step 2: Ethyl 3-(adamanty-1-yl)-pyrrole-5-carboxylate (0.29 g, 1.1 mmol, 1 eq), 1.000 N NaOH (2.20 mL, 2.2 mmol, 2 eq) and MeOH (15 mL) were mixed and stirred overnight. After only partial reaction, more 1.000 N NaOH (21 mL) together with more MeOH to dissolve were added and the contents refluxed for 4 hours. The contents were acidified to pH=1 with 1.0 N HCl. The MeOH was stripped off to yield solids and aqueous. The mixture was extracted with EtOAc, the EtOAc layers were combined, washed with brine, dried (MgSO4) and stripped to yield 250 mg of 3-(adamant-1-yl)-pyrrole-5-carboxylic acid as a white powder. MS found: (M+H)+=246.44

Preparation C6

Synthesis of 3-(Adamant-1-yl)-1-methylpyrrole-5-carboxylic acid

Preparation C6, Step 1. Ethyl 3-(adamant-1-yl)-pyrrole-5-carboxylate (0.20 g, 0.7 mmol, 1 eq) was dissolved in THF (20 mL). Potassium bis(trimethylsilyl)amide (0.5 M in Tol, 1.62 mL, 0.81 mmol, 1.1 eq) was added thereto followed by iodomethane (0.102 mL, 1.6 mmol, 2.2 eq). The next day, the same amounts of potassium bis(trimethylsilyl)amide and iodomethane were again added to drive the reaction to completion. In 4 h, the reaction was finished. Ethyl acetate was added (100 mL) and the organic layer was washed with water (2×), brine, dried ($MgSO_4$) and stripped to yield 600 mg of ethyl 3-(adamant-1-yl)-1-methylpyrrole-5-carboxylate, which was used as is in the next step. MS found: (M+H)+=288.16.

Preparation C6, Step 2: Saponification of ethyl 3-(adamant-1-yl)-1-methylpyrrole-5-carboxylate (entire contents from Step 1) by the procedure in Preparation C5, step 2 yielded 160 mg of 3-(adamant-1-yl)-1-methylpyrrole-5-carboxylic acid. MS found: (M−H)+=258.10.

Preparation C7

Synthesis of 6-tert-Butyl-4-chloro-pyrrolo[2,1-f][1,2,4]triazine

Preparation C7, Step 1: Ethyl pyrrole-2-carboxylate (7.24 g, 52 mmol, 1 eq), 2-chloro-2-methylpropane (6.18 mL, 57 mmol, 1.1 eq), gallium trichloride (10.0 g, 57 mMol, 1.1 eq), and carbon disulfide (200 mL) were mixed and refluxed for 45 min. The reaction was poured onto a mixture of ice and 1.0 N HCl. The aqueous mixture was extracted with chloroform, the chloroform layer was washed with saturated sodium bicarbonate, dried over magnesium sulfate, and stripped to yield 9.78 g of a golden oil, which eventually crystallized. Flash chromatography over silica gel in 9:1 hexane/ethyl acetate yielded 3.62 g of ethyl 4-tert-butyl-1H-pyrrole-2-carboxylate. MS found: (M−H)+=196.28.

Preparation C7, Step 2: Preparation of monochloramine by the method of John Hynes, Jr., et al., *J. Org. Chem.*, 2004, 69, 1368: $NH_4Cl$ (3 g, 56 mmol, was mixed in ether (110 mL) and cooled to −5° C. Concentrated $NH_4OH$ (4.7 mL) was then added followed by dropwise addition of bleach (Chlorox, 72 mL) over 15 minutes. The mixture was stirred for 15 minutes, the layers separated and the organic layer washed with brine. The organic layer was dried over powdered CaCl$_2$ in the freezer for 1 h and used for the subsequent step immediately. Ethyl 4-tert-butyl-1H-pyrrole-2-carboxylate (1.67 g, 8.6 mmol, 1 eq) was dissolved in DMF. Sodium hydride (60% suspension in oil) (0.41 g, 10 mmol, 1.2 eq) was then added thereto cautiously and stirred for 45 minutes at RT under nitrogen. Monochloramine was then added (0.15M in ether, 68.4 mL, 10 mmol, 1.2 eq). The next morning, the reaction is quenched with saturated aqueous Na$_2$S$_2$O$_3$, diluted with water and extracted into ether. The ether layer is dried, filtered and stripped to yield 3.19 g of ethyl 3-tert-butyl-1-aminopyrrole-5-carboxylate as a yellow oil which eventually crystallized as long needles. MS found: (M+H)+=211.34.

Preparation C7, Step 3: Ethyl 3-tert-butyl-1-aminopyrrole-5-carboxylate (1.00 g, 4.76 mmol, 1 eq), formamidine acetate (1.46 g, 14.3 mmol, 3 eq.) and 2-ethoxyethanol (10 mL) were mixed and refluxed for 3 hours. The solvent was stripped and then restripped from chloroform (3×) to yield a solid. This solid was stirred in 5 mL MeOH, filtered, and the collected solids rinsed with Et$_2$O and dried to yield 233 mg of 6-tert-butyl-pyrrolo[2,1-f][1,2,4]triazin-4-ol as a white solid. LCMS found: (M+H)+=191.

Preparation C7, Step 4: 6-tert-Butyl-pyrrolo[2,1-f][1,2,4]triazin-4-ol (0.43 mg, 2.26 mmol, 1 eq.) and POCl$_3$ (4.21 mL, 45.2 mmol, 20 eq.) were mixed and refluxed for 4 hours. The mixture was stripped then restripped 3× from methylene chloride and then dissolved in methylene chloride and rinsed 3× with sat'd NaHCO$_3$, 1× with brine. The organic layers were collected, dried and stripped in vacuo to yield 490 mg of 6-tert-butyl-4-chloro-pyrrolo[2,1-f][1,2,4]triazine as an amber oil. LCMS detects (M+H)+=210.

Preparation C8

Synthesis of 3-(tert-Butyl)-pyrrole-5-carboxylic Acid

Preparation C8, Step 1: Ethyl 4-tert-butyl-1H-pyrrole-2-carboxylate (from C7, Step 1) (38 mg, 1.95 mmol, 1 eq), 1.000 N NaOH (39 mL, 39 mmol, 20 eq) and MeOH (50 mL) were mixed and refluxed for 1 hour. The mixture was acidified with 1.0 N HCl, (1.0 N), the MeOH stripped, and the remaining aqueous extracted with ethyl acetate (2×). The organic layers were combined, dried (MgSO4), and stripped to yield 290 mg of an off-white solid. NMR (CDCl$_3$+2 drops DMSO-D6) δ 6.50 (s, 1H); 6.46 (s, 1H); 0.95 (s, 9H).

Preparation C9

Synthesis of 3-(tert-Butyl)-1-methylpyrrole-5-carboxylic Acid

Preparation C9, Step 1: Ethyl 4-tert-butyl-1H-pyrrole-2-carboxylate was first methylated by the method of C6, Step 1 and then saponified by the method of C8, Step 1 (reflux lasting 4 hours) yielding 3-(tert-butyl)-1-methylpyrrole-5-carboxylic acid. MS found: (M+H)+=182.10.

Preparation C10

Synthesis of lithium 2-tert-butyl-1-oxo-pyrimidine-4-carboxylate

The titled compound was prepared from 2-tert-butylpyrimidine-4-carboxylic acid utilizing the procedures used to synthesize lithium 2-phenylisonicotinate, N-oxide (Preparation H1). The synthesis yielded a 3:1 mixture of desired product, lithium 2-tert-butyl-1-oxo-pyrimidine-4-carboxylate, and the des-oxo derivative, lithium 2-tert-butylpyrimidine-4-carboxylate. This mixture was used as is. MS found: (M+H)+=197.24.

Preparation D1

Synthesis of 6-chloroquinazolin-4-ol

Preparation D1, Step 1: 2-Amino-5-chlorobenzoic acid (1.00 g, 5.86 mmol, 1 eq.) and formic acid (3.94 mL, 104 mmol, 17.8 eq.) were mixed at room temperature and then refluxed for 2.5 hours. Cooled to room temperature then added 15 mL of water. Solids precipitated. Stirred the solids for 10 minutes. The solids were filtered, rerinsed 2 times with of water (5 mL). The solids were filtered then stirred in of ethyl acetate (10 mL) for 5 minutes. Filtered the solids to give 6-chloroquinazolin-4-ol (800 mg) as tan solids. Yield=75%. Mass Spec (ESI) detects (M+H)+=180.8.

Preparation D1, Step 2: 6-Chloroquinazolin-4-ol (400 mg, 2.21 mmol, 1 eq.), phosphorus oxychloride (1.99 mL, 21.4 mmol, 9.64 eq.) and triethylamine (0.99 mL, 7.11 mmol, 3.21 eq.) were mixed at room temperature under nitrogen and then refluxed for 2.5 hours. Worked up by stripping the reaction, then re-rotovapping the residue 2 times from toluene to obtain brown solids. Methylene chloride (25 mL) was added to dissolve the solids. The organic mixture was then rinsed 2 times with saturated ammonium chloride (25 mL). The organic layer was dried (sodium sulfate) and stripped to give brown solids. The solids were purified over silica gel in 9:1 to 3:1 hexanes/ethyl acetate. Obtained 4,6-dichloroquinazoline (300 mg) as an off-white solid. Yield=68%. $^1$H NMR (400 MHz) (DMSO-D6) δ 9.16 (s, 1H): 8.33 (s, 1H), 8.17 (apparent t, 2H, J=7 Hz).

Preparation D2

Synthesis of 6-fluoroquinazolin-4-ol

Preparation D2, Step 1: 2-Amino-5-fluorobenzoic acid (2.00 g, 13.0 mmol, 1 eq.) and formic acid (8.72 mL, 231 mmol, 17.8 eq.) were mixed at room temperature and then refluxed for 2.5 hours. Cooled to room temperature then added 25 mL of water. Solids precipitated. Stirred the solids for 1 hour. The solids were filtered then stirred with hexanes (20 mL). The solids were filtered and dried at 110° C. under vacuum for 4 hours to give 6-fluoroquinazolin-4-ol (1.66 g) as a white solid. $^1$H NMR (400 MHz) (CD$_3$OD) δ 8.07 (s, 1H); 7.85 (D, 1h); 7.74 (T, 1h); 7.62 (M, 1h).

Preparation D2, Step 2: 6-fluoroquinazolin-4-ol (1.00 g, 6.09 mmol, 1 eq.), phosphorus oxychloride (3.41 mL, 36.6 mmol, 6 eq.) and triethylamine (5.09 mL, 36.6 mmol, 6 eq.) were mixed at room temperature and then refluxed for 2 hours. Worked up by stripping 3 times from methylene chloride. The residue was dissolved in methylene chloride (25 mL) and rinsed 3 times with saturated sodium bicarbonate (25 mL) and 1× with brine (25 mL). The organic layer was dried (sodium sulfate) and stripped to give a crude oil. Purified over silica gel in 9:1 to 3:1 hexanes/ethyl acetate. Obtained 4-chloro-6-fluoroquinazoline (0.96 g) as a tan solid. Yield=86%. LCMS detects (M+H)+=183.16.

Preparation D3

Synthesis of 4-chloro-6-(trifluoromethyl)quinazoline

Preparation D3, Step 1: A suspension of 2-(tert-butoxycarbonylamino)-5-(trifluoromethyl)benzoic acid (56.34 g, 185 mmol, see: S. Takagishi, et al., *Synlett* 1992) in dioxane (100 mL) was treated with the dropwise addition of 4 N hydrochloric acid solution in dioxane (250 mL, 1.0 mol), and the mixture was stirred for 4 h. Analysis by LC/MS indicated that the reaction was not complete, so additional 4 N hydrochloric acid solution in dioxane (250 mL, 1.0 mol) was added, and the mixture was stirred overnight. Analysis by LC/MS indicated that the reaction still contained c. 5% of the starting material, so additional 4 N hydrochloric acid solution in dioxane (100 mL, 0.4 mol) was added, and the mixture was stirred for 4 h. Analysis by LC/MS indicated that the reaction was now complete. The mixture was concentrated in-vacuo, and the residue was stripped 2× from methylene chloride to remove any remaining HCl. The 2-amino-5-(trifluoromethyl)benzoic acid, hydrochloride thus obtained was used immediately in the next step. MS (ES+)=206 (M+H+).

Preparation D3, Step 2: A suspension of 2-amino-5-(trifluoromethyl)benzoic acid, hydrochloride (44.7 g, 185 mmol) and formamidine acetate (38.52 g, 370 mmol) in 2-ethoxyethanol (200 mL) was heated at reflux overnight, during which time a clear solution was observed. The mixture was cooled to room temperature, and the resulting solids were collected by filtration, rinsed with a small amount of 2-ethoxyethanol followed by diethyl ether, and dried under vacuum to yield 9.7 g of an off-white solid, which was not desired product by NMR. The combined filtrates were concentrated in-vacuo, and the residue was crystallized from methanol to yield 31.07 g of 6-(trifluoromethyl)quinazolin-4-ol as off-white plates in two crops. $^1$H NMR (400 MHz, DMSO) δ ppm 12.60 (s, 1H), 8.35 (s, 1H), 8.24 (d, J=4.83 Hz, 1H), 8.13-8.09 (m, 1H), 7.85 (dd, J=8.35, 4.39 Hz, 1H). MS (ES+)=215 (M+H+).

Preparation D3, Step 3: A suspension of 6-(trifluoromethyl)quinazolin-4-ol (10.41 g, 48.4 mmol) in phosphorous oxychloride (100 mL) was heated at reflux for 3 h, during which time a clear, amber solution was observed. The solution was cooled to room temperature, concentrated in-vacuo, and stripped 3× from 150 mL methylene chloride to remove any remaining phosphorous oxychloride. The residue was partitioned between EtOAc and saturated sodium bicarbonate (1:1, 300 mL), and the mixture was stirred until gas evolution ceased. The layers were separated, the organic phase was washed successively with saturated sodium bicarbonate and brine, the combined aqueous phases were extracted with EtOAc (50 mL), and the combined organic phases were dried over sodium sulfate then concentrated in-vacuo. The residue was purified over silica gel, eluting with 25% EtOAc/Heptane, to yield 8.14 g of 4-chloro-6-(trifluoromethyl)quinazoline as a white solid. MS (ES+)=233, 235 (M+H+).

Preparation D4

Synthesis of 4-chloro-6-trifluoromethoxyquinazoline

Preparation D4, Step 1 (Synthesis of (4-Trifluoromethoxyphenyl)-carbamic acid tert-butyl ester): A solution of 4-(trifluoromethoxy)phenyl isocyanate (9.75 g, 48.0 mMol) in THF (100 mL) was cooled to 0° C., and a 1.0 M THF solution of potassium tert-butoxide (53 mL, 53 mMol) was added dropwise. The mixture was allowed to warm to room temperature, and stirred for 7 hours. The solution was poured into a mixture of saturated ammonium chloride solution (200 mL), and diethyl ether (200 mL). Enough water was added to redissolve the ammonium chloride that had crashed out, the mixture was shaken in a separatory funnel, and the layers were separated. The organic phase was washed with saturated ammonium chloride (100 mL), water (100 mL), brine (100 mL), dried over sodium sulfate, and concentrated in-vacuo. The residue was purified over silica gel, eluting with 10%-20% ethyl acetate/heptane to yield 11.7 g of white solids as product. NMR (500 MHz, DMSO) δ 9.54 (s, 1H), 7.54 (d, 2H, J=7 Hz), 7.23 (d, 2H, J=8 Hz), 1.45 (s, 9H). Yield=88%.

Preparation D4, Step 2 (Synthesis of 2-tert-Butoxycarbonylamino-5-trifluoromethoxy-benzoic acid): A solution of (4-trifluoromethoxy-phenyl)-carbamic acid tert-butyl ester (2.31 g, 8.33 mMol) in anhydrous THF (50 mL) at −78° C. was treated with a 1.4 M solution of sec-butyllithium in cyclohexane (13 mL, 18.33 mMol), at a rate which did not allow the internal temperature to exceed −60° C. The solution was stirred at −78° C. for 15 minutes, then allowed to warm to −40° C. and stirred for 2.5 hours. The reaction was treated with gaseous CO$_2$, stirred 30 minutes while warming to −20° C., then quenched with saturated ammonium chloride. The mixture was warmed to room temperature, and extracted with ethyl acetate (3×50 mL). The combined organic phases were washed with water (50 mL), brine (50 mL), dried over sodium sulfate, and concentrated in-vacuo. The residue was triturated with hot heptane to yield 1.9 g of white powder as product. NMR (500 MHz, DMSO) δ 12.89 (s, 1H), 8.24 (d, 1H, J=9 Hz), 7.84 (s, 1H), 7.21 (d, 1H, J=7 Hz), 1.51 (s, 9 Hz). Yield=72%.

Preparation D4, Step 3 (Synthesis of 2-Amino-5-trifluoromethoxy-benzoic acid, HCl salt): 2-tert-Butoxycarbonylamino-5-trifluoromethoxy-benzoic acid (1.9 g, 5.91 mMol) was dissolved in a 4 N HCl solution in dioxane (15 mL), and the resulting suspension was stirred at room temperature for 6 hours. Analysis by LC/MS showed that the reaction was incomplete, so concentrated HCl (1 mL) was added, followed by methylene chloride (20 mL) to dissolve the solids, and the reaction was stirred overnight at room temperature. The mixture was concentrated in-vacuo, then stripped from methanol (3×50 mL) to remove any excess HCl. The resulting solids were used as-is in the next step. MS (ES+)=222 (M+H)+.

Preparation D4, Step 4 (Synthesis of 6-Trifluoromethoxyquinazolin-4-ol): A mixture of 2-amino-5-trifluoromethoxybenzoic acid, HCl salt (1.52 g, 5.91 mMol), and formamidine acetate (1.84 g, 17.73 mMol) in 2-ethoxyethanol (20 mL) was heated at reflux for 2 hours. Analysis by LC/MS showed that the reaction was complete, so the mixture was concentrated in-vacuo, and the residue was purified over silica gel, eluting with 50% ethyl acetate/heptane–100% ethyl acetate, to yield 1.1 g of white solids as product. MS (ES+)=231 (M+H)+. Yield=82%.

Preparation D4, Step 5: A suspension of 6-(trifluoromethoxy)quinazolin-4-ol (515 mg, 2.23 mmol) in phosphorous oxychloride (1.9 mL) was treated with triethylamine (3 mL, 21.1 mmol), and the mixture was heated at reflux for 2 h. The resulting solution was cooled to room temperature, and stripped 3× from methylene chloride to remove residual phosphorous oxychloride. The residue was dissolved in 100 mL methylene chloride, 100 mL saturated sodium bicarbonate was carefully added, causing vigorous gas evolution, and the mixture was stirred for 10 min, until gas evolution had ceased. The layers were separated, and the organic phase was washed with saturated sodium bicarbonate (2×30 mL), followed by brine, dried over sodium sulfate, and concentrated in-vacuo. The residue was purified over silica gel, eluting with 40% EtOAc/heptane, to yield 377 mg of 4-chloro-6-(trifluoromethoxy)quinazoline as a colorless oil. $^1$H NMR (400 MHz, CDCl$_3$) δ ppm 9.10 (s, 1H), 8.16 (d, J=9.23 Hz, 1H), 8.10 (s, 1H), 7.83 (dd, J=9.23, 2.20 Hz, 1H). MS (ES+)=249 (M+H)$^+$.

Preparation D5

Synthesis of
2-tert-Butyl-8-chloro-pyrimido[5,4-d]pyrimidine

Preparation D5, Step 1 (Synthesis of 5-Bromo-2-tert-butyl-pyrimidine-4-carboxylic acid methyl ester): A 2.0 M hexanes solution of trimethylsilyldiazomethane (11.8 mL, 23.62 mMol) was added dropwise to a stirring solution of 5-bromo-2-tert-butyl-pyrimidine-4-carboxylic acid (6.12 g, 23.62 mMol) in 9:1 benzene/methanol (100 mL), and the reaction was stirred for 2 days. TLC analysis showed that the reaction was complete, so the mixture was concentrated in-vacuo. The residue was dissolved in ethyl acetate (100 mL), washed with water (3×20 mL), dried over sodium sulfate, then concentrated in-vacuo. Purified over silica gel, eluting with 10% ethyl acetate/hexanes, to yield 5.2 g of a colorless oil as product. MS (ES+)=273, 275 (M+H)$^+$. Yield=81%.

Preparation D5, Step 2 (Synthesis of 5-tert-Butoxycarbonylamino-2-tert-butyl-pyrimidine-4-carboxylic acid methyl ester): A flame dried reaction tube charged with tert-butylcarbamate (140 mg, 1.2 mMol), cesium carbonate (456 mg, 1.4 mMol), 4,5-bis(diphenylphosphino)-9,9-dimethylxanthane (18 mg, 0.03 mMol), and tris(dibenzylidineacetone)dipalladium(0) (19 mg, 0.02 mMol) was evacuated under vacuum, then backfilled with argon. Dioxane (2 mL) and 5-bromo-2-tert-butyl-pyrimidine-4-carboxylic acid methyl ester (273 mg, 1.0 mMol) were added, and the mixture was degassed under vacuum. The tube was then backfilled with argon, sealed, and heated at 100° C. for 2 hours. Analysis by LC/MS showed complete consumption of starting bromide. The mixture was diluted with methylene chloride (20 mL), filtered to remove solids, and concentrated in-vacuo. The residue was purified over silica gel, eluting with 10% ethyl acetate/heptane, to yield 152 mg of white solids as product. MS (ES+)=310 (M+H)$^+$. Yield=50%.

Preparation D5, Step 3 (Synthesis of 5-Amino-2-tert-butyl-pyrimidine-4-carboxylic acid methyl ester, HCl salt): 5-tert-Butoxycarbonylamino-2-tert-butyl-pyrimidine-4-carboxylic acid methyl ester (2.4 g, 7.75 mMol) was dissolved in a 4 M solution of HCl in dioxane (30 mL). After 10 minutes of stirring, a thick white solid precipitated. The reaction was allowed to stir overnight, during which time the mixture became a homogenous, amber solution. Concentrated in-vacuo, and the residue was stripped from toluene (2×50 mL) followed by methylene chloride (3×50 mL) to remove excess HCl. The resulting 1.85 g of yellow solids was used without further purification in the next step. MS (ES+)=210 (M+H)$^+$.

Preparation D5, Step 4 (Synthesis of 6-tert-Butyl-pyrimido[5,4-d]pyrimidin-4-ol): A mixture of 5-amino-2-tert-butyl-pyrimidine-4-carboxylic acid methyl ester, HCl salt (1.1 g, 4.48 mMol) and formamidine acetate (1.86 g, 17.90 mMol) in 2-ethoxyethanol (20 mL) was heated at reflux for 5 hours. LC/MS analysis showed the reaction to be essentially complete, so the mixture was cooled to room temperature, then concentrated in-vacuo. The residue was purified over silica gel, eluting with ethyl acetate, 1% methanol/ethyl acetate, then 2% methanol/ethyl acetate to yield 1.06 g of a beige solid as product. MS (ES+)=205 (M+H)$^+$. Yield=94%.

Preparation D5, Step 5 (Synthesis of 2-tert-Butyl-8-chloro-pyrimido[5,4-d]pyrimidine): 6-tert-Butyl-pyrimido[5,4-d]pyrimidin-4-ol (210 mg, 1.03 mMol) was dissolved in phosphorous oxychloride (10 mL), and the mixture was heated at reflux for 4 hours. The solution was concentrated in-vacuo, then stripped from methylene chloride (3×50 mL) to remove excess phosphorous oxychloride. The residue was stirred for 10 minutes in saturated sodium bicarbonate (50 mL), then extracted with ethyl acetate (3×30 mL). The combined organic phases were washed with water (30 mL), followed by brine (30 mL), dried over sodium sulfate, then concentrated in-vacuo. The residue was purified over silica gel, eluting with 50% ethyl acetate/heptane, to yield 150 mg of a white solid as product. NMR (500 MHz, CDCl3) δ 9.61 (s, 1H), 9.15 (S, 1H), 1.52 (s, 9H).

Preparation D6

Synthesis of
4-chloro-6-(2-methoxyphenyl)quinazoline

Preparation D6, Step 1: A suspension of 2-amino-5-bromobenzoic acid (2.00 g, 9.26 mmol) and formamidine acetate (3.86 g, 37.0 mmol) in 2-ethoxyethanol (20 mL) was heated at reflux for 2 hours, during which time, a clear solution was observed. The reaction was allowed to cool to room temperature, during which time solids precipitated. The precipitate was collected by filtration and rinsed with diethyl ether, to yield material which contained desired product, but was not pure by NMR analysis. The solids were partitioned between ethyl acetate and water, a small amount of material which did not dissolve was removed by filtration, and the layers were separated. The organic phase was washed twice with water, dried over sodium sulfate, and concentrated in-vacuo to yield 690 mg of 6-bromoquinazolin-4-ol as a tan solid. The initial organic filtrate was concentrated to give solids which were stirred in diethyl ether, collected by filtration, and air dried to yield 430 mg of 6-bromoquinazolin-4-ol as a tan solid. MS (ES+)=225/227 (M+H+).

Preparation D6, Step 2: A mixture of 6-bromoquinazolin-4-ol (227 mg, 1.01 mmol), 2-methoxyphenylboronic acid (307 mg, 2.02 mmol), 2.0 M potassium phosphate (aq) (1.5 mL, 3.0 mmol), and DMF (3 mL) in a 5 mL microwave tube was degassed under vacuum/Ar. A catalytic amount of tetrakis(triphenylphosphine)$_p$alladium(0) was added to the tube, the mixture was degassed again, the tube was sealed, and the reaction was heated at 150° C. in the microwave for 30 min. The resulting black mixture was filtered, then concentrated in-vacuo. The residue was taken up in 9:1 ethyl acetate/heptane (50 mL), washed with water (3×20 mL), then brine, then dried over sodium sulfate and concentrated in-vacuo. The residue was purified over silica gel, eluting with 1:1 ethyl acetate/heptane, 100% ethyl acetate, then 9:1 ethyl acetate/methanol, to yield 250 mg of 6-(2-methoxyphenyl)quinazolin-4-ol as a white powder. MS (ES+)=253 (M+H+).

Preparation D6, Step 3. A suspension of 6-(2-methoxyphenyl)quinazolin-4-ol (250 mg, 0.99 mmol) in POCl$_3$ (10 mL) was heated at reflux for 1 h, during which time a clear solution was observed. The mixture was cooled to room temperature, concentrated in-vacuo, then concentrated from methylene chloride (3×100 mL) to remove any remaining POCl$_3$. The residue was partitioned between ethyl acetate (25 mL) and saturated NaHCO$_3$ (30 mL), and the mixture was stirred until gas evolution ceased (10 min). The layers were separated, the organic phase was washed with saturated NaHCO$_3$, water, and brine, dried over sodium sulfate, and concentrated in-vacuo. The residue was purified over silica gel, eluting with 1:3 ethyl acetate/heptane, to yield 217 mg of 4-chloro-6-(2-methoxyphenyl)quinazoline as a white solid. $^1$H NMR (500 MHz, CDCl$_3$) δ ppm 9.03 (s, 1H), 8.36 (s, 1H), 8.19 (d, J=7.15 Hz, 1H), 8.10 (d, J=8.80 Hz, 1H), 7.42 (m, 2H), 7.10 (t, J=7.42 Hz, 1H), 7.04 (d, J=8.25 Hz, 1H), 3.86 (m, 3H).

Preparation D7

Synthesis of 3-(4-chloroquinazolin-6-yl)benzonitrile

The procedure described in Preparation D6 was followed, substituting 3-cyanobenzeneboronic acid for 2-methoxyphenylboronic acid in Preparation D6, step 2. MS (ES+)=266/268 (M+H+).

Preparation E1

4-tert-butylthiazole-2-carboxylic acid

A solution of ethyl thiooxamate (0.75 g, 5.6 mol) and 1-bromopinacolone (1.0 g, 5.6 mol) in ethanol was heated to reflux for 2 h. The solvent was removed in vacuo and the residue dissolved in $CH_2Cl_2$ and washed with water and brine, concentrated and the residue chromatographed on silica gel (10% Ethyl acetate/hexane) to give 0.8 g of ethyl 4-tert-butylthiazole-2-carboxylate as an oil. The ester was dissolved in methanol (5 ml) and treated with 1N NaOH (30 ml) and stirred overnight at room temperature. The solution was acidified with 1N HCl and extracted into $CH_2Cl_2$ and washed with water. The solvent was removed under vacuum to give 0.55 g of 4-tert-butylthiazole-2-carboxylic acid as a off-white solid. MS found: $(M+H)^+$=186.24

Preparation E2

4-(perfluoroethyl)thiazole-2-carboxylic acid

This was synthesized using the procedure described for Preparation E1. MS found: $(M+H)^+$=248

Preparation E3

4-(3-(trifluoromethyl)phenyl)thiazole-2-carboxylic acid

This was synthesized using the procedure described for Preparation E1. MS found: $(M+H)^+$=274.3

Preparation E4

4-phenylthiazole-2-carboxylic acid

This was synthesized using the procedure described for Preparation E1. MS found: $(M+H)^+$=206.17

Preparation E5

4-(4-chlorophenyl)thiazole-2-carboxylic acid

This was synthesized using the procedure described for Preparation E1. MS found: $(M+H)^+$=240.14

Preparation E6

4-(benzo[d]thiazol-2-yl)thiazole-2-carboxylic acid

This was synthesized using the procedure described for Preparation E1. MS found: $(M+H)^+$=263.13

Preparation E7

4-(1-adamantyl)thiazole-2-carboxylic acid

This was synthesized using the procedure described for Preparation E1. MS found: $(M-H)^-$=262.25

Preparation E8

4-(pyridin-2-yl)thiazole-2-carboxylic acid

This was synthesized using the procedure described for Preparation E1. MS found: $(M+H)^+$=207.22

Preparation E9

4-(thiophen-2-yl)thiazole-2-carboxylic acid

This was synthesized using the procedure described for Preparation E1. MS found: $(M+H)^+$=212.05

Preparation E10

4-(thiophen-3-yl)thiazole-2-carboxylic acid

This was synthesized using the procedure described for Preparation E1. MS found: $(M+H)^+$=212.05

Preparation F1

4-phenylfuran-2-carboxylic acid

Preparation F1, Step 1: Synthesis of 4-bromofuran-2-carboxylic acid: Commercially available 4,5-dibromofuran-2-carboxylic acid (6.1 g, 22.6 mol) was suspended in 100 ml of ammonium hydroxide and treated portion-wise with zinc dust (1.48 g, 22.6 mol) and stirred at room temperature for a few minutes. The reaction was filtered and the filtrate acidified with 5N HCl and extracted several times with methylene chloride. The extract was washed with brine and concentrated to give 2.93 g of a white solid consisting mainly of 4-bromofuran-2-carboxylic acid. MS $(ES^-)$found: $(M-H)^-$=190.95 and 188.95. NMR (500 MHz, DMSO-D6) δ 13.3 (bs, 1H), 8.14 (s, 1H), 7.36 (s, 1H). Product was contaminated with 25% furan-2-carboxylic acid by-product. NMR (500 MHz, DMSO-D6) δ 13.3 (bs, 1H), 7.90 (m, 1H), 7.19 (m, 1H), 6.64 (m, 1H).

Preparation F1, Step 2: Synthesis of 4-phenylfuran-2-carboxylic acid: A solution of 4-bromofuran-2-carboxylic acid (380 mg, 2 mmol), phenylboronic acid (488 mg, 4 mmol) in DMF (3 ml) was place in a microwave reaction tube and treated with a 2 M $K_3PO_4$ (aq) (2 ml, 4 mmol). The solution was purged with nitrogen for 10 minutes before adding Pd(PPh3)4 (1.5 mg) catalyst. The mixture was again purged with nitrogen for 5 minutes before the reaction tube was sealed. The mixture was heated in a microwave oven at 150° C. for 30 minutes. The reaction mixture was filtered and the filtrate poured into 1N HCl (100 ml) with stirring. The precipitate was filtered and air-dried to give 190 mg of 4-phenylfuran-2-carboxylic acid. MS $(ES^-)$ found: $(M-H)^-$=187.07.

Preparation F2

4-(4-methoxyphenyl)furan-2-carboxylic acid

This was synthesized using the procedure described for Preparation F1. MS $(ES^-)$ found: $(M-H)^-$=217.12

Preparation F3

4-(4-(trifluoromethyl)phenyl)furan-2-carboxylic acid

This was synthesized using the procedure described for Preparation F1. MS $(ES^-)$ found: $(M-H)^-$=255.14

Preparation G1

Synthesis of 5-phenylfuran-2-carboxylic acid.

A solution of 5-bromofuran-2-carboxylic acid (381 mg, 2 mmol), phenylboronic acid (488 mg, 4 mmol) in DMF (3 ml) was place in a microwave reaction tube and treated with a 2 M $K_3PO_4$ (aq) (2 ml, 4 mmol). The solution was purged with nitrogen for 10 minutes before adding $Pd(PPh_3)_4$ (1.5 mg) catalyst. The mixture was again purged with nitrogen for 5 minutes before the reaction tube was sealed. The mixture was heated in a microwave oven at 150° C. for 30 minutes. The reaction mixture was filtered and the filtrate poured into 1N HCl (100 ml) with stirring. The precipitate was filtered and air-dried to give 209 mg of 5-phenylfuran-2-carboxylic acid. MS ($ES^-$) found: $(M-H)^-=187.13$.

Preparation G2

Synthesis of 5-(4-(trifluoromethyl)phenyl)furan-2-carboxylic acid

This was synthesized using the procedure described for Preparation G1. MS ($ES^-$) found: $(M-H)^-=255.11$

Preparation G3

Synthesis of 5-(4-fluorophenyl)furan-2-carboxylic acid

This was synthesized using the procedure described for Preparation G1. MS ($ES^-$) found: $(M-H)^-=205.10$

Preparation G4

Synthesis of 5-(3-fluorophenyl)furan-2-carboxylic acid

This was synthesized using the procedure described for Preparation G1. MS ($ES^-$) found: $(M-H)^-=205.10$

Preparation G5

Synthesis of 5-(3,4-difluorophenyl)furan-2-carboxylic acid

This was synthesized using the procedure described for Preparation G1. MS ($ES^-$) found: $(M-H)^-=223.09$

Preparation G6

Synthesis of 5-(4-isopropylphenyl)furan-2-carboxylic acid

This was synthesized using the procedure described for Preparation G1. MS ($ES^-$) found: $(M-H)^-=229.15$

Preparation G7

Synthesis of 5-(3-methoxyphenyl)furan-2-carboxylic acid

This was synthesized using the procedure described for Preparation G1. MS ($ES^-$) found: $(M-H)^-=217.13$

Preparation G8

Synthesis of 5-(3-cyanophenyl)furan-2-carboxylic acid

This was synthesized using the procedure described for Preparation G1. MS ($ES^-$) found: $(M-H)^-=212.12$

Preparation G9

Synthesis of 5-(4-cyanophenyl)furan-2-carboxylic acid

This was synthesized using the procedure described for Preparation G1. MS ($ES^-$) found: $(M-H)^-=212.12$

Preparation H1

Synthesis of lithium 2-phenylisonicotinate, N-oxide

Preparation H1, Step 1: A mixture of 2-bromo-4-pyridinecarboxylic acid (1.1 g, 5.45 mmol), phenylboronic acid (1.3 g, 10.9 mmol), 2.0 M potassium phosphate (aq) (8.2 mL, 16.34 mmol), and DMF (10 mL) in a 20 mL microwave tube was degassed under vacuum/Ar. A catalytic amount of tetrakis(triphenylphosphine)palladium(0) was added to the tube, the mixture was degassed again, the tube was sealed, and the reaction was heated at 150° C. in the microwave for 30 min. The reaction mixture was filtered, the filtrate was concentrated in-vacuo, and the residue was dissolved in water (10 mL). The mixture was acidified to pH=6 with the addition of 1.0 N HCl, and the resulting precipitate was collected by filtration, rinsed with two portions of ice-cold water, and air dried to yield 575 mg of 2-phenylisonicotinic acid as an off-white solid. MS (ES+)=200 (M+H+).

Preparation H1, Step 2: A solution of 2-phenylisonicotinic acid (459 mg, 2.30 mmol) in 9:1 benzene/methanol (20 mL) was cooled to 0° C., and treated with the dropwise addition of a 2.0 M hexane solution of (trimethylsilyl)diazomethane (1.15 mL, 2.30 mmol). The mixture was allowed to come to room temperature and stirred for 6 h. Analysis by TLC indicated incomplete reaction, so the mixture was treated with additional (trimethylsilyl)diazomethane solution (230 µL, 0.23 mmol), and the reaction was stirred for an additional 2 h. TLC of the mixture remained unchanged. The solvent was stripped, and the residue was partitioned between ethyl acetate and saturated sodium bicarbonate. The layers were separated, the organic phase was washed 2× with saturated sodium bicarbonate, the combined aqueous phases were extracted with ethyl acetate, and the combined organic phases were washed with brine, dried over sodium sulfate, and concentrated in vacuo. The residue was purified over silica gel, eluting with 20% ethyl acetate/heptane, to yield 372 mg of methyl 2-phenylisonicotinate as a colorless oil. $^1$H NMR (400 MHz, $CDCl_3$) δ ppm 8.83 (d, J=5.27 Hz, 1H), 8.29 (s, 1H), 8.04 (d, J=7.03 Hz, 2H), 7.77 (d, J=3.52 Hz, 1H), 7.51-7.42 (m, 3H), 3.98 (s, 3H).

Preparation H1, Step 3: Methyl 2-phenylisonicotinate, N-oxide was prepared via the method of Sharpless, et. al., (J. Org. Chem. 1998, 63, 1740.). A solution of methyl 2-phenylisonicotinate (370 mg, 1.73 mmol) and methyltrioxorhenium (VII) (3 mg, 0.01 mmol) in methylene chloride (2 mL) was treated with 30% aqueous hydrogen peroxide (347 µL, 3.47 mmol), causing the colorless solution to turn yellow, and the mixture was stirred overnight. Analysis by LCMS indicated a 8:2 mixture of desired product to starting material, so additional methyltrioxorhenium(VII) (30 mg, 0.1 mmol) was added, and the mixture was allowed to stir for 6 h. A catalytic amount of manganese dioxide was added, and the mixture was stirred until gas evolution ceased (30 min). The mixture was diluted with methylene chloride (20 mL), the layers were separated, the aqueous was extracted with methylene chloride (5 mL), and the combined organic phases were dried over sodium sulfate, then concentrated in vacuo to 397 mg of a colorless glass. Analysis by LCMS indicates a ratio of 95:5 methyl 2-phenylisonicotinate, N-oxide/methyl 2-phenylisonicotinate. This material was used as-is in the next step. MS (ES+)=230 (M+H+).

Preparation H1, Step 4: A solution of methyl 2-phenylisonicotinate, N-oxide (397 mg, 1.73 mmol) in THF (6 mL) was treated with 0.5 N aqueous lithium hydroxide (3.65 mL, 1.81 mmol), and the mixture was stirred overnight. The THF was stripped, and the aqueous solution was freeze dried to yield lithium 2-phenylisonicotinate, N-oxide a colorless glass, which was used as-is in the next step.

Preparation H2

Synthesis of 5-phenylnicotinic acid

Preparation H2, Step 1: 5-bromonicotinic acid (500 mg, 2.48 mmol, 1 eq.), phenylboronic acid (454 mg, 3.71 mmol, 1.5 eq.), tetrakis(triphenylphosphine)palladium(0) (143 mg, 0.124 mmol, 0.05 eq.), and sodium carbonate (787 mg, 7.43 mmol, 3 eq.) were mixed in ethanol (5 mL), toluene (25 mL), and water (5 mL) at room temperature under nitrogen. The reaction was then refluxed for 20 hours. Worked up by adding water then stripping off the ethanol. Rinsed the aqueous layer 2 times with diethyl ether. Adjusted the aqueous layer pH=3 with conc. HCl. The acidic aqueous layer was extracted 3 times with ethyl acetate and a little THF. The ethyl acetate/THF layers were combined, dried over sodium sulfate and stripped to give 5-phenylnicotinic acid (332 mg) as a white solid. Yield=67%. LCMS detects (M+H)$^+$=198.1.

Preparation H3

Synthesis of 3'-trifluoromethylsulfonamido-[1,1'-biphenyl]-3-carboxylic acid

Preparation H3, Step 1: Ethyl 3-iodobenzoate (0.92 g, 3.34 mmol, 1 eq.), phenylboronic acid (0.87 g, 5.02 mmol, 1.5 eq.), palladium(II)acetate (37 mg, 0.167 mmol, 0.05 eq.) and sodium carbonate (706 mg, 6.66 mmol, 2 eq.) were dissolved in DMF (20 mL) at room temperature under nitrogen. The reaction was then heated at 80° C. for 1.5 hours. Worked up by adding ethyl acetate and rinsing 4 times with water. The organic layer was dried over sodium sulfate and stripped to give a dark oil. Purified over silica gel in 9:1 to 1:1 hexanes/ethyl acetate to obtain 3'-Amino-[1,1'-biphenyl]-3-carboxylic acid, ethyl ester (420 mg) as an oil. Yield=55%. LCMS detects (M+H)$^+$=242.41.

Preparation H3, Step 2: Ethyl-3-(3-aminophenyl)benzoate (100 mg, 0.44 mmol, 1 eq.) was dissolved in methylene chloride (10 mL) at room temperature and potassium carbonate (91 mg, 0.66 mmol, 1.5 eq.) was added. Cooled to −70° C. then added triflic anhydride (74 uL, 0.44 mmol, 1 eq.) dropwise via an addition funnel. After 1 hour, added 0.2 eq more of each of the above reagents. After 1 hour, the reaction was stripped to give 3'-trifluoromethylsulfonamido-[1,1'-biphenyl]-3-carboxylic acid, ethyl ester (150 mg) as an oil. Yield=91%. Mass Spec (ESI) detects (M+H)$^+$=372.1.

Preparation H3, Step 3: 3'-Trifluoromethylsulfonamido-[1,1'-biphenyl]-3-carboxylic acid, ethyl ester (150 mg, 0.40 mmol, 1 eq.) and 1.000 N NaOH (0.80 mL, 0.80 mmol, 2 eq.) were dissolved in THF (5 mL) at room temperature and stirred for 20 hours. Little reaction. Added 100 mg of NaOH and heated at 50° C. for 20 hours. Worked up by adding water then rinsing 2 times with diethyl ether. The aqueous layer's pH was adjusted to 3 with 1N HCl. The acidic aqueous layer was extracted 3 times with ethyl acetate. The ethyl acetate layers were combined, dried over sodium sulfate and stripped to give 3'-trifluoromethylsulfonamido-[1,1'-biphenyl]-3-carboxylic acid (90 mg) of an amber solid. Yield=65%. Mass Spec (ESI) detects (M+H)$^+$=344.0.

Preparation H4

Synthesis of 3-phenyl-4-hydroxybenzoic acid

Preparation H4, Step 1: 3-bromo-4-hydroxybenzoic acid (500 mg, 2.30 mmol, 1 eq.), phenylboronic acid (281 mg, 2.30 mmol, 1 eq.), palladium(II)acetate (16 mg, 0.069 mmol, 0.03 eq.) and 1.5M cesium carbonate (aqueous) (4.61 mL) were dissolved in DMF (10 mL) at room temperature under nitrogen then heated at 45° C. for 20 hours. Worked up by adding water (10 mL) then adjusting to pH=3 with 1N HCl. Extracted the acidic aqueous 3 times with ethyl acetate. The ethyl acetate layers were combined and rinsed 3 times with water (10 mL). The ethyl acetate layer was then dried over sodium sulfate and stripped to an oil. The oil was purified over silica gel in 1:1 hexanes/ethyl acetate. Obtained 3-phenyl-4-hydroxybenzoic acid (330 mg) as an oil which eventually solidified. Yield=67%. LCMS detects (M+H)$^+$=257.23.

Preparation H5

Synthesis of 2-Phenylpyrazine-6-carboxylic acid

Preparation H5, Step 1: 2-Phenylpyrazine-6-carboxylic acid was synthesized by the method of E. Felder, D. Pitre, S. Boveri and E. B. Grabitz, Chem. Ber. 100 (1967) 555-559. LCMS detects (M+H)$^+$=201.29.

Preparation H6

Synthesis of 3-tert-butyl-5-(2H-tetrazol-5-yl)benzoic acid

Preparation H6, Step 1: To a solution of dimethyl 5-tert-butylisophthalate (2.5 g, 10 mmol) in 20 mL of THF cooled to 0° C. was added dropwise a solution of lithium hydroxide monohydrate (168 mg, 7 mmol) in 5.0 mL of water. The reaction mixture was stirred at RT for 3 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 700 mg of 3-tert-butyl-5-(methoxycarbonyl)benzoic acid. MS found: (M+H)$^+$=237.

Preparation H6, Step 2: To a soultion of 3-tert-butyl-5-(methoxycarbonyl)benzoic acid (700 mg) in DMF (15 mL) at rt was added HATU (1.2 eq), 3-aminopropanenitrile (1.2 eq), and iPr$_2$NEt (1.2 eq). The mixture was stirred at rt for 16 h before water and EtOAc were added. The organic layer was separated and re-washed twice before it was collected, dried over Na$_2$SO$_4$, and concentrated to provide methyl 3-tert-butyl-5-((2-cyanoethyl)carbamoyl)benzoate as a glassy solid (520 mg). MS found: (M+H)$^+$=289.

Preparation H6, Step 3: To a soultion of 3-tert-butyl-5-((2-cyanoethyl)carbamoyl)benzoat (520 mg, 1.8 mmol) in MeCN (15 mL) at 0° C. was added NaN$_3$ (117 mg, 1.8 mmol), and Tf$_2$O (0.3 mL, 1.8 mmol). The mixture was stirred at rt for 16 h before aq NaHCO$_3$ and EtOAc were added. The organic layer was separated and re-washed twice before it was collected, dried over Na$_2$SO$_4$, and concentrated to methyl 3-tert-butyl-5-(2-(2-cyanoethyl)-2H-tetrazol-5-yl)benzoate as an oil (450 mg, 80% yield). MS found: (M+H)$^+$=314.

Preparation H6, Step 4: To a solution of methyl 3-tert-butyl-5-(2-(2-cyanoethyl)-2H-tetrazol-5-yl)benzoate (500 mg) in 20 mL of THF cooled to 0° C. was added dropwise a solution of lithium hydroxide monohydrate (76 mg) in 5.0 mL of water. The reaction mixture was stirred at RT for 16 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 3-tert-butyl-5-(2H-tetrazol-5-yl)benzoic acid. MS found: (M+H)$^+$=247.

Preparation H7

Synthesis of 3-(1H-tetrazol-5-yl)benzoic acid

Preparation H7, Step 1: To a soultion of 3-(methoxycarbonyl)benzoic acid (800 mg, 4.4 mmol) in DMF (15 mL) at rt was added HATU (2g, 5.3 mmol), 3-aminopropanenitrile (0.33 mL, 4.4 mmol), and iPr$_2$NEt (0.92 mL, 5.3 mmol). The mixture was stirred at rt for 16 h before water and EtOAc were added. The organic layer was separated and re-washed twice before it was collected, dried over Na$_2$SO$_4$, and concentrated to provide methyl 3-((2-cyanoethyl)carbamoyl)benzoate as a glassy solid (900 mg). MS found: (M+H)$^+$=233.

Preparation H7, Step 2: To a soultion of methyl 3-((2-cyanoethyl)carbamoyl)benzoate (400 mg, 1.7 mmol) in MeCN (15 mL) at 0° C. was added NaN$_3$ (111 mg, 1.7 mmol), and Tf$_2$O (0.3 mL, 1.7 mmol). The mixture was stirred at rt for 16 h before aq NaHCO$_3$ and EtOAc were added. The organic layer was separated and re-washed twice before it was collected, dried over Na$_2$SO$_4$, and concentrated to methyl 3-(1-(2-cyanoethyl)-1H-tetrazol-5-yl)benzoate as an oil (180 mg, 41% yield). MS found: (M+H)$^+$=258.

Preparation H7, Step 3: To a solution of methyl 3-(1-(2-cyanoethyl)-1H-tetrazol-5-yl)benzoate (180 mg, 0.7 mmol) in 20 mL of THF cooled to 0° C. was added dropwise a solution of lithium hydroxide monohydrate (50 mg, 2.1 mmol) in 5.0 mL of water. The reaction mixture was stirred at RT for 16 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 100 mg (58% yield) of 3-(1H-tetrazol-5-yl)benzoic acid. MS found: (M+H)$^+$=191.

Preparation H8

Synthesis of 3-(4-methylthiazol-2-yl)benzoic acid

The title compound was synthesized followd by the literature procedures described in *Bioorg. Med. Chem.* 1999, 8, 7, 1559-1566. MS found: (M+H)$^+$=220.

Preparation H9

Synthesis of 6-phenylpicolinic acid

Preparation H9, Step 1: 6-Bromopicolinic acid (1.0 g) was dissolved in 1,2-dimethoxyethane (15 mL) prior to the addition of palladium tetrakistriphenylphoshine (572 mg), 2M Na$_2$CO$_3$ (5 mL), and phenyl boronic acid (905 mg). The resulting solution was heated at reflux for 48 h. After cooling, 1N HCL was added to adjust the pH<4. A white precipitate was formed and was removed by filtration. A small portion of the filtrate was purified by reverse phase HPLC (gradient elution, water/acetonitrile/TFA) to afford 6-phenylpicolinic acid (25 mg). MS found: (M+H)$^+$=200.1.

Preparation H10

Synthesis of 5-phenylnicotinic acid N-oxide

Preparation H10, Step 1: 5-Phenylnicotinic acid (50 mg) was dissolved in dichloroethane (2 ml) prior to the addition of 77% mCPBA (250 mg). The reaction was stirred for 15 h and then it was concentrated, filtered, and purified by reverse phase HPLC (gradient elution, water/acetonitrile/TFA) to afford 5-phenylnicotinic acid N-oxide (20 mg). MS found: (M+H)$^+$=216.1.

Preparation H11

Synthesis of 3-(thiazol-2-yl)benzoic acid

Preparation H11, Step 1: 10 g (0.068 mol) of 3-cyano benzoic acid was taken in 150 ml of dry dichloromethane and cooled to 0° C. Added 50 ml of oxalyl chloride drop wise followed by 5 drops of dry DMF. The reaction mixture was stirred at RT overnight. Dichloromethane was removed and dry methanol (50 ml) was added and stirred at rt for 2 h. Excess methanol was removed and the residue was dissolved in ethyl acetate. The ethyl acetate layer was washed with 10% of sodium bicarbonate, brine and concentrated to give methyl 3-cyanobenzoate (7 g) as a white solid.

Preparation H11, Step 2: A solution of 2 g (0.01 mol) of methyl-3-cyanobenzoate in 32 ml of THF and 8 ml of water was charged with 2.3 g (0.012 mol) of diethyl dithiophosphate and heated at 80° C. for 24 h. THF was removed and the residue was taken in ethyl acetate. The extract was washed with water and concentrated to afford methyl 3-carbamothioylbenzoate (2.0 g) as a pale yellow solid.

Preparation H11, Step 3: A solution of 0.6 g (0.003 mol) of methyl 3-carbamothioylbenzoate in 6 ml of acetic acid was charged with 1.15 g (0.009 mol) of chloroacetaldehyde dimethyl acetal and a catalytic amount of PTSA. The RM was heated to 100° C. over night. Acetic acid was removed under vacuum and the crude product was purified by 60-120 silica gel column using 5% of ethyl acetate in pet ether as eluent to provide methyl 3-(thiazol-2-yl)benzoate (0.5 g) as a white solid.

Preparation H11, Step 4: A solution of 0.6 g (0.0027 mol) of methyl 3-(thiazol-2-yl)benzoate in 6 ml of THF and 1.2 ml of water was charged with 0.11 g (0.0046 mol) of lithium hydroxide. The reaction mixture was stirred at RT overnight. THF was removed and the aqueous layer was washed with ether and acidified with 1.5 N HCl. The solid product was extracted with ethyl acetate. The organic layer was washed with brine and concentrated to afford 3-(thiazol-2-yl)benzoic acid (0.4 g) as an off white solid obtained. $^1$H NMR (400

MHz, CDCl$_3$): 7.45 (d, 1H), 7.63 (m, 1H), 8.0 (d, 1H), 8.22 (d, 1H), 8.30 (d, 1H), 8.79 (s, 1H). MS found: (M–H)$^-$=204.

Examples 1a-1j

Example 1a

Synthesis of cis- and trans-(3S)-1-(4-(tert-butylamino)cyclohexyl)-3-(6-(trifluoromethyl)quinazolin-4-ylamino)pyrrolidin-2-one Example 1a, Step 1: 1,4-cyclohexanedione ethylene ketal (5.00 g, 32.0 mmol, 1 eq.), sodium triacetoxyborohydride (8.14 g, 38.4 mmol, 1.2 eq.) and benzylamine (3.50 mL, 32.0 mmol, 1 eq.) were mixed in methylene chloride (100 mL) at room temperature. Stirred for 20 hours. Added 50 mL of 1.0 N NaOH. Stirred for 10 minutes. Extracted 3 times with methylene chloride (50 mL). The organic layers were combined, dried over sodium sulfate and stripped to give N-(phenylmethyl)-1,4-Dioxaspiro[4.5]decan-8-amine (7.91 g) of a light amber oil as product. Yield=100%. LCMS detects (M+H)$^+$=248.26.

Example 1a, Step 2: 20% Palladium hydroxide (1.00 g) was carefully wetted down under nitrogen with methanol (50 mL) then N-(phenylmethyl)-1,4-Dioxaspiro[4.5]decan-8-amine (7.91 g) in methanol (50 mL) was added. The mixture was hydrogenated on a Parr shaker for 20 hours. Worked up by filtering off the catalyst under nitrogen through fiberglass filter paper. The filtrate was stripped to give 1,4-dioxaspiro[4.5]decan-8-amine (6.40 g) as an oily solid. Yield=100%. LCMS detects (M+H)$^+$=158.1.

Example 1a, Step 3: 1,4-Dioxaspiro[4.5]decan-8-amine (5.03 g, 32.0 mmol, 1 eq.), CBZ-L-methionine (10.90, 38.4 mmol, 1.2 eq.), 1-hydroxybenzotriazole hydrate (HOBT) (5.19 g, 38.4 mmol, 1.2 eq.), 1-[3-(dimethylamino)propyl]-3-ethylcarbodiimide HCl (EDCI) (7.36 g, 38.4 mmol, 1.2 eq.), triethylamine (8.92 mL, 64.0 mmol, 2 eq.) and methylene chloride (150 mL) were stirred at room temperature under nitrogen for 72 hours. Worked up by rinsing 3 times with saturated sodium bicarbonate (50 mL). The organic layer was dried over sodium sulfate and stripped to give an amber oil which solidified. The solids were triturated with diethyl ether (100 mL) and stirred overnight. The solids were filtered to give 8-((2S)-2-(benzyloxycarbonylamino)-4-(methylthio)butanamido)-1,4-dioxaspiro[4.5]decane (8.75 g) as a white solid. Yield=64%. Mass Spec (ESI) detects (M+H)$^+$=423.22.

Example 1a, Step 4a: 8-((2S)-2-(benzyloxycarbonylamino)-4-(methylthio)butanamido)-1,4-dioxaspiro[4.5]decane (8.75 g, 20.7 mmol, 1 eq.) was stirred in iodomethane (38.76 mL, 621.0 mmol, 30 eq.) at room temperature under nitrogen for 20 hours. The reaction was stripped 4 times from methylene chloride (50 mL) then 2 times from chloroform (50 mL). Obtained the corresponding sulfonium salt (12.0 g) as a tan amorphous solid. LCMS detects (M+)$^+$=437.06.

This sulfonium salt (11.7 g, 20.7 mmol, 1 eq.) and cesium carbonate (33.7 g, 103.5 mmol, 5 eq.) were stirred in DMF (75 mL) at room temperature under nitrogen for 20 hours. Added ethyl acetate (100 mL) and rinsed the organic layer 4 times with brine (50 mL). The organic layer was dried over sodium sulfate and stripped to give an oil. Purified over silica gel in 3:1 to 1:1 hexanes/ethyl acetate to 100% ethyl acetate. Obtained 8-((3S)-3-(benzyloxycarbonylamino)-2-oxopyrrolidin-1-yl)-1,4-dioxaspiro[4.5]decane (2.70 g) as a tan glass. Yield=35%. LCMS detects (M+)$^+$=375.14.

Example 1a, Step 4b: The sulfonium salt from 1a, Step4a, (1.00 g, 1.77 mmol, 1 eq.) was dissolved in THF at room temperature under nitrogen then 60% sodium hydride (370 mg, 9.30 mmol, 5 eq.) was added in 5 portions. Stirred for 20 hours. Worked up by adding saturated ammonium chloride (20 mL) then extracting 3 times with ethyl acetate. The organic extract were combined, dried over sodium sulfate and stripped to give an oil. Purified over silica gel in 3:1 to 1:1 hexanes/ethyl acetate to 100% ethyl acetate. Obtained 8-((3S)-3-(benzyloxycarbonylamino)-2-oxopyrrolidin-1-yl)-1,4-dioxaspiro[4.5]decane (460 mg) as a near-colorless oil as product. Yield=69%. LCMS detects (M+)$^+$=375.14.

Example 1a, Step 5: 8-((3S)-3-(benzyloxycarbonylamino)-2-oxopyrrolidin-1-yl)-1,4-dioxaspiro[4.5]decane (2.70 g, 7.21 mmol, 1 eq.) and p-toluene sulfonic acid (0.14 g, 0.721 mmol, 0.1 eq.) were dissolved in acetone (20 mL) at room temperature. Refluxed for 4 hours. Reaction was not complete by TLC. Added 1 N HCl (10 mL). Refluxed for 10 minutes. Stripped off the acetone. Added saturated sodium bicarbonate (25 mL). Extracted 3 times with methylene chloride (25 mL). The organic layers were combined, dried over sodium sulfate and stripped to give benzyl (3S)-2-oxo-1-(4-oxocyclohexyl)-pyrrolidin-3-ylcarbamate (2.40 g) as an amber glass. Yield=95%. LCMS detects (M+)$^+$=375.14.

Example 1a, Step 6: Benzyl (3S)-2-oxo-1-(4-oxocyclohexyl)-pyrrolidin-3-ylcarbamate (2.40 g, 7.26 mmol, 1 eq.), tert-butylamine (0.84 mL, 7.99 mmol, 1.1 eq.), and titanium isoproproxide (4.68 mL, 16.0 mmol, 2.2 eq.) were mixed and stirred at room temperature under nitrogen for 20 hours. Worked up by adding methanol (50 mL) and stirred for 1 hour then added sodium borohydride (pellets) (0.27 g, 7.26 mmol, 1 eq.). After 1 hour, added 50 mL of 1.0 N NaOH and stirred. After 20 minutes, extracted 3 times with methylene chloride (50 mL). The organic layers were combined, dried over sodium sulfate and stripped to give an amber oil. Purified over silica gel in 100% ethyl acetate to 4:1 methylene chloride/methanol. Obtained a mixture of cis and trans-isomers of benzyl (3S)-1-(4-(tert-butylamino)cyclohexyl)-2-oxopyrrolidin-3-ylcarbamate (700 mg) as an amber oil. Yield=25%. LCMS detects (M+H)$^+$=388.2.

Example 1a, Step 7: 20% Palladium hydroxide (150 mg) was carefully wetted down under nitrogen with methanol (10 mL) then the mixture of cis and trans-isomers of benzyl (3S)-1-(4-(tert-butylamino)cyclohexyl)-2-oxopyrrolidin-3-ylcarbamate (700 mg) dissolved in methanol were added. The mixture was hydrogenated on a Parr shaker for 20 hours. Worked up by filtering off the catalyst under nitrogen through fiberglass filter paper. The filtrate was stripped to give cis- and trans-(3S)-3-amino-1-(4-(tert-butylamino)-cyclohexyl)pyrrolidin-2-one (450 mg) as an oil. Yield=98%. LCMS detects (M+H)$^+$=254.26.

Example 1a and 1b, Step 8: The mixture of cis and trans-isomers of (3S)-3-amino-1-(4-(tert-butylamino)cyclohexyl) pyrrolidin-2-one (60 mg, 0.237 mmol, 1 eq.), 4-chloro-6-(trifluoromethyl)quinazoline (72 mg, 0.308 mmol, 1.3 eq.), and triethylamine (0.13 mL, 0.947 mmol, 4 eq.) were dissolved in ethanol at room temperature then microwaved at 100° C. for 1 hour. Purified by HPLC. Isolated two fractions: first fraction yielded a 1:1 mixture of cis:trans (3S)-1-(4-(tert-butylamino)cyclohexyl)-3-(6-(trifluoromethyl)quinazolin-4-ylamino)pyrrolidin-2-one, TFA salt (25 mg) as a white solid. LCMS detects (M+H)$^+$=450.17. Second fraction yielded 100% trans-(3S)-1-(4-(tert-butylamino)cyclohexyl)-

3-(6-(trifluoromethyl)quinazolin-4-ylamino)pyrrolidin-2-one, TFA salt (27 mg) as a white solid. LCMS detects (M+H)$^+$=450.17.

Examples 1e and 1f

Synthesis of cis- and trans-(3S)-3-tert-butyl-N-(1-(4-(tert-butylamino)cyclohexyl)-2-oxopyrrolidin-3-yl)-4-hydroxybenzamide Examples 1e and 1f, Step 1: The mixture of cis and trans-isomers of (3S)-3-amino-1-(4-(tert-butylamino)cyclohexyl)pyrrolidin-2-one (60 mg, 0.237 mmol, 1 eq.), tert-butyl-4-hydroxybenzoic acid (55 mg, 0.284 mmol, 1.2 eq.), 1-hydroxybenzotriazole hydrate (HOBT) (38 mg, 0.284 mmol, 1.2 eq.), 1-[3-(dimethylamino)propyl]-3-ethylcarbodiimide HCl (EDCI) (54 mg, 0.284 mmol, 1.2 eq.), triethylamine (66 uL, 0.474 mmol, 2 eq.) and methylene chloride (5 mL) were stirred at room temperature under nitrogen overnight. Purified by HPLC. Isolated two fractions. First fraction yielded a 3:1 mixture of cis- and trans-(3S)-3-tert-butyl-N-(1-(4-(tert-butylamino)-cyclohexyl)-2-oxopyrrolidin-3-yl)-4-hydroxybenzamide, TFA salt (10 mg) as a white solid. LCMS detects (M+H)$^+$=430.23. Second fraction yielded 100% trans-(3S)-3-tert-butyl-N-(1-(4-(tert-butylamino)cyclohexyl)-2-oxopyrrolidin-3-yl)-4-hydroxybenzamide, TFA salt (20 mg) as a white solid. LCMS detects (M+H)$^+$=430.23.

TABLE 1-A

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the (M + H)$^+$ ions in electrospray mass spectroscopy experiments.

| Example | R5 | R2 | Step Altered | MS Data |
|---|---|---|---|---|
| 1a | t-Bu-NH 1:1 mixture of cis & trans | 6-(trifluoromethyl)quinazolin-4-yl | n/a | 450.2 |
| 1b | t-Bu-NH 100% trans | 6-(trifluoromethyl)quinazolin-4-yl | n/a | 450.2 |
| 1c | t-Bu-NH 2:3 mix. Of cis & trans | tert-butyl-pyrrolo[1,2-b]pyridazinyl | 1a, Step 7 | 427.2 |
| 1d | t-Bu-NH 100% trans | tert-butyl-pyrrolo[1,2-b]pyridazinyl | 1a, Step 7 | 427.2 |
| 1e | t-Bu-NH 3:1 mix. Of cis & trans | 3-tert-butyl-4-hydroxybenzoyl | n/a | 430.2 |
| 1f | t-Bu-NH 100% trans | 3-tert-butyl-4-hydroxybenzoyl | n/a | 430.2 |
| 1g | t-Bu-NH 1:1 mix. of cis & trans | 4-tert-butyl-1H-pyrrole-2-carbonyl | 1e, Step 1 | 403.3 |
| 1h | t-Bu-NH 1:1 mix. of cis & trans | 4-tert-butyl-1-methyl-pyrrole-2-carbonyl | 1e, Step 1 | 417.2 |

TABLE 1-A-continued

| | | | | |
|---|---|---|---|---|
| 1i | t-Bu-NH 1:1 mix. of cis & trans | (structure) | 1e, Step 1 | 481.3 |
| 1j | t-Bu-NH 1:1 mix. of cis & trans | (structure) | 1e, Step 1 | 495.2 |

TABLE 1-B

The chemical names of the specific examples illustrated in Table 1-A are tabulated below.

| Example | Name |
|---|---|
| 1a | Cis-(3S)-1-(4-(tert-butylamino)cyclohexyl)-3-(6-(trifluoromethyl)quinazolin-4-ylamino)pyrrolidin-2-one |
| 1b | trans-(3S)-1-(4-(tert-butylamino)cyclohexyl)-3-(6-(trifluoromethyl)quinazolin-4-ylamino)pyrrolidin-2-one |
| 1c | Cis-(3S)-1-(4-(tert-butylamino)cyclohexyl)-3-(6-tert-butylpyrrolo[1,2-f][1,2,4]triazin-4-ylamino)pyrrolidin-2-one |
| 1d | trans-(3S)-1-(4-(tert-butylamino)cyclohexyl)-3-(6-tert-butylpyrrolo[1,2-f][1,2,4]triazin-4-ylamino)pyrrolidin-2-one |
| 1e | cis-(3S)-3-tert-butyl-N-(1-(4-(tert-butylamino)cyclohexyl)-2-oxopyrrolidin-3-yl)-4-hydroxybenzamide |
| 1f | trans-(3S)-3-tert-butyl-N-(1-(4-(tert-butylamino)cyclohexyl)-2-oxopyrrolidin-3-yl)-4-hydroxybenzamide |
| 1g | Cis- and trans-(3S)-4-tert-butyl-N-(1-(4-(tert-butylamino)cyclohexyl)-2-oxopyrrolidin-3-yl)-1H-pyrrole-2-carboxamide |
| 1h | Cis- and trans-(3S)-4-tert-butyl-N-(1-(4-(tert-butylamino)cyclohexyl)-2-oxopyrrolidin-3-yl)-1-methyl-1H-pyrrole-2-carboxamide |
| 1i | cis- and trans-(3S)-4-adamant-1-yl-N-(1-(4-(tert-butylamino)cyclohexyl)-2-oxopyrrolidin-3-yl)-1H-pyrrole-2-carboxamide |
| 1j | cis- and trans-(3S)-4-adamant-1-yl-N-(1-(4-(tert-butylamino)cyclohexyl)-2-oxopyrrolidin-3-yl)-1-methyl-1H-pyrrole-2-carboxamide |

Examples 2a-2bc

Example 2a

Synthesis of N-{(3S)-1-[(1S,2R,4R)-4-(Isopropylmethyl-amino)-2-propyl-cyclohexyl]-2-oxo-pyrrolidin-3-yl}-2-(3-isopropyl-ureido)-5-trifluoromethylbenzamide Example 2a, Step 1: To a cooled (0° C.) solution of (1R,2S,5R)-2-benzyloxycarbonylamino-7-oxo-6-aza-bicyclo[3.2.1]octane-6-carboxylic acid tert-butyl ester (4.6 g, 12.3 mmol) in CH$_2$Cl$_2$ (100 mL) was added DIBAL-H (37 mL of a 1.0 M solution in THF). The mixture was stirred for 105 min at 0° C. The reaction was quenched with 1N HCl and extracted with EtOAc (2×). The organic extracts were combined, washed with brine, dried (Na$_2$SO$_4$), filtered, and concentrated in vacuo to afford tert-butyl (1R,2S,5R,7R/S)-2-(benzyloxycarbonylamino)-7-hydroxy-6-aza-bicyclo[3.2.1]octane-6-carboxylate as a mixture of diastereomers. MS found: (M−H$_2$O+H)$^+$=359.2. This material was dissolved in THF (20 mL) and added by cannula (6 mL THF rinse) to a pre-mixed (15 min), pre-cooled (0° C.) solution of ethyltriphenylphosphonium iodide (6.4 g, 14.8 mmol) and KHMDS (31 mL of a 0.5 M solution in toluene). The reaction was stirred for 25 min at 0° C. before being quenched with the addition of sat. NH$_4$Cl. The biphasic mixture was extracted with EtOAc (2×). The organic extracts were combined, washed with brine, dried (Na$_2$SO$_4$), filtered, and concentrated in vacuo. Purification of the residue via flash chromatography afforded the desired [(1R,3R,4S)-(4-benzyloxycarbonyl-amino-3-propenyl-cyclohexyl)-carbamic acid tert-butyl ester as a colorless oil (3.44 g, 72% yield). MS found: (M+H)$^+$=389.3.

Example 2a, Step 2: A solution of [(1R,3R,4S)-(4-benzyloxycarbonyl-amino-3-propenyl-cyclohexyl)-carbamic acid tert-butyl ester (3.44 g) in MeOH (50 mL) was charged with 5% Pd/C, Degussa (1 g). The reaction flask was evacuated and then back-filled with hydrogen; this was repeated three more times. The reaction was stirred under 1 atm of H$_2$ for 4 h and then filtered and concentrated in vacuo to afford (1R,3R,4S)-(4-amino-3-propyl-cyclohexyl)-carbamic acid tert-butyl ester (quantitative). MS found: (M+H)$^+$=257.3.

Example 2a, Step 3: A sample of (1R,3R,4S)-(4-amino-3-propyl-cyclohexyl)-carbamic acid tert-butyl ester (1.9 mmol) was dissolved in 1:1 CH$_2$Cl$_2$/DMF (40 mL), and the resultant solution was charged with N-Cbz methionine (591 mg, 2.1 mmol), N,N-diethylisopropylamine (1 mL, 5.7 mmol), and BOP (1.0 g, 2.3 mmol). The reaction was stirred for 12 h at RT and then partitioned between EtOAc and sat. NaHCO$_3$; the aqueous phase was back extracted with EtOAc (1×). The organic phases were combined, washed with brine, dried (Na$_2$SO$_4$), filtered, and concentrated in vacuo. The residue was purified by flash chromatography to afford (1R,3R,4S)-[4-((2S)-2-benzyloxycarbonylamino-4-methylsulfanyl-butyrylamino)-3-propyl-cyclohexyl]-carbamic acid tert-butyl ester (375 mg). MS found: (M+H)$^+$=522.3.

Example 2a, Step 4: The compound (1R,3R,4S)-[4-((2S)-2-benzyloxycarbonylamino-4-methylsulfanyl-butyrylamino)-3-propyl-cyclohexyl]-carbamic acid tert-butyl ester (375 mg) was "wetted" with EtOAc, and then the majority of EtOAc was removed under nitrogen stream. The residue was dissolved in iodomethane (6 mL), and the resulting solution was stirred at RT for 48 h before being concentrated in vacuo. The residue was dissolved in methylene chloride, and the resulting solution was concentrated; this was repeated to afford the salt. MS found: (M+H)$^+$=536.3. This material was dissolved in DMF (12 mL) and the solution was charged with Cs$_2$CO$_3$ (470 mg, 1.4 mmol) and stirred for 12 h at RT before being partitioned between EtOAc and brine. The organic phase was dried (Na$_2$SO$_4$), filtered, and concentrated in vacuo. The residue was purified by flash chromatography to afford {(3S)-1-[(1S,2R,4R)-4-tert-butoxycarbonylamino-2-propyl-cyclohexyl]-2-oxo-pyrrolidin-3-yl}-carbamic acid benzyl ester (185 mg). MS found: (M+H)$^+$=474.3.

Example 2a, Step 5: A solution of {(3S)-1-[(1S,2R,4R)-4-tert-butoxycarbonylamino-2-propyl-cyclohexyl]-2-oxo-pyrrolidin-3-yl}-carbamic acid benzyl ester (185 mg, 0.54 mmol) in MeOH (8 mL) was charged with 5% Pd/C, Degussa (180 mg). The reaction flask was evacuated and then backfilled with hydrogen; this was repeated three more times. The reaction was stirred under 1 atm of $H_2$ for 12 h and then filtered and concentrated in vacuo to afford (1R,3R,4S)-{4-[(3S)-3-amino-2-oxo-pyrrolidin-1-yl]-3-propyl-cyclohexyl}-carbamic acid tert-butyl ester. MS found: $(M+H)^+$=340.3.

Example 2a, Step 6: A solution of (1R,3R,4S)-{4-[(3S)-3-amino-2-oxo-pyrrolidin-1-yl]-3-propyl-cyclohexyl}-carbamic acid tert-butyl ester (0.27 mmol assumed) in DMF (4 mL) was charged with 2-(3-isopropyl-ureido)-5-trifluoromethyl-benzoic acid (82 mg, 0.3 mmol), N,N-diethylisopropylamine (0.19 mL, 1.1 mmol), and BOP (142 mg, 0.32 mmol). The reaction was stirred for 48 h at RT and then partitioned between EtOAc and sat. $NaHCO_3$; the aqueous phase was back extracted with EtOAc (1×). The organic phases were combined, washed with brine, dried ($Na_2SO_4$), filtered, and concentrated in vacuo to afford (1R,3R,4S)-(4-{(3S)-3-[2-(3-isopropyl-ureido)-5-trifluoromethyl-benzoylamino]-2-oxo-pyrrolidin-1-yl}-3-propyl-cyclohexyl)-carbamic acid tert-butyl ester. MS found: $(M+H)^+$=612.3.

Example 2a, Step 7: A solution of (1R,3R,4S)-(4-{(3S)-3-[2-(3-isopropyl-ureido)-5-trifluoromethyl-benzoylamino]-2-oxo-pyrrolidin-1-yl}-3-propyl-cyclohexyl)-carbamic acid tert-butyl ester in $CH_2Cl_2$ (6 mL) was treated with trifluoroacetic acid (4 mL) and mixed. After 1 h, the reaction was concentrated in vacuo, and the resultant residue was again dissolved in $CH_2Cl_2$ (6 mL) and again charged with trifluoroacetic acid (4 mL). After 1 h, the reaction was concentrated in vacuo, and the resultant residue was partitioned between EtOAc and sat. $NaHCO_3$. The organic phase was washed with brine, dried ($Na_2SO_4$), filtered, and concentrated in vacuo to afford the amine. MS found: $(M+H)^+$=512.3. The amine was dissolved in MeOH (6 mL) and charged with acetone (~0.75 mL); the mixture was stirred for 5 min before being charged with $NaCNBH_3$ (~100 mg). The reaction was stirred for 4 h at RT and then charged with formaldehyde (~0.3 mL of a 30% aq. Solution). The mixture was stirred for 1.5 h, quenched with sat. $NaHCO_3$, and extracted with EtOAc (2×). The organic extracts were combined, washed with brine, dried ($Na_2SO_4$), filtered, and concentrated in vacuo. The residue was purified by reverse phase HPLC to afford the TFA salt of the title compound, N-{(3S)-1-[(1S,2R,4R)-4-(Isopropyl-methyl-amino)-2-propyl-cyclohexyl]-2-oxo-pyrrolidin-3-yl}-2-(3-isopropyl-ureido)-5-trifluoromethyl-benzamide (also known as 1-{2-[((S)-1-((1S,2R,4R)-4-(isopropyl(methyl)amino)-2-propylcyclohexyl)-2-oxopyrrolidin-3-yl)carbamoyl]-4-(trifluoromethyl)phenyl}-3-ethylurea), as a white powder (9 mg) after lyopholization. MS found: (free $M+H)^+$=568.3.

Example 2c

Synthesis of 1-{2-[((S)-1-((1S,2R,4R)-4-(isopropyl (methyl)amino)-2-propylcyclohexyl)-2-oxopyrrolidin-3-yl)carbamoyl]-4-(trifluoromethyl)phenyl}-3-ethylurea Example 2c, Step 1: To a solution of {(3S)-1-[(1S,2R,4R)-4-tert-butoxycarbonylamino-2-propyl-cyclohexyl]-2-oxo-pyrrolidin-3-yl}-carbamic acid benzyl ester (3.88 g, 8.2 mmol) in $CH_2Cl_2$ (90 mL) was added TFA (45 mL) at RT. The reaction was stirred for 5 h and concentrated in vacuo. The residue was partitioned between 1N NaOH (100 mL) and EtOAc (150 mL). The aqueous layer was extracted with EtOAc (2×50 mL) and the organic phases were combined, washed with brine (25 mL), dried ($Na_2SO_4$), filtered, and concentrated in vacuo to give benzyl (S)-1-[(1S,2R,4R)-4-amino-2-propylcyclohexyl]-2-oxopyrrolidin-3-ylcarbamate. MS found: $(M+H)^+$=374.3.

Example 2c, Step 2: The entirety of benzyl (S)-1-[(1S,2R,4R)-4-amino-2-propylcyclohexyl]-2-oxopyrrolidin-3-ylcarbamate prepared in Step 1 (assumed 8.2 mmol) was dissolved in methanol (40 mL). The resultant solution was charged with acetone (6 mL, 82 mmol) and stirred at RT for 10 min before sodium cyanoborohydride (2.6 g, 41 mmol) was added in one portion. The reaction was stirred at RT for 10 h and then charged successively with formaldehyde (3.0 mL of 37 wt % aq soln, 41 mmol) and sodium cyanoborohydride (0.52 g, 8.2 mmol). The reaction was stirred for another 9 h at RT and then quenched with sat. $NaHCO_3$ (150 mL). The aqueous mixture was extracted with EtOAc (200 mL, then 2×75 mL). The organic extracts were combined, washed with brine (30 mL), dried ($MgSO_4$), filtered, and concentrated in vacuo. After the resulting oil stood, some paraformaldehyde-related products solidified; these were removed by dissolving the mixture in a minimal volume of EtOAc and filtering. Subsequent concentration provided benzyl (S)-1-[(1S,2R,4R)-4-(isopropyl(methyl)amino)-2-propylcyclohexyl]-2-oxopyrrolidin-3-ylcarbamate. MS found: $(M+H)^+$=430.5.

Example 2c, Step 3: The entirety of benzyl (S)-1-[(1S,2R,4R)-4-(isopropyl(methyl)amino)-2-propylcyclohexyl]-2-oxopyrrolidin-3-ylcarbamate prepared in Step 2 (assumed 8.2 mmol) was wet with 3 mL of EtOAc and then charged with 30% HBr/AcOH (30 mL). The reaction vessel warms and a vigorous gas evolution occurs. The mixture was stirred for 25 min at RT and then the flask was placed in a cool water bath before the addition of 150 mL of 1:1 $Et_2O/H_2O$. This mixture was mixed and separated, and the aqueous phase was extracted once with $Et_2O$. The aqueous phase was basified to pH 14 through the addition of solid NaOH (the temperature of this exothermic process was controlled through the intermittent use of an external ice bath) and the resulting mixture was extracted with EtOAc (75 mL, then 2×35 mL). The organic extracts were combined, washed with brine (30 mL), dried ($Na_2SO_4$), filtered, and concentrated in vacuo to give an orange oil, contaminated with some powdery white solid (presumed to be formaldehyde-related). The mixture was dissolved in a minimal volume of EtOAc, filtered, and concentrated to provide (S)-3-amino-1-[(1S,2R,4R)-4-(isopropyl(methyl)amino)-2-propylcyclohexyl]pyrrolidin-2-one (2.31 g; 1H-NMR shows ~30% EtOAc, indicating an estimated 7.0 mmol of product from Steps 1-3). MS found: $(M+H)^+$=296.6.

Example 2c, Step 4: To a solution of (S)-3-amino-1-[(1S,2R,44R)-4-(isopropyl(methyl)amino)-2-propylcyclohexyl]pyrrolidin-2-one (77 mg, 0.26 mmol) in DMF (2 mL) was added N,N-diisopropylethylamine (0.32 mL), 2-(3-ethylureido)-5-(trifluoromethyl)benzoic acid (80 mg) and HATU (129 mg). The reaction was stirred at RT for 14 h, diluted with water, filtered, and purified by RP-HPLC to afford 1-{2-[((S)-1-((1S,2R,4R)-4-(isopropyl(methyl)amino)-2-propylcyclohexyl)-2-oxopyrrolidin-3-yl)carbamoyl]-4-(trifluoromethyl) phenyl}-3-ethylurea. MS found: $(M+H)^+$=554.4. [Note: for larger scale preparations, the reaction was frequently run with $CH_2Cl_2$ as a co-solvent, and the following aqueous workup was used before RP-HPLC purification. Volatiles were removed and the residue was dissolved in EtOAc. The organic

Example 2i

Synthesis of 6-tert-butyl-N-((3S)-1-((1S,2R,4R)-4-(isopropyl(methyl)amino)-2-propylcyclohexyl)-2-oxopyrrolidin-3-yl)picolinamide Example 2i, Step 1: (3S)-3-amino-1-((1S,2R,4R)-4-(isopropyl(methyl)amino)-2-propylcyclohexyl)pyrrolidin-2-one (41.7 mg, 0.14 mmol, 1 eq.), 6-tert-butylpicolinic acid HCl salt (37 mg, 0.168 mmol, 1.2 eq.), 1-hydroxybenzotriazole hydrate (HOBT) (19 mg, 0.168 mmol, 1.2 eq.), 1-[3-(dimethylamino)propyl]-3-ethylcarbodiimide HCl (EDCI) (28 mg, 0.168 mmol, 1.2 eq.), triethylamine (24 uL, 0.282 mmol, 2 eq.) and THF (5 mL) were stirred at room temperature under nitrogen overnight. Purified by RP-HPLC. Obtained 41 mg of the TFA salt of 6-tert-butyl-N-((3S)-1-((1S,2R,4R)-4-(isopropyl(methyl)amino)-2-propylcyclohexyl)-2-oxopyrrolidin-3-yl)picolinamide, bis TFA salt as a white solid after lyopholization. MS found: $(M+H)+=457.4$.

Example 2k

Synthesis of (S)-1-[(1S,2R,4R)-4-(isopropyl(methyl)amino)-2-propylcyclohexyl]-3-(6-(trifluoromethyl)quinazolin-4-ylamino)pyrrolidin-2-one Example 2k, Step 1: To a solution of (S)-3-amino-1-[(1S,2R,4R)-4-(isopropyl(methyl)amino)-2-propylcyclohexyl]pyrrolidin-2-one (7.0 mmol) in EtOH (23 mL) was added triethylamine (2.5 mL, 17.5 mmol) and 4-chloro-6-(trifluoromethyl)quinazoline (2.03 g, 8.75 mmol). The mixture was heated at 75° C. for 14 h and then concentrated in vacuo. [Note: on smaller reaction scales, this residue could be diluted in water/acetonitrile, filtered, and purified directly by RP-HPLC.] The residue was dissolved in 60 mL of 2:1 $H_2O$/AcOH and extracted with $Et_2O$ twice. The aqueous phase was basified to pH 14 with solid NaOH (the temperature of this exothermic process was controlled through the intermittent use of an external ice bath) and then extracted with EtOAc thrice. The organic extracts were combined, washed with brine, dried ($Na_2SO_4$), filtered, and concentrated in vacuo to give a solid. The material was recrystallized from EtOAc twice to provide the title compound, (S)-1-[(1S,2R,4R)-4-(isopropyl(methyl)amino)-2-propylcyclohexyl]-3-(6-(trifluoromethyl)quinazolin-4-ylamino)pyrrolidin-2-one, as a white microcrystalline solid (1.83 g, 52% yield). MS found: $(M+H)^+=492.4$. [Note: Purification of the the mother liquors using RP-HPLC provided more of the title compound as its bis-TFA salt.]

Example 2p

Synthesis of (3S)-1-((1S,2R,4R)-4-(isopropyl(methyl)amino)-2-propylcyclohexyl)-3-(6-(2-methoxyphenyl)quinazolin-4-ylamino)pyrrolidin-2-one Example 2p, Step 1: A solution of (3S)-3-amino-1-((1S,2R,4R)-4-(isopropyl(methyl)amino)-2-propylcyclohexyl)pyrrolidin-2-one (38 mg, 0.13 mmol), 4-chloro-6-(2-methoxyphenyl)quinazoline (42 mg, 0.15 mmol), and triethylamine (0.054 mL, 0.39 mmol) in ethanol (2 mL) in a sealed 5 mL microwave tube was heated in the microwave at 100° C. for 60 min. The reaction was cooled to room temperature, concentrated in-vacuo, and the residue was purified by RP-HPLC to afford the TFA salt of the title compound as a white powder after lyopholization (38 mg). MS found: $(M+H)^+=530$.

Examples 2r and 2s

Synthesis of (S)-3-(6-chloroquinazolin-4-ylamino)-1-((1S,2R,4R)-4-(isopropylamino)-2-propylcyclohexyl)pyrrolidin-2-one and (S)-3-(6-chloroquinazolin-4-ylamino)-1-((1S,2R,4R)-4-(ethyl(isopropyl)amino)-2-propylcyclohexyl)pyrrolidin-2-one Examples 2r and 2s, Step 1: A solution of (1R,3R,4S)-{4-[(3S)-3-amino-2-oxo-pyrrolidin-1-yl]-3-propyl-cyclohexyl}-carbamic acid tert-butyl ester (0.66 mmol) in EtOH (8 mL) was charged with triethylamine (0.5 mL, 3.3 mmol) and 4,6-dichloroquinazoline (200 mg, 1.0 mmol) before being heated at 80° C. for 12 h. The reaction mixture was cooled and purified by flash chromatography to afford tert-butyl (1R,3R,4S)-4-((S)-3-(6-chloroquinazolin-4-ylamino)-2-oxopyrrolidin-1-yl)-3-propylcyclohexylcarbamate. MS found: $(M+H)^+=502.2$.

Examples 2r and 2s, Step 2: A portion of tert-butyl (1R,3R,4S)-4-((S)-3-(6-chloroquinazolin-4-ylamino)-2-oxopyrrolidin-1-yl)-3-propylcyclohexylcarbamate was carried through the procedure outlined in Example 2a, Step 7, substituting acetaldehyde for formaldehyde. Purification by RP-HPLC provided two products: the TFA salt of (S)-3-(6-chloroquinazolin-4-ylamino)-1-((1S,2R,4R)-4-(isopropylamino)-2-propylcyclohexyl)pyrrolidin-2-one [MS found: $(M+H)^+=444$], and the TFA salt of (S)-3-(6-chloroquinazolin-4-ylamino)-1-((1S,2R,4R)-4-(ethyl(isopropyl)amino)-2-propylcyclohexyl)pyrrolidin-2-one [MS found: $(M+H)^+=472$].

Examples 2t and 2u

Synthesis of (S)-1-((1S,2R,4R)-4-(tert-butylamino)-2-propylcyclohexyl)-3-(6-(trifluoromethyl)quinazolin-4-ylamino)pyrrolidin-2-one and (S)-1-((1S,2R,4S)-4-(tert-butylamino)-2-propylcyclohexyl)-3-(6-(trifluoromethyl)quinazolin-4-ylamino)pyrrolidin-2-one Examples 2t and 2u, Step 1: A solution of 7-Oxo-6-oxabicyclo[3.2.1]oct-2-yl)-carbamic acid benzyl ester (2.2 g, 8.2 mmol) in toluene (80 mL) was cooled to −78° C. and treated with DIBAL-H (15 mL of a 1.5 M solution in toluene). The reaction was stirred for 4 h at −78° C. and quenched with 1 N HCl solution. The mixture was warmed to RT and extracted with EtOAc. The organic extracts were combined, washed with brine, dried, filtered, and concentrated in vacuo. The residue was dissolved in THF (20 mL) and added to a premixed (30 min), pre-cooled (0° C.) solution of ethyltriphenylphosphonium iodide (3.6 g, 9.8 mmol) and KHMDS (20.6 mL of a 0.5 M solution in toluene). The reaction was stirred at 0° C. for 20 min before being quenched with sat. ammonium chloride. The organic layer was separated, and the aqueous mixture was extracted with ethyl acetate. The combined organic phases were washed with brine, dried, filtered, and concentrated in vacuo. The residue was purified by flash chromatography to afford benzyl (1S,2S,4R)-4-hydroxy-2-((Z)-prop-1-enyl)cyclohexylcarbamate, contaminated with small amounts of its (E)-isomer (1.2 g). MS found: $(M+H)^+=290$.

Examples 2t and 2u, Step 2: A solution of benzyl (1S,2S,4R)-4-hydroxy-2-((Z)-prop-1-enyl)cyclohexylcarbamate (6.0 g, 20.7 mmol) in methylene chloride (60 mL) was treated with imidazole (2.1 g) and cooled to 0° C. The resultant solution was charged with tert-butylchlorodimethylsilane (3.4 g, 22.8 mmol) and then stirred for 18 h at 30° C. before being quenched with water. The organic phase was separated, and the aqueous phase was extracted with methylene chloride. The combined organic phases were washed with brine, dried, filtered, and concentrated in vacuo. The residue was purified by flash chromatography to afford benzyl (1S,2S, 4R)-4-(tert-butyldimethylsilyloxy)-2-((Z)-prop-1-enyl)cyclohexylcarbamate (6.0 g). MS found: $(M+H)^+=404$.

Examples 2t and 2u, Step 3: A solution of benzyl (1S,2S, 4R)-4-(tert-butyldimethylsilyloxy)-2-((Z)-prop-1-enyl)cyclohexylcarbamate (0.3 g, 0.74 mmol) in 10 mL of 7:3 EtOH:EtOAc was charged with palladium hydroxide and stirred under hydrogen atmosphere for 22 h. The palladium was removed by filtration and the solution was charged with fresh palladium hydroxide before again being placed under hydrogen atmosphere (5 kg pressure). After 3 h, the mixture was filtered through celite with EtOAc washings and concentrated in vacuo. The residue was dissolved in DMF (3 mL) and the resultant solution was cooled to 0° C. before being charged successively with (S)-Cbz methionine (0.31 g, 1.1 mmol), N-methyl morpholine (0.24 mL, 2.2 mmol), and BOP reagent (0.48 g, 1.1 mmol). The reaction was slowly warmed to 30° C. and then stirred for 12 h before being quenched water. The mixture was extracted with EtOAc, and the combined organic phases were washed with brine, dried, filtered, and concentrated in vacuo. The residue was purified by flash chromatography to afford benzyl (S)-1-((1S,2R,4R)-4-(tert-butyldimethylsilyloxy)-2-propylcyclohexylamino)-4-(methylthio)-1-oxobutan-2-ylcarbamate (0.25 g). blah, blah. MS found: $(M+H)^+=537$.

Examples 2t and 2u, Step 4: A sample of benzyl (S)-1-((1S, 2R,4R)-4-(tert-butyldimethylsilyloxy)-2-propylcyclohexylamino)-4-(methylthio)-1-oxobutan-2-ylcarbamate (4.0 g, 7.45 mmol) was dissolved in iodomethane (8 mL) and stirred at 30° C. for 3 days. The solution was concentrated in vacuo. The residue was dissolved in methylene chloride and the resultant solution was concentrated in vacuo again; this procedure was repeated twice before the residue was placed under high vacuum for 4 h. The resultant pale yellow foam solid was dissolved in THF (40 mL) and the resultant solution was cooled to 0° C. before being treated with sodium hydride (0.9 g, 37 mmol) in one portion. The mixture was slowly warmed to 30° C. and stirred for 12 h before being quenched with saturated ammonium chloride. The organic layer was separated and the aqueous layer was extracted with EtOAc. The combined organic phases were washed with brine, dried, filtered, and concentrated in vacuo. The residue was purified by flash chromatography to afford benzyl (S)-1-((1S,2R,4R)-4-(tert-butyldimethylsilyloxy)-2-propylcyclohexyl)-2-oxopyrrolidin-3-ylcarbamate (0.9 g). MS found: $(M+H)^+=489.2$.

Examples 2t and 2u, Step 5: A sample of benzyl (S)-1-((1S, 2R,4R)-4-(tert-butyldimethylsilyloxy)-2-propylcyclohexyl)-2-oxopyrrolidin-3-ylcarbamate (0.4 g, 0.82 mmol) was dissolved in 36 mL of 4:1:1 HOAc/THF/water and stirred at RT for 5 days. The volatiles were removed in vacuo and the residue was dissolved in EtOAc. The organic phase was washed with sat. $NaHCO_3$, dried ($MgSO_4$), filtered, and concentrated in vacuo. The residue was dissolved in methylene chloride (4 mL) and the resultant solution was cooled to 0° C. and charged with Dess-Martin periodinane (0.54 g, 1.27 mmol). After stirring for 2 h at RT, the solution was again cooled to 0° C. and charged with Dess-Martin periodinane (0.27 g). The reaction was stirred at RT for 14 h and treated with $Et_2O$. The resultant suspension was washed with 1 N NaOH, sat. $Na_2S_2O_3$, and sat. $NaHCO_3$. The organic phase was dried ($MgSO_4$), filtered, and concentrated in vacuo to afford benzyl (S)-2-oxo-1-((1S,2R)-4-oxo-2-propylcyclohexyl)pyrrolidin-3-ylcarbamate (114 mg). MS found: $(M+Na)^+=395.4$.

Examples 2t and 2u, Step 6: A sample of benzyl (S)-2-oxo-1-((1S,2R)-4-oxo-2-propylcyclohexyl)pyrrolidin-3-ylcarbamate (114 mg) was dissolved in $Ti(OiPr)_4$ (1.5 mL, 5.0 mmol) and tert-butylamine (0.14 mL, 1.8 mmol). The resultant solution was stirred at RT for 3 h before being cooled to 0° C. and charged successively with MeOH (2 mL) and $NaBH_4$ (22.8 mg, 0.6 mmol). The mixture was stirred for 90 min while the solution slowly warmed to RT. The solution was diluted with methylene chloride (10 mL) and 0.5 N NaOH was added. The resultant suspension was filtered through a pad of Celite with EtOAc washings and the filtrate was dried, filtered, and concentrated in vacuo to afford benzyl (S)-1-((1S,2R,4R/S)-4-(tert-butylamino)-2-propylcyclohexyl)-2-oxopyrrolidin-3-ylcarbamate as an inseparable mixture of diastereomers. MS found: $(M+H)^+=430.5$.

Examples 2t and 2u, Step 7: A sample of (S)-1-((1S,2R, 4R/S)-4-(tert-butylamino)-2-propylcyclohexyl)-2-oxopyrrolidin-3-ylcarbamate (110 mg) was dissolved in MeOH and the resultant solution was charged with 10% Pd/C, Degussa style (22 mg) before being evacuated and charged with hydrogen. The mixture was stirred for 14 h under 1 atm of hydrogen before being filtered through celite with EtOAc washings. The filtrate was concentrated in vacuo to afford a residue (41 mg), which was dissolved in EtOH. The resultant solution was charged with triethylamine (0.15 mL) and 4-chloro-6-trifluoromethylquinazoline before being heated at 80° C. for 14 h. The reaction was cooled to RT and concentrated in vacuo. The residue was dissolved in EtOAc and washed with sat. $NaHCO_3$, water, and sat. NaCl. The organic phase was dried ($MgSO_4$), filtered, and concentrated in vacuo. The residue was purified by RP-HPLC to afford the TFA salt of (S)-1-((1S,2R,4R)-4-(tert-butylamino)-2-propylcyclohexyl)-3-(6-(trifluoromethyl)quinazolin-4-ylamino)pyrrolidin-2-one as a white powder after lyopholization. MS found: $(M+H)^+=492.4$. The diastereomer of this product, (S)-1-((1S, 2R,4S)-4-(tert-butylamino)-2-propylcyclohexyl)-3-(6-(trifluoromethyl)quinazolin-4-ylamino)pyrrolidin-2-one, was also isolated from RP-HPLC. MS found: $(M+H)^+=492.4$.

Examples 2ai

Synthesis of 1-((S)-1-((1S,2R,4R)-4-(isopropyl(methyl)amino)-2-propylcyclohexyl)-2-oxopyrrolidin-3-yl)-3-(3-(trifluoromethyl)phenyl)urea Example 2ai, Step 1: A solution of (S)-3-amino-1-[(1S,2R, 4R)-4-(isopropyl(methyl)amino)-2-propylcyclohexyl]pyrrolidin-2-one (33 mg, 0.11 mmol) in acetonitrile (1 mL) was treated with N,N-diisopropylethylamine (0.12 mL, 0.66 mmol) and 1-isocyanato-3-(trifluoromethyl)benzene (0.05 mL, 0.33 mmol). The reaction was stirred for 14 h at RT, diluted with water, and filtered. The resulting solution was purified directly by RP-HPLC to afford the TFA salt of the title compound as a white powder (12.3 mg) after lyopholization. MS found: $(M+H)^+=483.4$.

Examples 2aj

Synthesis of 1-((S)-1-((1S,2R,4R)-4-(isopropyl(methyl)amino)-2-propylcyclohexyl)-2-oxopyrrolidin-3-yl)-3-(3-(trifluoromethyl)phenyl)urea Example 2aj, Step 1: A solution of (S)-3-amino-1-[(1S,2R, 4R)-4-(isopropyl(methyl)amino)-2-propylcyclohexyl]pyrrolidin-2-one (90 mg, 0.3 mmol) in MeOH (4 mL) was treated with 3-trifluoromethylbenzaldehyde (0.061 mL, 0.46 mmol) and stirred for 10 min at RT before being charged with sodium cyanoborohydride (60 mg, 0.92 mmol). The reaction was stirred for 14 h at RT and quenched with sat. NaHCO$_3$. This mixture was extracted with EtOAc thrice and the organic extracts were combined, washed with brine, dried (MgSO$_4$), filtered, and concentrated in vacuo. Purification of the residue by RP-HPLC afforded the TFA salt of the title compound as a white powder (45 mg) after lyopholization. MS found: (M+H)$^+$=454.3.

Examples 2al and 2am

Synthesis of (S)-1-((1S,2R,4R)-4-(isopropyl(methyl)amino)-2-propylcyclohexyl)-3-(6-(trifluoromethyl)quinolin-4-ylamino)pyrrolidin-2-one and (R)-1-((1S,2R,4R)-4-(isopropyl(methyl)amino)-2-propylcyclohexyl)-3-(6-(trifluoromethyl)quinolin-4-ylamino)pyrrolidin-2-one Examples 2al and 2am, Step 1: To a solution of (S)-3-amino-1-((1S,2R,4R)-4-(isopropyl(methyl)amino)-2-propylcyclohexyl)pyrrolidin-2-one (100 mg) in toluene (2 mL) was added sodium tert-butoxide (42 mg), acetato(2'-di-t-butylphosphino-1,1'-diphenyl-2-yl)palladium(II) (7.8 mg), and 4-chloro-6-(trifluoromethyl)quinoline (102.3 mg). The mixture was heated at 80° C. for 14 h before it was filtered and concentrated in vacuo. The residue was purified by chiral chromatography (OD column, 80/20/0.1 hexane/iPrOH/Et$_2$NH as mobile phase) to afford (R)-1-((1S,2R,4R)-4-(isopropyl(methyl)amino)-2-propylcyclohexyl)-3-(6-(trifluoromethyl)quinolin-4-ylamino)pyrrolidin-2-one [8 mg; MS found: (M+H)+=491.3] and (S)-1-((1S,2R,4R)-4-(isopropyl(methyl)amino)-2-propylcyclohexyl)-3-(6-(trifluoromethyl)quinolin-4-ylamino)pyrrolidin-2-one [18 mg; MS found: (M+H)+=491.3].

Example 2bb

Synthesis of 3-(((S)-1-((1S,2R,4R)-4-(isopropyl(methyl)amino)-2-propylcyclohexyl)-2-oxopyrrolidin-3-yl)carbamoyl)-5-tert-butylbenzoic acid Following the method described in Example 2c, Step 4, (S)-3-amino-1-[(1S,2R,4R)-4-(isopropyl(methyl)amino)-2-propylcyclohexyl]pyrrolidin-2-one (223 mg) was coupled with 3-tert-butyl-5-(methoxycarbonyl)benzoic acid (165 mg, see Preparation H6, Step 1) in 8 mL of DMF. After 14 h, 2 mL of this reaction mixture was removed and purified to provide Example 2ba. The remaining portion of the reaction mixture was charged successively with aq. LiOH (48 mg in 2 mL water) and MeOH (1 mL) before being stirred at RT for 14 h. The mixture was diluted with 2.0% TFA/water, filtered, and purified directly by RP-HPLC to afford the titled compound. MS found: (M+H)$^+$=500.4.

TABLE 2-A

The compounds in the following table were made using the methods exemplified above. See Table 1-A for a complete description of the table headings.

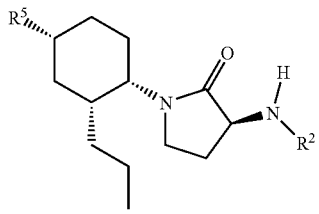

| Example | R$^5$ | R$^2$ | Step Altered | MS Data |
|---------|-------|-------|--------------|---------|
| 2a | i-Pr(Me)N | | n/a | 568.3 |

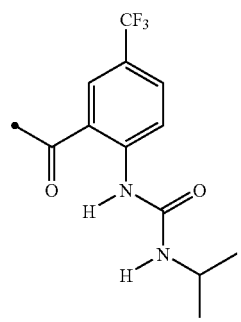

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2b | i-Pr(Me)N | | 2a, Step 6 | 566.3 |
| 2c | i-Pr(Me)N | | n/a | 554.4 |
| 2d | i-Pr(Me)N | | 2c, Step 4 | 566.4 |
| 2e | i-Pr(Me)N | | 2c, Step 4 | 468.3 |

TABLE 2-A-continued

The compounds in the following table were made using the methods exemplified above. See Table 1-A for a complete description of the table headings.

| Example | R$^5$ | R$^2$ | Step Altered | MS Data |
|---------|-------|-------|--------------|---------|
| 2f | i-Pr(Me)N | 3-tert-butylbenzoyl | 2c, Step 4 | 456.4 |
| 2g | i-Pr(Me)N | 2-tert-butylpyrimidine-4-carbonyl | 2c, Step 4 | 458.4 |
| 2h | i-Pr(Me)N | 3-tert-butyl-4-hydroxybenzoyl | 2c, Step 4 | 472.4 |
| 2i | i-Pr(Me)N | 6-tert-butylpyridine-2-carbonyl | n/a | 457.4 |
| 2j | i-Pr(Me)N | 2-tert-butylpyridine-4-carbonyl | 2i, Step 1 | 457.4 |

TABLE 2-A-continued

The compounds in the following table were made using the methods exemplified above. See Table 1-A for a complete description of the table headings.

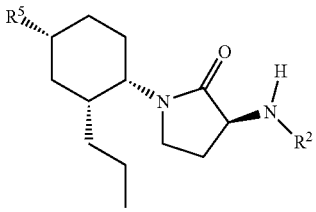

| Example | R⁵ | R² | Step Altered | MS Data |
|---|---|---|---|---|
| 2k | i-Pr(Me)N | 6-CF₃-quinazolin-4-yl | n/a | 492.4 |
| 2l | i-Pr(Me)N | 6-OCF₃-quinazolin-4-yl | 2k, Step 1 | 508.3 |
| 2m | i-Pr(Me)N | 6-Cl-quinazolin-4-yl | 2k, Step 1 | 458.3 |
| 2n | i-Pr(Me)N | 6-F-quinazolin-4-yl | 2k, Step 1 | 442.4 |
| 2o | i-Pr(Me)N | 2-t-Bu-pyrimido[5,4-d]pyrimidin-4-yl | 2k, Step 1 | 482 |

TABLE 2-A-continued
The compounds in the following table were made using the methods exemplified above. See Table 1-A for a complete description of the table headings.
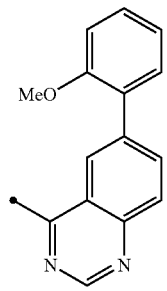
| Example | R⁵ | R² | Step Altered | MS Data |
|---|---|---|---|---|
| 2p | i-Pr(Me)N | 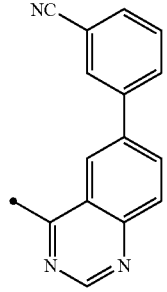 | n/a | 530 |
| 2q | i-Pr(Me)N | 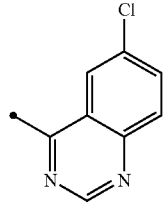 | 2p, Step 1 | 525 |
| 2r | i-Pr(H)N | 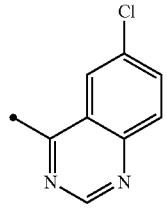 | n/a | 444 |
| 2s | i-Pr(Et)N | 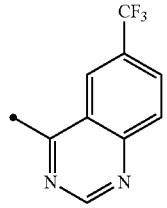 | n/a | 472 |
| 2t | i-Bu(H)N |  | n/a | 492.4 |

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2u | i-Bu(H)N [(S)-config.] | 4-(6-CF₃-quinazolinyl) | n/a | 492.4 |
| 2v | Me₂N | 4-(6-CF₃-quinazolinyl) | 2c, Steps 2 and 4 (see 2k) | 464.3 |
| 2w | Me₂N | 4-(6-OCF₃-quinazolinyl) | 2c, Steps 2 and 4 (see 2k) | 480.3 |
| 2x | Me₂N | 3-t-Bu-4-OH-benzoyl | 2c, Steps 2 and 4 | 444.3 |
| 2y | Me₂N | 3-CF₃-benzoyl | 2c, Steps 2 and 4 | 440.2 |

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2z | Me₂N | 2-tert-butylpyrimidin-4-yl carbonyl | 2c, Steps 2 and 4 | 430.3 |
| 2aa | Me₂N | 6-(2-methoxyphenyl)quinazolin-4-yl | 2c, Steps 2 and 4 (see 2p) | 502.3 |
| 2ab | Me₂N | 6-tert-butylpyridin-2-yl carbonyl | 2c, Steps 2 and 4 | 429.3 |
| 2ac | Me₂N | 5-(4-chlorophenyl)furan-2-yl carbonyl | 2c, Steps 2 and 4 | 472.2 |

TABLE 2-A-continued

The compounds in the following table were made using the methods exemplified above. See Table 1-A for a complete description of the table headings.

| Example | $R^5$ | $R^2$ | Step Altered | MS Data |
|---------|-------|-------|--------------|---------|
| 2ad | $Me_2N$ | (6-tert-butyl-pyrimido[5,4-d]pyrimidin-4-yl) | 2c, Steps 2 and 4 (see 2k) | 454.3 |
| 2ae | $Et_2N$ | (6-CF$_3$-quinazolin-4-yl) | 2c, Steps 2 and 4 (see 2k) | 492.5 |
| 2af | $Et_2N$ | (6-OCF$_3$-quinazolin-4-yl) | 2c, Steps 2 and 4 (see 2k) | 508.5 |
| 2ag | $Et_2N$ | (3-CF$_3$-benzoyl) | 2c, Steps 2 and 4 | 468.3 |
| 2ah | $Et_2N$ | (2-tert-butyl-pyrimidin-4-yl-carbonyl) | 2c, Steps 2 and 4 | 458.4 |

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2ai | i-Pr(Me)N | 3-(CF₃)C₆H₄NHC(O)CH₂- | n/a | 483.4 |
| 2aj | i-Pr(Me)N | 3-(CF₃)benzyl | n/a | 454.3 |
| 2ak | i-Pr(Me)N | 3,5-bis(CF₃)benzyl | 2aj | 522.3 |
| 2al | i-Pr(Me)N | 6-(CF₃)quinolin-4-ylmethyl | n/a | 491.3 |
| 2am (isomer of 1al) | i-Pr(Me)N | 6-(CF₃)quinolin-4-ylmethyl | n/a | 491.3 |
| 2an | i-Pr(Me)N | F₃SO₂NH-biphenyl-C(O)- | 2i, Step 1 | 623.3 |

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2ao | i-Pr(Me)N | 2-hydroxy-biphenyl-5-carbonyl | 2i, Step 1 | 492.4 |
| 2ap | i-Pr(Me)N | biphenyl-3-carbonyl | 2i, Step 1 | 475.7 |
| 2aq | i-Pr(Me)N | 2-phenylpyridine-4-carbonyl N-oxide | 2c, Step 4 | 493.4 |
| 2ar | i-Pr(Me)N | 1-methyl-1H-indole-3-carbonyl | 2c, Step 4 | 453 |
| 2as | i-Pr(Me)N | 1-methyl-1H-indole-2-carbonyl | 2c, Step 4 | 453 |

TABLE 2-A-continued
The compounds in the following table were made using the methods exemplified above. See Table 1-A for a complete description of the table headings.
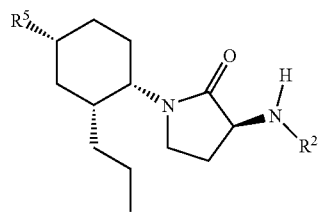
| Example | $R^5$ | $R^2$ | Step Altered | MS Data |
|---|---|---|---|---|
| 2at | i-Pr(Me)N | 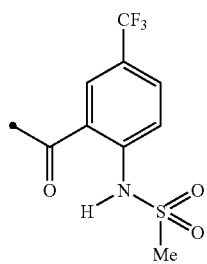 | 2c, Step 4 | 561 |
| 2au | i-Pr(Me)N | 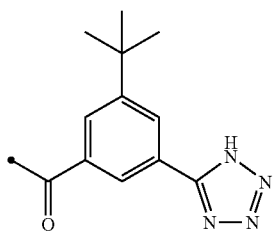 | 2c, Step 4 | 524 |
| 2av | i-Pr(Me)N | 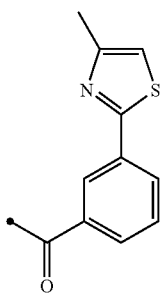 | 2c, Step 4 | 497 |
| 2aw | i-Pr(Me)N | 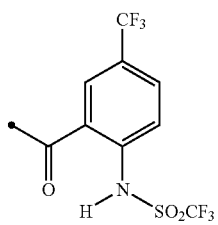 | 2c, Step 4 | 615 |

TABLE 2-A-continued

The compounds in the following table were made using the methods exemplified above. See Table 1-A for a complete description of the table headings.

| Example | R⁵ | R² | Step Altered | MS Data |
|---|---|---|---|---|
| 2ax | i-Pr(Me)N | 5-isopropyl-2-(trifluoromethylsulfonylamino)benzoyl | 2c, Step 4 | 589 |
| 2ay | i-Pr(Me)N | 2-chloro-5-(trifluoromethyl)benzoyl | 2c, Step 4 | 503 |
| 2az | i-Pr(Me)N | 3-(thiazol-2-yl)benzoyl | 2c, Step 4 | 483 |
| 2ba | i-Pr(Me)N | 3-tert-butyl-5-(methoxycarbonyl)benzoyl | 2c, Step 4 | 514.5 |
| 2bb | i-Pr(Me)N | 3-tert-butyl-5-carboxybenzoyl | n/a | 500.4 |

TABLE 2-A-continued

The compounds in the following table were made using the methods exemplified above. See Table 1-A for a complete description of the table headings.

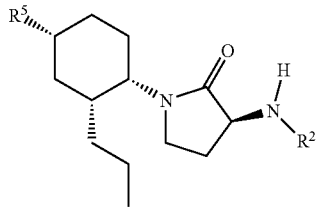

| Example | R⁵ | R² | Step Altered | MS Data |
|---|---|---|---|---|
| 2bc | i-Pr(Me)N | (2-tert-butyl-1-oxido-pyrimidin-4-yl carbonyl) | 2c, Step 4 | 474.4 |

TABLE 2-B

The chemical names of the specific examples illustrated in Table 2-A are tabulated below.

| Example | Name |
|---|---|
| 2a | N-{(3S)-1-[(1S,2R,4R)-4-(Isopropyl-methyl-amino)-2-propyl-cyclohexyl]-2-oxo-pyrrolidin-3-yl}-2-(3-isopropyl-ureido)-5-trifluoromethyl-benzamide |
| 2b | Azetidine-1-carboxylic acid (2-{(3S)-1-[(1S,2R,4R)-4-(isopropyl-methyl-amino)-2-propyl-cyclohexyl]-2-oxo-pyrrolidin-3-ylcarbamoyl}-4-trifluoromethyl-phenyl)-amide |
| 2c | 1-{2-[((S)-1-((1S,2R,4R)-4-(isopropyl(methyl)amino)-2-propylcyclohexyl)-2-oxopyrrolidin-3-yl)carbamoyl]-4-(trifluoromethyl)phenyl}-3-ethylurea |
| 2d | 1-(2-(((S)-1-((1S,2R,4R)-4-(isopropyl(methyl)amino)-2-propylcyclohexyl)-2-oxopyrrolidin-3-yl)carbamoyl)-4-(trifluoromethyl)phenyl)-3-cyclopropylurea |
| 2e | N-((S)-1-((1S,2R,4R)-4-(isopropyl(methyl)amino)-2-propylcyclohexyl)-2-oxopyrrolidin-3-yl)-3-(trifluoromethyl)benzamide |
| 2f | 3-tert-butyl-N-((S)-1-((1S,2R,4R)-4-(isopropyl(methyl)amino)-2-propylcyclohexyl)-2-oxopyrrolidin-3-yl)benzamide |
| 2g | 2-tert-butyl-N-((S)-1-((1S,2R,4R)-4-(isopropyl(methyl)amino)-2-propylcyclohexyl)-2-oxopyrrolidin-3-yl)pyrimidine-4-carboxamide |
| 2h | 3-tert-butyl-4-hydroxy-N-((S)-1-((1S,2R,4R)-4-(isopropyl(methyl)amino)-2-propylcyclohexyl)-2-oxopyrrolidin-3-yl)benzamide |
| 2i | 6-tert-butyl-N-((S)-1-((1S,2R,4R)-4-(isopropyl(methyl)amino)-2-propylcyclohexyl)-2-oxopyrrolidin-3-yl)picolinamide |
| 2j | 2-tert-butyl-N-((S)-1-((1S,2R,4R)-4-(isopropyl(methyl)amino)-2-propylcyclohexyl)-2-oxopyrrolidin-3-yl)isonicotinamide |

TABLE 2-B-continued

The chemical names of the specific examples illustrated in Table 2-A are tabulated below.

| Example | Name |
|---|---|
| 2k | (S)-1-[(1S,2R,4R)-4-(isopropyl(methyl)amino)-2-propylcyclohexyl]-3-(6-(trifluoromethyl)quinazolin-4-ylamino)pyrrolidin-2-one |
| 2l | (S)-1-((1S,2R,4R)-4-(isopropyl(methyl)amino)-2-propylcyclohexyl)-3-(6-(trifluoromethoxy)quinazolin-4-ylamino)pyrrolidin-2-one |
| 2m | (S)-3-(6-chloroquinazolin-4-ylamino)-1-((1S,2R,4R)-4-(isopropyl(methyl)amino)-2-propylcyclohexyl)pyrrolidin-2-one |
| 2n | (S)-3-(6-fluoroquinazolin-4-ylamino)-1-((1S,2R,4R)-4-(isopropyl(methyl)amino)-2-propylcyclohexyl)pyrrolidin-2-one |
| 2o | (S)-3-(6-tert-butylpyrimido[5,4-d]pyrimidin-4-ylamino)-1-((1S,2R,4R)-4-(isopropyl(methyl)amino)-2-propylcyclohexyl)pyrrolidin-2-one |
| 2p | (S)-1-((1S,2R,4R)-4-(isopropyl(methyl)amino)-2-propylcyclohexyl)-3-(6-(2-methoxyphenyl)quinazolin-4-ylamino)pyrrolidin-2-one |
| 2q | 3-(4-((S)-1-((1S,2R,4R)-4-(isopropyl(methyl)amino)-2-propylcyclohexyl)-2-oxopyrrolidin-3-ylamino)quinazolin-6-yl)benzonitrile |
| 2r | (S)-3-(6-chloroquinazolin-4-ylamino)-1-((1S,2R,4R)-4-(isopropylamino)-2-propylcyclohexyl)pyrrolidin-2-one |
| 2s | (S)-3-(6-chloroquinazolin-4-ylamino)-1-((1S,2R,4S)-4-(ethyl(isopropyl)amino)-2-propylcyclohexyl)pyrrolidin-2-one |
| 2t | (S)-1-((1S,2R,4R)-4-(tert-butylamino)-2-propylcyclohexyl)-3-(6-(trifluoromethyl)quinazolin-4-ylamino)pyrrolidin-2-one |

TABLE 2-B-continued

The chemical names of the specific examples illustrated in Table 2-A are tabulated below.

| Example | Name |
|---|---|
| 2u | (S)-1-((1S,2R,4S)-4-(tert-butylamino)-2-propylcyclohexyl)-3-(6-(trifluoromethyl)quinazolin-4-ylamino)pyrrolidin-2-one |
| 2v | (S)-1-((1S,2R,4R)-4-(dimethylamino)-2-propylcyclohexyl)-3-(6-(trifluoromethyl)quinazolin-4-ylamino)pyrrolidin-2-one |
| 2w | (S)-1-((1S,2R,4R)-4-(dimethylamino)-2-propylcyclohexyl)-3-(6-(trifluoromethoxy)quinazolin-4-ylamino)pyrrolidin-2-one |
| 2x | 3-tert-butyl-N-((S)-1-((1S,2R,4R)-4-(dimethylamino)-2-propylcyclohexyl)-2-oxopyrrolidin-3-yl)-4-hydroxybenzamide |
| 2y | N-((S)-1-((1S,2R,4R)-4-(dimethylamino)-2-propylcyclohexyl)-2-oxopyrrolidin-3-yl)-3-(trifluoromethyl)benzamide |
| 2z | N-((S)-1-((1S,2R,4R)-4-(dimethylamino)-2-propylcyclohexyl)-2-oxopyrrolidin-3-yl)-2-(trifluoromethyl)pyrimidine-4-carboxamide |
| 2aa | (S)-1-((1S,2R,4R)-4-(dimethylamino)-2-propylcyclohexyl)-3-(6-(2-methoxyphenyl)quinazolin-4-ylamino)pyrrolidin-2-one |
| 2ab | 6-tert-butyl-N-((S)-1-((1S,2R,4R)-4-(dimethylamino)-2-propylcyclohexyl)-2-oxopyrrolidin-3-yl)picolinamide |
| 2ac | 5-(4-chlorophenyl)-N-((S)-1-((1S,2R,4R)-4-(dimethylamino)-2-propylcyclohexyl)-2-oxopyrrolidin-3-yl)furan-2-carboxamide |
| 2ad | (S)-3-(6-tert-butylpyrimido[5,4-d]pyrimidin-4-ylamino)-1-((1S,2R,4R)-4-(dimethylamino)-2-propylcyclohexyl)pyrrolidin-2-one |
| 2ae | (S)-1-((1S,2R,4R)-4-(diethylamino)-2-propylcyclohexyl)-3-(6-(trifluoromethyl)quinazolin-4-ylamino)pyrrolidin-2-one |
| 2af | (S)-1-((1S,2R,4R)-4-(diethylamino)-2-propylcyclohexyl)-3-(6-(trifluoromethoxy)quinazolin-4-ylamino)pyrrolidin-2-one |
| 2ag | N-((S)-1-((1S,2R,4R)-4-(diethylamino)-2-propylcyclohexyl)-2-oxopyrrolidin-3-yl)-3-(trifluoromethyl)benzamide |
| 2ah | 2-tert-butyl-N-((S)-1-((1S,2R,4R)-4-(diethylamino)-2-propylcyclohexyl)-2-oxopyrrolidin-3-yl)pyrimidine-4-carboxamide |
| 2ai | 1-((S)-1-((1S,2R,4R)-4-(isopropyl(methyl)amino)-2-propylcyclohexyl)-2-oxopyrrolidin-3-yl)-3-(3-(trifluoromethyl)phenyl)urea |
| 2aj | (S)-3-(3-(trifluoromethyl)benzylamino)-1-((1S,2R,4R)-4-(isopropyl(methyl)amino)-2-propylcyclohexyl)pyrrolidin-2-one |
| 2ak | (S)-3-(3,5-bis(trifluoromethyl)benzylamino)-1-((1S,2R,4R)-4-(isopropyl(methyl)amino)-2-propylcyclohexyl)pyrrolidin-2-one |
| 2al | (S)-1-((1S,2R,4R)-4-(isopropyl(methyl)amino)-2-propylcyclohexyl)-3-(6-(trifluoromethyl)quinolin-4-ylamino)pyrrolidin-2-one |
| 2am | (R)-1-((1S,2R,4R)-4-(isopropyl(methyl)amino)-2-propylcyclohexyl)-3-(6-(trifluoromethyl)quinolin-4-ylamino)pyrrolidin-2-one |
| 2an | N-((S)-1-((1S,2R,4R)-4-(isopropyl(methyl)amino)-2-propylcyclohexyl)-2-oxopyrrolidin-3-yl)-3-(3-trifluoromethylsulfonamidophenyl)-benzamide |
| 2ao | 4-hydroxy-N-((S)-1-((1S,2R,4R)-4-(isopropyl(methyl)amino)-2-propylcyclohexyl)-2-oxopyrrolidin-3-yl)-3-phenyl-benzamide |
| 2ap | N-((S)-1-((1S,2R,4R)-4-(isopropyl(methyl)amino)-2-propylcyclohexyl)-2-oxopyrrolidin-3-yl)-3-phenyl-benzamide |
| 2aq | N-((S)-1-((1S,2R,4R)-4-(isopropyl(methyl)amino)-2-propylcyclohexyl)-2-oxopyrrolidin-3-yl)-2-phenyl-isonicotinamide N-oxide |
| 2ar | N-((S)-1-((1S,2R,4R)-4-(isopropyl(methyl)amino)-2-propylcyclohexyl)-2-oxopyrrolidin-3-yl)-1-methyl-1H-indole-3-carboxamide |
| 2as | N-((S)-1-((1S,2R,4R)-4-(isopropyl(methyl)amino)-2-propylcyclohexyl)-2-oxopyrrolidin-3-yl)-1-methyl-1H-indole-2-carboxamide |
| 2at | N-((S)-1-((1S,2R,4R)-4-(isopropyl(methyl)amino)-2-propylcyclohexyl)-2-oxopyrrolidin-3-yl)-2-(methylsulfonamido)-5-(trifluoromethyl)benzamide |
| 2au | 3-tert-butyl-N-((S)-1-((1S,2R,4R)-4-(isopropyl(methyl)amino)-2-propylcyclohexyl)-2-oxopyrrolidin-3-yl)-5-(1H-tetrazol-5-yl)benzamide |
| 2av | N-((S)-1-((1S,2R,4R)-4-(isopropyl(methyl)amino)-2-propylcyclohexyl)-2-oxopyrrolidin-3-yl)-3-(4-methylthiazol-2-yl)benzamide |
| 2aw | N-((S)-1-((1S,2R,4R)-4-(isopropyl(methyl)amino)-2-propylcyclohexyl)-2-oxopyrrolidin-3-yl)-5-(trifluoromethyl)-2-(trifluoromethylsulfonamido)benzamide |
| 2ax | 5-isopropyl-N-((S)-1-((1S,2R,4R)-4-(isopropyl(methyl)amino)-2-propylcyclohexyl)-2-oxopyrrolidin-3-yl)-2-(trifluoromethylsulfonamido)benzamide |
| 2ay | 2-chloro-N-((S)-1-((1S,2R,4R)-4-(isopropyl(methyl)amino)-2-propylcyclohexyl)-2-oxopyrrolidin-3-yl)-5-(trifluoromethyl)benzamide |
| 2az | N-((S)-1-((1S,2R,4R)-4-(isopropyl(methyl)amino)-2-propylcyclohexyl)-2-oxopyrrolidin-3-yl)-3-(thiazol-2-yl)benzamide |
| 2ba | methyl 3-(((S)-1-((1S,2R,4R)-4-(isopropyl(methyl)amino)-2-propylcyclohexyl)-2-oxopyrrolidin-3-yl)carbamoyl)-5-tert-butylbenzoate |
| 2bb | 3-(((S)-1-((1S,2R,4R)-4-(isopropyl(methyl)amino)-2-propylcyclohexyl)-2-oxopyrrolidin-3-yl)carbamoyl)-5-tert-butylbenzoic acid |
| 2bc | 2-tert-butyl-1-oxo-N-((S)-1-((1S,2R,4R)-4-(isopropyl(methyl)amino)-2-propylcyclohexyl)-2-oxopyrrolidin-3-yl)pyrimidine-4-carboxamide |

Examples 3a-3e

Example 3a

Synthesis of (S)-1-((1S,2S,4R)-2-isopropyl-4-(isopropyl(methyl)amino)cyclohexyl)-3-(6-(trifluoromethyl)quinazolin-4-ylamino)pyrrolidin-2-one and its diastereomer, (S)-1-((1S,2S,4S)-2-isopropyl-4-(isopropyl(methyl)amino)cyclohexyl)-3-(6-(trifluoromethyl)quinazolin-4-ylamino)pyrrolidin-2-one Example 3a, Step 1: N,O-Dimethylhydroxylamine hydrochloride (5.7 g) was suspended in $CH_2Cl_2$ (80 mL) and cooled to 0° C. prior to the addition of 2.0 M $AlMe_3$ (29.1 mL) in hexane. The mixture was warmed to rt over 1 h, then cooled to 0° C. prior to the addition of benzyl (1R,2S,5R)-7-oxo-6-oxa-bicyclo[3.2.1]octan-2-ylcarbamate (8.0 g) in $CH_2Cl_2$ (80 mL). After 5 h at 0° C., the reaction was quenched with a 10% Rochelle salt solution and extracted with EtOAc (2×). The organic extracts were combined, washed with brine, dried ($MgSO_4$), filtered, and concentrated. The resulting residue was dissolved in DMF (100 mL) prior to the addition of imidazole (1.97 g) and TBSCl (4.4 g). The reaction was stirred for 12 h at rt and then partitioned between EtOAc and a saturated brine solution. The organic phases were combined, dried ($MgSO_4$), filtered, and concentrated in vacuo. The residue was purified by flash chromatography to afford benzyl (1S,2R,4R)-4-(tert-butyldimethylsilyloxy)-2-(methoxy(methyl)carbamoyl)cyclohexylcarbamate (11.2 g). MS found: $(M+H)^+=451.3$.

Example 3a, Step 2: Benzyl (1S,2R,4R)-4-(tert-butyldimethylsilyloxy)-2-(methoxy(methyl)carbamoyl)cyclohexylcarbamate (4.0 g) was dissolved in THF (40 mL) and cooled to −22° C. prior to the addition of 1.6 M MeLi (14.5 mL) in $Et_2O$. After 40 min at −22° C., the reaction was quenched with 0.5 N HCl solution and extracted with EtOAc (2×). The organic extracts were combined, washed with brine, dried ($MgSO_4$), filtered, and concentrated. The resulting residue was purified by flash chromatography to afford benzyl (1S,2R,4R)-2-acetyl-4 -(tert-butyldimethylsilyloxy)cyclohexylcarbamate (5.7 g). MS found: $(M+H)^+=406.3$.

Example 3a, Step 3: Methyltriphenylphosphonium bromide (1.2 g) was suspended in toluene (16 mL) prior to the addition of 0.5M potassium bis(trimethylsilyl)amide (5.8 mL) in toluene. After 1 h, this solution was cooled to 0° C. prior to the addition of benzyl (1S,2R,4R)-2-acetyl-4-(tert-butyldimethylsilyloxy)cyclohexylcarbamate (660 mg) in toluene (5.4 mL). After 20 min at 0° C., the reaction was quenched with saturated $NH_4Cl$ solution and extracted with EtOAc (2×). The organic extracts were combined, washed with brine, dried ($MgSO_4$), filtered, and concentrated. The resulting residue was purified by flash chromatography to afford benzyl (1S,2S,4R)-4 -(tert-butyldimethylsilyloxy)-2-(prop-1-en-2-yl)cyclohexylcarbamate (380 mg). MS found: $(M+H)^+=404.2$.

Example 3a, Step 4: Benzyl (1S,2S,4R)-4-(tert-butyldimethylsilyloxy)-2-(prop-1-en-2-yl)cyclohexylcarbamate (4.8 g) in MeOH (40 mL) was charged with 10% Pd/C, Degussa (600 mg). The reaction flask was evacuated and then back-filled with hydrogen; this was repeated three more times. The reaction was stirred under 1 atm of $H_2$ for 4 h and then filtered and concentrated to provide (1S,2S,4R)-4-(tert-butyldimethylsilyloxy)-2-isopropylcyclohexanamine (2.9 g). MS (ES+)=272.3 $(M+H)^+$.

Example 3a, Step 5: (1S,2S,4R)-4-(Tert-butyldimethylsilyloxy)-2-isopropylcyclohexanamine (2.9 g) was dissolved in DMF (36 mL) and cooled to 0° C. prior to the addition of N-Cbz methionine (5.5 g), 4-methyl morpholine (3.8 g), and BOP (8.7 g). The reaction was stirred for 12 h at rt and then partitioned between EtOAc and 1N HCl solution. The organic phases were combined, washed with saturated $NaHCO_3$ and brine, dried ($MgSO_4$), filtered, and concentrated in vacuo. The residue was purified by flash chromatography to afford benzyl (S)-1-((1S,2S,4R)-4-(tert-butyldimethylsilyloxy)-2-isopropylcyclohexylamino)-4-(methylthio)-1-oxobutan-2-ylcarbamate (5.3 g). MS found: $(M+H)^+=537.3$.

Example 3a, Step 6: Benzyl (S)-1-((1S,2S,4R)-4-(tert-butyldimethylsilyloxy)-2-isopropylcyclohexylamino)-4-(methylthio)-1-oxobutan-2-ylcarbamate (5.3 g) was dissolved in iodomethane (90 mL), and the resulting solution was stirred at rt for 72 h before being concentrated in vacuo. The residue was dissolved in methylene chloride, and the resulting solution was concentrated; this was repeated to afford the salt. MS found: $(M+H)^+=586.5$. This material was dissolved in DMSO (30 mL) and the solution was charged with $Cs_2CO_3$ (12.7 g). After 6 h, the reaction was partitioned between EtOAc and brine. The organic phase was dried ($MgSO_4$), filtered, and concentrated in vacuo. The residue was purified by flash chromatography to afford benzyl (S)-1-((1S,2S,4R)-4-hydroxy-2-isopropylcyclohexyl)-2-oxopyrrolidin-3-ylcarbamate [580 mg; MS found: $(M+H)^+=375.3$] and benzyl (S)-1-((1S,2S,4R)-4-(tert-butyldimethylsilyloxy)-2-isopropylcyclohexyl)-2-oxopyrrolidin-3-ylcarbamate [1.0 g; MS found: $(M+H)^+=489.4$].

Example 3a, Step 7: Benzyl (S)-1-((1S,2S,4R)-4-(tert-butyldimethylsilyloxy)-2-isopropylcyclohexyl)-2-oxopyrrolidin-3-ylcarbamate (1.0 g) was dissolved in a 4/1/1 mixture of $AcOH/THF/H_2O$ (60 mL). After 72 h, additional 4/1/1 mixture of $AcOH/THF/H_2O$ (30 mL) was added. This solution was stirred an additional 24 h before it was concentrated. The residue was dissolved in EtOAc and washed with saturated $NaHCO_3$, dried ($MgSO_4$), filtered, and concentrated in vacuo to afford benzyl (S)-1-((1S,2S,4R)-4-hydroxy-2-isopropylcyclohexyl)-2-oxopyrrolidin-3-ylcarbamate (750 mg). MS found: $(M+H)^+=375.3$.

Example 3a, Step 8: Benzyl (S)-1-((1S,2S,4R)-4-hydroxy-2-isopropylcyclohexyl)-2-oxopyrrolidin-3-ylcarbamate (333 mg) was dissolved in $CH_2Cl_2$ (5 mL) and cooled to 0° C. prior to the addition of Dess-Martin reagent (678.9 mg). This solution was warmed to rt over 1 h, and then was cooled to 0° C. prior to the addition of more Dess-Martin reagent (260 mg). After 1 h at rt, the reaction was quenched with $Et_2O$ and 1N NaOH. The organic extracts were combined, washed with saturated $Na_2S_2O_3$ and $NaHCO_3$ solutions, dried ($MgSO_4$), filtered, and concentrated to afford benzyl (S)-1-((1S,2S)-2-isopropyl-4-oxocyclohexyl)-2-oxopyrrolidin-3-ylcarbamate (350 mg). MS found: $(M+H)^+=373.4$.

Example 3a, Step 9: Benzyl (S)-1-((1S,2S)-2-isopropyl-4-oxocyclohexyl)-2-oxopyrrolidin-3-ylcarbamate (350 mg) was dissolved in $Ti(Oi-Pr)_4$ (2 mL) prior to the addition of iPr(Me)NH (642 mg). After 3 h, this solution was cooled to 0° C. prior to the addition of MeOH (3 mL) and $NaBH_4$ (66.8 mg). After 1 h at rt, the reaction was quenched with 0.5N NaOH solution and extracted with $CH_2Cl_2$ (2×). The organic extracts were combined, dried ($MgSO_4$), filtered, and concentrated to a mixture of diastereomers benzyl (S)-1-((1S,2S,4R/S)-2-isopropyl-4-(isopropyl(methyl)amino)cyclohexyl)-2-oxopyrrolidin-3-ylcarbamate (162.4 mg). MS found: $(M+H)^+=430.5$.

Example 3a, Step 10: Benzyl (S)-1-((1S,2S,4R/S)-2-isopropyl-4-(isopropyl(methyl)amino)cyclohexyl)-2-oxopyrrolidin-3-ylcarbamate (160 mg) was dissolved in MeOH (6 mL) prior to the addition of 20% $Pd(OH)_2$ (50 mg) in a Parr bottle. The bottle was evacuated and then back-filled with hydrogen; this was repeated three more times. The reaction was stirred under 60 psi of $H_2$ for 5 h and then filtered and concentrated. The resulting residue was dissolved in MeOH (6 mL) prior to the addition of 20% $Pd(OH)_2$ (75 mg) in a Parr bottle. The bottle was evacuated and then back-filled with hydrogen; this was repeated three more times. The reaction was stirred under 5.0 psi of $H_2$ for 24 h and then filtered and concentrated to provide (S)-3-amino-1-((1S,2S,4R/S)-2-isopropyl-4-(isopropyl(methyl)amino)cyclohexyl)pyrrolidin-2-one (101 mg). MS (ES+)=296.3 $(M+H)^+$.

Example 3a, Step 11: To a solution of (S)-3-amino-1-((1S,2S,4R/S)-2-isopropyl-4-(isopropyl(methyl)amino)cyclohexyl)pyrrolidin-2-one (85 mg) in EtOH (2.5 mL) was added triethylamine (0.2 mL) and 4-chloro-6-(trifluoromethyl) quinazoline (100.1 mg). The mixture was heated at 80° C. for 14 h before it was filtered and concentrated in vacuo. The residue was purified by chiral chromatography (AD column, EtOH as mobile phase) to afford (S)-1-((1S,2S,4R)-2-isopropyl-4-(isopropyl(methyl)amino)cyclohexyl)-3-(6-(trifluoromethyl)quinazolin-4-ylamino)pyrrolidin-2-one [52 mg; MS found: $(M+H)^+=492.4$] and (S)-1-((1S,2S,4S)-2-isopropyl-4-(isopropyl(methyl)amino)cyclohexyl)-3-(6-(trifluoromethyl)quinazolin-4-ylamino)pyrrolidin-2-one [8 mg; MS found: $(M+H)^+=492.4$].

TABLE 3-A

The compounds in the following table were made using the methods exemplified above. See Table 1-A for a complete description of the table headings.

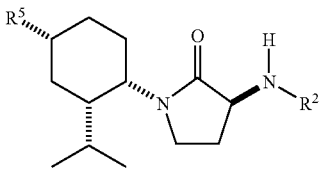

| Example | $R^5$ | $R^2$ | Step Altered | MS Data |
|---|---|---|---|---|
| 3a | i-Pr(Me)N | (4-quinazolinyl, 6-CF₃) | n/a | 492 |
| 3b | i-Pr(Me)N of (S) config. | (4-quinazolinyl, 6-CF₃) | See 3a | 492 |
| 3c | i-Pr(Me)N | (4-quinazolinyl, 6-OCF₃) | 3a, Step 11 | 508 |
| 3d | i-Pr(Me)N | (4-quinazolinyl, 6-Cl) | 3a, Step 11 | 458 |

TABLE 3-A-continued

The compounds in the following table were made using the methods exemplified above. See Table 1-A for a complete description of the table headings.

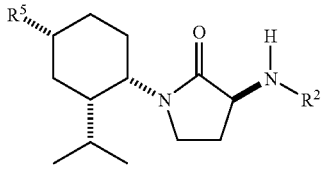

| Example | $R^5$ | $R^2$ | Step Altered | MS Data |
|---|---|---|---|---|
| 3e | i-Pr(Me)N | (6-tert-butyl-2-pyridyl carbonyl) | 3a, Step 11 | 457 |

TABLE 3-B

The chemical names of the specific examples illustrated in Table 3-A are tabulated below.

| Example | Name |
|---|---|
| 3a | (S)-1-((1S,2S,4R)-2-isopropyl-4-(isopropyl(methyl)amino)cyclohexyl)-3-(6-(trifluoromethyl)quinazolin-4-ylamino)pyrrolidin-2-one |
| 3b | (S)-1-((1S,2S,4S)-2-isopropyl-4-(isopropyl(methyl)amino)cyclohexyl)-3-(6-(trifluoromethyl)quinazolin-4-ylamino)pyrrolidin-2-one |
| 3c | (S)-1-((1S,2S,4R)-2-isopropyl-4-(isopropyl(methyl)amino)cyclohexyl)-3-(6-(trifluoromethoxy)quinazolin-4-ylamino)pyrrolidin-2-one |
| 3d | (S)-3-(6-chloroquinazolin-4-ylamino)-1-((1S,2S,4R)-2-isopropyl-4-(isopropyl(methyl)amino)cyclohexyl)pyrrolidin-2-one |
| 3e | 6-tert-butyl-N-((S)-1-((1S,2S,4R)-2-isopropyl-4-(isopropyl(methyl)amino)cyclohexyl)-2-oxopyrrolidin-3-yl)picolinamide |

Examples 4a-4d

Example 4a

Synthesis of N-((S)-1-((1S,2R,4R)-4-(isopropyl(methyl)amino)-2-methylcyclohexyl)-2-oxopyrrolidin-3-yl)-3-(trifluoromethyl)benzamide Example 4a, Step 1: (1R,2S,5R)-Tert-butyl 2-((S)-3-(benzyloxycarbonylamino)-2-oxopyrrolidin-1-yl)-7-oxo-6-azabicyclo[3.2.1]octane-6-carboxylate (2.0 g) was dissolved in THF (50 mL) and water (15 mL) prior to the addition of NaBH₄ (827 mg). After 5 h, the reaction was quenched with saturated NaHCO₃ solution and extracted with EtOAc (2×). The organic extracts were combined, dried (MgSO₄), filtered, and concentrated in vacuo to afford tert-butyl (1R,3R,4S)-4-

((S)-3-benzyloxycarbonylamino-2-oxopyrrolidin-1-yl)-3-(hydroxymethyl)cyclohexylcarbamate (2.1 g). MS (ES+)=462.5 (M+H)+.

Example 4a, Step 2: Tert-butyl (1R,3R,4S)-4-((S)-3-benzyloxycarbonylamino-2-oxopyrrolidin-1-yl)-3-(hydroxymethyl)cyclohexylcarbamate (2.0 g) was dissolved in THF (50 mL) prior to the addition of phenyl disulfide (190 mg) and n-BU$_3$P (0.16 mL). The reaction was heated at reflux for 12 h. After cooling to rt, the reaction was concentrated. The resulting residue was purified by flash chromatography to afford tert-butyl (1R,3R,4S)-4-((S)-3-benzyloxycarbonylamino-2-oxopyrrolidin-1-yl)-3-(phenylthiomethyl)cyclohexylcarbamate (200 mg). MS found: (M+H)+=554.4.

Example 4a, Step 3: Tert-butyl (1R,3R,4S)-4-((S)-3-benzyloxycarbonylamino-2-oxopyrrolidin-1-yl)-3-(phenylthiomethyl)cyclohexylcarbamate (150 mg) was dissolved in EtOH (2 mL) prior to the addition of Raney 2800 nickel (100 mg) in water. The reaction was heated at reflux for 12 h. After cooling to rt, the reaction was concentrated. The resulting residue was purified by flash chromatography to afford tert-butyl (1R,3R,4S)-4-((S)-3-benzyloxycarbonylamino-2-oxopyrrolidin-1-yl)-3-methylcyclohexylcarbamate (64 mg). MS found: (M+H)+=446.4.

Example 4a, Step 4: Tert-butyl (1R,3R,4S)-4-((S)-3-benzyloxycarbonylamino-2-oxopyrrolidin-1-yl)-3-methylcyclohexylcarbamate (91 mg) was dissolved in CH$_2$Cl$_2$ (3 mL) prior to the addition of trifluoroacetic acid (2 mL). After 1 h, the reaction was concentrated in vacuo. The resultant residue was dissolved in MeOH (3 mL) and charged with acetone (0.15 mL). The mixture was stirred for 5 min before being charged with NaCNBH$_3$ (68 mg). The reaction was stirred for 4 h and then charged with formaldehyde (0.5 mL of a 37% aq. solution). The mixture was stirred for 1.5 h, quenched with sat. NaHCO$_3$, and extracted with EtOAc (2×). The organic extracts were combined, dried (MgSO$_4$), filtered, and concentrated. The residue was purified by reverse phase HPLC (gradient elution, water/acetonitrile/TFA) to afford the TFA salt of (S)-3-benzyloxycarbonylamino-1-((1S,2R,4R)-4-(isopropyl(methyl)amino)-2-methylcyclohexyl)pyrrolidin-2-one (81 mg). MS found: (M+H)+=388.3.

Example 4a, Step 5: (S)-3-Benzyloxycarbonylamino-1-((1S,2R,4R)-4-(isopropyl(methyl)amino)-2-methylcyclohexyl)pyrrolidin-2-one (47 mg) in MeOH (5 mL) was charged with 20% Pd(OH)$_2$ (70 mg). The reaction flask was evacuated and then back-filled with hydrogen; this was repeated three more times. The reaction was stirred under 1 atm of H$_2$ for 4 h and then filtered and concentrated to provide (S)-3-amino-1-((1S,2R,4R)-4-(isopropyl(methyl)amino)-2-methylcyclohexyl)pyrrolidin-2-one (30 mg). MS (ES+)=268.3 (M+H)+.

Example 4a, Step 6: (S)-3-Amino-1-((1S,2R,4R)-4-(isopropyl(methyl)amino)-2-methylcyclohexyl)pyrrolidin-2-one (28 mg) was dissolved in DMF (1 mL) prior to the addition of 3-(trifluoromethyl)benzoic acid (37 mg), 4-methyl morpholine (0.07 mL), and BOP (86 mg). The reaction was stirred for 1 h before it was directly purified by reverse phase HPLC (gradient elution, water/acetonitrile/TFA) to afford the TFA salt of N-((S)-1-((1S,2R,4R)-4-(isopropyl(methyl)amino)-2-methylcyclohexyl)-2-oxopyrrolidin-3-yl)-3-(trifluoromethyl)benzamide (6 mg). MS found: (M+H)+=440.4.

Example 4d

Synthesis of (S)-1-((1S,2R,4R)-2-ethyl-4-(isopropyl (methyl)amino)-cyclohexyl)-3-(6-(trifluoromethyl) quinazolin-4-ylamino)pyrrolidin-2-one Example 4d, Step 1: Following the procedures described in Example 2a, Steps 1-4, and substituting methyl triphenylphosphonium iodide in Step 1, (1R,2S,5R)-2-benzyloxycarbonylamino-7-oxo-6-aza-bicyclo[3.2.1]octane-6-carboxylic acid tert-butyl ester was converted to {(3S)-1-[(1S,2R,4R)-4-tert-butoxycarbonylamino-2-ethyl-cyclohexyl]-2-oxo-pyrrolidin-3-yl}-carbamic acid benzyl ester. A portion of this material (995 mg, 2.2 mmol) was dissolved in 20 mL of 4:1 CH$_2$Cl$_2$/TFA. The resultant solution was stirred at RT for 3 h and concentrated in vacuo. The residue was dissolved in methylene chloride and concentrated in vacuo; this procedure was repeated twice more to afford benzyl (S)-1-((1S,2R,4R)-4-amino-2-ethylcyclohexyl)-2-oxopyrrolidin-3-ylcarbamate. MS found: (M+H)+=360.2.

Example 4d, Step 2: The benzyl (S)-1-((1S,2R,4R)-4-amino-2-ethylcyclohexyl)-2-oxopyrrolidin-3-ylcarbamate (assumed 2.2 mmol) was dissolved in 1,2-dichloroethane (27 mL) and the resulting solution was charged successively with acetic acid (0.27 mL), acetone, and NaHB(OAc)$_3$ (1.15 g) before being heated to 50° C. for 18 h. The reaction was concentrated in vacuo and the residue was dissolved in acetonitrile. The resulting solution was charged successively with formaldehyde and sodium cyanoborohydride. The reaction was concentrated in vacuo and purified via flash chromatography to afford benzyl (S)-1-((1S,2R,4R)-2-ethyl-4-(isopropyl(methyl)amino)cyclohexyl)-2-oxopyrrolidin-3-ylcarbamate (607 mg). MS found: (M+H)+=416.3.

Example 4d, Step 3: A sample of (S)-1-((1S,2R,4R)-2-ethyl-4-(isopropyl(methyl)amino)cyclohexyl)-2-oxopyrrolidin-3-ylcarbamate (100 mg) was dissolved in 2.5 mL of 33% HBr/AcOH and stirred for 25 min before being treated with Et$_2$O. A solid material appeared. The ether was decanted and the remaining solid was dried under vacuum to provide (S)-3-amino-1-((1S,2R,4R)-2-ethyl-4-(isopropyl(methyl) amino)cyclohexyl)pyrrolidin-2-one, bis-HBr salt, as a white solid (43 mg). MS found: (M+H)+=283.2.

Example 4d, Step 4: A sample of the bis-HBr salt of (S)-3-amino-1-((1S,2R,4R)-2-ethyl-4-(isopropyl(methyl) amino)cyclohexyl)pyrrolidin-2-one (147 mg) was dissolved in EtOH (5 mL) and the resulting solution was charged with triethylamine (0.55 mL) and 4-chloro-6-trifluoromethylquinazoline (183 mg) before being heated at 80° C. for 14 h. The reaction was cooled and concentrated under reduced pressure, and the residue was partitioned between diethyl ether and water. The organic phase was extracted twice with water. The combined aqueous extracts were lyophilized and the resultant powder was purified by RP-HPLC to afford (S)-1-((1S,2R,4R)-2-ethyl-4-(isopropyl(methyl)amino)cyclohexyl)-3-(6-(trifluoromethyl)quinazolin-4-ylamino)pyrrolidin-2-one. MS found: (M+H)+=478.4.

TABLE 4-A

The compounds in the following table were made using the methods exemplified above. See Table 1-A for a complete description of the table headings.

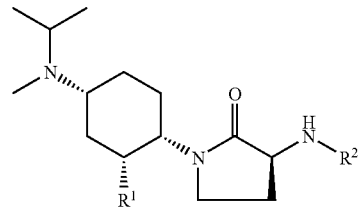

| Example | R¹ | R² | Step Altered | MS Data |
|---|---|---|---|---|
| 4a | Me | 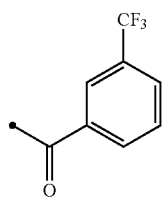 | n/a | 440 |
| 4b | Me | 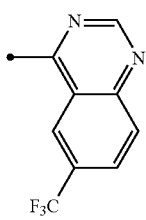 | 4a, Step 6 | 464 |
| 4c | Me | 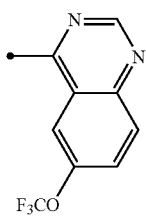 | 4a, Step 6 | 480 |
| 4d | Et | 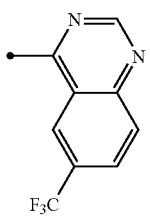 | n/a | 478 |

TABLE 4-B

The chemical names of the specific examples illustrated in Table 4-A are tabulated below.

| Example | Name |
|---|---|
| 4a | N-((S)-1-((1S,2R,4R)-4-(isopropyl(methyl)amino)-2-methylcyclohexyl)-2-oxopyrrolidin-3-yl)-3-(trifluoromethyl)benzamide |
| 4b | (S)-1-((1S,2R,4R)-4-(isopropyl(methyl)amino)-2-methylcyclohexyl)-3-(6-(trifluoromethyl)quinazolin-4-ylamino)pyrrolidin-2-one |
| 4c | (S)-1-((1S,2R,4R)-4-(isopropyl(methyl)amino)-2-methylcyclohexyl)-3-(6-(trifluoromethoxy)quinazolin-4-ylamino)pyrrolidin-2-one |
| 4d | (S)-1-((1S,2R,4R)-2-ethyl-4-(isopropyl(methyl)amino)-cyclohexyl)-3-(6-(trifluoromethyl)quinazolin-4-ylamino)pyrrolidin-2-one |

Examples 5a-5l

Example 5a

Synthesis of N-((S)-1-((1S,2R,4R)-4-(isopropyl(methyl)amino)-2-(methoxymethyl)cyclohexyl)-2-oxopyrrolidin-3-yl)-3-(trifluoromethyl)benzamide Example 5a, Step 1: A solution of (1R,2S,5R)-2-benzyloxycarbonyl-amino-7-oxo-6-aza-bicyclo[3.2.1]octane-6-carboxylic acid tert-butyl ester (2.0 g) in tetrahydrofuran (40 mL) was treated with water (8 mL) and then with sodium borohydride (1.01 g). The mixture was stirred at room temperature for 5 h, then was treated with aqueous sodium hydroxide (1.0 M, 100 mL) and stirred for 60 min. The mixture was extracted four times with ethyl acetate. The combined extracts were washed with saturated aqueous sodium chloride, dried over sodium sulfate, and concentrated under vacuum. The residue was recrystallized from ethyl acetate-hexane to provide (1R,3R,4S)-(4-benzyloxy-carbonylamino-3-hydroxymethyl-cyclohexyl)-carbamic acid tert-butyl ester as a white solid (1.44 g). MS found: $(M+H)^+=379.28$.

Example 5a, Step 2: (1R,3R,4S)-(4-benzyloxycarbonylamino-3-hydroxymethyl-cyclohexyl)carbamic acid tert-butyl ester (1.8 g) was dissolved in N,N-dimethylformamide (15 mL). Iodomethane (50 mL) was added, followed by silver oxide (5.52 g), and the mixture was stirred at room temperature overnight. The mixture was filtered through Celite and the solids were washed with ethyl acetate. The filtrate was washed sequentially with water and brine, dried over sodium sulfate and concentrated. The residue was purified by flash chromatography to provide (1R,3R,4S)-(4-benzyloxycarbonylamino-3-methoxymethylcyclohexyl)carbamic acid tert-butyl ester as a colorless gum (1.78 g). MS found: $(M+H)^+=393$.

Example 5a, Step 3: A solution of (1R,3R,4S)-(4-benzyloxycarbonylamino-3-methoxymethylcyclohexyl)carbamic acid tert-butyl ester (1.24 g) was dissolved in MeOH (20 mL) and the resultant solution was charged with 20 wt % Pd(OH)₂/C (300 mg) before being evacuated and purged with hydrogen. The reaction was stirred under 1 atm of H₂ for 3 h and then filtered through celite with EtOAc washings. The filtrate was concentrated in vacuo to provide (1R,3R,4S)-(4-amino-3-methoxymethyl-cyclohexyl)-carbamic acid tert-butyl ester (815 mg). MS found: $(M+H)^+=259.2$.

Example 5a, Step 4: A solution of (1R,3R,4S)-(4-amino-3-methoxymethyl-cyclohexyl)-carbamic acid tert-butyl ester (1.6 g, 6.2 mmol) in MeCN (30 mL) charged sequentially with N,N-diisopropylethylamine (2.2 mL, 12.4 mmol), N-Cbz Methionine (1.75 g, 6.2 mmol), and HATU (2.59 g, 6.82 mmol). The reaction was stirred overnight and concentrated in vacuo. The residue was dissolved in EtOAc and washed with 1 N HCl, sat. NaHCO₃, water, and brine. The organic phase was dried (Na₂SO₄), filtered, and concentrated in vacuo. The residue was chromatographed to provide (1R,3R,4S)-[4-(2S)-(2-benzyloxy-carbonylamino-4-methylsulfanylbutyrylamino)-3-methoxy-methylcyclohexyl]carbamic acid tert-butyl ester (1.74 g) as a white foam. MS found: $(M+H)^+=524.6$.

Example 5a, Step 5: A sample of (1R,3R,4S)-[4-(2S)-(2-benzyloxycarbonylamino-4-methylsulfanylbutyrylamino)-3-methoxymethylcyclohexyl]carbamic acid tert-butyl ester (0.95 g, 1.82 mmol) was dissolved in iodomethane (50 mL) with vigorous mechanical action and the resulting solution was stirred at RT for ca. 20 h before being concentrated in vacuo. The residue was dissolved in methylene chloride and the resultant solution was concentrated; this procedure was repeated twice more before the material was placed under high vacuum for 12 h. The product solid was dissolved in THF (50 mL) and the resultant solution was cooled to 0° C. and charged with sodium hydride (218 mg, 9.1 mmol) in one portion. The reaction was allowed to proceed for 2.5 h before being quenched with sat. NH₄Cl and extracted with EtOAc. The organic extracts were combined, dried, filtered, and concentrated in vacuo. The residue was purified by chromatography to afford (3S)-[1-(1S,2R,4R)-(4 -tert-butoxy-carbonylamino-2-methoxymethylcyclohexyl)-2-oxopyrrolidin-3-yl] carbamic acid benzyl ester (570 mg). MS found: (M+H)⁺=476.3.

Example 5a, Step 6: A sample of (3S)-[1-(1S,2R,4R)-(4-tert-butoxy-carbonylamino-2-methoxymethylcyclohexyl)-2-oxopyrrolidin-3-yl]carbamic acid benzyl ester (0.57 g) was subjected to the procedures described in Example 2c, Steps 1 and 2 to afford a crude product. This was purified by RP-HPLC to afford the TFA salt of benzyl (S)-1-((1S,2R,4R)-4-(isopropyl(methyl)amino)-2-(methoxymethyl)cyclohexyl)-2-oxopyrrolidin-3-ylcarbamate as a white powder (415 mg). MS found: (M+H)⁺=432.4.

Example 5a, Step 7: A sample of the TFA salt of benzyl (S)-1-((1S,2R,4R)-4-(isopropyl(methyl)amino)-2-(methoxymethyl)cyclohexyl)-2-oxopyrrolidin-3-ylcarbamate (75 mg) was converted to (S)-3-amino-1-((1S,2R,4R)-4-(isopropyl(methyl)amino)-2-(methoxymethyl)cyclohexyl)pyrrolidin-2-one (57 mg) using the method outlined in Example 5a, Step 3 (substituting EtOH for MeOH as solvent). MS found: (M+H)⁺=298.3.

Example 5a, Step 8: Following the procedure outlined in 2c, Step 4, a sample of (S)-3-amino-1-((1S,2R,4R)-4-(isopropyl(methyl)amino)-2-(methoxymethyl)cyclohexyl)pyrrolidin-2-one was converted to the title compound. Purification by RP-HPLC provided the TFA salt of N-((S)-1-((1S,2R,4R)-4-(isopropyl(methyl)amino)-2-(methoxymethyl)cyclohexyl)-2-oxopyrrolidin-3-yl)-3-(trifluoromethyl)benzamide as a white powder. MS found: (M+H)⁺=470.3.

Example 5j

Synthesis of N-((S)-1-((1S,2S,4R)-4-(isopropyl(methyl)amino)-2-(2-methoxyethyl)cyclohexyl)-2-oxopyrrolidin-3-yl)-3-(trifluoromethyl)benzamide Example 5j, Step 1: Following the protocol described above in Example 2a, Step 1, 1.3 g of tert-butyl (1R,2S,5R,7R/S)-2-(benzyloxycarbonylamino)-7-hydroxy-6-aza-bicyclo[3.2.1]octane-6-carboxylate was combined with a solution of ylide formed from 1.7 g of methyl triphenyl phosphonium iodide and 8.5 mL of 0.5 M KHMDS to afford [(1S,2R,4R)-[4-tert-butoxycarbonylamino-2-(vinyl)-cyclohexyl]-carbamic acid benzyl ester after silica gel chromatography (0.50 g). MS found: (M+H)⁺=375.2.

Example 5j, Step 2: The compound [(1S,2R,4R)-[4-tert-butoxycarbonylamino-2-(vinyl)-cyclohexyl]-carbamic acid benzyl ester (0.82 g, 2.2 mmol) was dissolved in THF (15 mL). The resultant solution was cooled to 0° C. and charged with 9-BBN (11 mL of a 0.5 M solution in THF). The mixture was stirred for 20 h at RT and then quenched sequentially with aqueous sodium acetate (0.6 g in 1.5 mL water) and 30% hydrogen peroxide (1.5 mL). This was stirred at RT for 14 h and partitioned between EtOAc and sat. NaHCO₃. The aqueous phase was extracted with EtOAc, and the combined organic extracts were washed with brine, dried (Na₂SO₄), filtered, and concentrated in vacuo. The residue was purified by silica gel chromatography to afford [(1S,2R,4R)-[4-tert-butoxycarbonylamino-2-(hydroxyethyl)-cyclohexyl]-carbamic acid benzyl ester (0.42 g) as a white foam. MS found: (M+H)⁺=393.

Example 5j, Step 3: A solution of [(1S,2R,4R)-[4-tert-butoxycarbonylamino-2-(hydroxyethyl)-cyclohexyl]-carbamic acid benzyl ester (0.42 g, 1.07 mmol) in DMF (4 mL) was charged with iodomethane (20 mL) and Ag₂O (1.24 g, 5.35 mmol) and stirred at RT for 14 h. The mixture was filtered and the filtrate was diluted with sat. NaHCO₃ and minimum EtOAc. The mixture was separated (organic on bottom). The aqueous was extracted with EtOAc, and the combined organic extracts were washed with brine, dried (Na₂SO₄), filtered, and concentrated in vacuo. The residue was purified by silica gel chromatography to afford [(1S,2R,4R)-[4-tert-butoxycarbonylamino-2-(methoxyethyl)-cyclohexyl]-carbamic acid benzyl ester (0.255 g). MS found: (M+H)⁺=429.2.

Example 5j, Step 4: A sample of [(1S,2R,4R)-[4-tert-butoxycarbonylamino-2(methoxyethyl)-cyclohexyl]-carbamic acid benzyl ester was carried through the procedures detailed in 5, Steps 3-8 to afford the title compound, N-((S)-1-((1S,2S,4R)-4-(isopropyl(methyl)amino)-2-(2-methoxyethyl)cyclohexyl)-2-oxopyrrolidin-3-yl)-3-(trifluoromethyl)benzamide, as a white powder after RP-HPLC purification and lyopholization. MS found: (M+H)⁺=484.4.

TABLE 5-A

The compounds in the following table were made using the methods exemplified above. See Table 1-A for a complete description of the table headings.

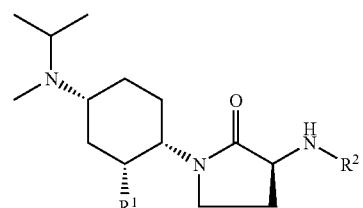

| Example | R¹ | R² | Step Altered | MS Data |
|---|---|---|---|---|
| 5a | MeOCH₂ | 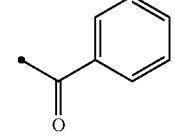 | n/a | 470.3 |
| 5b | MeOCH₂ | 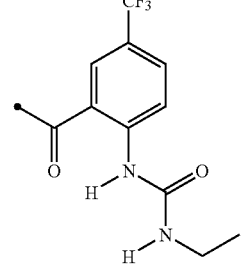 | 5a, Step 8 | 556.4 |

TABLE 5-A-continued

The compounds in the following table were made using the methods exemplified above. See Table 1-A for a complete description of the table headings.

| Example | R¹ | R² | Step Altered | MS Data |
|---------|-----|-----|-------------|---------|
| 5c | MeOCH₂ | 6-(CF₃)-quinazolin-4-yl | 5a, Step 8 (See 2k) | 494.3 |
| 5d | MeOCH₂ | 6-Cl-quinazolin-4-yl | 5a, Step 8 (See 2k) | 460.3 |
| 5e | MeOCH₂ | 6-(OCF₃)-quinazolin-4-yl | 5a, Step 8 (See 2k) | 510.3 |
| 5f | MeOCH₂ | 6-(2-MeO-phenyl)-quinazolin-4-yl | 5a, Step 8 (See 2k) | 532.5 |
| 5g | EtOCH₂ | 3-(CF₃)-benzoyl | 5a, Steps 2 & 8 | 484.4 |
| 5h | EtOCH₂ | 6-(CF₃)-quinazolin-4-yl | 5a, Steps 2 & 8 (See 2k) | 508.4 |
| 5i | EtOCH₂ | 2-(N'-ethylureido)-4-(CF₃)-benzoyl | 5a, Steps 2 & 8 | 570.5 |
| 5j | MeOCH₂CH₂ | 3-(CF₃)-benzoyl | n/a | 484.4 |
| 5k | MeOCH₂CH₂ | 2-(N'-ethylureido)-4-(CF₃)-benzoyl | 5j, final step | 570.5 |
| 5l | MeOCH₂CH₂ | 6-(CF₃)-quinazolin-4-yl | 5j, final step (see 2k) | 508.4 |

TABLE 5-B

The chemical names of the specific examples illustrated in Table 5-A are tabulated below.

| Example | Name |
|---|---|
| 5a | N-((S)-1-((1S,2R,4R)-4-(isopropyl(methyl)amino)-2-(methoxymethyl)cyclohexyl)-2-oxopyrrolidin-3-yl)-3-(trifluoromethyl)benzamide |
| 5b | 1-(2-(((S)-1-((1S,2R,4R)-4-(isopropyl(methyl)amino)-2-(methoxymethyl)cyclohexyl)-2-oxopyrrolidin-3-yl)carbamoyl)-4-(trifluoromethyl)phenyl)-3-ethylurea |
| 5c | (S)-1-((1S,2R,4R)-4-(isopropyl(methyl)amino)-2-(methoxymethyl)cyclohexyl)-3-(6-(trifluoromethyl)quinazolin-4-ylamino)pyrrolidin-2-one |
| 5d | (S)-3-(6-chloroquinazolin-4-ylamino)-1-((1S,2R,4R)-4-(isopropyl(methyl)amino)-2-(methoxymethyl)cyclohexyl)pyrrolidin-2-one |
| 5e | (S)-1-((1S,2R,4R)-4-(isopropyl(methyl)amino)-2-(methoxymethyl)cyclohexyl)-3-(6-(trifluoromethoxy)quinazolin-4-ylamino)pyrrolidin-2-one |
| 5f | (S)-1-((1S,2R,4R)-4-(isopropyl(methyl)amino)-2-(methoxymethyl)cyclohexyl)-3-(6-(2-methoxyphenyl)quinazolin-4-ylamino)pyrrolidin-2-one |
| 5g | N-((S)-1-((1S,2R,4R)-2-(ethoxymethyl)-4-(isopropyl(methyl)amino)cyclohexyl)-2-oxopyrrolidin-3-yl)-3-(trifluoromethyl)benzamide |
| 5h | (S)-1-((1S,2R,4R)-2-(ethoxymethyl)-4-(isopropyl(methyl)amino)cyclohexyl)-3-(6-(trifluoromethyl)quinazolin-4-ylamino)pyrrolidin-2-one |
| 5i | 1-(2-(((S)-1-((1S,2R,4R)-2-(ethoxymethyl)-4-(isopropyl(methyl)amino)cyclohexyl)-2-oxopyrrolidin-3-yl)carbamoyl)-4-(trifluoromethyl)phenyl)-3-ethylurea |
| 5j | N-((S)-1-((1S,2S,4R)-4-(isopropyl(methyl)amino)-2-(2-methoxyethyl)cyclohexyl)-2-oxopyrrolidin-3-yl)-3-(trifluoromethyl)benzamide |
| 5k | (S)-1-((1S,2S,4R)-4-(isopropyl(methyl)amino)-2-(2-methoxyethyl)cyclohexyl)-3-(6-(trifluoromethyl)quinazolin-4-ylamino)pyrrolidin-2-one |
| 5l | 1-(2-(((S)-1-((1S,2S,4R)-4-(isopropyl(methyl)amino)-2-(2-methoxyethyl)cyclohexyl)-2-oxopyrrolidin-3-yl)carbamoyl)-4-(trifluoromethyl)phenyl)-3-ethylurea |

Examples 6a-6k

Example 6a

Synthesis of 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one Example 6a, Step 1: To a stirred solution of (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate (520 mg, 1.14 mmol) in THF (16 mL) at 0° C. was added 2.0 M ethyl magnesium choride in THF (1.7 mL, 3.4 mmol). The mixture was stirred for 20 min at 0° C. and for 30 min at rt. After cooling to 0° C. the reaction was quenched with sat. NH$_4$Cl and extracted with EtOAc (2x). The organic extracts were combined, washed with brine, dried (Na$_2$SO$_4$), filtered, and concentrated in vacuo to afford the hemi-aminal as an oil. MS found: (M+H)$^+$=488.1.

Example 6a, Step 2: To a solution of the hemi-aminal (1.27 mmol) of the Step 1 in THF (12 mL) and water (6 mL) was added NaBH$_4$ (85 mg, 2.25 mmol) at 0° C., and the mixture was stirred for 20 min at 0° C. and for 40 min at rt. The reaction was quenched with sat. NH$_4$Cl, and the mixture was extracted with EtOAc (2x). The organic extracts were combined, washed with brine, dried (Na$_2$SO$_4$), filtered, and concentrated in vacuo. Purification of the residue via flash chromatography on silica gel with elution by 6:4, 7:3, then 8:2 EtOAc and hexane afforded two diasteromers (~1:5 fast and slow isomers) of the desired ((1R,3R,4S)-4-((S)-3-(benzyloxycarbonyl)amino-2-oxopyrrolidin-1-yl)-3-(1-hydroxypropyl)cyclohexyl)carbamic acid tert-buty ester as oils. MS found: (M+H)$^+$=490.3.

Example 6a, Step 3: To a solution of the slow isomer of the hydroxypropyl compound (419 mg, 0.86 mmol) of the Step 2 in CH$_2$Cl$_2$ (4 mL) was added trifluoroacetic acid (0.66 mL, 8.6 mmol), and the mixture was stirred for 75 min. The acid and solvent were evaporated off, and the residue was dissolved in CH$_2$Cl$_2$. The solution was washed with sat. Na$_2$CO$_3$, dried (Na$_2$SO$_4$), filtered, and concentrated in vacuo to afford the desired benzyl (S)-1-((1S,2R,4R)-4-amino-2-(1-hydroxypropyl)cyclohexyl)-2-oxopyrrolidin-3-ylcarbamate as an oil. MS found: (M+H)$^+$=390.2.

Example 6a, Step 4: To a solution of benzyl (S)-1-((1S,2R,4R)-4-amino-2-(1-hydroxypropyl)cyclohexyl)-2-oxopyrrolidin-3-ylcarbamate (0.86 mmol) in MeOH (5 mL) was added acetone (0.6 mL), and the mixture was stirred for 10 minutes. Then sodium triacetoxyborohydride (544 mg, 2.58 mmol) was added, and the mixture was stirred for 4 h at rt. At the end of the stirring 37% aq. HCHO (0.4 mL) was added, and the mixture was stirred for 30 min at rt. Finally additional sodium triacetoxyborohydride (181 mg, 0.86 mmol) was added, and the mixture was stirred for 18 h at rt. The reaction was quenched by addition of sat. Na$_2$CO$_3$, and the product was extracted with EtOAc (3x). The combined extracts were washed with brine, dried (Na$_2$SO$_4$), filtered, and concentrated in vacuo. Purification of the residue via flash chromatography on silica gel with elution by 1:9:90 cNH$_4$OH—MeOH—CH$_2$Cl$_2$ afforded the desired benzyl (S)-1-((1S,2R,4R)-2-(1-hydroxypropyl)-4-(isopropyl(methyl)amino)cyclohexyl)-2-oxopyrrolidin-3-ylcarbamate (267 mg) as an oil.

Example 6a, Step 5: A solution of benzyl (S)-1-((1S,2R,4R)-2-(1-hydroxypropyl)-4-(isopropyl(methyl)amino)cyclohexyl)-2-oxopyrrolidin-3-ylcarbamate (267 mg) in MeOH (15 mL) was charged with 10% Pd/C, Degussa (~100 mg). The reaction flask was evacuated and then back-filled with hydrogen; this was repeated two more times. The reaction was stirred under 60 psi of H$_2$ for 4 h and then filtered and concentrated in vacuo to afford the desired (S)-3-amino-1-((1S,2R,4R)-2-(1-hydroxypropyl)-4-(isopropyl(methyl)amino)cyclohexyl)pyrrolidin-2-one (190 mg) as an oil.

Example 6a, Step 6: A solution of (S)-3-amino-1-((1S,2R,4R)-2-(1-hydroxypropyl)-4-(isopropyl(methyl)amino)cyclohexyl)pyrrolidin-2-one (47.6 mg, 0.153 mmol) in EtOH (3 mL) was charged with 4-chloro-6-(trifluoromethyl)quinazoline (46.3 mg, 0.2 mmol) and triethylamine (0.064 mL, 0.46 mmol). The mixture was heated for 30 min at 100° C. in the microwave oven. Solvent was evaporated off, and the residue was purified by flash chromatography on silica gel with elution by 0.8:7.2:92 cNH$_4$OH—MeOH—CH$_2$Cl$_2$ to afford the titled compound 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one (47.3 mg) as a solid. MS found: $(M+H)^+=508.3$ Example 6b Synthesis of 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one The slow isomer of the hydroxypropyl compound of the Example 6a, Step 2 was converted to the titled compound 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one, which is isomeric to the Example 6a at the hydroxyl group of the propyl chain, by the methods described in the Example 6a, Steps 3-6. MS found: $(M+H)^+=508.3$ Example 6c Synthesis of N-(1-((1S,2R,4R)-2-(1-hydroxypropyl)-4-(isopropyl(methyl)amino)cyclohexyl)-2-oxopyrrolidin-3-yl)-3-(trifluoromethyl)benzamide To a solution of (S)-3-amino-1-((1S,2R,4R)-2-(1-hydroxypropyl)-4-(isopropyl(methyl)amino)cyclohexyl)pyrrolidin-2-one (47.6 mg, 0.153 mmol) in $CH_3CN$ (2 mL) were added triethylamine (0.08 mL, 0.46 mmol), 3-trifluoromethylbenzoic acid (38 mg, 0.2 mmol), and TBTU (73.7 mg, 0.23 mmol), and the mixture was stirred for 8 h at rt. The reaction mixture was diluted with EtOAc, and washed with 1N-NaOH and water. The organic layer was dried ($Na_2SO_4$), filtered, and concentrated in vacuo. The residue was purified by flash chromatography on silica gel with elution by 0.8:7.2:92 $cNH_4OH$—MeOH—$CH_2Cl_2$ to afford the titled compound N-(1-((1S,2R,4R)-2-((R)-1-hydroxypropyl)-4-(isopropyl(methyl)amino)cyclohexyl)-2-oxopyrrolidin-3-yl)-3-(trifluoromethyl)benzamide (38.5 mg) as a solid. MS found: $(M+H)^+=484.3$.

Example 6f

Synthesis of 1-((1S,2R,4R)-2-(1-hydroxyethyl)-4-(isopropyl(methyl)amino)cyclohexyl)-3-(6-(trifluoromethyl)quinazolin-4-ylamino)pyrrolidin-2-one The titled compound 1-((1S,2R,4R)-2-(1-hydroxyethyl)-4-(isopropyl(methyl)amino)cyclohexyl)-3-(6-(trifluoromethyl)quinazolin-4-ylamino)pyrrolidin-2-one was prepared by the methods described in the Example 6a, Steps 1-6 starting from (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate using methylmagnesium bromide instead of ethylmagnesium chloride in the Step 1. MS found: $(M+H)^+=494.3$.

Example 6g

Synthesis of N-(1-((1S,2R,4R)-2-(1-hydroxyethyl)-4-(isopropyl(methyl)amino)cyclohexyl)-2-oxopyrrolidin-3-yl)-3-(trifluoromethyl)benzamide The titled compound N-(1-((1S,2R,4R)-2-(1-hydroxyethyl)-4-(isopropyl(methyl)amino)cyclohexyl)-2-oxopyrrolidin-3-yl)-3-(trifluoromethyl)benzamide was prepared by the methods described in the Example 6c using (S)-3-amino-1-((1S,2R,4R.)-2-(1-hydroxyethyl)-4-(isopropyl(methyl)amino)cyclohexyl)pyrrolidin-2-one, which was prepared in the Step 5 of the Example 6f. MS found: $(M+H)^+=470.3$.

Example 6h

Synthesis of 1-((1S,2R,4R)-2-(hydroxymethyl)-4-(isopropyl(methyl)amino)cyclohexyl)-3-(6-(trifluoromethyl)quinazolin-4-ylamino)pyrrolidin-2-one To a solution of ((1R,2S,5R)-5-(isopropyl(methyl)amino)-2-(2-oxo-3-(6-(trifluoromethyl)quinazolin-4-ylamino)pyrrolidin-1-yl)cyclohexyl)methyl isobutyrate (Example 7a, 4 mg) in MeOH (1 mL) was added 1N-NaOH (0.1 mL), and the mixture was stirred for 9 h at rt. After neutralizing with sat. $NH_4Cl$, it was extracted with EtOAc (2×). The combined extracts were washed with brine, dried ($Na_2SO_4$), filtered, and concentrated in vacuo. The residue was purified by flash chromatography on silica gel with elution by 0.8:7.2:92 $cNH_4OH$—MeOH—$CH_2Cl_2$ to afford the titled compound 1-((1S,2R,4R)-2-(hydroxymethyl)-4-(isopropyl(methyl)amino)cyclohexyl)-3-(6-(trifluoromethyl)quinazolin-4-ylamino)pyrrolidin-2-one. MS found: $(M+H)^+=480.2$.

Example 6i

Synthesis of 1-((1S,2R,4R)-2-(2-hydroxypropan-2-yl)-4-(isopropyl(methyl)amino)cyclohexyl)-3-(6-(trifluoromethyl)quinazolin-4-ylamino)pyrrolidin-2-one Example 6i, Step 1: To 3M-methylmagnesium bromide in ether (1.1 mL, 3.3 mmol) at 0° C. was added a solution of (1R,2S,5R)-methyl 2-((S)-3-(benzyloxycarbonyl)amino-2-oxopyrrolidin-1-yl)-5-(isopropyl(methyl)-amino)cyclohexanecarboxylate (295 mg, 0.66 mmol) in THF dropwise, and the mixture was stirred for 2.5 h at 0~10° C. and for 40 min at 10~25° C. The reaction was quenched by addition of sat. $NH_4Cl$, and the product was extracted with EtOAc (3×). The combined extracts were washed with brine, dried ($Na_2SO_4$), filtered, and concentrated in vacuo. The residue was purified by flash chromatography on silica gel with elution by 0.8:7.2:92 $cNH_4OH$—MeOH—$CH_2Cl_2$ to afford the desired product benzyl (S)-1-((1S,2R,4R)-2-(2-hydroxypropan-2-yl)-4-(isopropyl(methyl)amino)cyclohexyl)-2-oxopyrrolidin-3-ylcarbamate (164 mg) and the recovered starting material (119 mg).

Example 6i, Step 2: A solution of benzyl (S)-1-((1S,2R,4R)-2-(2-hydroxypropan-2-yl)-4-(isopropyl(methyl)amino)cyclohexyl)-2-oxopyrrolidin-3-ylcarbamate (224 mg) in MeOH (15 mL) was charged with 10% Pd/C, Degussa (~100 mg). The reaction flask was evacuated and then back-filled with hydrogen; this was repeated two more times. The reaction was stirred under 60 psi of $H_2$ for 7 h and then filtered and concentrated in vacuo to afford the desired (S)-3-amino-1-((1S,2R,4R)-2-(2-hydroxypropan-2-yl)-4-(isopropyl(methyl)amino)cyclohexyl)pyrrolidin-2-one as an oil. MS found: (M+H)⁺=312.2.

Example 6i, Step 3: By the methods described in Example 6a, Step 6, (S)-3-amino-1-((1S,2R,4R)-2-(2-hydroxypropan-2-yl)-4-(isopropyl(methyl)amino)cyclohexyl)pyrrolidin-2-one was converted to the desired 1-((1S,2R,4R)-2-(2-hydroxypropan-2-yl)-4-(isopropyl(methyl)amino)cyclohexyl)-3-(6-(trifluoromethyl)quinazolin-4-ylamino)pyrrolidin-2-one. MS found: (M+H)⁺=508.3.

Example 6j

Synthesis of N-((S)-1-((1S,2R,4R)-2-(2-hydroxypropan-2-yl)-4-(isopropyl(methyl)amino)cyclohexyl)-2-oxopyrrolidin-3-yl)-3-(trifluoromethyl)benzamide By the methods described in Example 6c, (S)-3-amino-1-((1S,2R,4R)-2-(2-hydroxypropan-2-yl)-4-(isopropyl(methyl)amino)cyclohexyl)pyrrolidin-2-one was converted to the desired N-((S)-1-((1S,2R,4R)-2-(2-hydroxypropan-2-yl)-4-(isopropyl(methyl)amino)cyclohexyl)-2-oxopyrrolidin-3-yl)-3-(trifluoromethyl)benzamide. MS found: (M+H)⁺=484.4.

TABLE 6-A

The compounds in the following table were made using the methods exemplified above. See Table 1-A for a complete description of the table headings.

| Example | $R^{6'}$ | $R^{6''}$ | $R^2$ | Step Altered | MS Data |
|---------|----------|-----------|-------|--------------|---------|
| 6a | H | Et | 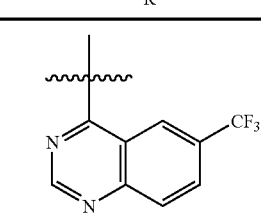 | n/a | 508.3 |
| 6b | H | Et | 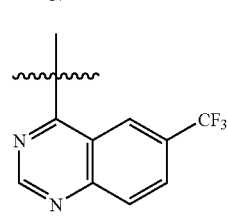 | n/a | 508.3 |
| 6c | H | Et | 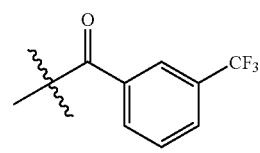 | n/a | 484.3 |
| 6d | H | Et | 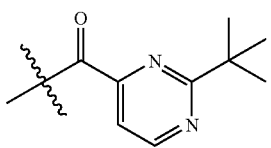 | 6c, Step 6 | 474.4 |
| 6e | H | Et | 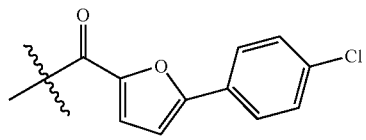 | 6c, Step 6 | 516.3 |

TABLE 6-A-continued
The compounds in the following table were made using the methods exemplified above. See Table 1-A for a complete description of the table headings.
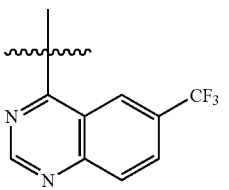
| Example | R⁶' | R⁶" | R² | Step Altered | MS Data |
|---------|-----|-----|-----|--------------|---------|
| 6f | H | Me | 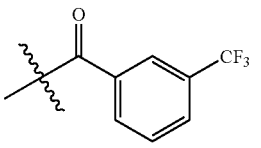 | n/a | 494.3 |
| 6g | H | Me | 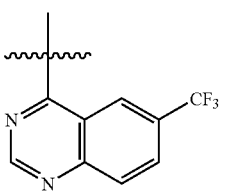 | n/a | 470.3 |
| 6h | H | H | 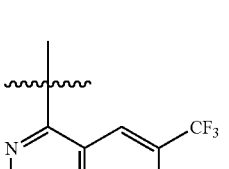 | n/a | 480.2 |
| 6i | Me | Me | 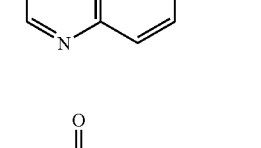 | n/a | 508.3 |
| 6j | Me | Me | 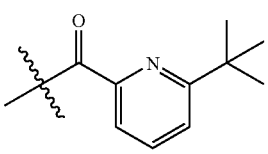 | n/a | 484.4 |
| 6k | Me | Me |  | 6j, Step 3 | 474.4 |

TABLE 6-B

The chemical names of the specific examples illustrated in Table 6-A are tabulated below.

| Example | Name |
| --- | --- |
| 6a | 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one |
| 6b (diastereomer of 6a) | 1-((1S,2R,4R)-2-(1-hydroxypropyl)-4-(isopropyl(methyl)amino)cyclohexyl)-3-(6-(trifluoromethyl)quinazolin-4-ylamino)pyrrolidin-2-one |
| 6c | N-(1-((1S,2R,4R)-2-(1-hydroxypropyl)-4-(isopropyl(methyl)amino)cyclohexyl)-2-oxopyrrolidin-3-yl)-3-(trifluoromethyl)benzamide |
| 6d | N-(1-((1S,2R,4R)-2-(1-hydroxypropyl)-4-(isopropyl(methyl)amino)cyclohexyl)-2-oxopyrrolidin-3-yl)-2-(tert-butyl)pyrimidine-4-carboxamide |
| 6e | 5-(4-chlorophenyl)-N-(1-((1S,2R,4R)-2-(1-hydroxypropyl)-4-(isopropyl(methyl)amino)cyclohexyl)-2-oxopyrrolidin-3-yl)furan-2-carboxamide |
| 6f | 1-((1S,2R,4R)-2-(1-hydroxyethyl)-4-(isopropyl(methyl)amino)cyclohexyl)-3-(6-(trifluoromethyl)quinazolin-4-ylamino)pyrrolidin-2-one |
| 6g | N-(1-((1S,2R,4R)-2-(1-hydroxyethyl)-4-(isopropyl(methyl)amino)cyclohexyl)-2-oxopyrrolidin-3-yl)-3-(trifluoromethyl)benzamide |
| 6h | 1-((1S,2R,4R)-2-(hydroxymethyl)-4-(isopropyl(methyl)amino)cyclohexyl)-3-(6-(trifluoromethyl)quinazolin-4-ylamino)pyrrolidin-2-one |
| 6i | 1-((1S,2R,4R)-2-(2-hydroxypropan-2-yl)-4-(isopropyl(methyl)amino)cyclohexyl)-3-(6-(trifluoromethyl)quinazolin-4-ylamino)pyrrolidin-2-one |
| 6j | N-((S)-1-((1S,2R,4R)-2-(2-hydroxypropan-2-yl)-4-(isopropyl(methyl)amino)cyclohexyl)-2-oxopyrrolidin-3-yl)-3-(trifluoromethyl)benzamide |
| 6k | 6-tert-butyl-N-((S)-1-((1S,2R,4R)-2-(2-hydroxypropan-2-yl)-4-(isopropyl(methyl)amino)cyclohexyl)-2-oxopyrrolidin-3-yl)picolinamide |

Examples 7a-7f

Example 7a

Synthesis of ((1R,2S,5R)-5-(isopropyl(methyl) amino)-2-(2-oxo-3-(6-(trifluoromethyl)quinazolin-4-ylamino)pyrrolidin-1-yl)cyclohexyl)methyl isobutyrate Example 7a, Step 1: To a solution of (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate (4.55 g, 9.94 mmol) in THF (50 mL) and water (50 mL) was added NaBH$_4$, and the mixture was stirred for 5 h at rt. After quenching the reaction with sat. NaHCO$_3$, the product was extracted with EtOAc (2×). The combined extracts were washed with brine, dried (MgSO$_4$), filtered, and concentrated in vacuo to give an oily residue, which crystallized upon tritulation with 4:6 EtOAc and hexane to provide pure ((1R,3R,4S)-4-((S)-3-(benzyloxycarbonyl)amino-2-oxopyrrolidin-1-yl)-3-(hydroxymethyl)cyclohexyl)carbamic acid tert-butyl ester (2.61 g).

Example 7a, Step 2: To a solution of the hydroxymethyl compound (2.61 g, 5.66 mmol) of the Step 1 in CH$_2$Cl$_2$ (22 mL) was added trifluoroacetic acid (4.36 mL, 56.6 mmol), and the mixture was stirred for 2 h at rt. The acid and solvent were evaporated off, and the residue was dissolved in EtOAc The solution was neutralized with sat. NaHCO$_3$, and EtOAc and water were evaporated off in vacuo. The solid residue was treated in MeOH and filtered. The filtrate was evaporated to give the desired benzyl (S)-1-((1S,2R,4R)-4-amino-2-(hydroxymethyl)cyclohexyl)-2-oxopyrrolidin-3-ylcarbamate as a waxy solid.

Example 7a, Step 3: To a solution of the crude product of the Step 2 in dichloroethane (52 mL) was added acetone (4.5 mL), and the mixture was stirred for 1 h at rt. Then sodium triacetoxyborohydride (3.9 g, 18.4 mmol) was added, and the mixture was stirred for 16 h at rt. A large amount of solid stayed out of the solution. At the end of the stirring 37% aq. HCHO (2.9 mL) was added, and MeOH (20 mL) was also added to make the solution homogeneous. After stirring for 1 h additional sodium triacetoxyborohydride (2 g, 9.4 mmol) was added, and the mixture was stirred for 2 h at rt. Then another 2 g portion of triacetoxyborohydride (9.4 mmol) was added and stirring continued for 20 h. The reaction was quenched by addition of sat. Na$_2$CO$_3$, and the product was extracted with EtOAc (3×). The combined extracts were washed with brine, dried (Na$_2$SO$_4$), filtered, and concentrated in vacuo. The residue was purified by column chromatography on silica gel with elution by 1:9:90 cNH$_4$OH—MeOH—CH$_2$Cl$_2$ to afford 0.8 g of benzyl (S)-1-((1S,2R,4R)-2-(hydroxymethyl)-4-(isopropyl(methyl)amino)cyclohexyl)-2-oxopyrrolidin-3-ylcarbamate, MS found: (M+H)$^+$=418.2, and 1.1 g of benzyl (S)-1-((1S,2R,4R)-4-(dimethylamino)-2-(hydroxymethyl)cyclohexyl)-2-oxopyrrolidin-3-ylcarbamate MS found: (M+H)$^+$=390.2, as crystals.

Example 7a, Step 4: To a stirred solution of (S)-1-((1S,2R,4R)-2-(hydroxymethyl)-4-(isopropyl(methyl)amino)cyclohexyl)-2-oxopyrrolidin-3-ylcarbamate (300 mg, 0.77 mmol) in pyridine (3 mL) were added isobutyryl chloride (0.16 mL, 1.54 mmol) and 4-(dimethylamino)pyridine (20 mg) and the mixture was stirred for 4 h at rt. The reaction was quenched by addition of MeOH (several drops) and stirring for 30 min. Then the volatile materials were evaporated off and the residue was partitioned between EtOAc and water. The aqueous layer was extracted with EtOAc (6×), and the combined extracts were washed with brine, dried (Na$_2$SO$_4$), filtered, and concentrated in vacuo to afford ((1R,2S,5R)-2-((S)-3-(benzyloxycarbonyl)-2-oxopyrrolidin-1-yl)-5-(isopropyl (methyl)amino)cyclohexyl)methyl isobutyrate as an oil.

Example 7a, Step 5: A solution of the crude product of Step 4 ((1R,2S,5R)-2-((S)-3-(benzyloxycarbonyl)-2-oxopyrrolidin-1-yl)-5-(isopropyl(methyl)amino)cyclohexyl)methyl isobutyrate (0.77 mmol) in MeOH (15 mL) was charged with 10% Pd/C, Degussa (~100 mg). The reaction flask was evacuated and then back-filled with hydrogen; this was repeated two more times. The reaction was stirred under 60 psi of $H_2$ for 4 h, and then filtered and concentrated in vacuo to afford the desired ((1R,2S,5R)-2-((S)-3-amino-2-oxopyrrolidin-1-yl)-5-(isopropyl(methyl)amino)cyclohexyl)methyl isobutyrate as an oil.

Example 7a, Step 6: By the methods described in Example 6a, Step 6, ((1R,2S,5R)-2-((S)-3-amino-2-oxopyrrolidin-1-yl)-5-(isopropyl(methyl)amino)cyclohexyl)methyl isobutyrate was converted to the desired ((1R,2S,5R)-5-(isopropyl(methyl)amino)-2-(2-oxo-3-(6-(trifluoromethyl)quinazolin-4-ylamino)pyrrolidin-1-yl)cyclohexyl)methyl isobutyrate. MS found: $(M+H)^+=550.4$.

Example 7b

Synthesis of ((1R,2S,5R)-5-(isopropyl(methyl)amino)-2-(2-oxo-3-(3-(trifluoromethyl)benzamido)pyrrolidin-1-yl)cyclohexyl)methyl isobutyrate By the methods described in Example 6c, ((1R,2S,5R)-2-((S)-3-amino-2-oxopyrrolidin-1-yl)-5-(isopropyl(methyl)amino)cyclohexyl)methyl isobutyrate was converted to the desired ((1R,2S,5R)-5-(isopropyl(methyl)amino)-2-(2-oxo-3-(3-(trifluoromethyl)benzamido)pyrrolidin-1-yl)cyclohexyl)methyl isobutyrate. MS found: $(M+H)^+=526.3$.

Example 7d

Synthesis of ((1R,2S,5R)-5-(dimethylamino)-2-(2-oxo-3-(6-(trifluoromethyl)quinazoline-4-carboxamido)pyrrolidin-1-yl)cyclohexyl)methyl isobutyrate By the methods described in Example 7a, Steps 4-6, (S)-1-((1S,2R,4R)-4-(dimethylamino)-2-(hydroxymethyl)cyclohexyl)-2-oxopyrrolidin-3-ylcarbamate, a product of Example 7a, Step 3, was converted to the desired ((1R,2S,5R)-5-(dimethylamino)-2-(2-oxo-3-(6-(trifluoromethyl)quinazoline-4-carboxamido)pyrrolidin-1-yl)cyclohexyl)methyl isobutyrate. MS found: $(M+H)^+=522.3$.

Example 7e

Synthesis of ((1R,2S,5R)-5-(dimethylamino)-2-(2-oxo-3-(3-(trifluoromethyl)benzamido)pyrrolidin-1-yl)cyclohexyl)methyl isobutyrate By the methods described in Example 6c, (S)-1-((1S,2R,4R)-4-(dimethylamino)-2-(hydroxymethyl)cyclohexyl)-2-oxopyrrolidin-3-ylcarbamate, a product of Example 7a, Step 3, was converted to the desired ((1R,2S,5R)-5-(dimethylamino)-2-(2-oxo-3-(3-(trifluoromethyl)benzamido)pyrrolidin-1-yl)cyclohexyl)methyl isobutyrate. MS found: $(M+H)^+=498.3$.

TABLE 7-A

The compounds in the following table were made using the methods exemplified above. See Table 1-A for a complete description of the table headings.

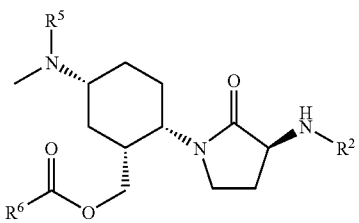

| Example | $R^5$ | $R^6$ | $R^2$ | Step Altered | MS Data |
|---|---|---|---|---|---|
| 7a | iPr | iPr | 4-(6-(trifluoromethyl)quinazolinyl) | n/a | 550.4 |
| 7b | iPr | iPr | 3-(trifluoromethyl)benzoyl | n/a | 526.3 |
| 7c | iPr | iPr | 1-methyl-3-tert-butyl-pyrazole-5-carbonyl | 7b, Step 6 | 518.4 |
| 7d | Me | iPr | 4-(6-(trifluoromethyl)quinazolinyl) | n/a | 522.3 |
| 7e | Me | iPr | 3-(trifluoromethyl)benzoyl | n/a | 498.3 |
| 7f | Me | iPr | 1-methyl-3-tert-butyl-pyrazole-5-carbonyl | 7e, Step 6 | 490.4 |

TABLE 7-B

The chemical names of the specific examples illustrated in Table 7-A are tabulated below.

| Example | Name |
|---|---|
| 7a | ((1R,2S,5R)-5-(isopropyl(methyl)amino)-2-(2-oxo-3-(6-(trifluoromethyl)quinazolin-4-ylamino)pyrrolidin-1-yl)cyclohexyl)methyl isobutyrate |
| 7b | ((1R,2S,5R)-5-(isopropyl(methyl)amino)-2-(2-oxo-3-(3-(trifluoromethyl)benzamido)pyrrolidin-1-yl)cyclohexyl)methyl isobutyrate |
| 7c | ((1R,2S,5R)-2-(3-(3-tert-butyl-1-methyl-1H-pyrazole-5-carboxamido)-2-oxopyrrolidin-1-yl)-5-(isopropyl(methyl)amino)cyclohexyl)methyl isobutyrate |
| 7d | ((1R,2S,5R)-5-(dimethylamino)-2-(2-oxo-3-(6-(trifluoromethyl)quinazoline-4-carboxamido)pyrrolidin-1-yl)cyclohexyl)methyl isobutyrate |
| 7e | ((1R,2S,5R)-5-(dimethylamino)-2-(2-oxo-3-(3-(trifluoromethyl)benzamido)pyrrolidin-1-yl)cyclohexyl)methyl isobutyrate |
| 7f | ((1R,2S,5R)-2-(3-(3-tert-butyl-1-methyl-1H-pyrazole-5-carboxamido)-2-oxopyrrolidin-1-yl)-5-(dimethylamino)cyclohexyl)methyl isobutyrate |

Examples 8a-8s

Example 8a

Synthesis of N-((S)-1-((1S,2R,4R)-4-(isopropyl(methyl)amino)-2-(methylsulfonylmethyl)cyclohexyl)-2-oxopyrrolidin-3-yl)-3-(trifluoromethyl)benzamide Example 8a, Step 1: (1R,2S,5R)-2-Benzyloxycarbonylamino-7-oxo-6-aza-bicyclo[3.2.1]octane-6-carboxylic acid tert-butyl ester (500 mg, 1.3 mmol) was dissolved in THF (10 mL) and water (2.2 mL) prior to the addition of NaBH$_4$ (252.4 mg). After 5 h, the reaction was quenched with saturated NaHCO$_3$ solution and extracted with EtOAc (2×). The organic extracts were combined, dried (MgSO$_4$), filtered, and concentrated in vacuo to afford tert-butyl (1R,3R,4S)-4-benzyloxycarbonylamino-3-(hydroxymethyl)cyclohexylcarbamate (505 mg). MS (ES+)=375.4 (M+H)$^+$.

Example 8a, Step 2: Tert-butyl (1R,3R,4S)-4-benzyloxycarbonylamino-3-(hydroxymethyl)cyclohexylcarbamate (500 mg) was dissolved in CH$_2$Cl$_2$ (4.5 mL) prior to the addition of Et$_3$N (186.9 mg). After cooling to 0° C., methanesulfonyl chloride (196.7 mg) was added dropwise. The solution was warmed to rt over 1 h before it was quenched with saturated NaHCO$_3$ solution and extracted with CH$_2$Cl$_2$ (2×). The organic extracts were combined, dried (MgSO$_4$), filtered, and concentrated in vacuo to afford ((1R,2S,5R)-2-benzyloxycarbonylamino-5-(tert-butoxycarbonyl)cyclohexyl)methyl methanesulfonate (MS (ES+)=457.4 (M+H)$^+$) as a foam. This was immediately dissolved in DMF and added dropwise into a flask containing sodium thiomethoxide (370 mg) in DMF (7 mL) and water (0.5 mL) at 10° C. After 20 min, the reaction was quenched with saturated NaHCO$_3$ solution and extracted with EtOAc (2×). The organic extracts were combined, dried (MgSO$_4$), filtered, and concentrated. The resulting residue was dissolved in MeOH (15 mL) and water (4 mL). After cooling to 0° C., oxone (2.1 g) was added. This was stirred for 5 h before it was filtered and concentrated. The residue was purified by flash chromatography to provide tert-butyl (1R,3R,4S)-4-benzyloxycarbonylamino-3-(methylsulfonylmethyl)cyclohexylcarbamate (348 mg). MS (ES+)=441.2 (M+H)$^+$.

Example 8a, Step 3: A solution of tert-butyl (1R,3R,4S)-4-benzyloxycarbonylamino-3-(methylsulfonylmethyl)cyclohexylcarbamate (5.5 g) in MeOH (40 mL) was charged with 10% Pd/C, Degussa (800 mg). The reaction flask was evacuated and then back-filled with hydrogen; this was repeated three more times. The reaction was stirred under 1 atm of H$_2$ for 3 h and then filtered and concentrated. The resulting residue was dissolved in DMF (41 mL) and cooled to 0° C. prior to the addition of N-Cbz methionine (6.35 g), 4-methyl morpholine (4.4 g), and BOP (9.92 g). The reaction was stirred for 12 h at RT and then partitioned between EtOAc and 1N HCl solution. The organic phases were combined, washed with saturated NaHCO$_3$ and brine, dried (MgSO$_4$). filtered, and concentrated in vacuo. The residue was purified by flash chromatography to afford tert-butyl (1R,3R,4S)-4-((S)-2-benzyloxycarbonylamino-4-(methylthio)butanamido)-3-(methylsulfonylmethyl)cyclohexylcarbamate (6.9 g). MS found: (M+H)$^+$=572.4.

Example 8a, Step 4: Tert-butyl (1R,3R,4S)-4-((S)-2-benzyloxycarbonylamino-4-(methylthio)butanamido)-3-(methylsulfonylmethyl)cyclohexylcarbamate (6.9 g) was dissolved in iodomethane (100 mL), and the resulting solution was stirred at rt for 72 h before being concentrated in vacuo. The residue was dissolved in methylene chloride, and the resulting solution was concentrated; this was repeated to afford the salt. MS found: (M+H)$^+$=586.5. This material was dissolved in DMF (20 mL) and the solution was charged with Cs$_2$CO$_3$ (12.0 g). After 12 h, the reaction was partitioned between EtOAc and brine. The organic phase was dried (MgSO$_4$), filtered, and concentrated in vacuo. The residue was purified by flash chromatography to afford tert-butyl (1R,3R,4S)-4-((S)-3-benzyloxycarbonylamino-2-oxopyrrolidin-1-yl)-3-(methylsulfonylmethyl)cyclohexylcarbamate (2.4 g). MS found: (M+H)$^+$=524.3.

Example 8a, Step 5: A solution of tert-butyl (1R,3R,4S)-4-((S)-3-benzyloxycarbonylamino-2-oxopyrrolidin-1-yl)-3-(methylsulfonylmethyl)cyclohexylcarbamate (835 mg) in MeOH (5 mL) was charged with 10% Pd/C, Degussa (800 mg). The reaction flask was evacuated and then back-filled with hydrogen; this was repeated three more times. The reaction was stirred under 1 atm of H$_2$ for 2 h and then filtered and concentrated to afford tert-butyl (1R,3R,4S)-4-((S)-3-amino-2-oxopyrrolidin-1-yl)-3-(methylsulfonylmethyl)cyclohexylcarbamate (566 mg). MS found: (M+H)$^+$=390.3.

Example 8a, Step 6: 3-(Trifluoromethyl)benzoic acid (252.4 mg) was dissolved in DMF (5 mL) and 4-methyl morpholine (0.42 mL) was added prior to the addition of BOP (511 mg). After 10 min, tert-butyl (1R,3R,4S)-4-((S)-3-amino-2-oxopyrrolidin-1-yl)-3-(methylsulfonylmethyl)cyclohexylcarbamate (300 mg) was added. The reaction was stirred for 1 h before it was partitioned between EtOAc and 1N HCl solution. The organic phases were combined, washed with saturated NaHCO$_3$ and brine, dried (MgSO$_4$), filtered, and concentrated in vacuo. The residue was purified by flash chromatography to afford tert-butyl (1R,3R,4S)-3-(methylsulfonylmethyl)-4-((S)-2-oxo-3-(3-(trifluoromethyl)benzamido)pyrrolidin-1-yl)cyclohexylcarbamate (560 mg). MS found: (M+H)$^+$=562.2.

Example 8a, Step 7: Tert-butyl (1R,3R,4S)-3-(methylsulfonylmethyl)-4-((S)-2-oxo-3-(3-(trifluoromethyl)benzamido)pyrrolidin-1-yl)cyclohexylcarbamate (560 mg) was dissolved in CH$_2$Cl$_2$ (5 mL) prior to the addition of trifluoroacetic acid (5 mL). After 1 h, the reaction was concentrated in vacuo. The resultant residue was dissolved in MeOH (5 mL)

and charged with acetone (0.6 mL) and NaOAc (316 mg). The mixture was stirred for 5 min before being charged with NaCNBH₃ (261 mg). The reaction was stirred for 4 h and then charged with formaldehyde (~0.3 mL of a 37% aq. solution). The mixture was stirred for 1.5 h, quenched with sat. NaHCO₃, and extracted with EtOAc (2×). The organic extracts were combined, dried (MgSO₄), filtered, and concentrated. The residue was purified by reverse phase HPLC (gradient elution, water/acetonitrile/TFA) to afford the TFA salt of N-((S)-1-((1S,2R,4R)-4-(isopropyl(methyl)amino)-2-(methylsulfonylmethyl)cyclohexyl)-2-oxopyrrolidin-3-yl)-3-(trifluoromethyl)benzamide (347 mg). MS found: (M+H)⁺=504.2.

Example 8p

Synthesis of (S)-1-((1S,2R,4R)-4-(isopropyl(methyl)amino)-2-(methylsulfonylmethyl)cyclohexyl)-3-(6-(trifluoromethyl)quinazolin-4-ylamino)pyrrolidin-2-one Example 8p, Step 1: Tert-butyl (1R,3R,4S)-4-((S)-3-benzyloxycarbonylamino-2-oxopyrrolidin-1-yl)-3-(methylsulfonylmethyl)cyclohexylcarbamate (714 mg) was dissolved in CH₂Cl₂ (15 mL) prior to the addition of trifluoroacetic acid (7 mL). After 1 h at rt, the reaction was concentrated in vacuo. This residue was dissolved in MeOH (15 mL) and charged with acetone (1.0 mL) and NaOAc (558 mg). The mixture was stirred for 5 min before being charged with NaCNBH₃ (461 mg). The reaction was stirred for 2 h and then charged with formaldehyde (0.5 mL of a 37% aq. solution) and NaCNBH₃ (461 mg). The mixture was stirred for 1 h, quenched with sat. NaHCO₃, and extracted with EtOAc (2×). The organic extracts were combined, dried (MgSO₄), filtered, and concentrated to afford the benzyl (S)-1-((1S,2R,4R)-4-(isopropyl(methyl)amino)-2-(methylsulfonylmethyl)cyclohexyl)-2-oxopyrrolidin-3-ylcarbamate (1.5 g). MS found: (M+H)⁺=466.4.

Example 8p, Step 2: The material from above benzyl (S)-1-((1S,2R,4R)-4-(isopropyl(methyl)amino)-2-(methylsulfonylmethyl)cyclohexyl)-2-oxopyrrolidin-3-ylcarbamate (600 mg) was dissolved in 33% HBr/AcOH (10 mL) at rt. The solution was stirred for 30 min before Et₂O was added. This resulted in a precipitate which was isolated to afford the bis-hydrogen bromide salt of (S)-3-amino-1-((1S,2R,4R)-4-(isopropyl(methyl)amino)-2-(methylsulfonylmethyl)cyclohexyl)pyrrolidin-2-one (525 mg). MS found: (M+H)⁺=346.5.

Example 8p, Step 3: To a solution of (S)-3-amino-1-((1S,2R,4R)-4-(isopropyl(methyl)amino)-2-(methylsulfonylmethyl)cyclohexyl)pyrrolidin-2-one (100 mg) in EtOH (5 mL) was added triethylamine (0.14 mL) and 4-chloro-6-(trifluoromethyl)quinazoline (68.7 mg). The mixture was heated at 80° C. for 14 h before it was filtered and concentrated in vacuo. The residue was purified by reverse phase HPLC (gradient elution, water/acetonitrile/TFA) to afford the TFA salt of (S)-1-((1S,2R,4R)-4-(isopropyl(methyl)amino)-2-(methylsulfonylmethyl)cyclohexyl)-3-(6-(trifluoromethyl)quinazolin-4-ylamino)pyrrolidin-2-one (30 mg). MS found: (M+H)⁺=542.6.

TABLE 8-A

The compounds in the following table were made using the methods exemplified above. See Table 1-A for a complete description of the table headings.

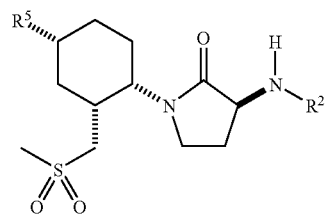

| Example | R⁵ | R² | Step Altered | MS Data |
|---|---|---|---|---|
| 8a | i-Pr(Me)N | ![CF₃-phenyl carbonyl] | n/a | 518 |
| 8b | i-Pr(Me)N | ![OCF₃, NH₂-phenyl carbonyl] | 8a, Step 6 | 549 |
| 8c | i-Pr(Me)N | ![tert-butyl-N-methylpyrazole carbonyl] | 8a, Step 6 | 510 |
| 8d | i-Pr(Me)N | ![tert-butyl pyridine carbonyl] | 8a, Step 6 | 507 |
| 8e | i-Pr(Me)N | ![CF₃-pyridine carbonyl] | 8a, Step 6 | 519 |

TABLE 8-A-continued

The compounds in the following table were made using the methods exemplified above. See Table 1-A for a complete description of the table headings.

| Example | R⁵ | R² | Step Altered | MS Data |
|---|---|---|---|---|
| 8f | i-Pr(Me)N | 6-Ph-pyridin-2-yl-C(O)- | 8a, Step 6 | 527 |
| 8g | i-Pr(Et)N | 3-CF₃-phenyl-C(O)- | 8a, Step 7 | 532 |
| 8h | tert-BuCH₂(H)N | 3-CF₃-phenyl-C(O)- | 8a, Step 7 | 532 |
| 8i | i-Pr(Me)N | 3-CF₃-4-Me-phenyl-C(O)- | 8a, Step 6 | 532 |
| 8j | i-Pr(Me)N | 3-CF₃-4-Cl-phenyl-C(O)- | 8a, Step 6 | 552 |
| 8k | i-Pr(Me)N | 3-tert-Bu-phenyl-C(O)- | 8a, Step 6 | 506 |
| 8l | i-Pr(Me)N | 3-Ph-phenyl-C(O)- | 8a, Step 6 | 526 |
| 8m | i-Pr(Me)N | 6-Ph-pyrazin-2-yl-C(O)- | 8a, Step 6 | 528 |
| 8n | i-Pr(Me)N | 3-CF₃-5-F-phenyl-C(O)- | 8a, Step 6 | 536 |
| 8o | i-Pr(Me)N | 3-OCF₃-phenyl-C(O)- | 8a, Step 6 | 534 |
| 8p | i-Pr(Me)N | 6-CF₃-quinazolin-4-yl | n/a | 542 |

TABLE 8-A-continued

The compounds in the following table were made using the methods exemplified above. See Table 1-A for a complete description of the table headings.

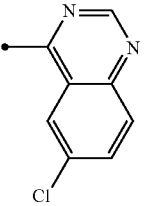

| Example | R⁵ | R² | Step Altered | MS Data |
|---|---|---|---|---|
| 8q | i-Pr(Me)N | (4-chloroquinazolin-2-yl) | 8p, Step 3 | 508 |
| 8r | i-Pr(Me)N | (3,5-bis(trifluoromethyl)benzoyl) | 8a, Step 6 | 586 |
| 8s | i-Pr(Me)N | (3,5-dichlorobenzoyl) | 8a, Step 6 | 518 |

TABLE 8-B

The chemical names of the specific examples illustrated in Table 8-A are tabulated below.

| Example | Name |
|---|---|
| 8a | N-((S)-1-((1S,2R,4R)-4-(isopropyl(methyl)amino)-2-(methylsulfonylmethyl)cyclohexyl)-2-oxopyrrolidin-3-yl)-3-(trifluoromethyl)benzamide |
| 8b | 2-amino-N-((S)-1-((1S,2R,4R)-4-(isopropyl(methyl)amino)-2-(methylsulfonylmethyl)cyclohexyl)-2-oxopyrrolidin-3-yl)-5-(trifluoromethoxy)benzamide |
| 8c | 3-tert-butyl-N-((S)-1-((1S,2R,4R)-4-(isopropyl(methyl)amino)-2-(methylsulfonylmethyl)cyclohexyl)-2-oxopyrrolidin-3-yl)-1-methyl-1H-pyrazole-5-carboxamide |
| 8d | 6-tert-butyl-N-((S)-1-((1S,2R,4R)-4-(isopropyl(methyl)amino)-2-(methylsulfonylmethyl)cyclohexyl)-2-oxopyrrolidin-3-yl)picolinamide |
| 8e | N-((S)-1-((1S,2R,4R)-4-(isopropyl(methyl)amino)-2-(methylsulfonylmethyl)cyclohexyl)-2-oxopyrrolidin-3-yl)-6-(trifluoromethyl)picolinamide |

TABLE 8-B-continued

The chemical names of the specific examples illustrated in Table 8-A are tabulated below.

| Example | Name |
|---|---|
| 8f | N-((S)-1-((1S,2R,4R)-4-(isopropyl(methyl)amino)-2-(methylsulfonylmethyl)cyclohexyl)-2-oxopyrrolidin-3-yl)-6-phenylpicolinamide |
| 8g | N-((S)-1-((1S,2R,4R)-4-(ethyl(isopropyl)amino)-2-(methylsulfonylmethyl)cyclohexyl)-2-oxopyrrolidin-3-yl)-3-(trifluoromethyl)benzamide |
| 8h | N-((S)-1-((1S,2R,4R)-2-(methylsulfonylmethyl)-4-(neopentylamino)cyclohexyl)-2-oxopyrrolidin-3-yl)-3-(trifluoromethyl)benzamide |
| 8i | N-((S)-1-((1S,2R,4R)-4-(isopropyl(methyl)amino)-2-(methylsulfonylmethyl)cyclohexyl)-2-oxopyrrolidin-3-yl)-4-methyl-3-(trifluoromethyl)benzamide |
| 8j | 4-chloro-N-((S)-1-((1S,2R,4R)-4-(isopropyl(methyl)amino)-2-(methylsulfonylmethyl)cyclohexyl)-2-oxopyrrolidin-3-yl)-3-(trifluoromethyl)benzamide |
| 8k | 3-tert-butyl-N-((S)-1-((1S,2R,4R)-4-(isopropyl(methyl)amino)-2-(methylsulfonylmethyl)cyclohexyl)-2-oxopyrrolidin-3-yl)benzamide |
| 8l | 3-phenyl-N-((S)-1-((1S,2R,4R)-4-(isopropyl(methyl)amino)-2-(methylsulfonylmethyl)cyclohexyl)-2-oxopyrrolidin-3-yl)benzamide |
| 8m | N-((S)-1-((1S,2R,4R)-4-(isopropyl(methyl)amino)-2-(methylsulfonylmethyl)cyclohexyl)-2-oxopyrrolidin-3-yl)-6-phenylpyrazine-2-carboxamide |
| 8n | 3-fluoro-N-((S)-1-((1S,2R,4R)-4-(isopropyl(methyl)amino)-2-(methylsulfonylmethyl)cyclohexyl)-2-oxopyrrolidin-3-yl)-5-(trifluoromethyl)benzamide |
| 8o | N-((S)-1-((1S,2R,4R)-4-(isopropyl(methyl)amino)-2-(methylsulfonylmethyl)cyclohexyl)-2-oxopyrrolidin-3-yl)-3-(trifluoromethoxy)benzamide |
| 8p | (S)-1-((1S,2R,4R)-4-(isopropyl(methyl)amino)-2-(methylsulfonylmethyl)cyclohexyl)-3-(6-(trifluoromethyl)quinazolin-4-ylamino)pyrrolidin-2-one |
| 8q | (S)-3-(6-chloroquinazolin-4-ylamino)-1-((1S,2R,4R)-4-(isopropyl(methyl)amino)-2-(methylsulfonylmethyl)cyclohexyl)pyrrolidin-2-one |
| 8r | N-((S)-1-((1S,2R,4R)-4-(isopropyl(methyl)amino)-2-(methylsulfonylmethyl)cyclohexyl)-2-oxopyrrolidin-3-yl)-3,5-bis(trifluoromethyl)benzamide |
| 8s | 3,5-dichloro-N-((S)-1-((1S,2R,4R)-4-(isopropyl(methyl)amino)-2-(methylsulfonylmethyl)cyclohexyl)-2-oxopyrrolidin-3-yl)benzamide |

Examples 9a-9m

Example 9a

Synthesis of N-((S)-1-((1S,2R,4R)-2-(tert-butylsulfonylmethyl)-4-(isopropyl(methyl)amino)cyclohexyl)-2-oxopyrrolidin-3-yl)-4-fluoro-3-(trifluoromethyl)benzamide Example 9a, Step 1: ((1R,2S,5R)-2-Benzyloxycarbonylamino-5-(tert-butoxycarbonyl)cyclohexyl)methyl methanesulfonate (12.1 g) was dissolved in DMF (50 mL) and HMPA (25 mL) at 0° C. prior to the addition of sodium 2-methyl-2-propanethiolate (6.3 g) in DMF (50 mL). After warming to rt, the reaction was quenched with cold water and extracted with EtOAc (2×). The organic extracts were combined, washed with brine, dried (MgSO$_4$), filtered, and concentrated. The residue was purified by flash chromatography to provide tert-butyl (1R,3R,4S)-4-benzyloxycarbonylamino-3-(tert-butylthiomethyl)cyclohexylcarbamate (13.0 g). MS (ES+)=451.4 (M+H)$^+$.

Example 9a, Step 2: Tert-butyl (1R,3R,4S)-4-benzyloxycarbonylamino-3-(tert-butylthiomethyl)cyclohexylcarbamate (12.1 g) was dissolved in MeOH (120 mL) and water (60 mL). After cooling to 0° C., oxone (41.0 g) was added. This was stirred for 5 h before it was filtered and concentrated. The residue was purified by flash chromatography to provide tert-butyl (1R,3R,4S)-4-benzyloxycarbonylamino-3-(tert-butylsulfonylmethyl)cyclohexylcarbamate (7.35 g). MS (ES+)=483.3 (M+H)$^+$.

Example 9a, Step 3: A solution of tert-butyl (1R,3R,4S)-4-benzyloxycarbonylamino-3-(tert-butylsulfonylmethyl)cyclohexylcarbamate (7.3 g) in MeOH (80 mL) was charged with 10% Pd/C, Degussa (5.0 g). The reaction flask was evacuated and then back-filled with hydrogen; this was repeated three more times. The reaction was stirred under 1 atm of H$_2$ for 3 h and then filtered and concentrated to provide tert-butyl (1R,3R,4S)-4-amino-3-(tert-butylthiomethyl)cyclohexylcarbamate (5.0 g). MS (ES+)=349.3 (M+H)$^+$.

Example 9a, Step 4: A solution of tert-butyl (1R,3R,4S)-4-amino-3-(tert-butylthiomethyl)cyclohexylcarbamate (4.8 g) was dissolved in DMF (40 mL) and cooled to 0° C. prior to the addition of N-Cbz methionine (4.3 g), 4-methyl morpholine (7.6 g), and BOP (7.9 g). The reaction was stirred for 12 h at RT and then partitioned between EtOAc and 1N HCl solution. The organic phases were combined, washed with saturated NaHCO$_3$ and brine, dried (MgSO$_4$), filtered, and concentrated in vacuo. The residue was purified by flash chromatography to afford tert-butyl (1R,3R,4S)-4-((S)-2-benzyloxycarbonylamino-4-(methylthio)butanamido)-3-(tert-butylsulfonylmethyl)cyclohexylcarbamate (8.4 g). MS found: (M+H)$^+$=614.4.

Example 9a, Step 5: Tert-butyl (1R,3R,4S)-4-((S)-2-benzyloxycarbonylamino-4-(methylthio)butanamido)-3-(tert-butylsulfonylmethyl)cyclohexylcarbamate (6.2 g) was dissolved in iodomethane (60 mL) and CH$_2$Cl$_2$ (15 mL). The resulting solution was stirred at rt for 72 h before being concentrated in vacuo. The residue was dissolved in methylene chloride, and the resulting solution was concentrated; this was repeated to afford the salt. This material was dissolved in DMF (60 mL) and the solution was charged with Cs$_2$CO$_3$ (13.2 g). After 12 h, the reaction was partitioned between EtOAc and brine. The organic phase was dried (MgSO$_4$), filtered, and concentrated to afford tert-butyl (1R,3R,4S)-4-((S)-3-benzyloxycarbonylamino-2-oxopyrrolidin-1-yl)-3-(tert-butylsulfonylmethyl)cyclohexylcarbamate (5.5 g). MS found: (M+H)$^+$=566.5.

Example 9a, Step 6: Tert-butyl (1R,3R,4S)-4-((S)-3-benzyloxycarbonylamino-2-oxopyrrolidin-1-yl)-3 -(tert-butylsulfonylmethyl)cyclohexylcarbamate (880 mg) was dissolved in CH$_2$Cl$_2$ (5 mL) at 0° C. prior to the addition of trifluoroacetic acid (10 mL). After 1 h at rt, the reaction was concentrated in vacuo. The resultant residue was dissolved in EtOAc and was washed with sat. Na$_2$CO$_3$ solution. The organic phase was dried (MgSO$_4$), filtered, and concentrated. This residue was dissolved in dichloroethane (6 ml) and acetone (6 mL) prior to the addition of NaBH(OAc)$_3$ (637.6 mg). After 2 h, formaldehyde (6.0 mL of a 37% aq. solution) was added along with NaBH(OAc)$_3$ (310 mg). The mixture was stirred for 1 h, quenched with sat. Na$_2$CO$_3$, and extracted with EtOAc (2×). The organic extracts were combined, dried (MgSO$_4$), filtered, and concentrated to afford benzyl (S)-1-((1S,2R,4R)-2-(tert-butylsulfonylmethyl)-4-(isopropyl(methyl)amino)cyclohexyl)-2-oxopyrrolidin-3-ylcarbamate (1.0 g). MS found: (M+H)$^+$=522.5.

Example 9a, Step 7: The material from above benzyl (S)-1-((1S,2R,4R)-2-(tert-butylsulfonylmethyl)-4-(isopropyl(methyl)amino)cyclohexyl)-2-oxopyrrolidin-3-ylcarbamate (1.0 g) was dissolved in 33% HBr/AcOH (5 mL) at rt. The solution was stirred for 30 min before Et$_2$O was added. This resulted in a precipitate which was isolated. The solid was dissolved in EtOAc and was washed with sat. Na$_2$CO$_3$ solution. The organic phase was dried (MgSO$_4$), filtered, and concentrated to afford (S)-3-amino-1-((1S,2R,4R)-2-(tert-butylsulfonylmethyl)-4-(isopropyl(methyl)amino)cyclohexyl)pyrrolidin-2-one (250 mg). MS found: (M+H)$^+$=388.4.

Example 9a, Step 8: (S)-3-Amino-1-((1S,2R,4R)-2-(tert-butylsulfonylmethyl)-4-(isopropyl(methyl)amino)cyclohexyl)pyrrolidin-2-one (23 mg) was dissolved in DMF (1.5 mL) and cooled to 0° C. prior to the addition of 4-fluoro-3-(trifluoromethyl)benzoic acid (23 mg), 4-methyl morpholine (0.02 mL), and BOP (49 mg). The reaction was stirred for 12 h at RT and then partitioned between EtOAc and saturated Na$_2$CO$_3$ solution. The organic phases were combined, dried (MgSO$_4$), filtered, and concentrated in vacuo. The residue was purified by reverse phase HPLC (gradient elution, water/acetonitrile/TFA) to afford the TFA salt of N-((S)-1-((1S,2R,4R)-2-(tert-butylsulfonylmethyl)-4-(isopropyl(methyl)amino)cyclohexyl)-2-oxopyrrolidin-3-yl)-4-fluoro-3-(trifluoro-methyl)benzamide (8 mg). MS found: (M+H)$^+$=578.3.

Example 9j

Synthesis of (S)-1-((1S,2R,4R)-4-(isopropyl(methyl)amino)-2-(tert-butylsulfonylmethyl)cyclohexyl)-3-(6-(trifluoromethyl)quinazolin-4-ylamino)pyrrolidin-2-one Example 9j, Step 1: To a solution of (S)-3-amino-1-((1S,2R,4R)-4-(isopropyl(methyl)amino)-2 -(tert-butylsulfonylmethyl)cyclohexyl)pyrrolidin-2-one bis-hydrogen bromide (100 mg) in EtOH (2 mL) was added triethylamine (0.076 mL) and 4-chloro-6-(trifluoromethyl)quinazoline (63 mg). The mixture was heated at 80° C. for 6 h before it was filtered and concentrated in vacuo. The residue was purified by reverse phase HPLC (gradient elution, water/acetonitrile/TFA) to afford the TFA salt of (S)-1-((1S,2R,4R)-4-(isopropyl(methyl)amino)-2-(tert-butylsulfonylmethyl)cyclohexyl)-3-(6-(trifluoromethyl)quinazolin-4-ylamino)pyrrolidin-2-one (63 mg). MS found: (M+H)$^+$=584.6.

TABLE 9-A

The compounds in the following table were made using the methods exemplified above. See Table 1-A for a complete description of the table headings.

| Example | R⁵ | R² | Step Altered | MS Data |
|---------|-----|-----|--------------|---------|
| 9a | i-Pr(Me)N | 3-CF₃, 4-F-benzoyl | n/a | 578 |
| 9b | i-Pr(Me)N | 6-CF₃-pyridine-2-carbonyl | 9a, Step 8 | 561 |
| 9c | i-Pr(Me)N | 3-CF₃-benzoyl | 9a, Step 8 | 560 |
| 9d | i-Pr(Me)N | 6-t-Bu-pyridine-2-carbonyl | 9a, Step 8 | 549 |
| 9e | i-Pr(Me)N | 3-OCF₃-benzoyl | 9a, Step 8 | 576 |
| 9f | i-Pr(Me)N | 3-CF₃, 5-F-benzoyl | 9a, Step 8 | 578 |
| 9g | i-Pr(Me)N | 2-NH₂, 5-OCF₃-benzoyl | 9a, Step 8 | 591 |
| 9h | i-Pr(Me)N | 3-NH₂, 5-CF₃-benzoyl | 9a, Step 8 | 575 |
| 9i | i-Pr(Me)N | 5-Ph-pyridine N-oxide-3-carbonyl | 9a, Step 8 | 585 |
| 9j | i-Pr(Me)N | 6-CF₃-quinazolin-4-yl | n/a | 584 |

TABLE 9-A-continued

The compounds in the following table were made using the methods exemplified above. See Table 1-A for a complete description of the table headings.

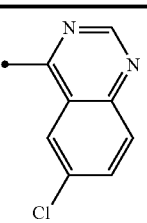

| Example | R⁵ | R² | Step Altered | MS Data |
|---|---|---|---|---|
| 9k | i-Pr(Me)N | 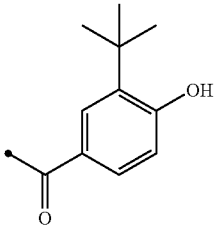 | 9j, Step 1 | 550 |
| 9l | i-Pr(Me)N | 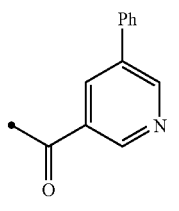 | 9a, Step 8 | 564 |
| 9m | i-Pr(Me)N | Ph | 9a, Step 8 | 569.5 |

TABLE 9-B

The chemical names of the specific examples illustrated in Table 9-A are tabulated below.

| Example | Name |
|---|---|
| 9a | N-((S)-1-((1S,2R,4R)-2-(tert-butylsulfonylmethyl)-4-(isopropyl(methyl)amino)cyclohexyl)-2-oxopyrrolidin-3-yl)-4-fluoro-3-(trifluoromethyl)benzamide |
| 9b | N-((S)-1-((1S,2R,4R)-2-(tert-butylsulfonylmethyl)-4-(isopropyl(methyl)amino)cyclohexyl)-2-oxopyrrolidin-3-yl)-6-(trifluoromethyl)picolinamide |
| 9c | N-((S)-1-((1S,2R,4R)-2-(tert-butylsulfonylmethyl)-4-(isopropyl(methyl)amino)cyclohexyl)-2-oxopyrrolidin-3-yl)-3-(trifluoromethyl)benzamide |
| 9d | 6-tert-butyl-N-((S)-1-((1S,2R,4R)-2-(tert-butylsulfonylmethyl)-4-(isopropyl(methyl)amino)cyclohexyl)-2-oxopyrrolidin-3-yl)picolinamide |

TABLE 9-B-continued

The chemical names of the specific examples illustrated in Table 9-A are tabulated below.

| Example | Name |
|---|---|
| 9e | N-((S)-1-((1S,2R,4R)-2-(tert-butylsulfonylmethyl)-4-(isopropyl(methyl)amino)cyclohexyl)-2-oxopyrrolidin-3-yl)-3-(trifluoromethoxy)benzamide |
| 9f | N-((S)-1-((1S,2R,4R)-2-(tert-butylsulfonylmethyl)-4-(isopropyl(methyl)amino)cyclohexyl)-2-oxopyrrolidin-3-yl)-3-fluoro-5-(trifluoromethyl)benzamide |
| 9g | 2-amino-N-((S)-1-((1S,2R,4R)-2-(tert-butylsulfonylmethyl)-4-(isopropyl(methyl)amino)cyclohexyl)-2-oxopyrrolidin-3-yl)-5-(trifluoromethoxy)benzamide |
| 9h | 3-amino-N-((S)-1-((1S,2R,4R)-2-(tert-butylsulfonylmethyl)-4-(isopropyl(methyl)amino)cyclohexyl)-2-oxopyrrolidin-3-yl)-5-(trifluoromethyl)benzamide |
| 9i | N-((S)-1-((1S,2R,4R)-2-(tert-butylsulfonylmethyl)-4-(isopropyl(methyl)amino)cyclohexyl)-2-oxopyrrolidin-3-yl)-5-phenylnicotinamide N-oxide |
| 9j | (S)-1-((1S,2R,4R)-2-(tert-butylsulfonylmethyl)-4-(isopropyl(methyl)amino)cyclohexyl)-3-(6-(trifluoromethyl)quinazolin-4-ylamino)pyrrolidin-2-one |
| 9k | (S)-1-((1S,2R,4R)-2-(tert-butylsulfonylmethyl)-4-(isopropyl(methyl)amino)cyclohexyl)-3-(6-chloroquinazolin-4-ylamino)pyrrolidin-2-one |
| 9l | 3-tert-butyl-N-((S)-1-((1S,2R,4R)-2-(tert-butylsulfonylmethyl)-4-(isopropyl(methyl)amino)cyclohexyl)-2-oxopyrrolidin-3-yl)-4-hydroxybenzamide |
| 9m | N-((S)-1-((1S,2R,4R)-2-(tert-butylsulfonylmethyl)-4-(isopropyl(methyl)amino)cyclohexyl)-2-oxopyrrolidin-3-yl)-5-phenylnicotinamide |

Examples 10a-10m

Example 10a

Synthesis of N-((S)-1-((1S,2R,4R)-4-(isopropyl(methyl)amino)-2-(isopropylsulfonylmethyl)cyclohexyl)-2-oxopyrrolidin-3-yl)-3-(trifluoromethyl)benzamide Example 10a, Step 1: To a solution of N-(1S,2R,4R)-4-(Benzyloxycarbonylamino-3-hydroxymethyl-cyclohexyl)-carbamic acid tert-butyl ester (440 mg, 1.16 mmol, See Example 5a, Step 1) in 20 mL of $CH_2Cl_2$ cooled to 0° C. was added $Et_3N$ (0.3 mL, 2 mmol) and MsCl (0.1 mL, 1.39 mmol). The reaction mixture was stirred at rt for 2 h before water was added. The aqueous phase was extracted with EtOAc (2×25 mL) and concentrated to an oil for further use. In a separate flask, propane-2-thiol (0.22 mL, 2.3 mmol) was dissolved in 10 mL of DMF, cooled to 0° C., and followed by NaH (93 mg, 2.32 mmol). The reaction mixture was stirred at rt for 2 h before a solution of the just prepared oil in 10 mL of DMF was slowly added. The mixture was stirred at rt for 16 h before water and EtOAc were added. The organic layer was separated, dried over $Na_2SO_4$, and concentrated to afford an oil which was purified by colum chromatography on silica gel with EtOAc:hexane (30:70) to give N-(1S,2R,4R)-4-Benzyloxycarbonylamino-3-isopropylsulfanylmethyl-cyclohexyl)-carbamic acid tert-butyl ester (160 mg, 33%). MS [M+H]$^+$ 437.

Example 10a, Step 2: To a soultion of N-(1S,2R,4R)-4-Benzyloxycarbonylamino-3-isopropylsulfanylmethyl-cyclohexyl)-carbamic acid tert-butyl ester (1 g, 2.3 mmol) in iPrOH (20 mL) at rt was added Oxone (2.8 g, 4.6 mmol) in water (10 mL). The mixture was stirred at rt for 16 h before water and EtOAc were added. The organic layer was separated, dried over $Na_2SO_4$, and concentrated to afford to crude N-(1S,2R,4R)-4-Benzyloxycarbonylamino-3-(propane-2-sulfonylmethyl)-cyclohexyl]-carbamic acid tert-butyl ester (900 mg, 90%). MS [M+H]$^+$ 469.

Example 10a, Step 3: A solution of N-(1S,2R,4R)-4-Benzyloxycarbonylamino-3-(propane-2-sulfonylmethyl)-cyclohexyl]-carbamic acid tert-butyl ester (2 g) in MeOH (50 mL) was charged with 10% Pd/C, Degussa (1.5 g). The reaction flask was evacuated and then back-filled with hydrogen; this was repeated three more times. The reaction was stirred under 1 atm of $H_2$ for 4 h and then filtered and concentrated in vacuo to afford tert-butyl (1R,3R,4S)-4-amino-3-(isopropylsulfonylmethyl)cyclohexylcarbamate (1 g). MS found: $(M+H)^+=335$.

Example 10a, Step 4: A sample of tert-butyl (1R,3R,4S)-4-amino-3-(isopropylsulfonylmethyl)cyclohexylcarbamate (1 g, 2.9 mmol) was dissolved in DMF (20 mL), and the resultant solution was charged with N-Cbz methionine (850 mg, 2.9 mmol), N,N-diethylisopropylamine (0.5 mL, 2.9 mmol), and HATU (1.1 g, 2.9 mmol). The reaction was stirred for 12 h at RT and then partitioned between EtOAc and sat. $NaHCO_3$; the aqueous phase was back extracted with EtOAc (1×). The organic phases were combined, washed with brine, dried ($Na_2SO_4$), filtered, and concentrated in vacuo. The residue was purified by flash chromatography to afford benzyloxycarbonyl tert-butyl (1R,3R,4S)-4-((S)-2-amino-4-(methylthio)butanamido)-3-(isopropylsulfonylmethyl)cyclohexylcarbamate (1.4 g, 82%). MS found: $(M+H)^+=599$.

Example 10a, Step 5: The compound benzyloxycarbonyl tert-butyl (1R,3R,4S)-4-((S)-2-amino-4-(methylthio)butanamido)-3-(isopropylsulfonylmethyl)cyclohexylcarbamate (1.4 g) was "wetted" with EtOAc, and then the majority of EtOAc was removed under nitrogen stream. The residue was dissolved in iodomethane (20 mL), and the resulting solution was stirred at RT for 48 h before being concentrated in vacuo. The residue was dissolved in methylene chloride, and the resulting solution was concentrated; this was repeated to afford the salt. MS found: $(M+H)^+=616$. This material was dissolved in DMF (20 mL) and the solution was charged with $Cs_2CO_3$ (2.2 g) and stirred for 12 h at RT before being partitioned between EtOAc and brine. The organic phase was dried ($Na_2SO_4$), filtered, and concentrated in vacuo. The residue was purified by flash chromatography to afford benzyloxycarbonyl tert-butyl (1R,3R,4S)-4-((S)-3-amino-2-oxopyrrolidin-1-yl)-3-(isopropylsulfonylmethyl)cyclohexylcarbamate (185 mg). MS found: $(M+H)^+=552$.

Example 10a, Step 6: A solution of benzyloxycarbonyl tert-butyl (1R,3R,4S)-4-((S)-3-amino-2-oxopyrrolidin-1-yl)-3-(isopropylsulfonylmethyl)cyclohexylcarbamate (1 g) in MeOH (20 mL) was charged with 10% Pd/C, Degussa (250 mg). The reaction flask was evacuated and then back-filled with hydrogen; this was repeated three more times. The reaction was stirred under 1 atm of $H_2$ for 12 h and then filtered and concentrated in vacuo to afford tert-butyl (1R,3R,4S)-4-((S)-3-amino-2-oxopyrrolidin-1-yl)-3-(isopropylsulfonylmethyl)cyclohexylcarbamate. MS found: $(M+H)^+=418$.

Example 10a, Step 7: A sample of tert-butyl (1R,3R,4S)-4-((S)-3-amino-2-oxopyrrolidin-1-yl)-3-(isopropylsulfonylmethyl)cyclohexylcarbamate (200 mg, 0.47 mmol) in DMF (10 mL) was charged with 3-(trifluoromethyl)benzoic acid (109 mg, 0.57 mmol), N,N-diethylisopropylamine (0.1 mL, 0.57 mmol), and HATU (216 mg, 0.57 mmol). The reaction was stirred for 48 h at RT and then partitioned between EtOAc and sat. $NaHCO_3$; the aqueous phase was back extracted with EtOAc (1×). The organic phases were combined, washed with brine, dried ($Na_2SO_4$), filtered, and concentrated in vacuo to afford tert-butyl (1R,3R,4S)-3-(isopropylsulfonylmethyl)-4-((S)-2-oxo-3-(3-(trifluoromethyl)benzamido)pyrrolidin-1-yl)cyclohexylcarbamate. MS found: $(M+H)^+=590$.

Example 10a, Step 8: A solution of tert-butyl (1R,3R,4S)-3-(isopropylsulfonylmethyl)-4-((S)-2-oxo-3-(3-(trifluoromethyl)benzamido)pyrrolidin-1-yl)cyclohexylcarbamate in $CH_2Cl_2$ (10 mL) was treated with trifluoroacetic acid (4 mL). After 1 h, the reaction was concentrated in vacuo, and the resultant residue was partitioned between EtOAc and sat. $NaHCO_3$. The organic phase was washed with brine, dried ($Na_2SO_4$), filtered, and concentrated in vacuo to afford the amine. MS found: $(M+H)^+=490$. The amine (30 mg, 0.06 mmol) was dissolved in $CH_2Cl_2$ (10 mL) and charged with acetone (~2 mL); the mixture was stirred for 5 min before being charged with $NaCNBH_3$ (50 mg, 0.12 mmol). The reaction was stirred for 4 h at RT and then charged with formaldehyde (2 mL of a 30% aq. Solution). The mixture was stirred for 1.5 h, quenched with sat. $NaHCO_3$, and extracted with EtOAc (2×). The organic extracts were combined, washed with brine, dried ($Na_2SO_4$), filtered, and concentrated in vacuo. The residue was purified by reverse phase HPLC to afford the TFA salt of the title compound, N-((S)-1-((1S,2R,4R)-4-(isopropyl(methyl)amino)-2-(isopropylsulfonylmethyl)cyclohexyl)-2-oxopyrrolidin-3-yl)-3-(trifluoromethyl)benzamide, as a white powder (15 mg) after lyopholization. MS found: $(M+H)^+=546$.

Example 10b

Synthesis of (S)-1-((1S,2R,4R)-4-(isopropyl(methyl)amino)-2-(isopropylsulfonylmethyl)cyclohexyl)-3-(6-(trifluoromethyl)quinazolin-4-ylamino)pyrrolidin-2-one Example 10b, Step 1: To a solution of benzyloxycarbonyl tert-butyl (1R,3R,4S)-4-((S)-3-amino-2-oxopyrrolidin-1-yl)-3-(isopropylsulfonylmethyl)cyclohexylcarbamate (1 g) in $CH_2Cl_2$ (30 mL) was added TFA (6 mL) at RT. The reaction was stirred for 5 h and concentrated in vacuo. The residue was partitioned between 1N NaOH (100 mL) and EtOAc (150 mL). The aqueous layer was extracted with EtOAc (2×50 mL) and the organic phases were combined, washed with brine (25 mL), dried ($Na_2SO_4$), filtered, and concentrated in vacuo to give benzyl (S)-1-((1S,2R,4R)-4-amino-2-(isopropylsulfonylmethyl)cyclohexyl)-2-oxopyrrolidin-3-ylcarbamate. MS found: $(M+H)^+=452$.

Example 10b, Step 2: The entirety of benzyl benzyl (S)-1-((1S,2R,4R)-4-amino-2-(isopropylsulfonylmethyl)cyclohexyl)-2-oxopyrrolidin-3-ylcarbamate prepared in Step 1 (1 eq) was dissolved in $CH_2Cl_2$ (20 mL). The resultant solution was charged with acetone (10 eq) and stirred at RT for 10 min before sodium cyanoborohydride (2 eq) was added in one portion. The reaction was stirred at RT for 10 h and then charged successively with formaldehyde (10 eq. in 37 wt % aq soln) and sodium cyanoborohydride (2 eq). The reaction was stirred for another 9 h at RT and then quenched with sat. $NaHCO_3$. The aqueous mixture was extracted with EtOAc (200 mL, then 2×75 mL). The organic extracts were combined, washed with brine (30 mL), dried ($MgSO_4$), filtered, and concentrated in vacuo. After the resulting oil stood, some paraformaldehyde-related products solidified; these were removed by dissolving the mixture in a minimal volume of EtOAc and filtering. Subsequent concentration provided benzyl (S)-1-((1S,2R,4R)-4-(isopropyl(methyl)amino)-2-(isopropylsulfonylmethyl)cyclohexyl)-2-oxopyrrolidin-3-ylcarbamate. MS found: $(M+H)^+=508$.

Example 10b, Step 3: The entirety of benzyl (S)-1-((1S,2R,4R)-4-(isopropyl(methyl)amino)-2-(isopropylsulfonylmethyl)cyclohexyl)-2-oxopyrrolidin-3-ylcarbamate prepared in Step 2 (250 mg, 0.5 mmol) was charged with 30% HBr/AcOH (5 mL). The reaction vessel warms and a vigorous gas evolution occurs. The mixture was stirred for 25 min at RT and then the flask was placed in a cool water bath before the addition of 20 mL of $Et_2O$. The resulting solid was collected, washed with $Et_2O$ twice, and concentrated in vacuo to give (S)-3-amino-1-((1S,2R,4R)-4-(isopropyl(methyl)amino)-2-(isopropylsulfonylmethyl)cyclohexyl)pyrrolidin-2-one (240 mg, 91% yield). MS found: $(M+H)^+=374$.

Example 10b, Step 4: To a solution of (S)-3-amino-1-((1S,2R,4R)-4-(isopropyl(methyl)amino)-2-(isopropylsulfonylmethyl)cyclohexyl)pyrrolidin-2-one (75 mg, 0.14 mmol) in EtOH (2 mL) was added triethylamine (0.12 mL, 0.84 mmol) and 4-chloro-6-(trifluoromethyl)quinazoline (39 mg, 0.16 mmol). The mixture was heated at 80° C. for 14 h and then concentrated in vacuo. The residue was pjurified by HPLC to provide the title compound, (S)-1-((1S,2R,4R)-4-(isopropyl (methyl)amino)-2-(isopropylsulfonylmethyl)cyclohexyl)-3-(6-(trifluoromethyl)quinazolin-4-ylamino)pyrrolidin-2-one (35 mg, 44% yield). MS found: $(M+H)^+=570$.

Example 10c

Synthesis of 3-tert-butyl-N-((S)-1-((1S,2R,4R)-4-(isopropyl(methyl)amino)-2-(isopropylsulfonylmethyl)cyclohexyl)-2-oxopyrrolidin-3-yl)-1-methyl-1H-pyrazole-5-carboxamide Example 10c, Step 1: To a solution of (S)-3-amino-1-((1S,2R,4R)-4-(isopropyl(methyl)amino)-2-(isopropylsulfonylmethyl)cyclohexyl)pyrrolidin-2-one (40 mg, 0.08 mmol) in DMF (2 mL) was added diisopropylethylamine (0.1 mL, 0.6 mmol), 3-tert-butyl-1-methyl-1H-pyrazole-5-carboxylic acid (18 mg, 0.1 mmol) and HATU (38 mg, 0.1 mmol). The reaction was stirred at RT for 14 h, partially concentrated, and purified by RP-HPLC to affor 20 mg of the title compound. MS found: $(M+H)^+=538$.

TABLE 10-A

The compounds in the following table were made using the methods exemplified above. See Table 1-A for a complete description of the table headings.

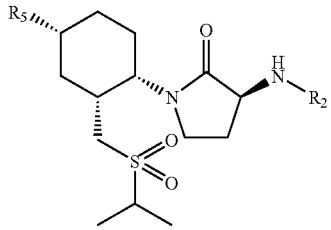

| Example | $R^5$ | $R^2$ | Step Altered | MS Data |
|---|---|---|---|---|
| 10a | i-Pr(Me)N | 3-(trifluoromethyl)benzoyl | n/a | 546 |
| 10b | i-Pr(Me)N | 6-(trifluoromethyl)quinazolin-4-yl | n/a | 570 |
| 10c | i-Pr(Me)N | 3-tert-butyl-1-methyl-1H-pyrazole-5-carbonyl | n/a | 538 |
| 10d | Pyrrolidine | 3-(trifluoromethyl)benzoyl | 10a, Step 8 | 544 |
| 10e | i-Pr(Me)N | 3-tert-butylbenzoyl | 10a, Step 6 | 534 |

TABLE 10-A-continued

The compounds in the following table were made using the methods exemplified above. See Table 1-A for a complete description of the table headings.

| Example | R⁵ | R² | Step Altered | MS Data |
|---|---|---|---|---|
| 10f | i-Pr(Et)N | 6-(trifluoromethyl)quinazolin-4-yl | 10b, Step 1 | 584 |
| 10g | i-Pr(Et)N | 3-tert-butylbenzoyl | 10a, Steps 6 and 8 | 548 |
| 10h | i-Pr(Pr)N | 3-tert-butylbenzoyl | 10a, Steps 6 and 8 | 562 |
| 10i | i-Pr(Me)N | 6-(trifluoromethoxy)quinazolin-4-yl | 10b, Step 4 | 586 |
| 10j | i-Pr(Et)N | 6-(trifluoromethoxy)quinazolin-4-yl | 10b, Steps 2 and 4 | 600 |
| 10k | i-Pr(Et)N | 6-CF₃-quinazolin-4-yl | 10b, Step 2 | 584 |
| 10l | i-Pr(Me)N | 1-methyl-1H-indole-2-carbonyl | 10a, Step 6 | 531 |
| 10m | i-Pr(Et)N | 3-(1H-tetrazol-5-yl)benzoyl | 10b, Steps 2 & 4 (See 10c) | 560 |

TABLE 10-B

The chemical names of the specific examples illustrated in Table 10-A are tabulated below.

| Example | Name |
|---|---|
| 10a | N-((S)-1-((1S,2R,4R)-4-(isopropyl(methyl)amino)-2-(isopropylsulfonylmethyl)cyclohexyl)-2-oxopyrrolidin-3-yl)-3-(trifluoromethyl)benzamide |
| 10b | (S)-1-((1S,2R,4R)-4-(isopropyl(methyl)amino)-2-(isopropylsulfonylmethyl)cyclohexyl)-3-(6-(trifluoromethyl)quinazolin-4-ylamino)pyrrolidin-2-one |
| 10c | 3-tert-butyl-N-((S)-1-((1S,2R,4R)-4-(isopropyl(methyl)amino)-2-(isopropylsulfonylmethyl)cyclohexyl)-2-oxopyrrolidin-3-yl)-1-methyl-1H-pyrazole-5-carboxamide |
| 10d | N-((S)-1-((1S,2R,4R)-2-(isopropylsulfonylmethyl)-4-(pyrrolidin-1-yl)cyclohexyl)-2-oxopyrrolidin-3-yl)-3-(trifluoromethyl)benzamide |

TABLE 10-B-continued

The chemical names of the specific examples illustrated in Table 10-A are tabulated below.

| Example | Name |
|---|---|
| 10e | 3-tert-butyl-N-((S)-1-((1S,2R,4R)-4-(isopropyl(methyl)amino)-2-(isopropylsulfonylmethyl)cyclohexyl)-2-oxopyrrolidin-3-yl)benzamide |
| 10f | (S)-1-((1S,2R,4R)-4-(ethyl(isopropyl)amino)-2-(isopropylsulfonylmethyl)cyclohexyl)-3-(6-(trifluoromethyl)quinazolin-4-ylamino)pyrrolidin-2-one |
| 10g | 3-tert-butyl-N-((S)-1-((1S,2R,4R)-4-(ethyl(isopropyl)amino)-2-(isopropylsulfonylmethyl)cyclohexyl)-2-oxopyrrolidin-3-yl)benzamide |
| 10h | 3-tert-butyl-N-((S)-1-((1S,2R,4R)-4-(isopropyl(propyl)amino)-2-(isopropylsulfonylmethyl)cyclohexyl)-2-oxopyrrolidin-3-yl)benzamide |
| 10i | (S)-1-((1S,2R,4R)-4-(isopropyl(methyl)amino)-2-(isopropylsulfonylmethyl)cyclohexyl)-3-(6-(trifluoromethoxy)quinazolin-4-ylamino)pyrrolidin-2-one |
| 10j | (S)-1-((1S,2R,4R)-4-(ethyl(isopropyl)amino)-2-(isopropylsulfonylmethyl)cyclohexyl)-3-(6-(trifluoromethoxy)quinazolin-4-ylamino)pyrrolidin-2-one |
| 10k | (S)-1-((1S,2R,4R)-4-(ethyl(isopropyl)amino)-2-(isopropylsulfonylmethyl)cyclohexyl)-3-(6-(trifluoromethyl)quinazolin-4-ylamino)pyrrolidin-2-one |
| 10l | N-((S)-1-((1S,2R,4R)-4-(isopropyl(methyl)amino)-2-(isopropylsulfonylmethyl)cyclohexyl)-2-oxopyrrolidin-3-yl)-1-methyl-1H-indole-2-carboxamide |
| 10m | N-((S)-1-((1S,2R,4R)-4-(ethyl(isopropyl)amino)-2-(isopropylsulfonylmethyl)cyclohexyl)-2-oxopyrrolidin-3-yl)-3-(2H-tetrazol-5-yl)benzamide |

Examples 11a-11e

Example 11a

Synthesis of N-((S)-1-((1S,2R,4R)-2-(ethylsulfonylmethyl)-4-(isopropyl(methyl)amino)cyclohexyl)-2-oxopyrrolidin-3-yl)-3-(trifluoromethyl)benzamide Example 11a, Step 1: To a solution of benzyloxycarbonyl tert-butyl (1R,3R,4S)-4-amino-3-(hydroxymethyl)cyclohexylcarbamate (5.60 g, 14.7 mmol) in $CH_2Cl_2$ (32 mL) at 0° C. was added $NEt_3$ (4.73 g, 44.2 mmol), and methanesulfonyl chloride (1.71 mL, 22.1 mmol). The reaction mixture was stirred at room temperature for 2 h under nitrogen atmosphere, then cooled to 0° C. and quenched with satd $NH_4Cl$ (200 mL). The organic layer was washed with satd $NaHCO_3$ (250 mL) and brine (100 mL), dried ($Na_2SO_4$), and concentrated in vacuo to give the intermediate as a yellow foam and used without futher purification for next step: $^1$H NMR (300 MHz, $CDCl_3$) δ 7.40-7.31 (m, 5H), 5.25 (s, 2H), 4.85-4.83 (m, 2H), 4.39 (s, 1H), 4.17-3.96 (m, 3H), 3.70-3.35 (m, 1H), 3.30-3.20 (m, 1H), 2.96 (s, 3H), 2.10-0.94 (m, 7H), 1.44 (s, 9H); ESI MS m/z 457 $[C_{21}H_{34}N_2O_7S+H]^+$.

A solution of ethanethiol (908 μL, 12.3 mmol) and anhyd DMF (31 mL) was cooled to 0° C. under nitrogen atmosphere, then sodium hydride (60% dispersion in mineral oil; 491 mg, 12.3 mmol) was added. To this mixture, a solution of the intermediate just prepared above (2.80 g, 6.1 mmol) in anhyd DMF (30 mL) was added at 0° C. The reaction mixture was warmed to room temperature, stirred for 12 h, cooled back to 0° C., and quenched with satd $NH_4Cl$ (200 mL). The mixture was extracted with EtOAc (500 mL) and the organic layer was washed with 5% LiCl (2×250 mL), dried ($Na_2SO_4$), and concentrated to give benzyloxycarbonyl tert-butyl (1R,3R,4S)-4-amino-3-(ethylthiomethyl)cyclohexylcarbamate (3.00 g). $^1$H NMR (300 MHz, $CDCl_3$) δ 7.61-7.20 (m, 5H), 5.10 (s, 2H), 4.45-4.30 (m, 1H), 4.12-4.02 (m, 2H), 3.52-3.35 (m, 1H) 2.78-2.41 (m, 4H), 2.40-2.25 (m, 1H), 2.20-0.72 (m, 9H), 1.44 (s, 9H); ESI MS m/z 423 $[C_{22}H_{34}N_2O_4S+H]^+$.

Example 11a, Step 2: To a solution of benzyloxycarbonyl tert-butyl (1R,3R,4S)-4-amino-3-(ethylthiomethyl)cyclohexylcarbamate (3.00 g, 6.13 mmol) in 2-PrOH (16 mL) at 0° C. was added a suspension of Oxone® (23.0 g, 36.8 mmol) in water (30 mL). The reaction mixture was stirred at room temperature for 12 h, then diluted with water (200 mL) and extracted with EtOAc (3×250 mL). The organic layer was washed with brine (50 mL), dried ($Na_2SO_4$), and concentrated in vacuo. Purification of the residue by column chromatography (silica gel, 50 g, EtOAc) gave benzyloxycarbonyl tert-butyl (1R,3R,4S)-4-amino-3-(ethylsulfonylmethyl)cyclohexylcarbamate (1.89 g, 68%) as a white solid: mp 54-58° C.; $^1$H NMR (300 MHz, $CDCl_3$) δ 7.60-7.32 (m, 5H), 5.10 (s, 2H), 4.90-4.87 (m, 1H), 4.41-4.30 (m, 1H), 4.07-3.98 (m, 1H), 3.58-3.35 (m, 1H), 3.28-3.10 (m, 1H), 3.08-2.88 (m, 2H), 2.72-2.65 (m, 1H), 2.50-2.18 (m, 2H), 2.08-0.80 (m, 8H), 1.43 (s, 9H); ESI MS m/z 455 $[C_{22}H_{34}N_2O_6S+H]^+$; HPLC 95.7% (area percent), $t_R$=3.76 min.

Example 11a, Step 3: A portion of benzyloxycarbonyl tert-butyl (1R,3R,4S)-4-amino-3-(ethylsulfonylmethyl)cyclohexylcarbamate (1.7 g) in MeOH (30 mL) was charged with 10% Pd/C, Degussa (300 mg). The reaction flask was evacuated and then back-filled with hydrogen; this was repeated three more times. The reaction was stirred under 1 atm of $H_2$ for 4 h and then filtered and concentrated in vacuo to afford tert-butyl (1R,3R,4S)-4-amino-3-(ethylsulfonylmethyl)cyclohexylcarbamate (1.1 g). MS found: $(M+H)^+$=321.

Example 11a, Step 4: A sample of tert-butyl (1R,3R,4S)-4-amino-3-(ethylsulfonylmethyl)cyclohexylcarbamate (1.1 g, 3.4 mmol) was dissolved in DMF (20 mL), and the resultant solution was charged with N-Cbz methionine (1.15 g, 4.08 mmol), N,N-diethylisopropylamine (0.7 mL, 4.08 mmol), and HATU (1.55 g, 4.08 mmol). The reaction was stirred for 12 h at RT and then partitioned between EtOAc and sat. $NaHCO_3$; the aqueous phase was back extracted with EtOAc (1×). The organic phases were combined, washed with brine, dried ($Na_2SO_4$), filtered, and concentrated in vacuo. The residue was purified by flash chromatography to afford benzyloxycarbonyl tert-butyl (1R,3R,4S)-4-((S)-2-amino-4-(methylthio)butanamido)-3-(ethylsulfonylmethyl)cyclohexylcarbamate (2.2 g). MS found: $(M+H)^+$=586.

Example 11a, Step 5: The compound benzyloxycarbonyl tert-butyl (1R,3R,4S)-4-((S)-2-amino-4-(methylthio)butanamido)-3-(ethylsulfonylmethyl)cyclohexylcarbamate (3.4 mmol) was "wetted" with EtOAc, and then the majority of EtOAc was removed under nitrogen stream. The residue was dissolved in iodomethane (20 mL), and the resulting solution was stirred at RT for 48 h before being concentrated in vacuo.

The residue was dissolved in methylene chloride, and the resulting solution was concentrated; this was repeated to afford the salt. MS found: (M+H)⁺=602. This material was dissolved in DMF (20 mL) and the solution was charged with Cs₂CO₃ (3.3 g, 10.2 mmol) and stirred for 12 h at RT before being partitioned between EtOAc and brine. The organic phase was dried (Na₂SO₄), filtered, and concentrated in vacuo. The residue was purified by flash chromatography to afford benzyloxycarbonyl tert-butyl (1R,3R,4S)-4-((S)-3-amino-2-oxopyrrolidin-1-yl)-3-(ethylsulfonylmethyl)cyclohexylcarbamate (1 g). MS found: (M+H)⁺=538.

Example 11a, Step 6: A solution of benzyloxycarbonyl tert-butyl (1R,3R,4S)-4-((S)-3-amino-2-oxopyrrolidin-1-yl)-3-(ethylsulfonylmethyl)cyclohexylcarbamate (1 g) in MeOH (20 mL) was charged with 10% Pd/C, Degussa (250 mg). The reaction flask was evacuated and then back-filled with hydrogen; this was repeated three more times. The reaction was stirred under 1 atm of H₂ for 12 h and then filtered and concentrated in vacuo to afford tert-butyl (1R,3R,4S)-4-((S)-3-amino-2-oxopyrrolidin-1-yl)-3-(isopropylsulfonylmethyl)cyclohexylcarbamate. MS found: (M+H)⁺=404.

Example 11a, Step 7: A sample of tert-butyl (1R,3R,4S)-4-((S)-3-amino-2-oxopyrrolidin-1-yl)-3-(ethylsulfonylmethyl)cyclohexylcarbamate (100 mg, 0.25 mmol) in DMF (10 mL) was charged with 3-(trifluoromethyl)benzoic acid (57 mg, 0.29 mmol), N,N-diethylisopropylamine (0.05 mL, 0.29 mmol), and HATU (114 mg, 0.29 mmol). The reaction was stirred for 48 h at RT and then partitioned between EtOAc and sat. NaHCO₃; the aqueous phase was back extracted with EtOAc (1×). The organic phases were combined, washed with brine, dried (Na₂SO₄), filtered, and concentrated in vacuo to afford tert-butyl (1R,3R,4S)-3-(ethylsulfonylmethyl)-4-((S)-2-oxo-3-(3-(trifluoromethyl)benzamido)pyrrolidin-1-yl)cyclohexylcarbamate. MS found: (M+H)⁺=578.

Example 11a, Step 8: A solution of tert-butyl (1R,3R,4S)-3-(etylsulfonylmethyl)-4-((S)-2-oxo-3-(3-(trifluoromethyl)benzamido)pyrrolidin-1-yl)cyclohexylcarbamate (0.25 mmol) in CH₂Cl₂ (10 mL) was treated with trifluoroacetic acid (4 mL). After 1 h, the reaction was concentrated in vacuo, and the resultant residue was partitioned between EtOAc and sat. NaHCO₃. The organic phase was washed with brine, dried (Na₂SO₄), filtered, and concentrated in vacuo to afford the amine. MS found: (M+H)⁺=476. The amine (0.25 mmol) was dissolved in CH₂Cl₂ (10 mL) and charged with acetone (~2 mL); the mixture was stirred for 5 min before being charged with NaCNBH₃ (1 mmol). The reaction was stirred for 4 h at RT and then charged with formaldehyde (2 mL of a 30% aq. Solution). The mixture was stirred for 1.5 h, quenched with sat. NaHCO₃, and extracted with EtOAc (2×). The organic extracts were combined, washed with brine, dried (Na₂SO₄), filtered, and concentrated in vacuo. The residue was purified by reverse phase HPLC to afford the TFA salt of the title compound, N-((S)-1-((1S,2R,4R)-4-(isopropyl(methyl)amino)-2-(ethylsulfonylmethyl)cyclohexyl)-2-oxopyrrolidin-3-yl)-3-(trifluoromethyl)benzamide, as a white powder (42 mg) after lyopholization. MS found: (M+H)⁺=532.

Example 11b

Synthesis of (S)-1-((1S,2R,4R)-4-(isopropyl(methyl)amino)-2-(ethylsulfonylmethyl)cyclohexyl)-3-(6-(trifluoromethyl)quinazolin-4-ylamino)pyrrolidin-2-one Example 11b, Step 1: To a solution of benzyloxycarbonyl tert-butyl (1R,3R,4S)-4-((S)-3-amino-2-oxopyrrolidin-1-yl)-3-(ethylsulfonylmethyl)cyclohexylcarbamate (1 g) in CH₂Cl₂ (30 mL) was added TFA (6 mL) at RT. The reaction was stirred for 5 h and concentrated in vacuo. The residue was partitioned between 1N NaOH (100 mL) and EtOAc (150 mL). The aqueous layer was extracted with EtOAc (2×50 mL) and the organic phases were combined, washed with brine (25 mL), dried (Na₂SO₄), filtered, and concentrated in vacuo to give benzyl (S)-1-((1S,2R,4R)-4-amino-2-(ethylsulfonylmethyl)cyclohexyl)-2-oxopyrrolidin-3-ylcarbamate. MS found: (M+H)⁺=438.

Example 11b, Step 2: The entirety of benzyl (S)-1-((1S,2R,4R)-4-amino-2-(ethylsulfonylmethyl)cyclohexyl)-2-oxopyrrolidin-3-ylcarbamate prepared in Step 1 (1 eq) was dissolved in CH₂Cl₂ (20 mL). The resultant solution was charged with acetone (10 eq) and stirred at RT for 10 min before sodium cyanoborohydride (2 eq) was added in one portion. The reaction was stirred at RT for 10 h and then charged successively with formaldehyde (10 eq in 37 wt % aq soln) and sodium cyanoborohydride (2 eq). The reaction was stirred for another 9 h at RT and then quenched with sat. NaHCO₃. The aqueous mixture was extracted with EtOAc (200 mL, then 2×75 mL). The organic extracts were combined, washed with brine (30 mL), dried (MgSO₄), filtered, and concentrated in vacuo. After the resulting oil stood, some paraformaldehyde-related products solidified; these were removed by dissolving the mixture in a minimal volume of EtOAc and filtering. Subsequent concentration provided benzyl (S)-1-((1S,2R,4R)-4-(isopropyl(methyl)amino)-2-(ethylsulfonylmethyl)cyclohexyl)-2-oxopyrrolidin-3-ylcarbamate. MS found: (M+H)⁺=494.

Example 11b, Step 3: The entirety of benzyl (S)-1-((1S,2R,4R)-4-(isopropyl(methyl)amino)-2-(ethylsulfonylmethyl)cyclohexyl)-2-oxopyrrolidin-3-ylcarbamate prepared in Step 2 (250 mg) was charged with 30% HBr/AcOH (5 mL). The reaction vessel warms and a vigorous gas evolution occurs. The mixture was stirred for 25 min at RT and then the flask was placed in a cool water bath before the addition of 20 mL of Et₂O. The resulting solid was collected, washed with Et₂O twice, and concentrated in vacuo to give (S)-3-amino-1-((1S,2R,4R)-4-(isopropyl(methyl)amino)-2-(ethylsulfonylmethyl)cyclohexyl)pyrrolidin-2-one (150 mg). MS found: (M+H)⁺=360.

Example 11b, Step 4: To a solution of (S)-3-amino-1-((1S,2R,4R)-4-(isopropyl(methyl)amino)-2-(ethylsulfonylmethyl)cyclohexyl)pyrrolidin-2-one (50 mg, 0.1 mmol) in EtOH (2 mL) was added triethylamine (0.1 mL, 0.6 mmol) and 4-chloro-6-(trifluoromethyl)quinazoline (27 mg, 0.11 mmol). The mixture was heated at 80° C. for 14 h and then concentrated in vacuo. The residue was pjurified by HPLC to provide the title compound, (S)-1-((1S,2R,4R)-4-(isopropyl(methyl)amino)-2-(ethylsulfonylmethyl)cyclohexyl)-3-(6-(trifluoromethyl)quinazolin-4-ylamino)pyrrolidin-2-one (35 mg). MS found: (M+H)⁺=556.

TABLE 11-A

The compounds in the following table were made using the methods exemplified above. See Table 1-A for a complete description of the table headings.

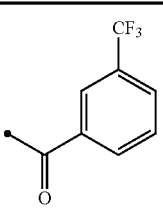

| Example | R⁵ | R² | Step Altered | MS Data |
|---|---|---|---|---|
| 11a | i-Pr(Me)N | 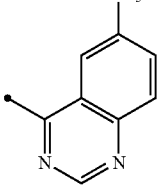 (3-CF₃-benzoyl) | n/a | 532 |
| 11b | i-Pr(Me)N | 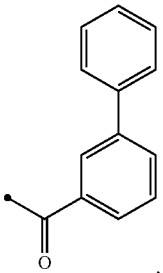 (6-CF₃-quinazolin-4-yl) | n/a | 556 |
| 11c | i-Pr(Me)N | (3-phenylbenzoyl) | 11a, Step 6 | 540 |
| 11d | i-Pr(Me)N | 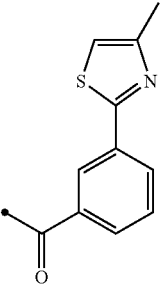 (4-methylthiazol-2-yl-benzoyl) | 11a, Step 6 | 561 |
| 11e | i-Pr(Me)N | 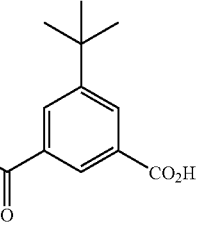 (3-tBu-5-CO₂H-benzoyl) | 11a, Step 6 | 564 |

TABLE 11-B

The chemical names of the specific examples illustrated in Table 11-A are tabulated below.

| Example | Name |
|---|---|
| 11a | N-((S)-1-((1S,2R,4R)-2-(ethylsulfonylmethyl)-4-(isopropyl(methyl)amino)cyclohexyl)-2-oxopyrrolidin-3-yl)-3-(trifluoromethyl)benzamide |
| 11b | (S)-1-((1S,2R,4R)-2-(ethylsulfonylmethyl)-4-(isopropyl(methyl)amino)cyclohexyl)-3-(6-(trifluoromethyl)quinazolin-4-ylamino)pyrrolidin-2-one |
| 11c | N-((S)-1-((1S,2R,4R)-2-(ethylsulfonylmethyl)-4-(isopropyl(methyl)amino)cyclohexyl)-2-oxopyrrolidin-3-yl)-3-(phenyl)benzamide |
| 11d | N-((S)-1-((1S,2R,4R)-2-(ethylsulfonylmethyl)-4-(isopropyl(methyl)amino)cyclohexyl)-2-oxopyrrolidin-3-yl)-3-(4-methylthiazol-2-yl)benzamide |
| 11e | 3-(((S)-1-((1S,2R,4R)-2-(ethylsulfonylmethyl)-4-(isopropyl(methyl)amino)cyclohexyl)-2-oxopyrrolidin-3-yl)carbamoyl)-5-tert-butylbenzoic acid |

Examples 12a-12bh

Example 12a

Synthesis of (1R,2S,5R)-methyl 5-(isopropyl(methyl)amino)-2-((S)-2-oxo-3-(3-(trifluoromethyl)benzamido)pyrrolidin-1-yl)cyclohexanecarboxylate Example 12a, Step 1: A solution of (1R,2S,5R)-tert-butyl 2-(benzyloxycarbonyl-amino)-7-oxo-6-aza-bicyclo[3.2.1]octane-6-carboxylate (9.6 g, 0.025 mmol) in methanol was treated with 2.5 g of 10% Pd/C and hydrogenated at 55 psi of H₂ in a Parr shaker overnight. The mixure was filtered and the filtrate was concentrated in-vacuo to give an oil consisting of a mixture of (1R,2S,5R)-methyl 2-amino-5-(tert-butoxy-carbonylamino)cyclohexanecarboxylate and (1R,2S,5R)-tert-butyl 2-amino-7-oxo-6-aza-bicyclo[3.2.1]octane-6-carboxylate. This was used without further purification. LCMS found two peaks: (M+H)⁺=273 and (M+H–BOC)⁺=141.

Example 12a, Step 2: A solution of crude amine from step 1 above in CH₂Cl₂ was treated with CBZ-L-Met (8.49 g, 0.03 mol), EDCI (5.7 g, 0.03 mol), HOBT (4.1 g, 0.03 mol), Et₃N (3.0 g 0.03 mol), and the resulting reaction solution was stirred overnight at room temperature. The solution was washed with water, brine, dried (MgSO₄), filtered, and concentrated in vacuo and the residue chromatographed on silica gel (50-70% ethyl acetate/hexane) to give 5.5 grams (40% yield) of (1R,2S,5R)-methyl 2-((R)-2-(benzyloxycarbonylamino)-3-(methylthio)propanamido)-5-(tert-butoxycarbonylamino)cyclohexanecarboxylate as a solid. MS found: (M+H)⁺=538.

Example 12a, Step 3: A solution of (1R,2S,5R)-methyl 2-((R)-2-(benzyloxycarbonylamino)-3-(methylthio)propanamido)-5-(tert-butoxycarbonylamino)-cyclohexanecarboxylate in MeI (and minimal amount of CH₂Cl₂) was stirred 24 h at room temperature before being concentrated in vacuo. The residue was titurated with hexane and resulting suspension was concentrated; this was repeated several times to afford 7 g of the salt as a white solid. MS found: (M+H)⁺=552.2. This material was dissolved in DMF (75 mL) and the solution was charged with Cs₂CO₃ (6.6 g, 20 mmol) and stirred at RT for 20 h. The reaction mixture was poured into a mixture of ice/1 N HCl while stirring and then further diluted with water (total volume 1 L). The solid that precipitated was filtered and air dried to give 1.6 g (30% yield) of (1R,2S,5R)-methyl 2-((S)-3-(benzyloxycarbonylamino)-2-oxopyrrolidin-1-yl)-5-(tert-butoxycarbonylamino)-cyclohexanecarboxylate which was used without further purification. MS found: $(M+H)^+=490.3$.

Example 12a, Step 4: A solution of (1R,2S,5R)-methyl 2-((S)-3-(benzyloxycarbonylamino)-2-oxopyrrolidin-1-yl)-5-(tert-butoxycarbonylamino)-cyclohexanecarboxylate in $CH_2Cl_2$ (10 mL) was treated with TFA (15 mL) and stirred at room temperature for 2 h. The reaction mixture was concentrated in vacuo and the residue dissolved in $CH_2Cl_2$ and washed with $NaHCO_{3(aq)}$, brine, and dried over $MgSO_4$. The solution was filtered and concentrated in vacuo to give 0.75 g (59%) of (1R,2S,5R)-methyl 5-amino-2-((S)-3-(benzyloxycarbonylamino)-2-oxopyrrolidin-1-yl)cyclohexanecarboxylate as a white solid. MS found: $(M+H)^+=390.3$.

Example 12a, Step 5: A solution of (1R,2S,5R)-methyl 5-amino-2-((S)-3-(benzyloxycarbonylamino)-2-oxopyrrolidin-1-yl)cyclohexanecarboxylate from step 4 (0.75 g, 1.9 mmol) in $CH_2Cl_2$ (10 ml) was treated with acetone (1 ml) and $NaBH(OAc)_3$ (0.85 g, 4 mmol) and stired at room temperature for 6 h. A solution of 37% aq formaldehyde (2 ml) was added and stirred at room temperature overnight. The solution was diluted with $CH_2Cl_2$ (50 ml) and washed with 1 N NaOH, water, brine, concentrated in vacuo and the residue chromatographed (1:9:90 $NH_4OH:MeOH:CH_2Cl_2$) to give 0.4 g (50%) of (1R,2S,5R)-methyl 2-((S)-3-(benzyloxycarbonylamino)-2-oxopyrrolidin-1-yl)-5-(isopropyl(methyl)amino)-cyclohexanecarboxylate as a white foam. MS found: $(M+H)^+=446.3$.

Example 12a, Step 6: A solution of (1R,2S,5R)-methyl 2-((S)-3-(benzyloxycarbonylamino)-2-oxopyrrolidin-1-yl)-5-(isopropyl(methyl)amino)-cyclohexanecarboxylate (0.6 g, 1.3 mmol) in methanol was treated with 150 mg of 10% Pd/C and hydrogenated at 55 psi of $H_2$ in a Parr shaker overnight. The catalyst was filtered and the filtrate concentrated in vacuo to give 0.4 g of (1R,2S,5R)-methyl 2-((S)-3-amino-2-oxopyrrolidin-1-yl)-5-(isopropyl(methyl)amino)cyclohexanecarboxylate as a white solid. This was used without further purification. MS found: $(M+H)^+=312.3$.

Example 12a, Step 7: A solution of (1R,2S,5R)-methyl 2-((S)-3-amino-2-oxopyrrolidin-1-yl)-5-(isopropyl(methyl)amino)-cyclohexanecarboxylate (50 mg, 0.16 mmol), 3-(trifluoromethyl)benzoic acid (38 mg, 0.20 mol), EDCI (38 mg, 0.20 mmol), HOBT (27 mg, 0.20 mmol), and $Et_3N$ (20 mg 0.20 mmol) in $CH_2Cl_2$ was stirred overnight at room temperature. The solution was washed with water and brine, concentrated in vacuo and the residue chromatographed on silica gel (3%-5%-10% ($NH_4OH/MeOH$)/$CH_2Cl_2$) to give 30 mg of the title product as a white solid. MS found: $(M+H)^+=484.25$ Example 12b Synthesis of (1R,2S,5R)-methyl 5-(tert-butylamino)-2-((S)-2-oxo-3-(3-(trifluoromethyl)benzamido)pyrrolidin-1-yl)cyclohexanecarboxylate Example 12b, Step 1: A solution of benzyl (1R,2S,5R)-7-oxo-6-oxa-bicyclo[3.2.1]octan-2-ylcarbamate (20 g, 72.6 mmol) in ethyl acetate (125 mL) was treated with 1.3 g of 10% Pd/C and hydrogenated overnight at 55 psi of $H_2$ in a Parr shaker overnight. The catalyst was filtered and the filtrate concentrated in vacuo to give 10.2 g (100%) of (1R,2S,5R)-2-amino-6-oxa-bicyclo[3.2.1]octan-7-one as an oil. This was used without further purification. MS found: $(M+H)^+=142.06$.

Example 12b, Step 2: A solution of (1R,2S,5R)-2-amino-6-oxa-bicyclo-[3.2.1]octan-7-one (10.2 g, 72.6 mmol) from step 1 above in $CH_2Cl_2$ was treated with CBZ-L-Met (22.7 g, 80 mmol), EDCI (15.3 g, 80 mmol), HOBT (10.8 g, 80 mmol), $Et_3N$ (8.1 g 80 mmol), and the resulting reaction solution was stirred overnight at room temperature. The solution was washed with water, brine, dried ($MgSO_4$), filtered, and concentrated in vacuo to give 29.5 grams (100% yield) of benzyl (R)-3-(methylthio)-1-oxo-1-((1R,2S,5R)-7-oxo-6-oxa-bicyclo[3.2.1]octan-2-ylamino)propan-2-ylcarbamate as a solid. This was used without further purification. MS found: $(M+H)^+=407.3$.

Example 12b, Step 3: A solution of benzyl (R)-3-(methylthio)-1-oxo-1-((1R,2S,SR)-7-oxo-6-oxa-bicyclo[3.2.1]octan-2-ylamino)propan-2-ylcarbamate (29.5 g, 72.6 mmol)in MeI (80 ml and minimal amount of $CH_2Cl_2$) was stirred 24 h at room temperature before being diluted with $CH_2Cl_2$ and then concentrated in vacuo. The residue was titurated with hexane and resulting suspension was concentrated; this was repeated several times to afford 40 g of the salt as a white solid. MS found: $(M+H)^+=421.22$. This material was dissolved in DMF (150 mL) and the solution was charged with $CS_2CO_3$ (47.19 g, 145 mmol) and stirred at room temperature for 25 h. The reaction mixture was poured into a mixture of ice/1 N HCl while stirring and then further diluted with water (total volume 1 L). The solid that precipitated was extracted into $CH_2Cl_2$ and washed with water and brine. The solvent was removed in vacuo and the resulting solid recrystallized from ethyl acetate to give 11.3 g (43%) of benzyl (S)-2-oxo-1-((1R,2S,5R)-7-oxo-6-oxa-bicyclo[3.2.1]octan-2-yl)pyrrolidin-3-ylcarbamate as a light yellow solid. The mother liquor was concentrated in vacuo and the resulting residue chromatographed to give an additional 4.5 g (61% total yield). MS found: $(M+H)^+=359.24$ Example 12b, Step 4: A solution of benzyl (S)-2-oxo-1-((1R,2S,5R)-7-oxo-6-oxa-bicyclo[3.2.1]octan-2-yl)pyrrolidin-3-ylcarbamate (11.3 g, 31.5 mol) in methanol was treated with solid $NaHCO_3$ (4.0 g, 47.6 mol) and stirred at room temperature for 2 h. Water (100 ml) was added and the mixture extracted into $CH_2Cl_2$. The extract was washed with water, brine and concentrated to give 12.3 g of an apparent equilibrium mixture of lactone and desired alcohol ester (in 40:60 ratio). This mixture was used without further purification. MS found: $(M+H)^+=391.29$.

Example 12b, Step 5: A solution of the mixture of lactone and alcohol ester from step 4 above (12.3 g, 31.5 mol) in acetone was treated with Jone's Reagent (35 ml) while stirring at room temperature. The excess reagent was quenched with isopropyl alcohol and the mixture neutralized with sat'd NaHCO3. The resulting mixture was partitioned between water and ethyl acetate and the organic layer was washed with water and brine. The solvent was removed under vacuum and the residue recrystallized from ethyl acetate to give, in two crops, 6.6 g (54%) of (1R,2S)-methyl 2-((S)-3-(benzyloxycarbonylamino)-2-oxopyrrolidin-1-yl)-5-oxocyclohexanecarboxylate. MS found: $(M+H)^+=389.17$ The mother liquor consists mainly of the lactone, benzyl (S)-2-oxo-1-((1R,2S,5R)-7-oxo-6-oxa-bicyclo[3.2.1]octan-2-yl)pyrrolidin-3-ylcarbamate, which was recycled in step 4.

Example 12b, Step 6: A solution of (1R,2S)-methyl 2-((S)-3-(benzyloxy-carbonylamino)-2-oxopyrrolidin-1-yl)-5-oxo-cyclo-hexanecarboxylate (3.1 g, 8 mmol) in DMSO (7 ml) was treated with t-butylamine (1.75 g, 24 mol) and strirred for 10 minutes before $Ti(i-OPr)_4$ (6.8 g, 24 mol) was added and the resulting mixture was stirred at room temperature for 2.5 h. Then NaBH$_4$ (0.3 g, 8 mol) was added and stirred for 1.5 h before diluting slowly with methanol (gas evolution) and the resulting solution stirred an additional 1 h. While stiring vigorously, a sat'd solution of NaHCO$_3$ was added, and the resulting suspension was filtered through Celite. The filter cake was washed thoroughly with CH$_2$Cl$_2$ several times and the combined washes were transferred to a separatory funnel. The organic layer was separated and washed with water and brine, concentrated and the residue chromatographed on silica gel (5% MeOH/CH$_2$Cl$_2$-8% NH$_4$OH/MeOH/CH$_2$Cl$_2$) to give 3.0 g (80%) of (1R,2S,5R)-methyl 2-((S)-3-(benzyloxycarbonylamino)-2-oxopyrrolidin-1-yl)-5-(tert-butylamino) cyclohexane-carboxylate. MS found: (M+H)$^+$=446.30. Also obtained was 400 mg of the isomeric (1R,2S,5S)-methyl 2-((S)-3-(benzyloxycarbonylamino)-2-oxopyrrolidin-1-yl)-5-(tert-butylamino)cyclohexanecarboxylate. MS found: (M+H)$^+$=446.3.

Example 12b, Step 7: A solution of (1R,2S,5R)-methyl 2-((S)-3-(benzyloxycarbonylamino)-2-oxopyrrolidin-1-yl)-5-(tert-butylamino)-cyclohexanecarboxylate (2.42 g, 5.43 mmol) in methanol was treated with 600 mg of 10% Pd/C and hydrogenated at 55 psi of H$_2$ in a Parr shaker overnight. The catalyst was filtered and the filtrate concentrated in vacuo to give 1.64 g of (1R,2S,5R)-methyl 2-((S)-3-amino-2-oxopyrrolidin-1-yl)-5-(tert-butylamino)-cyclohexanecarboxylate as a white solid. This was used without further purification. MS found: (M+H)$^+$=312.32.

Example 12b, Step 8: A solution of (1R,2S,5R)-methyl 2-((S)-3-amino-2-oxopyrrolidin-1-yl)-5 -(tert-butylamino)-cyclohexanecarboxylate (56 mg, 0.18 mmol), 3-(trifluoromethyl)benzoic acid (42 mg, 0.22 mol), EDCI (42 mg, 0.22 mmol), HOBT (30 mg, 0.22 mmol), and Et$_3$N (22 mg 0.20 mmol) in CH$_2$Cl$_2$ was stirred overnight at room temperature. The solution was washed with water and brine, concentrated in vacuo and the residue chromatographed on silica gel (3%-5%-10% (NH$_4$OH/MeOH)/CH$_2$Cl$_2$) to give 34 mg of the title product, (1R,2S,5R)-methyl 5-(tert-butylamino)-2-((S)-2-oxo-3-(3-(trifluoromethyl)-benzamido)pyrrolidin-1-yl)cyclohexanecarboxylate, as a white solid. MS found: (M+H)$^+$=484.24.

Example 12c

Synthesis of (1R,2S,5R)-methyl 5-(tert-butyl(methyl)amino)-2-((S)-2-oxo-3-(3-(trifluoromethyl)-benzamido)pyrrolidin-1-yl)cyclohexanecarboxylate Example 12c, Step 1: A solution of (1R,2S,SR)-methyl 2-((S)-3-(benzyloxycarbonylamino)-2-oxopyrrolidin-1-yl)-5-(tert-butylamino)cyclohexanecarboxylate (460 mg, 1.0 mol) (from Example 12b, Step 6 above) in CH$_2$Cl$_2$ was treated with a solution of 37% aq formaldehyde (1 ml) and NaBH(OAc)$_3$ (436 mg, 2.0 mol) and stirred at room temperature overnight. The solution was diluted with CH$_2$Cl$_2$ (50 ml) and washed with 1 N NaOH, water, brine, concentrated in vacuo and the residue chromatographed (1:9:90 NH$_4$OH:MeOH:CH$_2$Cl$_2$) to give 330 mg (70%) of (1R,2S,5R)-methyl 2-((S)-3-(benzyloxycarbonylamino)-2-oxopyrrolidin-1-yl)-5-(tert-butyl(methyl)amino)-cyclohexanecarboxylate. MS found: (M+H)$^+$=460.49

Example 12c, Step 2: A solution of (1R,2S,5R)-methyl 2-((S)-3-(benzyloxycarbonylamino)-2-oxopyrrolidin-1-yl)-5-(tert-butyl(methyl)amino)cyclohexanecarboxylate (330 mg, 0.65 mmol) in methanol was treated with 100 mg of 10% Pd/C and hydrogenated at 55 psi of H$_2$ in a Parr shaker overnight. The catalyst was filtered and the filtrate concentrated in vacuo to give 200 mg of (1R,2S,5R)-methyl 2-((S)-3-amino-2-oxopyrrolidin-1-yl)-5-(tert-butyl(methyl)amino)-cyclohexanecarboxylate as a white solid. This was used without further purification. MS found: (M+H)$^+$=326.50

Example 12c, Step 3: A solution of (1R,2S,5R)-methyl 2-((S)-3-amino-2-oxopyrrolidin-1-yl)-5-(tert-butyl(methyl)amino)-cyclohexanecarboxylate (58 mg, 0.18 mmol), 3-(trifluoromethyl)benzoic acid (42 mg, 0.22 mol), EDCI (30 mg, 0.21 mmol), HOBT (30 mg, 0.21 mmol), and Et$_3$N (21 mg 0.21 mmol) in CH$_2$Cl$_2$ was stirred overnight at room temperature. The solution was washed with water and brine, concentrated in vacuo and the residue chromatographed on silica gel (3%-5%-10% (NH$_4$OH/MeOH)/CH$_2$Cl$_2$) to give 34 mg of the title product, (1R,2S,5R)-methyl 5-(tert-butyl(methyl)amino)-2-((S)-2-oxo-3-(3-(trifluoromethyl)-benzamido)pyrrolidin-1-yl)cyclohexanecarboxylate, as a white solid. MS found: (M+H)$^+$=498.40.

Example 12d

Synthesis of (1R,2S,5R)-methyl 5-(isopropyl(methyl)amino)-2-((S)-2-oxo-3-(6-(trifluoromethyl)quinazolin-4-ylamino)pyrrolidin-1-yl)cyclohexanecarboxylate Example 12d, Step 1: A solution of (1R,2S,5R)-methyl 2-((S)-3-amino-2-oxopyrrolidin-1-yl)-5-(isopropyl(methyl)amino)-cyclohexanecarboxylate (50 mg, 0.16 mol), 4-chloro-6-(trifluoromethyl)quinazoline (48 mg, 0.20 mol) and Et$_3$N (100 mg, 1.0 mol) in EtOH (2 ml) was added to a microwave reaction tube, sealed, and heated in a microwave oven at 100° C. for 60 minutes. The reaction mixture was concentrated in vacuo and the residue chromatographed on silica gel (3%-5% (NH$_4$OH/MeOH)/CH$_2$Cl$_2$) to give 25 mg of the title product, (1R,2S,5R)-methyl 5-(isopropyl(methyl)amino)-2-((S)-2-oxo-3-(6-(trifluoromethyl)quinazolin-4-ylamino)pyrrolidin-1-yl)cyclohexanecarboxylate, as a white solid. MS found: (M+H)$^+$=508.24.

Example 12bh

Synthesis of (1R,2S,5S)-methyl 5-(tert-butylamino)-2-((S)-2-oxo-3-(3-(trifluoromethyl)-benzamido)pyrrolidin-1-yl)cyclohexanecarboxylate Example 12bh, Step 1: A solution of (1R,2S,5S)-methyl 2-((S)-3-(benzyloxycarbonylamino)-2-oxopyrrolidin-1-yl)-5-(tert-butylamino)cyclohexanecarboxylate (200 mg, 0.4 mmol, obtained from Example 12b, Step 6 above), in methanol was treated with 60 mg of 10% Pd/C and hydrogenated at 55 psi of H$_2$ in a Parr shaker overnight. The catalyst was filtered and the filtrate concentrated in vacuo to give 130 mg of (1R,2S,5S)-methyl 2-((S)-3-amino-2-oxopyrrolidin-1-yl)-5-(tert-butylamino)-cyclohexanecarboxylate as a white solid. This was used without further purification. MS found: (M+H)$^+$=312.3.

Example 12bh, Step 2: A sample of (1R,2S,5S)-methyl 2-((S)-3-amino-2-oxopyrrolidin-1-yl)-5 -(tert-butylamino)-cyclohexanecarboxylate was carried through the procedure outlined in Example 12b, Step 8 to provide the title compound, (1R,2S,5S)-methyl 5-(tert-butylamino)-2-((S)-2-oxo-3-(3-(trifluoromethyl)-benzamido)pyrrolidin-1-yl)cyclohexanecarboxylate, as a white solid after flash chromatography. MS found: (M+H)$^+$=484.2.

TABLE 12-A

The compounds in the following table were made using the methods exemplified above. See Table 1-A for a complete description of the table headings.

| Example | R⁵ | R² | Step Altered | MS Data |
|---|---|---|---|---|
| 12a | i-Pr(Me)N | 3-(trifluoromethyl)benzoyl | n/a | 484.2 |
| 12b | t-Bu(H)N | 3-(trifluoromethyl)benzoyl | n/a | 484.2 |
| 12c | t-Bu(Me)N | 3-(trifluoromethyl)benzoyl | n/a | 498.4 |
| 12d | i-Pr(Me)N | 6-(trifluoromethyl)quinazolin-4-yl | n/a | 508.2 |
| 12e | i-Pr(Me)N | 6-(trifluoromethoxy)quinazolin-4-yl | 12d, Step 1 | 524.2 |

TABLE 12-A-continued
The compounds in the following table were made using the methods exemplified above. See Table 1-A for a complete description of the table headings.
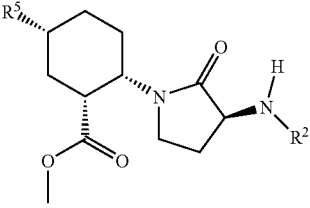
| Example | R⁵ | R² | Step Altered | MS Data |
|---|---|---|---|---|
| 12f | i-Pr(Me)N | 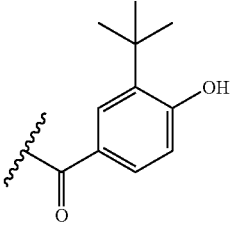 | 12a, Step 7 | 488.3 |
| 12g | i-Pr(Me)N | 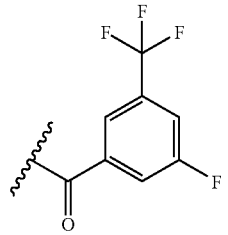 | 12a, Step 7 | 502.2 |
| 12h | i-Pr(Me)N | 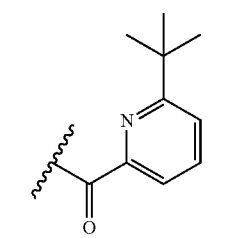 | 12a, Step 7 | 473.3 |
| 12i | t-Bu(H)N | 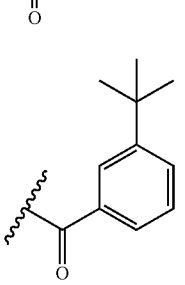 | 12b, Step 8 | 488.3 |
| 12j | t-Bu(H)N |  | 12b, Step 8 | 472.4 |

TABLE 12-A-continued

The compounds in the following table were made using the methods exemplified above. See Table 1-A for a complete description of the table headings.

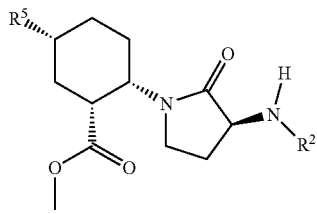

| Example | R⁵ | R² | Step Altered | MS Data |
|---|---|---|---|---|
| 12k | t-Bu(H)N | (2-t-Bu-pyrimidin-4-yl-carbonyl) | 12b, Step 8 | 474.3 |
| 12l | t-Bu(H)N | (6-t-Bu-pyridin-2-yl-carbonyl) | 12b, Step 8 | 473.3 |
| 12m | t-Bu(H)N | (3-Ph-phenylcarbonyl) | 12b, Step 8 | 492.5 |
| 12n | t-Bu(H)N | (6-Ph-pyrazin-2-yl-carbonyl) | 12b, Step 8 | 494.5 |
| 12o | t-Bu(H)N | (4-F-3-CF₃-phenylcarbonyl) | 12b, Step 8 | 502.4 |

TABLE 12-A-continued

The compounds in the following table were made using the methods exemplified above. See Table 1-A for a complete description of the table headings.

| Example | R⁵ | R² | Step Altered | MS Data |
|---------|-----|-----|--------------|---------|
| 12p | t-Bu(Me)N | 5-(4-chlorophenyl)furan-2-carbonyl | 12c, Step 3 | 530.3 |
| 12q | t-Bu(Me)N | 6-(trifluoromethoxy)quinazolin-4-yl | 12c, Step 3 (See 12d) | 538.4 |
| 12r | t-Bu(Me)N | 6-(trifluoromethyl)quinazolin-4-yl | 12c, Step 3 (See 12d) | 522.4 |
| 12s | t-Bu(H)N | 4-(pentafluoroethyl)thiazole-2-carbonyl | 12b, Step 8 | 541.4 |
| 12t | t-Bu(H)N | 4-tert-butylthiazole-2-carbonyl | 12b, Step 8 | 479.5 |
| 12u | t-Bu(H)N | 4-(3-(trifluoromethyl)phenyl)thiazole-2-carbonyl | 12b, Step 8 | 567.4 |

TABLE 12-A-continued
The compounds in the following table were made using the
methods exemplified above. See Table 1-A for a complete
description of the table headings.
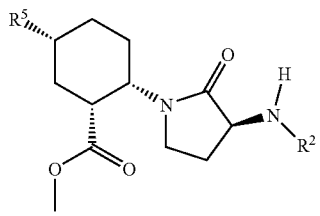
| Example | R⁵ | R² | Step Altered | MS Data |
|---------|------|------|---------|---------|
| 12v | t-Bu(H)N | 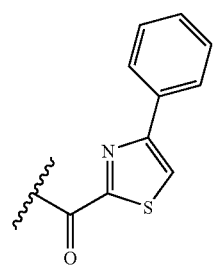 | 12b, Step 8 | 499.4 |
| 12w | t-Bu(H)N | 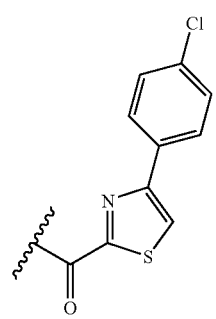 | 12b, Step 8 | 533.4 |
| 12x | t-Bu(H)N | 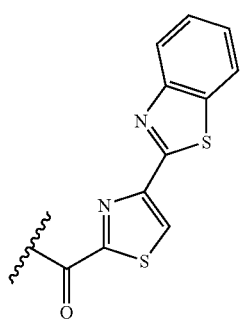 | 12b, Step 8 | 556.4 |
| 12y | t-Bu(H)N | 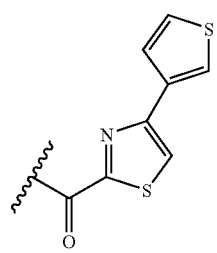 | 12b, Step 8 | 502.2 |

TABLE 12-A-continued

The compounds in the following table were made using the methods exemplified above. See Table 1-A for a complete description of the table headings.

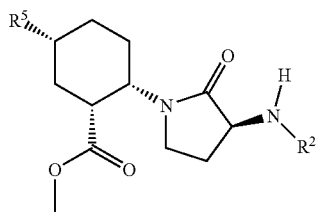

| Example | $R^5$ | $R^2$ | Step Altered | MS Data |
|---|---|---|---|---|
| 12z | t-Bu(H)N | (4-(thiophen-2-yl)thiazol-2-yl)carbonyl | 12b, Step 8 | 502.2 |
| 12aa | t-Bu(H)N | (4-(adamantan-1-yl)thiazol-2-yl)carbonyl | 12b, Step 8 | 557.2 |
| 12ab | t-Bu(H)N | (4-(pyridin-2-yl)thiazol-2-yl)carbonyl | 12b, Step 8 | 500.2 |
| 12ac | t-Bu(H)N | (2-phenylthiazol-4-yl)carbonyl | 12b, Step 8 | 499.4 |

TABLE 12-A-continued
The compounds in the following table were made using the methods exemplified above. See Table 1-A for a complete description of the table headings.
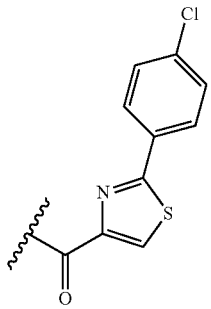
| Example | R⁵ | R² | Step Altered | MS Data |
|---------|-----|-----|--------------|---------|
| 12ad | t-Bu(H)N | 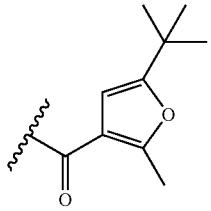 | 12b, Step 8 | 533.3 |
| 12ae | t-Bu(H)N | 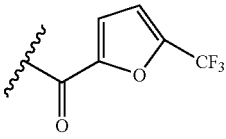 | 12b, Step 8 | 476.5 |
| 12af | t-Bu(H)N | 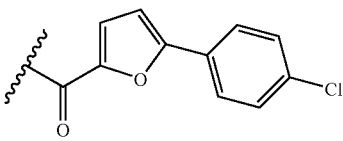 | 12b, Step 8 | 474.4 |
| 12ag | t-Bu(H)N | 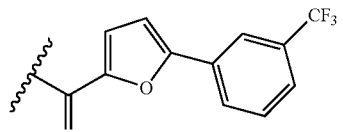 | 12b, Step 8 | 516.1 |
| 12ah | t-Bu(H)N | 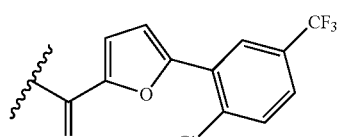 | 12b, Step 8 | 550.3 |
| 12ai | t-Bu(H)N |  | 12b, Step 8 | 584.2 |

TABLE 12-A-continued

The compounds in the following table were made using the methods exemplified above. See Table 1-A for a complete description of the table headings.

| Example | R⁵ | R² | Step Altered | MS Data |
|---|---|---|---|---|
| 12aj | t-Bu(H)N | furan-2,5-diyl-C(O)– linked to 2,5-dichlorophenyl | 12b, Step 8 | 550.2 |
| 12ak | t-Bu(H)N | furan-2,5-diyl-C(O)– linked to 4-isopropylphenyl | 12b, Step 8 | 524.4 |
| 12al | t-Bu(H)N | furan-2,5-diyl-C(O)– linked to 4-fluorophenyl | 12b, Step 8 | 500.4 |
| 12am | t-Bu(H)N | furan-2,5-diyl-C(O)– linked to phenyl | 12b, Step 8 | 482.4 |
| 12an | t-Bu(H)N | furan-2,5-diyl-C(O)– linked to 3-fluorophenyl | 12b, Step 8 | 500.3 |
| 12ao | t-Bu(H)N | furan-2,5-diyl-C(O)– linked to 3-cyanophenyl | 12b, Step 8 | 507.4 |
| 12ap | t-Bu(H)N | furan-2,5-diyl-C(O)– linked to 3-methoxyphenyl | 12b, Step 8 | 512.5 |
| 12aq | t-Bu(H)N | furan-2,5-diyl-C(O)– linked to 4-cyanophenyl | 12b, Step 8 | 507.3 |

TABLE 12-A-continued
The compounds in the following table were made using the methods exemplified above. See Table 1-A for a complete description of the table headings.
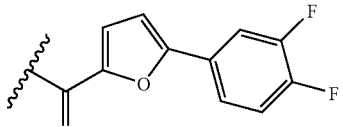
| Example | R⁵ | R² | Step Altered | MS Data |
|---|---|---|---|---|
| 12ar | t-Bu(H)N | 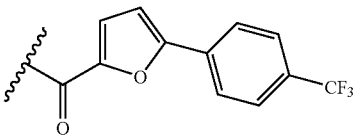 | 12b, Step 8 | 518.3 |
| 12as | t-Bu(H)N | 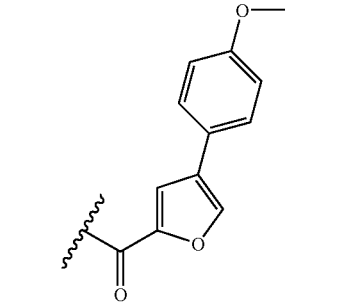 | 12b, Step 8 | 550.4 |
| 12at | t-Bu(H)N | 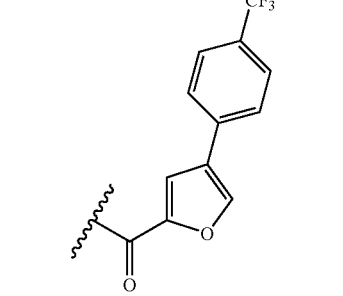 | 12b, Step 8 | 512.2 |
| 12au | t-Bu(H)N | 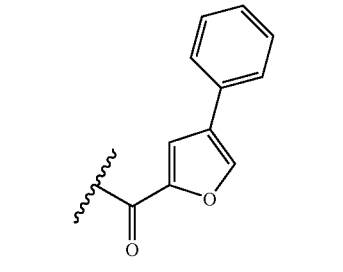 | 12b, Step 8 | 550.2 |
| 12av | t-Bu(H)N | | 12b, Step 8 | 482.4 |

TABLE 12-A-continued

The compounds in the following table were made using the methods exemplified above. See Table 1-A for a complete description of the table headings.

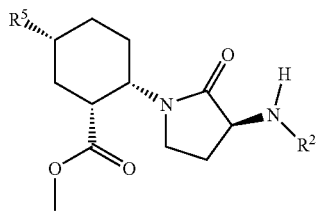

| Example | R⁵ | R² | Step Altered | MS Data |
|---|---|---|---|---|
| 12aw | t-Bu(H)N | 4-phenylthiophene-2-carbonyl | 12b, Step 8 | 498.3 |
| 12ax | t-Bu(H)N | 5-(pyridin-2-yl)thiophene-2-carbonyl | 12b, Step 8 | 499.4 |
| 12ay | t-Bu(H)N | 5-(thiophen-2-yl)thiophene-2-carbonyl | 12b, Step 8 | 504.3 |
| 12az | t-Bu(H)N | 5-phenylthiophene-2-carbonyl | 12b, Step 8 | 492.4 |
| 12ba | t-Bu(H)N | 5-(4-methoxyphenyl)thiophene-2-carbonyl | 12b, Step 8 | 528.4 |
| 12bb | t-Bu(H)N | 1-methyl-3-phenyl-1H-pyrazole-5-carbonyl | 12b, Step 8 | 496.2 |

TABLE 12-A-continued

The compounds in the following table were made using the methods exemplified above. See Table 1-A for a complete description of the table headings.

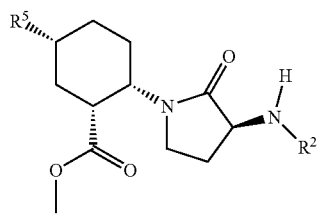

| Example | R⁵ | R² | Step Altered | MS Data |
|---|---|---|---|---|
| 12bc | t-Bu(H)N | 3-phenylisoxazol-5-yl carbonyl | 12b, Step 8 | 483.4 |
| 12bd | t-Bu(H)N | 6-(trifluoromethyl)quinazolin-4-yl | 12b, Step 8 (See 12d) | 508.2 |
| 12be | t-Bu(H)N | 2-tert-butylpyrimido[4,5-d]pyrimidin-4-yl | 12b, Step 8 (See 12d) | 498.4 |
| 12bf | t-Bu(H)N | 6-chloroquinazolin-4-yl | 12b, Step 8 (See 12d) | 474.2 |
| 12bg | t-Bu(H)N | 6-(trifluoromethoxy)quinazolin-4-yl | 12b, Step 8 (See 12d) | 524.2 |

TABLE 12-A-continued

The compounds in the following table were made using the methods exemplified above. See Table 1-A for a complete description of the table headings.

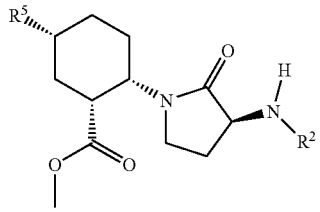

| Example | R⁵ | R² | Step Altered | MS Data |
|---|---|---|---|---|
| 12bh | t-BuN (S)-sterochem | (3-(trifluoromethyl)benzoyl group) | n/a | 484.2 |

TABLE 12-B

The chemical names of the specific examples illustrated in Table 12-A are tabulated below.

| Example | Name |
|---|---|
| 12a | (1R,2S,5R)-methyl 5-(isopropyl(methyl)amino)-2-((S)-2-oxo-3-(3-(trifluoromethyl)benzamido)pyrrolidin-1-yl)cyclohexanecarboxylate |
| 12b | (1R,2S,5R)-methyl 5-(tert-butylamino)-2-((S)-2-oxo-3-(3-(trifluoromethyl)benzamido)pyrrolidin-1-yl)cyclohexanecarboxylate |
| 12c | (1R,2S,5R)-methyl 5-(tert-butyl(methyl)amino)-2-((S)-2-oxo-3-(3-(trifluoromethyl)benzamido)pyrrolidin-1-yl)cyclohexanecarboxylate |
| 12d | (1R,2S,5R)-methyl 5-(isopropyl(methyl)amino)-2-((S)-2-oxo-3-(6-(trifluoromethyl)quinazolin-4-ylamino)pyrrolidin-1-yl)cyclohexanecarboxylate |
| 12e | (1R,2S,5R)-methyl 5-(isopropyl(methyl)amino)-2-((S)-2-oxo-3-(6-(trifluoromethoxy)quinazolin-4-ylamino)pyrrolidin-1-yl)cyclohexanecarboxylate |
| 12f | (1R,2S,5R)-methyl 2-((S)-3-(3-tert-butyl-4-hydroxybenzamido)-2-oxopyrrolidin-1-yl)-5-(isopropyl(methyl)amino)-cyclohexanecarboxylate |
| 12g | (1R,2S,5R)-methyl 2-((S)-3-(3-fluoro-5-(trifluoromethyl)benzamido)-2-oxopyrrolidin-1-yl)-5-(isopropyl(methyl)amino)-cyclohexanecarboxylate |
| 12h | (1R,2S,5R)-methyl 2-((S)-3-(2-tert-butylpicolinamido)-2-oxopyrrolidin-1-yl)-5-(isopropyl(methyl)amino)-cyclohexanecarboxylate |
| 12i | (1R,2S,5R)-methyl 2-((S)-3-(3-tert-butyl-4-hydroxybenzamido)-2-oxopyrrolidin-1-yl)-5-(tert-butylamino)cyclohexanecarboxylate |
| 12j | (1R,2S,5R)-methyl 2-((S)-3-(3-tert-butylbenzamido)-2-oxopyrrolidin-1-yl)-5-(tert-butylamino)cyclohexanecarboxylate |
| 12k | (1R,2S,5R)-methyl 5-(tert-butylamino)-2-((S)-3-(2-tert-butylpyrimidine-4-carboxamido)-2-oxopyrrolidin-1-yl)cyclohexanecarboxylate |
| 12l | (1R,2S,5R)-methyl 5-(tert-butylamino)-2-((S)-3-(2-tert-butylpicolinamido)-2-oxopyrrolidin-1-yl)cyclohexanecarboxylate |
| 12m | (1R,2S,5R)-methyl 5-(tert-butylamino)-2-((S)-3-(3-phenylbenzamido)-2-oxopyrrolidin-1-yl)cyclohexanecarboxylate |
| 12n | (1R,2S,5R)-methyl 5-(tert-butylamino)-2-((S)-2-oxo-3-(2-phenylpyrazine-6-carboxamido)pyrrolidin-1-yl)cyclohexanecarboxylate |
| 12o | (1R,2S,5R)-methyl 5-(tert-butylamino)-2-((S)-3-(4-fluoro-3-(trifluoromethyl)-benzamido)-2-oxopyrrolidin-1-yl)cyclohexanecarboxylate |
| 12p | (1R,2S,5R)-methyl 5-(tert-butyl(methyl)amino)-2-((S)-3-(2-(4-chlorophenyl)furan-5-carboxamido)-2-oxopyrrolidin-1-yl)cyclohexanecarboxylate |
| 12q | (1R,2S,5R)-methyl 5-(tert-butyl(methyl)amino)-2-((S)-2-oxo-3-(6-(trifluoromethoxy)quinazolin-4-ylamino)pyrrolidin-1-yl)cyclohexanecarboxylate |
| 12r | (1R,2S,5R)-methyl 5-(tert-butyl(methyl)amino)-2-((S)-2-oxo-3-(6-(trifluoromethyl)quinazolin-4-ylamino)pyrrolidin-1-yl)cyclohexanecarboxylate |
| 12s | (1R,2S,5R)-methyl 5-(tert-butylamino)-2-((S)-2-oxo-3-(4-(perfluoroethyl)thiazole-2-carboxamido)pyrrolidin-1-yl)cyclohexanecarboxylate |
| 12t | (1R,2S,5R)-methyl 5-(tert-butylamino)-2-((S)-3-(4-tert-butylthiazole-2-carboxamido)-2-oxopyrrolidin-1-yl)cyclohexanecarboxylate |

TABLE 12-B-continued

The chemical names of the specific examples illustrated in Table 12-A are tabulated below.

| Example | Name |
| --- | --- |
| 12u | (1R,2S,5R)-methyl 5-(tert-butylamino)-2-((S)-2-oxo-3-(4-(3-(trifluoromethyl)-phenyl)thiazole-2-carboxamido)pyrrolidin-1-yl)cyclohexanecarboxylate |
| 12v | (1R,2S,5R)-methyl 5-(tert-butylamino)-2-((S)-2-oxo-3-(4-phenylthiazole-2-carboxamido)pyrrolidin-1-yl)cyclohexanecarboxylate |
| 12w | (1R,2S,5R)-methyl 5-(tert-butylamino)-2-((S)-3-(4-(4-chlorophenyl)thiazole-2-carboxamido)-2-oxopyrrolidin-1-yl)cyclohexanecarboxylate |
| 12x | (1R,2S,5R)-methyl 2-((S)-3-(4-(benzo[d]thiazol-2-yl)thiazole-2-carboxamido)-2-oxopyrrolidin-1-yl)-5-(tert-butylamino)cyclohexanecarboxylate |
| 12y | (1R,2S,5R)-methyl 5-(tert-butylamino)-2-((S)-2-oxo-3-(4-(thiophen-3-yl)thiazole-2-carboxamido)pyrrolidin-1-yl)cyclohexanecarboxylate |
| 12z | (1R,2S,5R)-methyl 5-(tert-butylamino)-2-((S)-2-oxo-3-(4-(thiophen-2-yl)thiazole-2-carboxamido)pyrrolidin-1-yl)cyclohexanecarboxylate |
| 12aa | (1R,2S,5R)-methyl 2-((S)-3-(4-(adamant-1-yl)thiazole-2-carboxamido)-2-oxopyrrolidin-1-yl)-5-(tert-butylamino)cyclohexanecarboxylate |
| 12ab | (1R,2S,5R)-methyl 5-(tert-butylamino)-2-((S)-2-oxo-3-(4-(pyridin-2-yl)thiazole-2-carboxamido)pyrrolidin-1-yl)cyclohexanecarboxylate |
| 12ac | (1R,2S,5R)-methyl 5-(tert-butylamino)-2-((S)-2-oxo-3-(2-phenylthiazole-4-carboxamido)pyrrolidin-1-yl)cyclohexanecarboxylate |
| 12ad | (1R,2S,5R)-methyl 5-(tert-butylamino)-2-((S)-3-(2-(4-chlorophenyl)thiazole-4-carboxamido)-2-oxopyrrolidin-1-yl)cyclohexanecarboxylate |
| 12ae | (1R,2S,5R)-methyl 2-((S)-3-(2-tert-butyl-5-methylfuran-4-carboxamido)-2-oxopyrrolidin-1-yl)-5-(tert-butylamino)cyclohexane-carboxylate |
| 12af | (1R,2S,5R)-methyl 5-(tert-butylamino)-2-((S)-2-oxo-3-(2-(trifluoromethyl)furan-5-carboxamido)pyrrolidin-1-yl)cyclohexanecarboxylate |
| 12ag | (1R,2S,5R)-methyl 5-(tert-butylamino)-2-((S)-3-(2-(4-chlorophenyl)furan-5-carboxamido)-2-oxopyrrolidin-1-yl)cyclohexanecarboxylate |
| 12ah | (1R,2S,5R)-methyl 5-(tert-butylamino)-2-((S)-2-oxo-3-(2-(3-(trifluoromethyl)phenyl)furan-5-carboxamido)pyrrolidin-1-yl)cyclohexanecarboxylate |
| 12ai | (1R,2S,5R)-methyl 5-(tert-butylamino)-2-((S)-3-(2-(2-chloro-5-(trifluoromethyl)phenyl)furan-5-carboxamido)-2-oxopyrrolidin-1-yl)cyclohexanecarboxylate |
| 12aj | (1R,2S,5R)-methyl 5-(tert-butylamino)-2-((S)-3-(2-(2,5-dichlorophenyl)furan-5-carboxamido)-2-oxopyrrolidin-1-yl)cyclohexanecarboxylate |
| 12ak | (1R,2S,5R)-methyl 5-(tert-butylamino)-2-((S)-3-(2-(4-isopropylphenyl)furan-5-carboxamido)-2-oxopyrrolidin-1-yl)cyclohexanecarboxylate |
| 12al | (1R,2S,5R)-methyl 5-(tert-butylamino)-2-((S)-3-(2-(4-fluorophenyl)furan-5-carboxamido)-2-oxopyrrolidin-1-yl)cyclohexanecarboxylate |
| 12am | (1R,2S,5R)-methyl 5-(tert-butylamino)-2-((S)-2-oxo-3-(2-phenylfuran-5-carboxamido)pyrrolidin-1-yl)cyclohexanecarboxylate |
| 12an | (1R,2S,5R)-methyl 5-(tert-butylamino)-2-((S)-3-(2-(3-fluorophenyl)furan-5-carboxamido)-2-oxopyrrolidin-1-yl)cyclohexanecarboxylate |
| 12ao | (1R,2S,5R)-methyl 5-(tert-butylamino)-2-((S)-3-(2-(3-cyanophenyl)furan-5-carboxamido)-2-oxopyrrolidin-1-yl)cyclohexanecarboxylate |
| 12ap | (1R,2S,5R)-methyl 5-(tert-butylamino)-2-((S)-3-(2-(3-methoxyphenyl)furan-5-carboxamido)-2-oxopyrrolidin-1-yl)cyclohexanecarboxylate |
| 12aq | (1R,2S,5R)-methyl 5-(tert-butylamino)-2-((S)-3-(2-(4-cyanophenyl)furan-5-carboxamido)-2-oxopyrrolidin-1-yl)cyclohexanecarboxylate |
| 12ar | (1R,2S,5R)-methyl 5-(tert-butylamino)-2-((S)-3-(2-(3,4-difluorophenyl)furan-5-carboxamido)-2-oxopyrrolidin-1-yl)cyclohexanecarboxylate |
| 12as | (1R,2S,5R)-methyl 5-(tert-butylamino)-2-((S)-2-oxo-3-(2-(4-(trifluoromethyl)phenyl)furan-5-carboxamido)pyrrolidin-1-yl)cyclohexanecarboxylate |
| 12at | (1R,2S,5R)-methyl 5-(tert-butylamino)-2-((S)-3-(3-(4-methoxyphenyl)furan-5-carboxamido)-2-oxopyrrolidin-1-yl)cyclohexanecarboxylate |
| 12au | (1R,2S,5R)-methyl 5-(tert-butylamino)-2-((S)-2-oxo-3-(3-(4-(trifluoromethyl)phenyl)furan-5-carboxamido)pyrrolidin-1-yl)cyclohexanecarboxylate |
| 12av | (1R,2S,5R)-methyl 5-(tert-butylamino)-2-((S)-2-oxo-3-(3-phenylfuran-5-carboxamido)pyrrolidin-1-yl)cyclohexanecarboxylate |
| 12aw | (1R,2S,5R)-methyl 5-(tert-butylamino)-2-((S)-2-oxo-3-(3-phenylthiophene-5-carboxamido)pyrrolidin-1-yl)cyclohexanecarboxylate |
| 12ax | (1R,2S,5R)-methyl 5-(tert-butylamino)-2-((S)-2-oxo-3-(2-(pyridin-2-yl)thiophene-5-carboxamido)pyrrolidin-1-yl)cyclohexanecarboxylate |
| 12ay | (1R,2S,5R)-methyl 5-(tert-butylamino)-2-((S)-2-oxo-3-(2-(thiophen-2-yl)thiophene-5-carboxamido)pyrrolidin-1-yl)cyclohexanecarboxylate |
| 12az | (1R,2S,5R)-methyl 5-(tert-butylamino)-2-((S)-2-oxo-3-(2-phenylthiophene-5-carboxamido)pyrrolidin-1-yl)cyclohexanecarboxylate |
| 12ba | (1R,2S,5R)-methyl 5-(tert-butylamino)-2-((S)-3-(2-(4-methoxyphenyl)thiophene-5-carboxamido)-2-oxopyrrolidin-1-yl)cyclohexanecarboxylate |
| 12bb | (1R,2S,5R)-methyl 5-(tert-butylamino)-2-((S)-3-(1-methyl-3-phenyl-1H-pyrazole-5-carboxamido)-2-oxopyrrolidin-1-yl)cyclohexanecarboxylate |
| 12bc | (1R,2S,5R)-methyl 5-(tert-butylamino)-2-((S)-2-oxo-3-(3-phenylisoxazole-5-carboxamido)pyrrolidin-1-yl)cyclohexanecarboxylate |
| 12bd | (1R,2S,5R)-methyl 5-(tert-butylamino)-2-((S)-2-oxo-3-(6-(trifluoromethyl)quinazolin-4-ylamino)pyrrolidin-1-yl)cyclohexanecarboxylate |
| 12be | (1R,2S,5R)-methyl 5-(tert-butylamino)-2-((S)-3-(6-tert-butylpyrimido[5,4-d]pyrimidin-4-ylamino)-2-oxopyrrolidin-1-yl)cyclohexanecarboxylate |
| 12bf | (1R,2S,5R)-methyl 5-(tert-butylamino)-2-((S)-3-(6-chloroquinazolin-4-ylamino)-2-oxopyrrolidin-1-yl)cyclohexanecarboxylate |
| 12bg | (1R,2S,5R)-methyl 5-(tert-butylamino)-2-((S)-2-oxo-3-(6-(trifluoromethoxy)-quinazolin-4-ylamino)pyrrolidin-1-yl)cyclohexanecarboxylate |
| 12bh | (1R,2S,5S)-methyl 5-(tert-butylamino)-2-((S)-2-oxo-3-(3-(trifluoromethyl)-benzamido)pyrrolidin-1-yl)cyclohexanecarboxylate |

Examples 13a-13f

Example 13a

Synthesis of (1S,2S,5R)-methyl 5-(isopropyl(methyl)amino)-2-((S)-2-oxo-3-(3-(trifluoromethyl)benzamido)pyrrolidin-1-yl)cyclohexanecarboxylate Example 13a, Step 1 (Isomerization of the cis ester to the corresponding trans ester): To a solution of (1R,2S,5R)-methyl 2-((S)-3-(benzyloxycarbonylamino)-2-oxopyrrolidin-1-yl)-5-(tert-butoxycarbonylamino)-cyclohexanecarboxylate (281 mg, 0.573 mmol, see Example 12a, Step 3) in anhydrous DMF was added cesium carbonate (747 mg, 2.29 mmol), and the mixture was stirred for 16 h at rt. At the end of the stirring the mixture was poured into water, and extracted with EtOAc (3×). The combined extracts were washed with water, dried ($Na_2SO_4$), filtered, and concentrated in vacuo. The residue was purified by flash chromatograpy on silica gel with elution by EtOAc to afford pure trans isomer, (1S,2S,5R)-methyl 2-((S)-3-(benzyloxycarbonyl)amino-2-oxopyrrolidin-1-yl)-5-(tert-butoxycarbonyl)amino-cyclohexanecarboxylate (214 mg) as an oil.

Example 13a, Step 2: To a solution of (1S,2S,5R)-methyl 2-((S)-3-(benzyloxycarbonyl)amino-2-oxopyrrolidin-1-yl)-5-(tert-butoxycarbonyl)amino-cyclohexanecarboxylate (677 mg, 1.383 mmol) in $CH_2Cl_2$ (7 mL) was added trifluoroacetic acid (1.07 mL, 13.83 mmol), and the mixture was stirred for 75 min at rt. The acid and solvent were evaporated off and the residue was dried under vacuum to afford the trifluoroacetic acid salt of (1S,2S,5R)-methyl 5-amino-2-((S)-3-(benzyloxycarbonyl)amino-2-oxopyrrolidin-1-yl)cyclohexanecarboxylate as an oil.

Example 13a, Step 3: A solution of the crude product of the Step 2 and acetone (0.96 mL, 13.1 mmol) in MeOH (8 mL) was stirred for 20 min at rt, and was added sodium triacetoxyborohydride (880 mg, 4.15 mmol). After stirring for 2.5 h at rt was added 37% aq. HCHO (1 mL), and the mixture was stirred for 1 hr. Then additional sodium triacetoxyborohydride (440 mg, 2.07 mmol) was added and the mixture continued to stirred for additional 3 h. The reaction was quenched with sat. $Na_2CO_3$ and the product was extracted with EtOAc (3×). The combined extracts were washed with brine, dried ($Na_2SO_4$), filtered, and concentrated in vacuo. Mass spectrum of the crude product showed that the product was mainly a mixture of (1S,2S,5R)-methyl 2-((S)-3-(benzyloxycarbonyl)amino-2-oxopyrrolidin-1-yl)-5-(isopropylamino)cyclohexanecarboxylate and (1S,2S,5R)-methyl 2-((S)-3-(benzyloxycarbonyl)amino-2-oxopyrrolidin-1-yl)-5-(dimethylamino)cyclohexanecarboxylate. The product was re-dissolved in $CH_2Cl_2$ (8 mL) and was added 37% aq. HCHO (1 mL). The mixture was stirred for 30 min, and was added sodium triacetoxyborohydride (660 mg, 3.1 mmol). Then it was continued to stir for 16 h and was worked up as above. The residue after concentration was purified by flash chromatography on silica gel with elution by 0.5:4.5:95 $cNH_4OH$-MeOH—$CH_2Cl_2$ followed by 0.7:6.3:93 $cNH_4OH$-MeOH—$CH_2Cl_2$ to provide (1S,2S,5R)-methyl 2-((S)-3-(benzyloxycarbonyl)-2-oxopyrrolidin-1-yl)amino-5-(isopropyl(methyl)amino)cyclohexanecarboxylate (224.4 mg), MS found: $(M+H)^+=446.2$, and (1S,2S,5R)-methyl 2-((S)-3-(benzyloxycarbonyl)amino-2-oxopyrrolidin-1-yl)-5-(dimethylamino)cyclohexanecarboxylate (238 mg), MS found: $(M+H)^+=418.2$.

Example 13a, Step 4: By the methods described in Example 6a, Step 5, (1S,2S,5R)-methyl 2-((S)-3-(benzyloxycarbonyl)-2-oxopyrrolidin-1-yl)amino-5-(isopropyl(methyl)amino)cyclohexanecarboxylate (224 mg) was converted to (1S,2S,5R)-methyl 2-((S)-3-amino-2-oxopyrrolidin-1-yl)-5-(isopropyl(methyl)amino)cyclohexanecarboxylate (134 mg).

Example 13a, Step 5: By the methods described in Example 6c, (1S,2S,5R)-methyl 2-((S)-3-amino-2-oxopyrrolidin-1-yl)-5-(isopropyl(methyl)amino)cyclohexanecarboxylate (33.5 mg) was converted to the titled compound (1S,2S,5R)-methyl 5-(isopropyl(methyl)amino)-2-((S)-2-oxo-3-(3-(trifluoromethyl)benzamido)pyrrolidin-1-yl)cyclohexanecarboxylate (19.3 mg). MS found: $(M+H)^+=484.4$.

Example 13d

Synthesis of (1S,2S,5R)-ethyl 2-((S)-3-(2-(4-chlorophenyl)furan-5-carboxamido)-2-oxopyrrolidin-1-yl)-5-(isopropyl(methyl)amino)cyclohexanecarboxylate Example 13d, Step 1: A solution of (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate (0.80 g, 1.75 mol) in EtOH was treated with NaH (84 mg, 2.1 mol) portion-wise while stirring at rt. After 10 minutes of sirring the reaction was diluted with water and extracted into $CH_2Cl_2$. The extracts were washed with water and brine, concentrated, and the residue chromatographed on silica gel to give 810 mg of isomerized ester (1S,2S,5R)-ethyl 2-((S)-3-(benzyloxycarbonylamino)-2-oxopyrrolidin-1-yl)-5-(tert-butoxycarbonylamino)cyclohexanecarboxylate. MS found: $(M+H)^+=504.46$; $(M+H-BOC)^+=404.46$.

Example 13d, Step 2: A solution of (1S,2S,5R)-ethyl 2-((S)-3-(benzyloxycarbonylamino)-2-oxopyrrolidin-1-yl)-5-(tert-butoxycarbonylamino)cyclohexanecarboxylate (810 mg, 1.61 mol) in $CH_2Cl_2$ (10 mL) was treated with TFA (15 mL) and stirred at room temperature for 2 h. The reaction mixture was concentrated in vacuo and the residue dissolved in $CH_2Cl_2$. The solution was concentrated in vacuo, and this was repeated several times. The final crude (1S,2S,5R)-ethyl 5-amino-2-((S)-3-(benzyloxycarbonylamino)-2-oxopyrrolidin-1-yl)cyclohexanecarboxylate was used with further purification.

Example 13d, Step 3: A solution of (1S,2S,5R)-ethyl 5-amino-2-((S)-3-(benzyloxycarbonylamino)-2-oxopyrrolidin-1-yl)cyclohexanecarboxylate from step 2 in $CH_2Cl_2$ (10 ml) was treated with acetone (1 ml) and $NaBH(OAc)_3$ (1.7 g, 8 mmol) and stirred at room temperature overnight. A solution of 37% aq formaldehyde (2 ml) was added and stirred at room temperature for 1 h. The solution was diluted with $CH_2Cl_2$ (50 ml) and washed with 1 N NaOH, water, brine, concentrated in vacuo and the residue chromatographed (4%

NH$_4$OH:MeOH:CH$_2$Cl$_2$) to give 540 mg (73%) of (1S,2S, 5R)-ethyl 2-((S)-3-(benzyloxycarbonylamino)-2-oxopyrrolidin-1-yl)-5-(isopropyl(methyl)amino)-cyclohexanecarboxylate as a white foam. MS found: (M+H)$^+$=460.51

Example 13d, Step 4: A solution of (1S,2S,5R)-ethyl 2-((S)-3-(benzyloxycarbonylamino)-2-oxopyrrolidin-1-yl)-5-(isopropyl(methyl)amino)-cyclohexanecarboxylate (530 mg, 1.1 mmol) in methanol was treated with 150 mg of 10% Pd/C and hydrogenated at 55 psi of H$_2$ in a Parr shaker overnight. The catalyst was filtered and the filtrate concentrated in vacuo to give 360 mg of (1S,2S,5R)-ethyl 2-((S)-3-amino-2-oxopyrrolidin-1-yl)-5-(isopropyl(methyl)amino) cyclohexanecarboxylate. This was used without further purification. MS found: (M+H)$^+$=326.3

Example 13d, Step 5: Using the methods outlined in Example 12a, Step 7 (and substituting 5-(4-chlorophenyl) furan-2-carboxylic acid), a sample of (1S,2S,5R)-ethyl 2-((S)-3-amino-2-oxopyrrolidin-1-yl)-5-(isopropyl(methyl) amino)cyclohexanecarboxylate was converted to the title compound, (1S,2S,5R)-ethyl 2-((S)-3-(2-(4-chlorophenyl) furan-5-carboxamido)-2-oxopyrrolidin-1-yl)-5-(isopropyl (methyl)amino)cyclohexanecarboxylate. MS found: (M+H)+=530.4.

Example 13e

Synthesis of ethyl 3-((1S,2S,5R)-5-(isopropyl(methyl)amino)-2-((S)-2-oxo-3-(3-(trifluoromethyl)benzamido)pyrrolidin-1-yl)cyclohexyl)propanoate Example 13e, Step 1: A solution of oxalyl chloride (2.0 M in dichloromethane, 370 µL, 735 µmol) in dichloromethane (1.6 mL) was stirred at −78° C. Dimethyl sulfoxide (108 µL, 1.51 mmol) was added dropwise over about 2 min, and the mixture was stirred for 35 min. A solution of tert-butyl (1R, 3R,4S)-4-((S)-3-benzyloxycarbonylamino-2-oxopyrrolidin-1-yl)-3-(hydroxymethyl)cyclohexylcarbamate (219 mg, 475 µmol, See Example 4a, Step 1) in dichloromethane (1.5 mL) was added and the solution was stirred at −78° C. for 65 min. Triethylamine (215 µL, 1.54 mmol) was added, and after 10 min the mixture was warmed to 0° C. and stirred for 2 h. The mixture was diluted with dichloromethane, washed with saturated aqueous ammonium chloride, then with water, and was dried over sodium sulfate and concentrated under vacuum to provide tert-butyl (1R,4S)-4-((S)-3-benzyloxycarbonylamino-2-oxopyrrolidin-1-yl)-3-formylcyclohexylcarbamate as a tan glassy foam (220 mg). MS found: (M+Na)$^+$=482.37.

Example 13e, Step 2: Sodium hydride (60% in mineral oil, 67 mg, 1.66 mmol) was suspended in tetrahydrofuran (1 mL) and treated dropwise with triethyl phosphonoacetate (330 µL, 1.66 mmol). After stirring for 20 min, the mixture was cooled to 0° C. and treated with a solution of tert-butyl (1R,4S)-4-((S)-3-benzyloxycarbonylamino-2-oxopyrrolidin-1-yl)-3-formylcyclohexylcarbamate (220 mg, 475 µmol) in tetrahydrofuran (2 mL). The mixture was stirred at room temperature for 21 h, then was quenched by the addition of saturated aqueous ammonium chloride. The mixture was extracted three times with ethyl acetate, and the combined organic phases were dried over sodium sulfate and concentrated. The residue was purified by flash column chromatography on silica gel, eluting with 3:7 hexane-ethyl acetate, to provide a mixture. of (E)-ethyl 3-((2S,5R)-2-((S)-3-benzyloxycarbonylamino-2-oxopyrrolidin-1-yl)-5-(tert-butoxycarbonyl)cyclohexyl)acrylate and (1R,2S,5R,7R)-tert-butyl 2-((S)-3-(benzyloxycarbonyl)-2-oxopyrrolidin-1-yl)-7-(2-ethoxy-2-oxoethyl)-6-aza-bicyclo[3.2.1]octane-6-carboxylate (56 mg) as a white glassy foam. MS found: (M+H)$^+$=530.48.

Example 13e, Step 3: Following the procedure of Example 5a, Step 3, the mixture of (E)-ethyl 3-((2S,5R)-2-((S)-3-benzyloxycarbonylamino-2-oxopyrrolidin-1-yl)-5-(tert-butoxycarbonyl)cyclohexyl)acrylate and (1R,2S,5R,7R)-tert-butyl 2-((S)-3-(benzyloxycarbonyl)-2-oxopyrrolidin-1-yl)-7-(2-ethoxy-2-oxoethyl)-6-aza-bicyclo[3.2.1]octane-6-carboxylate prepared above in step 2 was converted to a mixture of ethyl 3-((2S,5R)-2-((S)-3-amino-2-oxopyrrolidin-1-yl)-5-(tert-butoxycarbonylamino)cyclohexyl)propanoate and (1R, 2S,5R,7R)-tert-butyl 2-((S)-3-amino-2-oxopyrrolidin-1-yl)-7-(2-ethoxy-2-oxoethyl)-6-aza-bicyclo[3.2.1]octane-6-carboxylate (48 mg) as an off-white solid. MS found: (M+H)+=398.36, 396.36.

Example 13e, Step 4: Following the procedures outlined in Example 2a, Steps 6 and 7, the mixture of ethyl 3-((2S,5R)-2-((S)-3-amino-2-oxopyrrolidin-1-yl)-5-(tert-butoxycarbonylamino)cyclohexyl)propanoate and (1R,2S,5R,7R)-tert-butyl 2-((S)-3-amino-2-oxopyrrolidin-1-yl)-7-(2-ethoxy-2-oxoethyl)-6-aza-bicyclo[3.2.1]octane-6-carboxylate prepared in step 3 above (48 mg) was converted, after reverse phase HPLC and lyophilization, to the TFA salt of the title product, ethyl 3-((1S,2S,5R)-5-(isopropyl(methyl)amino)-2-((S)-2-oxo-3-(3-(trifluoromethyl)benzamido)pyrrolidin-1-yl)cyclohexyl)propanoate, as a white powder (12 mg). MS found: (M+H)$^+$=526.37.

Example 13f

Synthesis of 3-((1S,2S,5R)-5-(isopropyl(methyl) amino)-2-((S)-2-oxo-3-(3-(trifluoromethyl)benzamido)pyrrolidin-1-yl)cyclohexyl)propanoic acid Example 13f, Step 1: A solution of ethyl 3-((2S,5R)-5-(isopropyl(methyl)amino)-2-((S)-2-oxo-3-(3-(trifluoromethyl)benzamido)pyrrolidin-1-yl)-cyclohexyl)propanoate, trifluoroacetic acid salt (10 mg, 15 µmol) in tetrahydrofuran (0.5 mL) was treated with a solution of lithium hydroxide in water (1.0 M, 0.5 mL, 0.5 mmol) and the mixture was stirred for 18 h at room temperature. The mixture was treated with 1.0 N HCl (0.5 mL) and concentrated under vacuum. The residue was purified by reverse phase HPLC to provide the TFA salt of the title product, 3-((1S,2S,5R)-5-(isopropyl(methyl)amino)-2-((S)-2-oxo-3-(3-(trifluoromethyl)benzamido) pyrrolidin-1-yl)cyclohexyl)propanoic acid, as a white powder after lyophilization (7 mg). MS found: (M+H)$^+$=498.41.

TABLE 13-A

The compounds in the following table were made using the methods exemplified above. See Table 1-A for a complete description of the table headings.

| Example | R¹ | R² | Step Altered | MS Data |
|---|---|---|---|---|
| 13a | CO$_2$Me | (3-trifluoromethyl)benzoyl | n/a | 484.4 |
| 13b | CO$_2$Me | 5-(4-chlorophenyl)furan-2-carbonyl | 13a, Step 5 | 516.3 |
| 13c | CO$_2$Me | 3-tert-butyl-4-hydroxybenzoyl | 13a, Step 5 | 488.4 |
| 13d | CO$_2$Et | 5-(4-chlorophenyl)furan-2-carbonyl | n/a | 530.4 |
| 13e | (CH$_2$)$_2$CO$_2$Et | (3-trifluoromethyl)benzoyl | n/a | 526.4 |
| 13f | (CH$_2$)$_2$CO$_2$H | (3-trifluoromethyl)benzoyl | n/a | 498.4 |

TABLE 13-B

The chemical names of the specific examples illustrated in Table 13-A are tabulated below.

| Example | Name |
|---|---|
| 13a | (1S,2S,5R)-methyl 5-(isopropyl(methyl)amino)-2-((S)-2-oxo-3-(3-(trifluoromethyl)benzamido)pyrrolidin-1-yl)cyclohexanecarboxylate |
| 13b | (1S,2S,5R)-methyl 2-((S)-3-(2-(4-chlorophenyl)furan-5-carboxamido)-2-oxopyrrolidin-1-yl)-5-(isopropyl(methyl)amino)cyclohexanecarboxylate |

TABLE 13-B-continued

The chemical names of the specific examples illustrated in Table 13-A are tabulated below.

| Example | Name |
|---|---|
| 13c | (1S,2S,5R)-methyl 2-((S)-3-(3-tert-butyl-4-hydroxybenzamido)-2-oxopyrrolidin-1-yl)-5-(isopropyl(methyl)amino)cyclohexanecarboxylate |
| 13d | (1S,2S,5R)-ethyl 2-((S)-3-(2-(4-chlorophenyl)furan-5-carboxamido)-2-oxopyrrolidin-1-yl)-5-(isopropyl(methyl)amino)cyclohexanecarboxylate |
| 13e | ethyl 3-((1S,2S,5R)-5-(isopropyl(methyl)amino)-2-((S)-2-oxo-3-(3-(trifluoromethyl)benzamido)pyrrolidin-1-yl)cyclohexyl)propanoate |
| 13f | 3-((1S,2S,5R)-5-(isopropyl(methyl)amino)-2-((S)-2-oxo-3-(3-(trifluoromethyl)benzamido)pyrrolidin-1-yl)cyclohexyl)propanoic acid |

Examples 14a-14g

Example 14a

Synthesis of (S)-1-((1S,2R,4R)-4-isopropoxy-2-(isopropylsulfonylmethyl)cyclohexyl)-3-(6-(trifluoromethyl)quinazolin-4-ylamino)pyrrolidin-2-one Example 14a, Step a: Sodium hydride (60% dispersion; 45 g, 1.17 mol) was washed with 500 ml of hexane (2×), suspended in 750 mL of THF and treated with diethylcarbonate (112.5 g, 0.94 mol). The suspension was heated to reflux and treated drop-wise with a solution of 1,4-cyclohexanedione mono-ethylene ketal (60.0 g, 0.384 mol) in THF (250 mL). After the addition was complete the suspension was heated to reflux for an additional 4 hours. The mixture was cooled in an ice bath to 0° C. and then poured, while vigorously stirring, into a mixture of ice (1 L), water (100 mL) and acetic acid (100 mL). The resulting mixture was extracted with hexane (2 L total) and the extracts washed with water and brine. The hexane extract was dried over $Na_2SO_4$, filtered and concentrated to give 8-Oxo-1,4-dioxa-spiro[4.5]decane-7-carboxylic acid ethyl ester as a pale yellow oil. This was used without further purification.

$^1$H NMR (300 MHz, CDCl$_3$) δ(TMS): 12.25 (s, 1H), 4.20 (q, J=7 Hz, 2H), 4.06-3.96 (m, 4H), 2.53-2.48 (m, 4H), 1.84 (t, J=6.6 Hz, 2H), 1.29 (t, J=7 Hz, 3H).

Example 14a, Step b: A solution of the crude ester of the Step 1 (0.384 mol) in benzene (375 mL) was treated with (S)-1-phenyl-ethylamine (46.4 g, 0.384 mol) and Yb(OTf)$_3$ catalyst (0.6 g) and heated to reflux for 2-3 hours with the removal of water with a Dean-Stark trap. The resulting solution was concentrated on a rotary evaporator. The residue was passed through a plug of silica gel with 4:6 EtOAc-hexane, and the solvent was evaporated off to give an oily residue, which was crystallized from hexane to give 59 grams of crystalline 8-(S-1-phenyl-ethylamino)-1,4-dioxa-spiro[4.5]dec-7-ene-7-carboxylic acid ethyl ester.

$^1$H NMR (300 MHz, CDCl$_3$) δ(TMS): 9.41 (d, J=7.4 Hz, 1H), 7.35-7.20 (m, 5H), 4.64-4.58 (m, 1H), 4.14 (q, J=7 Hz, 2H), 4.02-3.88 (m, 4H), 2.57-2.49 (m, 3H), 2.25-2.15 (m, 1H), 1.72-1.65 (m, 2H), 1.48 (d, J=7.4 Hz, 3H), 1.28 (t, J=7 Hz, 3H).

Example 14a, Step c: A solution of 8-(S-1-Phenyl-ethylamino)-1,4-dioxa-spiro[4.5]dec-7-ene-7-carboxylic acid ethyl ester (59 g, 0.178 mol) in 110 mL of acetonitrile and 54 mL of acetic acid was cooled in an ice bath and treated with NaBH(OAc)$_3$ (55.9 g, 0.263 mol) and stirred for 30 minutes, removed ice bath, and stirred overnight at room temperature. The solution was concentrated on a rotary evaporator and the residue dissolved in CH$_2$Cl$_2$ The solution was made basic with solid NaHCO$_3$ and partitioned between CH$_2$Cl$_2$ and water. The organic layer was washed with water and brine, dried over Na$_2$SO$_4$, filtered and concentrated on a rotary evaporator. The residue was filtered through a plug of silica gel with 4:6 EtOAc-hexane, and the solvent was evaporated off to give 28.7 g of pure (7R,8S)-8-(S-1-phenyl-ethylamino)-1,4-dioxa-spiro[4.5]decane-7-carboxylic acid ethyl ester.

$^1$H NMR (300 MHz, CDCl$_3$) δ(TMS): 7.34-7.21 (m, 5H), 4.18 (q, J=7 Hz, 2H), 3.95-3.88 (m, 4H), 3.73 (q, J=7 Hz, 1H), 3.14 (m, 1H), 2.81 (m, 1H), 2.08 (m, 1H), 1.80-1.38 (m, 6H), 1.32-1.25 (m, 6H).

Example 14a, Step d: A solution of (7R,8S)-8-(S-1-phenyl-ethylamino)-1,4-dioxa-spiro[4.5]decane-7-carboxylic acid ethyl ester (28.7 g, 0.086 mol) in THF (400 mL) was cooled to 0° C. in an ice bath and treated slowly with 1.0M-LAH in ether (86 mL, 0.086 mol), and the mixture was stirred for 2 h, and quenched with portion-wise addition of Na$_2$SO$_4$.10H$_2$O. The mixture was filtered through Celite and concentrated to give a colorless syrup of [(7R,8S)-8-(S-1-phenyl-ethylamino)-1,4-dioxa-spiro[4.5]dec-7-yl]-methanol (quantitative yield). This was used without further purification.

Example 14a, Step e: A solution of crude [(7R,8S)-8-(S-1-phenyl-ethylamino)-1,4-dioxa-spiro[4.5]dec-7-yl]-methanol (0.086 mol) in 250 mL of MeOH was treated with 4 g of 20% Pd(OH)$_2$/C and hydrogenated overnight at 55 psi. The mixture was filtered through Celite and concentrated on a rotary evaporator to give the desired ((7R,8S)-8-Amino-1,4-dioxa-spiro[4.5]dec-7-yl)-methanol as a syrup. This was used without further purification.

Example 14a, Step f: A solution of crude ((7R,8S)-8-Amino-1,4-dioxa-spiro[4.5]dec-7-yl)-methanol (0.086 mol) in 300 mL of CH$_2$Cl$_2$ was treated with a 120 mL of saturated Na$_2$CO$_3$, and cooled in an ice bath. The mixture was stirred vigorously while benzyl chloroformate (17.3 mL, 0.108 mol) was added slowly. After the addition was complete the mixture was stirred for an additional 30 min. The organic layer was separated and washed with water, brine and concentrated to give 33 g of crude product. This was recrystallized from hexane to give pure Benzyl (1S,2R)-2-(hydroxymethyl)-4-(1,3-dioxolane)cyclohexylcarbamate.

$^1$H NMR (300 MHz, CDCl$_3$) δ(TMS):

Example 14a, Step 1: Benzyl (1S,2R)-2-(hydroxymethyl)-4-(1,3-dioxolane)cyclohexylcarbamate was dissolved in dry CH$_2$Cl$_2$ prior to the addition of triethylamine (9.4 mL). This solution was cooled to 0° C. and methanesulfonyl chloride (3.4 mL) was added. The resulting solution was stirred 2 h before saturated sodium bicarbonate was added. The organic layer was separated and the aqueous layer re-extracted with CH$_2$Cl$_2$. The combined organic layer was washed with brine and dried (Na$_2$SO$_4$). It was then filtered, concentrated and dried in vacuo to get (1R,2S)-2-(benzyloxycarbonyl)-5-(1,3-dioxolane)-cyclohexyl)methyl methanesulfonate as a pale yellow oil. It was used without any further purification.

Example 14a, Step 2: To a solution of isopropanethiol (6.3 ml, 67.72 mMol) in anhydrous DMF at 0° C. was added sodium hydride (2.7 g, 67.72 mMol) in small portions under a nitrogen flush. After the effervescence subsided, the cooling was removed and stirring continued at rt for 90 min after which ((1R,2S)-2-(benzyloxycarbonyl)-5-(1,3-dioxolane)-cyclohexyl)methylmethane sulfonate (33.86 mMol) was dissolved in DMF (50 mL) and added slowly to the reaction. After 4 h, saturated NH$_4$Cl was added to the reaction. Partitioned between ethyl acetate and water. Aqueous layer was re-extracted with ethyl acetate. The combined organic layer was washed with brine and dried (MgSO$_4$) After filteration and concentration, a flash column yielded benzyl (1S,2R)-2-(isopropylthiomethyl)-4-(1,3-dioxolane)cyclohexyl carbamate as a pale oil (8.16 gm, 63% yield over two steps).

Example 14a, Step 3: A sample of benzyl (1S,2R)-2-(isopropylthiomethyl)-4-(1,3-dioxolane)cyclohexyl carbamate (8.15 g) was dissolved in acetonitrile (50 mL) prior to the addition of 1N HCl (50 mL). After 30 h the reaction was made basic by portionwise addition of saturated NaHCO$_3$. It was then partitioned between EtOAc and water. The aqueous layer was re-extracted with EtOAc. The combined organic layer was washed with brine and dried (MgSO$_4$). Filtered, concentrated and dried in vacuo to result in benzyl (1S,2R)-2-(isopropylthiomethyl)-4-oxocyclohexylcarbamate as a clear oil (6.57 g, quant. yield). MS found: (M+H)$^+$=336.1.

Example 14a, Step 4: A sample of benzyl (1S,2R)-2-(isopropylthiomethyl)-4-oxocyclohexylcarbamate (8.66 g, 25.81 mMol) was dissolved in a mixture of iPrOH (50 mL) and triisopropyl orthoformate (50 mL) prior to the portionwise addition of camphorsulfonic acid (1.2 g, 5.16 mMol). After overnight stirring at rt, the reaction was quenched by addition of saturated sodium bicarbonate. Partitioned between EtOAc and water. The aq. layer was re-extracted with EtOAc. Combined organic layer was washed with brine and dried (MgSO$_4$). Filtered, concentrated and flash chromatographed to yield benzyl (1S,2R)-4,4-diisopropoxy-2-(isopropylthiomethyl)cyclohexylcarbamate as a foamy solid (8.376 g, yield=74%)

Example 14a, Step 5: A sample of benzyl (1S,2R)-4,4-diisopropoxy-2-(isopropylthiomethyl)cyclohexylcarbamate (8.376 g, 19.16 mMol) was dissolved in CH$_2$Cl$_2$ (75 mL). This was cooled in an ice bath prior to the addition of triethylsilane (4.6 mL, 28.74 mMol) followed by BF$_3$.Et$_2$O (4.96 mL, 40.23 mMol). After 2 h, the resulting solution was quenched with saturated aq. NaHCO$_3$. Partitioned between water and CH$_2$Cl$_2$. The aq. layer was re-extracted with CH$_2$Cl$_2$. The combined organic layer was washed with brine, dried (MgSO$_4$), filtered, and concentrated to get benzyl (1S,2R)-4-isopropoxy-2-(isopropylthiomethyl)cyclohexyl carbamate as a clear oil which was used without any further purification.

Example 14a, Step 6: A sample of benzyl (1S,2R)-4-isopropoxy-2-(isopropylthiomethyl)cyclohexylcarbamate (27.59 mMol) was dissolved in iPrOH (200 mL) prior to the addition of Oxone® (33.92 g, 55.18 mMol) as a solution in 300 mL of water. The reaction was stirred at rt overnight. Partitoned between EtOAc and water. Aqueous layer was re-extracted with EtOAc and combined organic layer was washed with brine and dried (MgSO$_4$). Filtered, concentrated and flash chromatographed to yield benzyl (1S,2R)-4-isopropoxy-2-(isopropylsulfonylmethyl)cyclohexylcarbamate as a clear oil (7.73 g, 68% over steps 5 and 6). MS found: (M+H)$^+$=412.35.

Example 14a, Step 7: A sample of benzyl (1S,2R)-4-isopropoxy-2-(isopropylsulfonylmethyl)cyclohexylcarbamate (7.73 g, 18.8 mMol) and Pd/C (2 g) were taken in MeOH (250 mL) and stirred at rt under 50 psi hydrogen. After 2.5 h the reaction was filtered through Celite with EtOAc. The resulting solution was concentrated and dried in vacuo to yield (1S,2R)-4-isopropoxy-2-(isopropylsulfonylmethyl)cyclohexanamine as a clear oil which was used without any further purification.

Example 14a, Step 8: A sample of (1S,2R)-4-isopropoxy-2-(isopropylsulfonylmethyl)cyclohexanamine (18.8 mMol) was dissolved in MeCN (60 mL) prior to the addition of, in sequence, diisopropylamine (6.55 mL, 37.6 mMol), N-carbobenzyloxy-1-methionine (5.86 g, 20.68 mMol) and TBTU (7.8 g, 24.44 mMol). The resulting pale solution was stirred for 2 h. The reaction was diluted with EtOAc and washed, in sequence, with 1N HCl, saturated NaHCO$_3$ and brine. Dried (MgSO$_4$), filtered, concentrated and flash chromatographed to get benzyl (S)-1-((1S,2R)-4-isopropoxy-2-(isopropylsulfonylmethyl)cyclohexylamino)-4-(methylthio)-1-oxobutan-2-ylcarbamate as a white solid (8.76 g, 86%). MS found: (M+H)$^+$=543.2.

Example 14a, Step 9: A solution of benzyl (S)-1-((1S,2R)-4-isopropoxy-2-(isopropylsulfonyl methyl)cyclohexylamino)-4-(methylthio)-1-oxobutan-2-ylcarbamate (2.8 g, 5.16 mMol) was stirred at rt. After 24 h the solution was evaporated. The residue was redissolved in CH$_2$Cl$_2$ and evaporated. This process was repeated four more times. The residue was dried in vacuo to get a yellow foamy solid. This solid was dissolved in DMSO and treated with Cs$_2$CO$_3$ (3.36 g, 10.32 mMol). The reaction was set to stir at rt. After 4 h, the reaction was quenched with saturated aq. NH$_4$Cl. Extracted the reaction mixture with EtOAc three times. The combined organic layer was washed with brine twice. It was dried (MgSO$_4$), filtered, concentrated and chromatographed to get benzyl (S)-1-((1S,2R,4R)-4-isopropoxy-2-(isopropylsulfonylmethyl)cyclohexyl)-2-oxopyrrolidin-3-ylcarbamate A (faster isomer, 0.41 g, oil) and benzyl (S)-1-((1S,2R,4R)-4-isopropoxy-2-(isopropylsulfonylmethyl)cyclohexyl)-2-oxopyrrolidin-3-ylcarbamate B (slower isomer, 0.62 g, white solid).

Example 14a, Step 10: A sample of benzyl (S)-1-((1S,2R,4R)-4-isopropoxy-2-(isopropylsulfonylmethyl)cyclohexyl)-2-oxopyrrolidin-3-ylcarbamate A (faster ismer, 0.41 g) and Pd/C (0.08 g) were taken in MeOH (20 mL) and stirred at rt under 50 psi hydrogen pressure. After stirring overnight, the reaction mixture was filtered through Celite using EtOAc. Upon concentration and drying in vacuo, (S)-3-amino-1-((1S,2R,4R)-4-isopropoxy-2-(isopropylsulfonylmethyl)cyclohexyl)pyrrolidin-2-one was obtained as a clear viscous oil.

Example 14a, Step 11: A mixture of (S)-3-amino-1-((1S,2R,4R)-4-isopropoxy-2-(isopropylsulfonylmethyl)cyclohexyl)pyrrolidin-2-one (0.04 g, 0.128 mMol), triethylamine (71 uL, 0.512 mMol) and 4-chloro-6-(trifluoromethyl)quinazoline (0.035 g, 0.192 mMol) were taken in EtOH and microwaved at 100° C. for 45 min. The reaction mixture was concentrated and chromatographed to yield (S)-1-((1S,2R,4R)-4-isopropoxy-2-(isopropylsulfonyl methyl)cyclohexyl)-3-(6-(trifluoro methyl)quinazolin-4-ylamino)pyrrolidin-2-one as a white solid (0.04 g). MS found: (M+H)$^+$=557.2

Example 14b

Synthesis of (S)-1-((1S,2R,4R)-4-methoxy-2-(methylsulfonylmethyl)cyclohexyl)-3-(6-(trifluoromethyl)quinazolin-4-ylamino)pyrrolidin-2-one Example 14b, Step 1: A sample of benzyl (1R,2S,5R)-7-oxo-6-oxa-bicyclo[3.2.1]octan-2-ylcarbamate (2.8 g) was dissolved in anhydrous THF prior to the addition of LiBH$_4$ (0.44 g) in one portion. The reaction mixture was stirred at rt overnight. The reaction was quenched with saturated NH$_4$Cl and extracted with EtOAc. The organic layer was washed with brine and dried (MgSO$_4$). Filtered, concentrated and chromatographed to get benzyl (1S,2R,4R)-4-hydroxy-2-(hydroxymethyl)cyclohexylcarbamate as a white foamy solid.

Example 14b, Step 2: A sample of benzyl (1S,2R,4R)-4-hydroxy-2-(hydroxymethyl)cyclohexylcarbamate (8.78 g, 31.42 mMol) was dissolved in anhydrous $CH_2Cl_2$ prior to the addition of triethylamine (11 mL, 78.55 mMol) followed by DMAP (0.05 g) and then trityl chloride (10.52 g, 37.7 mMol) in one portion. The reaction mixture was stirred at rt overnight. The reaction was partitioned between $CH_2Cl_2$ and water. The organic layer was washed with brine and dried ($MgSO_4$), filtered, concentrated and chromatographed. Benzyl (1S,2R,4R)-4-hydroxy-2-(trityloxymethyl)cyclohexylcarbamate was obtained as a white foamy solid (9.85 g, yield=60%).

Example 14b, Step 3: A sample of benzyl (1S,2R,4R)-4-hydroxy-2-(trityloxymethyl)cyclohexylcarbamate (6.9 g, 13.24 mMol) was dissolved in a mixture of MeI (12.4 mL, 198.6 mMol) and anhydrous DMF (15 mL) prior to the addition of $Ag_2O$ (6.1 g, 26.48 mMol) in one portion under an argon flush. The reaction was set to stir at rt in the dark. After stirring for 30 hr (the reaction was incomplete), it was diluted with $CH_2Cl_2$ and filtered through Celite. Filtered and concentrated to a yellow oil and flash chromatographed to get benzyl (1S,2R,4R)-4-methoxy-2-(trityloxymethyl)cyclohexylcarbamate (3.48 g) as a white foamy solid and recover the starting material.

Example 14b, Step 4: A sample of benzyl (1S,2R,4R)-4-methoxy-2-(trityloxymethyl)cyclohexylcarbamate (0.53 g) was dissolved in a mixture of 70% aqueous acetic acid (10 mL) and MeCN (10 mL) and stirred at 60° C. for 2 h. Reaction mixture was cooled and evaporated. Dissolved in EtOAc and washed with saturated $NaHCO_3$ followed by brine and then dried ($MgSO_4$). Filtered, concentrated and chromatographed to get benzyl (1S,2R,4R)-2-(hydroxyl methyl)-4-methoxycyclohexylcarbamate (0.24 g, yield=83%) as a clear oil. MS found: $(M+H)^+=294.29$ Example 14b, Step 5: A sample of benzyl (1S,2R,4R)-2-(hydroxymethyl)-4-methoxycyclohexylcarbamate (0.298 g) was used to synthesize ((1R,2S,5R)-2-(benzyloxycarbonyl)-5-methoxycyclohexyl)methylmethane sulfonate by the same procedure as that of Example 14a, step 1. The product was obtained as a yellow foamy solid which was used without any further purification.

Example 14b, Step 6: A sample of sodium thiomethoxide (0.28 g, 4.04 mMol) was taken in DMF (4 mL) at 0° C. under nitrogen and water was added to it dropwise until the suspension becomes a homogenous mixture. A sample of ((1R,2S,5R)-2-(benzyloxycarbonyl)-5-methoxycyclohexyl)methyl methanesulfonate (1.01 mMol) in DMF (6 mL) was added slowly to the thiolate mixture. Stirring was continued for 1 h at 0° C. and then quenched with saturated $NaHCO_3$. Extracted with EtOAc twice. Combined organic layer was washed with water twice and then with brine. Dried ($MgSO_4$), filtered and concentrated to get benzyl (1S,2R,4R)-4-methoxy-2-(methylthiomethyl)cyclohexyl carbamate as a pale solid. MS found: $(M+H)^+=324.27$ Example 14b, Step 7: As per the procedure of Example 14a, Step 6; the desired product, benzyl (1S,2R,4R)-4-methoxy-2-(methylsulfonylmethyl)cyclohexylcarbamate (0.318 g, yield=89%) was obtained as a white solid starting with a sample of benzyl (1S,2R,4R)-4-methoxy-2-(methylthiomethyl)cyclohexylcarbamate (1.01 mMol). MS found: $(M+H)^+=356.1$ Example 14b, Step 8: As per the procedure of Example 14a, Step 7; the desired product, (1S,2R,4R)-4-methoxy-2-(methylsulfonylmethyl)cyclohexan-amine (0.2 g, quantitative yield) was obtained as an oil starting with a sample of benzyl (1S,2R,4R)-4-methoxy-2-(methylsulfonyl methyl)cyclohexylcarbamate (0.318 g). MS found: $(M+H)^+=222.19$ Example 14b, Step 9: As per the procedure of Example 14a, Step 8; the desired product, benzyl (S)-1-((1S,2R,4R)-4-methoxy-2-(methylsulfonylmethyl)cyclohexylamino)-4-(methylthio)-1-oxobutan-2-ylcarbamate (1.5 g, yield=60.5%) was obtained as a translucent viscous oil starting with a sample of (1S,2R,4R)-4-methoxy-2-(methylsulfonylmethyl)cyclohexanamine (5.1 mMol). MS found: $(M+H)^+=487.38$ Example 14b, Step 10: As per the procedure of Example 14a, Step 9; the desired product, benzyl (S)-1-((1S,2R,4R)-4-methoxy-2-(methylsulfonylmethyl)cyclohexyl)-2-oxopyrrolidin-3-ylcarbamate (1.15 g, yield=80%) was obtained as a foamy solid starting with a sample of benzyl (S)-1-((1S,2R,4R)-4-methoxy-2-(methylsulfonyl methyl)cyclohexylamino)-4-(methylthio)-1-oxobutan-2-ylcarbamate (1.5 g). MS found: $(M+H)^+=439.4$ Example 14b, Step 11: As per the procedure of Example 14a, Step 10; the desired product, (S)-3-amino-1-((1S,2R,4R)-4-methoxy-2-(methylsulfonylmethyl)cyclohexyl)pyrrolidin-2-one (0.44 g, quantitative yield) was obtained as a viscous oil starting with a sample of benzyl (S)-1-((1S,2R,4R)-4-methoxy-2-(methylsulfonylmethyl)cyclohexyl)-2-oxopyrrolidin-3-ylcarbamate (0.65 g).

Example 14b, Step 12: As per the procedure of Example 14a, Step 11; the desired product, (S)-1-((1S,2R,4R)-4-methoxy-2-(methylsulfonylmethyl)cyclohexyl)-3-(6-(trifluoromethyl)quinazolin-4-ylamino)pyrrolidin-2-one (0.0462 g, yield=77%) was obtained as a white solid starting with a sample of (S)-3-amino-1-((1S,2R,4R)-4-methoxy-2-(methylsulfonylmethyl)cyclohexyl)pyrrolidin-2-one (0.0364 g). MS found: $(M+H)^+=501.39$ Example 14c Synthesis of 2-tert-butyl-N-((S)-1-((1S,2R,4R)-4-methoxy-2-(methylsulfonylmethyl)cyclo hexyl)-2-oxopyrrolidin-3-yl)pyrimidine-4-carboxamide Example 14c, Step 13: As per the procedure of Example 14a, Step 8; the desired product, 2-tert-butyl-N-((S)-1-((1S,2R,4R)-4-methoxy-2-(methylsulfonylmethyl)cyclo hexyl)-2-oxopyrrolidin-3-yl)pyrimidine-4-carboxamide (0.0403 g, yield=74%) was obtained as a white solid starting with a sample of (S)-3-amino-1-((1S,2R,4R)-4-methoxy-2-(methylsulfonylmethyl)cyclohexyl)pyrrolidin-2-one (0.0364 g) and 2-tert-butylpyrimidine-4-carboxylic acid. MS found: $(M+H)^+=467.42$ Example 14e Synthesis of (S)-1-((1S,2R,4S)-4-isopropoxy-2-(isopropylsulfonylmethyl)cyclohexyl)-3-(6-(trifluoromethyl)quinazolin-4-ylamino)pyrrolidin-2-one Example 14e, Step 1: By the method described in Example 14a, Steps 10-11, the slower isomer of the Example 14a, Step 9, benzyl (S)-1-((1S,2R,4S)-4-isopropoxy-2-(isopropylsulfonylmethyl)cyclohexyl)-2-oxopyrrolidin-3-ylcarbamate was converted to the titled (S)-1-((1S,2R,4S)-4-isopropoxy-2-(isopropylsulfonylmethyl)cyclohexyl)-3-(6-(trifluoromethyl)quinazolin-4-ylamino)pyrrolidin-2-one. MS found: $(M+H)^+=557.2$.

Example 14g

Synthesis of 5-(3-(((S)-1-((1S,2R,4R)-4-methoxy-2-(methylsulfonylmethyl)cyclohexyl)-2-oxopyrrolidin-3-yl)carbamoyl)phenyl)phenyl-3-carboxylic acid A solution of methyl 5-(3-(((S)-1-((1S,2R,4R)-4-methoxy-2-(methylsulfonylmethyl)cyclohexyl)-2-oxopyrrolidin- 3-yl)carbamoyl)phenyl)phenyl-3-carboxylate (27 mg, Example 14f) in MeOH (3.5 mL) was charged with 1N NaOH (1.5 mL) and stirred at RT for 3 h before being partitioned between EtOAc and water. The aqueous phase was acidified with 1 N HCl and extracted with EtOAc twice. The combined organic extracts were washed with brine, dried (magnesium sulfate), filtered, and concentrated in vacuo to afford the titled carboxylic acid as a white solid. MS found: $(M+H)^+=529.4$.

TABLE 14-A

The compounds in the following table were made using the methods exemplified above. See Table 1-A for a complete description of the table headings.

| Example | $R^5$ | $R^6$ | $R^2$ | Step Altered | MS Data |
|---------|-------|-------|-------|--------------|---------|
| 14a | iPrO | iPr | 4-(6-CF$_3$-quinazolinyl) | n/a | 557.2 |
| 14b | MeO | Me | 4-(6-CF$_3$-quinazolinyl) | n/a | 501.39 |
| 14c | MeO | Me | 2-tBu-pyrimidin-4-yl carbonyl | n/a | 467.42 |
| 14d | MeO | Me | 5-(4-Cl-phenyl)furan-2-yl carbonyl | 14c, Step 13 | 509.36 |
| 14e | iPrO (S)-diast. | iPr | 4-(6-CF$_3$-quinazolinyl) | n/a | 557.2 |
| 14f | MeO | Me | 3'-MeO$_2$C-biphenyl-3-yl carbonyl | 14c, Step 13 | 543.4 |

TABLE 14-A-continued

The compounds in the following table were made using the methods exemplified above. See Table 1-A for a complete description of the table headings.

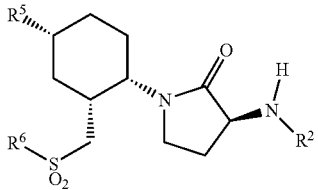

| Example | R⁵ | R⁶ | R² | Step Altered | MS Data |
|---|---|---|---|---|---|
| 14g | MeO | Me | (structure with biphenyl-CO-, HO₂C) | n/a | 529.4 |

TABLE 14-B

The chemical names of the specific examples illustrated in Table 14-A are tabulated below.

| Example | Name |
|---|---|
| 14a | (S)-1-((1S,2R,4R)-4-isopropoxy-2-(isopropylsulfonylmethyl)cyclohexyl)-3-(6-(trifluoromethyl)quinazolin-4-ylamino)pyrrolidin-2-one |
| 14b | (S)-1-((1S,2R,4R)-4-methoxy-2-(methylsulfonylmethyl)cyclohexyl)-3-(6-(trifluoromethyl)quinazolin-4-ylamino)pyrrolidin-2-one |
| 14c | 2-tert-butyl-N-((S)-1-((1S,2R,4R)-4-methoxy-2-(methylsulfonylmethyl)cyclohexyl)-2-oxopyrrolidin-3-yl)pyrimidine-4-carboxamide |
| 14d | 5-(4-chlorophenyl)-N-((S)-1-((1S,2R,4R)-4-methoxy-2-(methylsulfonylmethyl)cyclohexyl)-2-oxopyrrolidin-3-yl)furan-2-carboxamide |
| 14e | (S)-1-((1S,2R,4S)-4-isopropoxy-2-(isopropylsulfonylmethyl)cyclohexyl)-3-(6-(trifluoromethyl)quinazolin-4-ylamino)pyrrolidin-2-one |
| 14f | methyl 5-(3-(((S)-1-((1S,2R,4R)-4-methoxy-2-(methylsulfonylmethyl)cyclohexyl)-2-oxopyrrolidin-3-yl)carbamoyl)phenyl)phenyl-3-carboxylate |
| 14g | 5-(3-(((S)-1-((1S,2R,4R)-4-methoxy-2-(methylsulfonylmethyl)cyclohexyl)-2-oxopyrrolidin-3-yl)carbamoyl)phenyl)phenyl-3-carboxylic acid |

Examples 15a-15h

Example 15a

Synthesis of (3S)-1-((3R,4S)-1-isopropyl-3-propylpiperidin-4-yl)-3-(6-(trifluoromethyl)quinazolin-4-ylamino)pyrrolidin-2-one Example 15a, Step a: To a solution of (3R,4S)-1-tert-butyl 3-methyl 4-((S)-1-phenylethylamino)piperidine-1,3-dicarboxylate (47 g, 0.13 mol, See: S. S. Ko, et al, WO PCT 2002002525 for preparation of the enantiomer of this compound) in anhydrous ether (500 mL) at 0° C. was added 1M-LAH (100 mL, 0.1 mol) dropwise, and the mixture was stirred at 0~15° C. for 3 h. The reaction was quenched with a portion-wise addition of Na₂SO₄.10H₂O (excess) and stirring for 1 h at rt. It was filtered through Celite and the solvent was evaporated off to give (3R,4S)-tert-butyl 3-(hydroxymethyl)-4-((S)-1-phenylethylamino)piperidine-1-carboxylate (quantitative yield).

Example 15a, Step 1: A mixture of (3R,4S)-tert-butyl 3-(hydroxymethyl)-4-((S)-1-phenylethylamino)piperidine-1-carboxylate (38 g, 113.6 mMol) and Pd(OH)₂ (5 g) were stirred in methanol (250 mL) at rt under 50 psi hydrogen. After overnight stirring, the reaction mixture was filtered through Celite. The solution was concentrated to get the desired product, (3R,4S)-tert-butyl 4-amino-3-(hydroxymethyl)piperidine-1-carboxylate as a pale oil (quantitative yield).

Example 15a, Step 2: A sample of (3R,4S)-tert-butyl 4-amino-3-(hydroxymethyl)piperidine-1-carboxylate (113.6 mMol) was dissolved in CH₂Cl₂ prior to the addition of saturated sodium carbonate (180 mL). This mixture was cooled to 0° C. and then benzyl chloroformate (21.76 mL, 136.32 mMol) was added slowly. The cooling was removed and stirring continued overnight. Partitioned the mixture between water and CH₂Cl₂. Aqueous layer was re-extracted with CH₂Cl₂. Combined organic layer was washed with brine and dried (MgSO₄). Filtered, concentrated and dried in vacuo to get the desired product, (3R,4S)-tert-butyl 4-(benzyloxycarbonyl)-3-(hydroxymethyl)piperidine-1-carboxylate as a yellow oil.

Example 15a, Step 3: To a stirring solution of anhydrous DMSO (1.8 mL, 25.36 mMol) in CH₂Cl₂ (40 mL) at −78° C. was added oxalyl chloride (2 mL, 23.78 mMol) slowly. After 20 min, a sample of (3R,4S)-tert-butyl 4-(benzyloxycarbonyl)-3-(hydroxymethyl)piperidine-1-carboxylate (5.78 g, 15.85 mMol) dissolved in CH₂Cl₂ (30 mL) was added to the reaction slowly. Stirring was continued for 1 h. Triethylamine (6.6 mL, 47.55 mMol) was added dropwise. Stirring was then continued with a gradual warm up to 0° C. over 1 h. Partitioned the mixture between water and CH₂Cl₂. Aqueous layer was re-extracted with CH₂Cl₂. Combined organic layer was washed with brine and dried (Na₂SO₄). Filtered, concentrated and chromatographed to get the desired product, (3R,4S)-tert-butyl 4-(benzyloxycarbonyl)-3-formylpiperidine-1-carboxylate as a pale oil (3.8 g, yield=67%).

Example 15a, Step 4: To a stirring suspension of EtPPh₃Br (4.7 g, 12.59 mMol) in anhydrous THF (70 mL) in a −5° C. (approx.) bath was added KHMDS (13.12 mMol) slowly. The resulting reddish solution was stirred for 20 min. While maintaining the same low temperature, a solution of (3R,4S)-tert-butyl 4-(benzyloxycarbonyl)-3-formylpiperidine-1-carboxylate in anhydrous THF (30 mL) was added to the reaction mixture. After the addition was completed, the reaction was stirred for 30 min. The reaction was quenched with saturated NH₄Cl. Partitioned between EtOAc and water. The organic layer was washed with brine and dried (MgSO₄). Filtered, concentrated and chromatographed to get the desired product, (4S,E)-tert-butyl 4-(benzyloxycarbonyl)-3-(prop-1-enyl)piperidine-1-carboxylate, apparent mixture of diastereomers, as a pale oil (3.2 g, yield=82%).

Example 15a, Step 5: A mixture of (3R,4S,E)-tert-butyl 4-(benzyloxycarbonyl)-3-(prop-1-enyl)piperidine-1-carboxylate (2.85 g), Pd/C (0.28 g) in MeOH (75 mL) was set to stir at rt under 50 psi hydrogen. After overnight stirring the reaction mixture was filtered through Celite to yield the desired product, (4S)-tert-butyl 4-amino-3-propylpiperidine-1-carboxylate (1.72 g, yield=93%) as a pale oil. It was used without any further purification.

Example 15a, Step 6: As per the procedure in Example 14a, Step 8, the desired product was obtained using (4S)-tert-butyl 4-amino-3-propylpiperidine-1-carboxylate (1.72 g) as the starting material. The desired product, (4S)-tert-butyl 4-((S)-2-(benzyloxycarbonyl)-4-(methylthio)butanamido)-3-propylpiperidine-1-carboxylate, apparent mixture of diastereomers, was obtained as a white solid (3.174 g, yield=88%) after a flash column.

Example 15a, Step 7: As per the procedure in Example 14a, step 9, the desired product was obtained using (4S)-tert-butyl 4-((S)-2-(benzyloxycarbonyl)-4-(methylthio)butanamido)-3-propylpiperidine-1-carboxylate (3.174 g) as the starting material. The crude product mixture was chromatographed. Two products were obtained which were found to be isomers. Based on the TLC, they will be called the following here: (3R,4S)-tert-butyl 4-((S)-3-(benzyloxycarbonyl)-2-oxopyrrolidin-1-yl)-3-propylpiperidine-1-carboxylate (Faster) and (3S,4S)-tert-butyl 4-((S)-3-(benzyloxycarbonyl)-2-oxopyrrolidin-1-yl)-3-propylpiperidine-1-carboxylate (Slower).

Example 15a, Step 8: A sample of (3R,4S)-tert-butyl 4-((S)-3-(benzyloxycarbonyl)-2-oxopyrrolidin-1-yl)-3-propylpiperidine-1-carboxylate (Faster, 0.341 g) was dissolved in CH₂Cl₂ (10 mL) prior to the addition of trifluoroacetic acid (0.82 mL, 11.14 mMol). After 2.5 h, the reaction was evaporated and redissloved in CH₂Cl₂. The solution was washed with saturated NaHCO₃ followed by brine. It was dried (Na₂SO₄), filtered, concentrated and dried in vacuo to get the desired amine (0.25 g, yield=94%) as a clear oil.

Example 15a, Step 9: A sample of amine from Step 8 (0.25 g) was dissolved in 1,2-dicholoroethane prior to the addition of acetone (0.26 mL, 3.475 mMol). Stirring was contined at rt for 1 h after which sodium triacetoxyborohydride (0.29 g, 1.39 mMol) was added to the reaction. Reaction was stirred for 5 h and then quenched with saturated NaHCO₃. Partitioned between CH₂Cl₂ and water. Organic layer was washed with brine and dried (MgSO₄). Filtered, concentrated and dried in vacuo to yield the desired product, benzyl (S)-1-((3R, 4S)-1-isopropyl-3-propylpiperidin-4-yl)-2-oxopyrrolidin-3-yl carbamate (Faster) (0.262 g, yield=94%) as a clear oil. MS found: (M+H)⁺=402.2

Example 15a, Step 10: A mixture of benzyl (S)-1-((3R,4S)-1-isopropyl-3-propylpiperidin-4-yl)-2-oxopyrrolidin-3-yl-carbamate (faster) (0.262 g) and Pd/C (0.056 g) in MeOH were stirred at rt under 50 psi hydrogen. After overnight stirring, the reaction was filtered through Celite. Concentrated and dried in vacuo to get the desired product, (3S)-3-amino-1-((3R,4S)-1-isopropyl-3-propylpiperidin-4-yl)pyrrolidin-2-one (faster) (0.166 g, yield=95%) as a clear oil.

Example 15a, Step 11: As per the procedure in Example 14a, Step 11, the desired product, (3S)-1-((3R,4S)-1-isopropyl-3-propylpiperidin-4-yl)-3-(6-(trifluoromethyl)quinazolin-4-ylamino)pyrrolidin-2-one (faster) was obtained as a white solid (0.045 g, yield=65%) using (3S)-3-amino-1-((3R,4S)-1-isopropyl-3-propylpiperidin-4-yl)pyrrolidin-2-one (faster) (0.0399 g) as a starting material. MS found: (M+H)⁺=464.2

Example 15c

Synthesis of 5-(4-chlorophenyl)-N-((S)-1-((3R,4S)-1-isopropyl-3-propylpiperidin-4-yl)-2-oxopyrrolidin-3-yl)furan-2-carboxamide Example 15c, Step 1: As per the procedure in Example 14a, Step 8, the desired product, 5-(4-chlorophenyl)-N-((S)-1-((3R,4S)-1-isopropyl-3-propylpiperidin-4-yl)-2-oxopyrrolidin-3-yl)furan-2-carboxamide) (faster) was obtained as a white solid (0.0401 g, yield=63%) using (3S)-3-amino-1-((3R,4S)-1-isopropyl-3-propylpiperidin-4-yl)pyrrolidin-2-one (faster) (0.036 g) and 5-(4-chlorophenyl)furan-2-carboxylic acid (0.027 g, 0.148 mMol) as starting materials. MS found: (M+H)⁺=472.2

Example 15e

Synthesis of (S)-1-((3S,4S)-1-isopropyl-3-propylpiperidin-4-yl)-3-(6-(trifluoromethyl)quinazolin-4-ylamino)pyrrolidin-2-one Example 15e, Step 1: A sample of (3S,4S)-tert-butyl 4-((S)-3-(benzyloxycarbonyl)-2-oxopyrrolidin-1-yl)-3-propylpiperidine-1-carboxylate (slower isomer from Example 15a, Step 7) was carried through the procedures outlined above in Example 15a, Steps 8-11.

Example 15i

Synthesis of (3R,4S)-methyl 1-isopropyl-4-((S)-2-oxo-3-(6-(trifluoromethyl)quinazolin-4-ylamino)pyrrolidin-1-yl)piperidine-3-carboxylate Example 15i, Step 1: Methyl 4-oxopiperidine-3-carboxylate hydrochloride (10.0 g, 51.6 mmol, 1 eq.) was dissolved in water (60 mL) at room temperature then cooled to 0° C. Added sodium carbonate (6.02 g, 56.8 mmol, 1.05 eq.) followed by the dropwise addition of BOC anhydride (11.84 g, 51.6 mmol, 1 eq.) in THF (50 mL) via an addition funnel. Stirred at 0° C. for 1 hour. Worked up by extracting 3 times with diethyl ether (50 mL). The diethyl ether extracts were combined and rinsed once (50 mL) with brine. The diethyl ether layer was dried over sodium sulfate and stripped to give 1-tert-butyl 3-methyl 4-oxopiperidine-1,3-dicarboxylate (13.29 g) as an amber oil. Yield=100%. ¹H NMR (400 MHz) (CDCl3) δ 4.02 (s, 2H); 3.77 (s, 3H); 3.59 (s, 2H); 2.37 (s, 2H); 1.47 (s, 9H).

Example 15i, Step 2: 1-tert-butyl 3-methyl 4-oxopiperidine-1,3-dicarboxylate (13.29 g, 51.6 mmol, 1 eq.), (S)-(–)-α-methylbenzylamine (6.66 mL, 51.6 mmol, 1 eq.), acetic acid (5.91 mL, 103.0 mmol, 2 eq.) and benzene (200 mL) were mixed at room temperature then refluxed using a Dean-Stark trap for 4 hours. Cooled to 0° C. Added acetic acid (23.66 mL, 412.8 mmol, 8 eq.) followed by the addition of sodium triacetoxyborohydride (21.90 g, 103.0 mmol, 2 eq.). Stirred for 20 minutes at 0° C. then allowed the reaction to warm to room temperature and stirred for 20 hours. Worked up by carefully (foaming) adding sodium carbonate until the pH=10. Extracted the aqueous 3 times with ethyl acetate. The ethyl acetate layers were combined, rinsed once with brine, then dried over sodium sulfate and stripped to give (3R,4S)-1-tert-butyl 3-methyl 4-((1S)-1-phenylethylamino)-piperidine-1,3-dicarboxylate (18.7 g) of an oil as product. Yield=100%. Mass Spec (ESI) detects (M+H)$^+$=363.2.

Example 15i, Step 3: 20% Palladium hydroxide (1.87 g) was carefully wetted down under nitrogen with isopropanol (50 mL) then (3R,4S)-1-tert-butyl 3-methyl 4-((1S)-1-phenylethylamino)-piperidine-1,3-dicarboxylate (18.7 g, 51.6 mmol, 1 eq.) in isopropanol (50 mL) was added. The mixture was hydrogenated on a Parr shaker for 20 hours. Worked up by filtering off the catalyst under nitrogen through fiberglass filter paper. The filtrate was stripped to give an oil which was purified over silica gel in 1:1 hexanes/ethyl acetate to 100% ethyl acetate to 4:1 methylene chloride/methanol. Obtained (3R,4S)-1-tert-butyl 3-methyl 4-aminopiperidine-1,3-dicarboxylate (11.2 g) as a colorless oil. Yield=84%. Mass Spec (ESI) detects (M+H)$^+$=259.1.

Example 15i, Step 4: (3R,4S)-1-tert-butyl 3-methyl 4-aminopiperidine-1,3-dicarboxylate (10.0 g, 38.7 mmol, 1 eq.), CBZ-L-methionine (13.16 g, 46.5 mmol, 1.2 eq.), 1-hydroxybenzotriazole hydrate (HOBT) (6.28 g, 46.5 mmol, 1.2 eq.), 1-[3-(dimethylamino)propyl]-3-ethylcarbodiimide HCl (EDCI) (8.91 g, 46.5 mmol, 1.2 eq.), triethylamine (10.79 mL, 77.4 mmol, 2 eq.) and methylene chloride (100 mL) were stirred at room temperature under nitrogen overnight. Worked up by rinsing 3 times with water. The organic layer was dried over sodium sulfate and stripped to give an oil. Purified over silica gel in 3:1 to 1:1 hexanes/ethyl acetate. Obtained (3R,4S)-1-tert-butyl 3-methyl 4-((2S)-2-(benzyloxycarbonylamino)-4-(methylthio)butanamido)-piperidine-1,3-dicarboxylate (19.7 g) as a white glass. Yield=97%. LCMS detects (M+Na)$^+$=546.26.

Example 15i, Step 5: (3R,4S)-1-tert-butyl 3-methyl 4-((2S)-2-(benzyloxycarbonylamino)-4 (methylthio)butanamido)-piperidine-1,3-dicarboxylate (19.7 g, 37.6 mmol, 1 eq.) and iodomethane (23.5 mL, 376.0 mmol, 10 eq.) were stirred in methylene chloride under nitrogen at room temperature for 20 hours. The reaction was stripped 5 times from chloroform (50 mL). Obtained 27.1 g of the sulfonium salt as an off-white glass. Yield=100%. LCMS detects (M+H)$^+$=538.38. The sulfonium salt (1.00 g, 1.50 mmol, 1 eq.) and cesium carbonate (1.96 g, 6.01 mmol, 4 eq.) were stirred in DMF (10 mL) at room temperature under nitrogen for 20 hours. Worked up by adding ethyl acetate (25 mL) and rinsing 3 times with brine (25 mL). The organic layer was dried over sodium sulfate and stripped to give an amber oil. Purified over silica gel in 3:1 to 1:1 hexanes/ethyl acetate. Obtained (3R,4S)-1-tert-butyl 3-methyl 4-((3S)-3-(benzyloxycarbonylamino)-2-oxopyrrolidin-1-yl)piperidine-1,3-dicarboxylate (450 mg) as a white glass. Yield=63%. LCMS detects (M+H)$^+$=476.30.

Example 15i, Step 6: (3R,4S)-1-tert-butyl 3-methyl 4-((3S)-3-(benzyloxycarbonylamino)-2-oxopyrrolidin-1-yl)piperidine-1,3-dicarboxylate (7.45 g) was dissolved in methylene chloride (20 mL) at room temperature under nitrogen, then TFA (10 mL) was added. After 3 hours, stripped the reaction 3 times from methylene chloride (25 mL). Obtained an oil which was dissolved in ethyl acetate (25 mL) and rinsed 4 times with 1.000 N NaOH (25 mL). The ethyl acetate layer was dried over sodium sulfate and stripped to give (3R,4S)-methyl 4-((3S)-3-(benzyloxycarbonylamino)-2-oxopyrrolidin-1-yl)piperidine-3-carboxylate (4.30 g) as a white glass. Yield=73%. LCMS detects (M+H)$^+$=376.1.

Example 15i, Step 7: (3R,4S)-Methyl 4-((3S)-3-(benzyloxycarbonylamino)-2-oxopyrrolidin-1-yl)piperidine-3-carboxylate (1.00 g, 2.66 mmol, 1 eq.), sodium triacetoxyborohydride (0.85 g, 4.00 mmol, 1.5 eq.) and acetone (0.59 mL, 7.99 mmol, 3 eq.) were mixed in methylene chloride (15 mL) and stirred for 20 hours at room temperature. Worked up by adding 20 mL of 1.000 N NaOH. Stirred 10 minutes then extracted 3 times with methylene chloride. The organic layers were combined, dried over sodium sulfate and stripped to give methyl 4-((3S)-3-(benzyloxycarbonylamino)-2-oxopyrrolidin-1-yl)-1-isopropyl-piperidine-3-carboxylate (1.10 g) of a white glass. Yield=99%. LCMS detects (M+H)$^+$=418.41.

Example 15i, Step 8: 20% Palladium hydroxide (0.30 g) was carefully wetted down under nitrogen with isopropanol (10 mL) then (3R,4S)-methyl 4-((3S)-3-(benzyloxycarbonylamino)-2-oxo-pyrrolidin-1-yl)-1-isopropylpiperidine-3-carboxylate (1.10 g) in isopropanol (10 mL) was added. The mixture was hydrogenated on a Parr shaker for 20 hours. Worked up by filtering off the catalyst under nitrogen through fiberglass filter paper. The filtrate was stripped to give (3R,4S)-methyl 4-((3S)-3-amino-2-oxopyrrolidin-1-yl)-1-isopropylpiperidine-3-carboxylate (695 mg) as an oil. Yield=93%. LCMS detects (M+H)$^+$=284.34.

Example 15i, Step 9: (3R,4S)-Methyl 4-((3S)-3-amino-2-oxopyrrolidin-1-yl)-1-isopropylpiperidine-3-carboxylate (50 mg, 0.176 mmol, 1 eq.), 4-chloro-6-(trifluoromethyl)-quinazoline (45 mg, 0.194 mmol, 1.1 eq.) and triethylamine (98 uL, 0.706 mmol, 4 eq.) were dissolved in ethanol (3 mL) at room temperature then microwaved at 100° C. for 1 hour. Purified by HPLC. Obtained (3R,4S)-methyl 1-isopropyl-4-(2-oxo-(3S)-3-(6-(trifluoromethyl)quinazolin-4-ylamino) pyrrolidin-1-yl)piperidine-3-carboxylate, bis TFA salt (88 mg) as a white solid. LCMS detects (M+H)$^+$=480.39. $^1$H NMR (400 MHz) (CD$_3$OD) δ 8.82 (s, 1H, J=7 Hz); 8.20 (s, 1H, J=7 Hz); 8.78 (s, 1H, J=7 Hz); 7.91 (d, 1H, J=7 Hz); 7.30-7.10 (m, 1H); 5.37 (m, 1H); 4.3-4.05 (m, 1H); 3.80-3.00 (m, 9H); 2.60-2.45 (m, 1H); 2.45-2.10 (m, 2H); 2.10-1.80 (m, 2H); 1.27 (m, 6H).

Example 15j

Synthesis of (3S,4S)-methyl 1-isopropyl-4-((S)-2-oxo-3-(6-(trifluoromethyl)quinazolin-4-ylamino) pyrrolidin-1-yl)piperidine-3-carboxylate Example 15j, Step 1: The synthesis of the lactam of 15i, Step 5, was scaled up 21.5 fold. Normal workup gave a white solid instead of an amber oil. This white solid was stirred in diethyl ether (50 mL) and the solids were filtered to yield 7.00 g of a white solid. This product was identical to the lactam (3R,4S)-(1-tert-butyl 3-methyl 4-((3S)-3-(benzyloxycarbonylamino)-2-oxopyrrolidin-1-yl)piperidine-1,3-dicarboxylate) that was previously isolated in 15i, Step 5. The filtrate was stripped and purified over silica gel in 3:1 to 1:1 hexanes/ethyl acetate to give 2.77 g of the diastereomeric (3S,4S)-1-tert-butyl 3-methyl 4-((3S)-3-(benzyloxycarbonylamino)-2-oxopyrrolidin-1-yl)piperidine-1,3-dicarboxylate.

Example 15j, Step 2: (3S,4S)-1-tert-butyl 3-methyl 4-((3S)-3-(benzyloxycarbonylamino)-2-oxopyrrolidin-1-yl) piperidine-1,3-dicarboxylate underwent the reaction sequence described in 15i, Steps 6-9 to yield (3S,4S)-methyl 1-isopropyl-4-(2-oxo-(3S)-3-(6-(trifluoromethyl)quinazolin-4-ylamino)pyrrolidin-1-yl)piperidine-3-carboxylate, bis TFA salt. LCMS detects (M+H)$^+$=480.39. $^1$H NMR (400 MHz) (CD$_3$OD) δ 8.79 (s, 2H); 8.27 (d, 1H, J=7 Hz,; 7.96 (d, 1H, J=7 Hz); 5.50-5.25 (m, 1H); 4.30-4.10 (m, 1H); 3.74 (s, 3H); 3.70-3.50 (m, 3H); 3.40-3.20 (m, 1H); 2.80-2.60 (m, 1H); 2.50-2.00 (m, 3H); 1.37 (s, 6H).

TABLE 15-A

The compounds in the following table were made using the methods exemplified above. See Table 1-A for a complete description of the table headings.

| Example | R$^1$ | R$^2$ | Step Altered | MS Data |
|---|---|---|---|---|
| 15a | (R)-nPr | 4-quinazolinyl-6-CF$_3$ | n/a | 464.2 |
| 15b | (R)-nPr | 4-quinazolinyl-6-OCF$_3$ | 15a, Step 11 | 480.2 |
| 15c | (R)-nPr | C(O)-5-(4-chlorophenyl)furan-2-yl | n/a | 472.2 |
| 15d | (R)-nPr | C(O)-3-CF$_3$-phenyl | 15c, Step 1 | 440.2 |
| 15e | (S)-nPr | 4-quinazolinyl-6-CF$_3$ | n/a | 464.43 |
| 15f | (S)-nPr | 4-quinazolinyl-6-OCF$_3$ | 15e, Step 1 | 480.38 |

TABLE 15-A-continued

The compounds in the following table were made using the methods exemplified above. See Table 1-A for a complete description of the table headings.

| Example | R¹ | R² | Step Altered | MS Data |
|---|---|---|---|---|
| 15g | (S)-nPr | (3-CF₃-benzoyl) | 15e, Step 1 (See 15c) | 440.41 |
| 15h | (S)-nPr | (5-(4-chlorophenyl)furan-2-yl carbonyl) | 15e, Step 1 (See 15c) | 472.37 |
| 15i | (R)-CO₂Me | (6-CF₃-quinazolin-4-yl) | n/a | 480.4 |
| 15j | (S)-CO₂Me | (6-CF₃-quinazolin-4-yl) | n/a | 480.4 |

TABLE 15-B

The chemical names of the specific examples illustrated in Table 15-A are tabulated below.

| Example | Name |
|---------|------|
| 15a | (S)-1-((3R,4S)-1-isopropyl-3-propylpiperidin-4-yl)-3-(6-(trifluoromethyl)quinazolin-4-ylamino)pyrrolidin-2-one |
| 15b | (S)-1-((3R,4S)-1-isopropyl-3-propylpiperidin-4-yl)-3-(6-(trifluoromethoxy)quinazolin-4-ylamino)pyrrolidin-2-one |
| 15c | 5-(4-chlorophenyl)-N-((S)-1-((3R,4S)-1-isopropyl-3-propylpiperidin-4-yl)-2-oxopyrrolidin-3-yl)furan-2-carboxamide |
| 15d | N-((S)-1-((3R,4S)-1-isopropyl-3-propylpiperidin-4-yl)-2-oxopyrrolidin-3-yl)-3-(trifluoromethyl)benzamide |
| 15e | (S)-1-((3S,4S)-1-isopropyl-3-propylpiperidin-4-yl)-3-(6-(trifluoromethyl)quinazolin-4-ylamino)pyrrolidin-2-one |
| 15f | (S)-1-((3S,4S)-1-isopropyl-3-propylpiperidin-4-yl)-3-(6-(trifluoromethoxy)quinazolin-4-ylamino)pyrrolidin-2-one |
| 15g | N-((S)-1-((3S,4S)-1-isopropyl-3-propylpiperidin-4-yl)-2-oxopyrrolidin-3-yl)-3-(trifluoromethyl)benzamide |
| 15h | 5-(4-chlorophenyl)-N-((S)-1-((3S,4S)-1-isopropyl-3-propylpiperidin-4-yl)-2-oxopyrrolidin-3-yl)furan-2-carboxamide |
| 15i | (3R,4S)-methyl 1-isopropyl-4-(2-oxo-(3S)-3-(6-(trifluoromethyl)quinazolin-4-ylamino)pyrrolidin-1-yl)piperidine-3-carboxylate |
| 15j | (3S,4S)-methyl 1-isopropyl-4-(2-oxo-(3S)-3-(6-(trifluoromethyl)quinazolin-4-ylamino)pyrrolidin-1-yl)piperidine-3-carboxylate |

Examples 16a-16c

Example 16a

Synthesis of N-((S)-1-((3R,4S)-1-isopropyl-3-(isopropylsulfonylmethyl)piperidin-4-yl)-2-oxopyrrolidin-3-yl)-3-(trifluoromethyl)benzamide Example 16a, Step 1: As per the procedure in Example 14a, Step 1, the desired product, (3R,4S)-tert-butyl 4-(benzyloxycarbonyl)-3-((methylsulfonyloxy)methyl)piperidine-1-carboxylate was obtained using (3R,4S)-tert-butyl 4-(benzyloxycarbonyl)-3-(hydroxymethyl)piperidine-1-carboxylate (5.38 g) as the starting materiel. The desired product was obtained as a pale yellow oil which was dried in vacuo and used without any further purification.

Example 16a, Step 2: As per the procedure in Example 14a, Step 2, the desired product was obtained using (3R,4S)-tert-butyl 4-(benzyloxycarbonyl)-3-((methylsulfonyloxy)methyl)piperidine-1-carboxylate (14.76 mMol) as the starting material. The desired product, (3R,4S)-tert-butyl 4-(benzyloxycarbonyl)-3-(isopropylthiomethyl)piperidine-1-carboxylate was obtained as a yellow oil which was dried in vacuo and used without any further purification.

Example 16a, Step 3: As per the procedure in Example 14a, Step 6, the desired product was obtained using (3R,4S)-tert-butyl 4-(benzyloxycarbonyl)-3-(isopropylthiomethyl)piperidine-1-carboxylate (14.76 mMol) as the starting material. The crude product was chromatographed. The desired product, (3R,4S)-tert-butyl 4-(benzyloxycarbonyl)-3-(isopropylsulfonylmethyl)piperidine-1-carboxylate was obtained as white foamy solid. The net yield over three steps was 3.16 g (yield=47%).

Example 16a, Step 4: A mixture of (3R,4S)-tert-butyl 4-(benzyloxycarbonyl)-3-(isopropylsulfonylmethyl)piperidine-1-carboxylate (3.15 g) and Pd/C (0.6 g) in 200 mL of EtOAc was set to stir at rt under 50 psi hydrogen. After stirring for 24 h the reaction was filtered through Celite and concentrated to a light brown oil. A quantitative yield was assumed. The desired product, (3R,4S)-tert-butyl 4-amino-3-(isopropylsulfonylmethyl)piperidine-1-carboxylate was used without any further purification.

Example 16a, Step 5: As per the procedure in Example 14a, Step 8, the desired product, (3R,4S)-tert-butyl 4-((S)-2-(benzyloxycarbonyl)-4-(methylthio)butanamido)-3-(isopropylsulfonylmethyl)piperidine-1-carboxylate was obtained as a "glassy" solid (3.46 g, yield=85%) using (3R,4S)-tert-butyl 4-amino-3-(isopropylsulfonylmethyl)piperidine-1-carboxylate as the starting material (6.929 mMol).

Example 16a, Step 6: As per the procedure in Example 14a, Step 9, the desired product, (3R,4S)-tert-butyl 4-((S)-3-(benzyloxycarbonyl)-2-oxopyrrolidin-1-yl)-3-(isopropylsulfonylmethyl)piperidine-1-carboxylate was obtained as white crystalline solid (1.92 g, yield=60%) using (3R,4S)-tert-butyl 4-((S)-2-(benzyloxycarbonyl)-4-(methylthio)butanamido)-3-(isopropylsulfonylmethyl)piperidine-1-carboxylate (3.46 g, 5.9 mMol).

Example 16a, Step 7: A mixture of (3R,4S)-tert-butyl 4-((S)-3-(benzyloxycarbonyl)-2-oxopyrrolidin-1-yl)-3-(isopropylsulfonylmethyl)piperidine-1-carboxylate (0.7 g), Pd/C (0.14 g) in MeOH (20 mL) was stirred at rt under 50 psi hydrogen. After 2.5 h, the reaction mixture was filtered through Celite. It was then concentrated and dried in vacuo to yield the desired product, (3R,4S)-tert-butyl 4-((S)-3-amino-2-oxopyrrolidin-1-yl)-3-(isopropylsulfonyl methyl)piperidine-1-carboxylate (quantitative yield assumed)as a clear "glassy" solid. This material was used without any further purification.

Example 16a, Step 8: As per the procedure in Example 14a, Step 8, the desired product, (3R,4S)-tert-butyl 3-(isopropylsulfonylmethyl)-4-((S)-2-oxo-3-(3-(trifluoro methyl)benzamido)pyrrolidin-1-yl)piperidine-1-carboxylate was obtained as a reddish foamy solid (0.688 g, yield=92%) using (3R,4S)-tert-butyl 4-((S)-3-amino-2-oxopyrrolidin-1-yl)-3-(isopropylsulfonylmethyl)piperidine-1-carboxylate (1.3 mMol) and 3-(trifluoromethyl)benzoic acid (0.26 g, 1.365 mMol) as starting materials.

Example 16a, Step 9: A sample of (3R,4S)-tert-butyl 3-(isopropylsulfonylmethyl)-4-((S)-2-oxo-3-(3-(trifluoromethyl)benzamido)pyrrolidin-1-yl)piperidine-1-carboxylate (0.688 g) was dissolved in $CH_2Cl_2$ (10 mL) prior to the addition of trifluoroacetic acid (0.92 mL, 11.9 mMol). After 4 h, the reaction was made basic with saturated $NaHCO_3$. Extracted with $CH_2Cl_2$. The organic layer was washed with brine and dried ($MgSO_4$). Concentrated and dried in vacuo to yield the desired product, N-((S)-1-((3R,4S)-3-(isopropylsulfonylmethyl)piperidin-4-yl)-2-oxopyrrolidin-3-yl)-3-(trifluoromethyl)benzamide) (0.482 g, yield=85%). MS found: $(M+H)^+=476.31$ Example 16a, Step 10: A sample of N-((S)-1-((3R,4S)-3-(isopropylsulfonylmethyl)piperidin-4-yl)-2-oxopyrrolidin-3-yl)-3-(trifluoromethyl)benzamide (0.05 g) was dissolved in 1,2-dichloroethane (3 mL) prior to the addition of acetone (0.38 mL, 0.525 mMol). After stirring at rt for 1 h, sodium triacetoxyborohydride (0.445 g, 0.21 mMol) was added to the reaction. Stirring was continued for 2 h when the reaction was quenched with saturated $NaHCO_3$. Partitioned between EtOAc and water. Organic layer was washed with brine and dried ($MgSO_4$). Filtered, concentrated and chromatographed. The desired product, N-((S)-1-((3R,4S)-1-isopropyl-3-(isopropylsulfonylmethyl)piperidin-4-yl)-2-oxopyrrolidin-3-yl)-3-(trifluoromethyl)benzamide (0.0086 g, yield=16%) was obtained as a white solid. MS found: $(M+H)^+=518.2$

TABLE 16-A

The compounds in the following table were made using the methods exemplified above. See Table 1-A for a complete description of the table headings.

| Example | R⁵  | R⁶  | R²                                    | Step Altered    | MS Data |
|---------|-----|-----|---------------------------------------|-----------------|---------|
| 16a     | iPr | iPr | —C(O)-C₆H₄-3-CF₃                      | n/a             | 518.2   |
| 16b     | iBu | iPr | —C(O)-C₆H₄-3-CF₃                      | 16a, Step 10    | 532.3   |
| 16c     | Et  | iPr | —C(O)-C₆H₄-3-CF₃                      | 16a, Step 10    | 504.33  |

TABLE 16-B

The chemical names of the specific examples illustrated in Table 16-A are tabulated below.

| Example | Name |
|---------|------|
| 16a | N-((S)-1-((3R,4S)-1-isopropyl-3-(isopropylsulfonylmethyl)piperidin-4-yl)-2-oxopyrrolidin-3-yl)-3-(trifluoromethyl)benzamide |
| 16b | N-((S)-1-((3R,4S)-1-isobutyl-3-(isopropylsulfonylmethyl)piperidin-4-yl)-2-oxopyrrolidin-3-yl)-3-(trifluoromethyl)benzamide |
| 16c | N-((S)-1-((3R,4S)-1-ethyl-3-(isopropylsulfonylmethyl)piperidin-4-yl)-2-oxopyrrolidin-3-yl)-3-(trifluoromethyl)benzamide |

Examples 17a-17b

Example 17a

Synthesis of 1-((1S,2R,4R)-4-(isopropyl(ethyl)amino)-2-(isopropylsulfonylmethyl)cyclohexyl)-4-(3-(trifluoromethyl)phenyl)-5,6-dihydropyridin-2(1H)-one Example 17a, Step 1: A solution of 3-trifluoromethylbenzaldehyde (6.7 mL) in tetrahydrofuran (40 mL) was stirred on an ice bath and treated dropwise over 25 min with a solution of vinylmagnesium bromide in tetrahydrofuran (1.0 M, 60 mL). The mixture was stirred for 2 h while allowing to warm slowly to room temperature, then was treated with saturated aqueous ammonium chloride. The mixture was extracted with ether, and the organic extracts were washed with water and brine, then dried over sodium sulfate and concentrated under vacuum. Purification by flash column chromatography, eluting with 10% ethyl acetate in hexane, provided 1-(3-trifluoromethylphenyl)prop-2-en-1-ol (2.33 g) as a colorless oil. MS found: $(M+H-H_2O)^+=185.19$.

Example 17a, Step 2: A solution of 1-(3-trifluoromethylphenyl)prop-2-en-1-ol (1.0 g) in acetone (10 mL) was stirred on an ice bath and treated dropwise with Jones reagent (1.4 mL). After 30 min, isopropanol was added to discharge the yellow-orange color, and the mixture was filtered through Celite. The filtrate was concentrated under vacuum and the residue was purified by flash column chromatography, eluting with 10% ethyl acetate in hexane, to provide 1-(3-trifluoromethylphenyl)propenone (672 mg) as a colorless liquid. $^1$H-NMR (CDCl₃): δ 8.21 (s, 1H), 8.15 (d, J=7.6 Hz, 1H), 7.86 (d, J=7.6 Hz, 1H), 7.66 (t, J=7.6 Hz, 1H), 7.18 (dd, J=17.3, 10.4 Hz, 1H), 6.51 (dd, J=17.3, 1.5 Hz, 1H), 6.04 (dd, J=10.4, 1.5 Hz, 1H).

Example 17a, Step 3: A solution of tert-butyl (1R,3R,4S)-4-amino-3-(isopropylsulfonylmethyl)cyclohexylcarbamate (1.09 g, see procedure 10a, Step 3) in methanol (10 mL) was stirred on an ice bath and treated dropwise over 5 min with a solution of 1-(3-trifluoromethylphenyl)propenone (655 mg)

in methanol (5 mL). The mixture was stirred at room temperature for 4.75 h, then was concentrated under vacuum. Purification by flash column chromatography, eluting with 75% ethyl acetate in hexane, provided (1R,3R,4S)-[4-[3-oxo-3-(3-trifluoromethylphenyl)propylamino]-3-(propane-2-sulfonylmethyl)cyclohexyl]-carbamic acid tert-butyl ester (1.0 g) as a white glassy solid. MS found: (M+H)$^+$=535.3.

Example 17a, Step 4: A suspension of sodium hydride (60%, 82 mg) in tetrahydrofuran (2.5 mL) was stirred on an ice bath and treated dropwise over 5 min with tert-butyl dimethyl-phosphonoacetate (0.37 mL). The mixture was stirred at room temperature for 15 min, then was cooled on ice and treated with a solution of (1R,3R,4S)-[4-[3-oxo-3-(3-trifluoro-methylphenyl)propylamino]-3-(propane-2-sulfonylmethyl)-cyclohexyl]carbamic acid tert-butyl ester (500 mg) in tetrahydrofuran (2.5 mL). The resulting mixture was stirred at room temperature for 2.5 h, then was treated with saturated aqueous ammonium chloride. The mixture was extracted with ethyl acetate and the organic phase was dried over sodium sulfate and concentrated under vacuum. Flash column chromatography, eluting with 50% ethyl acetate in hexane, provided the E isomer of 5-[(1R,2R,4S)-4-tert-butoxycarbonylamino-2-(propane-2-sulfonylmethyl)-cyclohexylamino]-3-(3-trifluoromethylphenyl)pent-2-enoic acid tert-butyl ester (300 mg) as a white glassy solid. MS found: (M+H)$^+$=633.37. Further elution provided the Z isomer of the same compound (232 mg) as a white glassy solid.

Example 17a, Step 5: A solution of the E isomer of 5-[(1R,2R,4S)-4-tert-butoxycarbonylamino-2-(propane-2-sulfonylmethyl)-cyclohexylamino]-3-(3-trifluoromethylphenyl)pent-2-enoic acid tert-butyl ester (293 mg) in dichloromethane (6 mL) was treated with trifluoroacetic acid (3 mL) and stirred at room temperature. After 2 h, the mixture was concentrated under vacuum to provide the E isomer of 5-[(1R,2R,4S)-4-amino-2-(propane-2-sulfonylmethyl)cyclohexylamino]-3-(3-trifluoromethylphenyl)pent-2-enoic acid, bis-trifluoroacetic acid salt, (387 mg) as a white glassy powder. MS found: (M+H)$^+$=477.35.

Example 17a, Step 6: A solution of the E isomer of 5-[(1R,2R,4S)-4-amino-2-(propane-2-sulfonylmethyl)cyclohexylamino]-3-(3-trifluoromethylphenyl)pent-2-enoic acid, bis-trifluoroacetic acid salt, (387 mg) in dichloromethane (3 mL) was treated sequentially with diisopropylethylamine (0.323 mL), 4-(N,N-dimethylamino)pyridine (57 mg) and TBTU (164 mg). The mixture was stirred at room temperature for 4.75 h, then was washed with saturated aqueous sodium bicarbonate, water, and brine, and dried over sodium sulfate. The solution was concentrated under vacuum and the residue was purified by reverse phase HPLC to provide, after lyophilization, 1-[(1R,2R,4S)-4-amino-2-(propane-2-sulfonylmethyl)cyclohexyl]-4-(3-trifluoromethylphenyl)-5,6-dihydro-1H-pyridin-2-one, trifluoroacetate salt (143 mg) as a white powder. MS found: (M+H)$^+$=459.35.

Example 17a, Step 7: The free base (94 mg) obtained from 1-[(1R,2R,4S)-4-amino-2-(propane-2-sulfonylmethyl)cyclohexyl]-4-(3-trifluoro-methylphenyl)-5,6-dihydro-1H-pyridin-2-one, trifluoroacetate salt, was dissolved in 1,2-dichloroethane (2 mL) and treated sequentially with acetone (0.045 mL), acetic acid (0.059 mL) and sodium triacetoxyborohydride (130 mg). The mixture was stirred at room temperature for 4.5 h, then was concentrated under vacuum. The residue was partitioned between ethyl acetate and saturated aqueous sodium bicarbonate, and the organic phase was dried over sodium sulfate and concentrated to provide 1-[(1R,2R,4S)-4-isopropylamino-2-(propane-2-sulfonylmethyl)cyclohexyl]-4-(3-trifluoromethylphenyl)-5,6-dihydro-1H-pyridin-2-one (103 mg) as a white glassy solid. MS found: (M+H)$^+$=501.37.

Example 17a, Step 8: A solution of 1-[(1R,2R,4S)-4-isopropylamino-2-(propane-2-sulfonylmethyl)cyclohexyl]-4-(3-trifluoromethyl-phenyl)-5,6-dihydro-1H-pyridin-2-one (43 mg) in methanol (1 mL) was treated with acetaldehyde (0.025 mL) and stirred at room temperature. After 35 min, sodium cyanoborohydride (8 mg) was added, and the mixture was stirred at room temperature for 22.5 h. The mixture was concentrated and partitioned between water and ethyl acetate. The aqueous phase was extracted with additional ethyl acetate, and the combined organic phases were dried over sodium sulfate and concentrated under vacuum to provide 1-((1S,2R,4R)-4-(isopropyl(ethyl)amino)-2-(isopropylsulfonylmethyl)cyclohexyl)-4-(3-(trifluoromethyl)phenyl)-5,6-dihydropyridin-2(1H)-one (41 mg) as a white glassy solid. MS found: (M+H)$^+$=529.39.

TABLE 17-A

The compounds in the following table were made using the methods exemplified above. See Table 1-A for a complete description of the table headings.

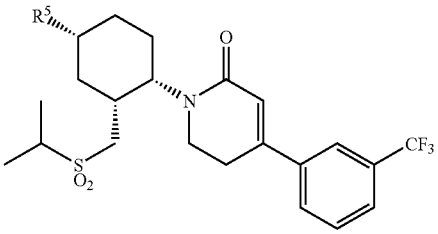

| Example | R$^5$ | Step Altered | MS Data |
|---|---|---|---|
| 17a | i-Pr(Et)N | n/a | 529.4 |
| 17b | i-Pr(Me)N | 17a, Step 8 | 515.4 |

TABLE 17-B

The chemical names of the specific examples illustrated in Table 17-A are tabulated below.

| Example | Name |
|---|---|
| 17a | 1-((1S,2R,4R)-4-(isopropyl(ethyl)amino)-2-(isopropylsulfonylmethyl)cyclohexyl)-4-(3-(trifluoromethyl)phenyl)-5,6-dihydropyridin-2(1H)-one |
| 17b | 1-((1S,2R,4R)-4-(isopropyl(methyl)amino)-2-(isopropylsulfonylmethyl)cyclohexyl)-4-(3-(trifluoromethyl)phenyl)-5,6-dihydropyridin-2(1H)-one |

Examples 18a and 18b

Example 18a

Synthesis of (S)-1-((1R,2S,4S)-4-(isopropyl(methyl)amino)-2-methoxycyclohexyl)-3-(6-(trifluoromethyl)quinazolin-4-ylamino)pyrrolidin-2-one Example 18a, Step 1: A solution of racemic 4-cis-(benzyloxy)-2-trans-methoxycyclohexanol (3.24 g, see *J. Org. Chem.* 1990, 55, 4265) and triethylamine (5.73 mL) in dichloromethane (35 mL) was stirred on an ice bath and treated dropwise over about 1 min with methanesulfonyl chloride. The mixture was stirred on an ice bath for 2 h, then was treated with saturated aqueous NH$_4$Cl. The layers were separated, the organic layer was washed with saturated aqueous NaHCO$_3$, then with brine, and then was dried over Na$_2$SO$_4$ and concentrated under vacuum to provide racemic 4-cis-(benzyloxy)-2-trans-methoxycyclohexyl methanesulfonate as an orange gum (4.36 g), used without further purification. MS found: (M+H)$^+$=315.1.

Example 18a, Step 2: A solution of racemic 4-cis-(benzyloxy)-2-trans-methoxycyclohexyl methanesulfonate (1.0 g) in dimethyl sulfoxide (12 mL) was treated with sodium azide (1.03 g) and heated at 60° C. for 16 h, then at 80° C. for 4.5 days. The mixture was cooled to rt, diluted with ethyl acetate, and washed five times with water and once with brine. The solution was dried over Na$_2$SO$_4$ and concentrated under vacuum to provide racemic 1-((4-trans-azido-3-trans-methoxycyclohexyloxy)methyl)benzene as a brown oil (756 mg) used without further purification. MS found: (M+Na)$^+$=284.5.

Example 18a, Step 3: A solution of racemic 1-((4-trans-azido-3-trans-methoxycyclohexyloxy)methyl)benzene (750 mg) in ethanol (20 mL) was treated with Pearlman's catalyst (20% Pd(OH)$_2$ on charcoal, 150 mg) and stirred under an atmosphere of hydrogen (maintained by a hydrogen-filled balloon) for 2.5 h. The mixture was filtered through Celite and the solids were rinsed with ethanol. The combined filtrates were concentrated under vacuum to provide racemic 4-trans-(benzyloxy)-2-cis-methoxycyclohexanamine as an oil (678 mg), used without further purification. MS found: (M+H)$^+$=236.1.

Example 18a, Step 4: A solution of racemic 4-trans-(benzyloxy)-2-cis-methoxycyclohexanamine (675 mg) and (S)-2-(tert-butoxycarbonyl)-4-(methylthio)butanoic acid (787 mg) in dichloromethane (15 mL) was treated with diisopropylethylamine (1.1 mL) and TBTU (1.01 g). The mixture was stirred at rt for 3.5 h, then was diluted with dichloromethane. The mixture was washed with 1.0 M aqueous HCl, saturated aqueous NaHCO$_3$, and water, then was dried over Na$_2$SO$_4$ and concentrated under vacuum. The residue was purified by flash column chromatography on silica gel, eluting with 6:4 v/v hexane-ethyl acetate, to provide a mixture of tert-butyl (S)-1-((1S,2R,4S)-4-(benzyloxy)-2-methoxycyclohexylamino)-4-(methylthio)-1-oxobutan-2-ylcarbamate and tert-butyl (S)-1-((1R,2S,4R)-4-(benzyloxy)-2-methoxycyclohexylamino)-4-(methylthio)-1-oxobutan-2-ylcarbamate as a sticky white solid (893 mg). MS found: (M+H)$^+$=467.4.

Example 18a, Step 5: A solution of the mixture of tert-butyl (S)-1-((1S,2R,4S)-4-(benzyloxy)-2-methoxycyclohexylamino)-4-(methylthio)-1-oxobutan-2-ylcarbamate and tert-butyl (S)-1-((1R,2S,4R)-4-(benzyloxy)-2-methoxycyclohexylamino)-4-(methylthio)-1-oxobutan-2-ylcarbamate from Example 18a, Step 4 (870 mg) in dichloromethane (2 mL) was treated with iodomethane (20 mL) and the solution was stirred at rt for 24 h. The mixture was concentrated under vacuum, then was dissolved in fresh dichloromethane and concentrated under vacuum. The dissolution in dichloromethane and concentration was repeated four more times to provide a mixture of (S)-4-((1S,2R,4S)-4-(benzyloxy)-2-methoxycyclohexylamino)-3-(tert-butoxycarbonylamino)-4-oxobutane-1-dimethylsulfonium iodide and (S)-4-((1R,2S,4R)-4-(benzyloxy)-2-methoxycyclohexylamino)-3-(tert-butoxycarbonylamino)-4-oxobutane-1-dimethylsulfonium iodide as a pale yellowish powder (1.019 g). MS found: (M−Me$_2$S)$^+$=419.4.

Example 18a, Step 6: A solution of the mixture of (S)-4-((1S,2R,4S)-4-(benzyloxy)-2-methoxycyclohexylamino)-3-(tert-butoxycarbonylamino)-4-oxobutane-1-dimethylsulfonium iodide and (S)-4-((1R,2S,4R)-4-(benzyloxy)-2-methoxycyclohexylamino)-3-(tert-butoxycarbonylamino)-4-oxobutane-1-dimethylsulfonium iodide from Example 18a, Step 5 (1.013 g) in tetrahydrofuran (10 mL) was stirred on an ice bath and treated with NaH (60% in mineral oil, 266 mg). After 30 min, the bath was removed and the mixture was stirred at rt. After 22 h, the mixture was diluted with water and ethyl acetate. The layers were separated and the aqueous layer was extracted three times with ethyl acetate. The combined organic layers were dried over Na$_2$SO$_4$ and concentrated under vacuum. The residue was purified by flash column chromatography on silica gel, eluting with 35:65 v/v hexane-ethyl acetate, to provide a mixture of tert-butyl (S)-1-((1S,2R,4S)-4-(benzyloxy)-2-methoxycyclohexyl)-2-oxopyrrolidin-3-ylcarbamate and tert-butyl (S)-1-((1R,2S,4R)-4-(benzyloxy)-2-methoxycyclohexyl)-2-oxopyrrolidin-3-ylcarbamate as a white glassy foam (386 mg). MS found: (M+H)$^+$=419.4.

Example 18a, Step 7: Following the procedure of Example 18a, Step 3, the mixture of tert-butyl (S)-1-((1S,2R,4S)-4-(benzyloxy)-2-methoxycyclohexyl)-2-oxopyrrolidin-3-ylcarbamate and tert-butyl (S)-1-((1R,2S,4R)-4-(benzyloxy)-2-methoxycyclohexyl)-2-oxopyrrolidin-3-ylcarbamate from Example 18a, Step 6 (374 mg) was converted, in two batches, to a mixture of tert-butyl (S)-1-((1S,2R,4S)-4-hydroxy-2-methoxycyclohexyl)-2-oxopyrrolidin-3-ylcarbamate and tert-butyl (S)-1-((1R,2S,4R)-4-hydroxy-2-methoxycyclohexyl)-2-oxopyrrolidin-3-ylcarbamate as a white glassy foam (293 mg). MS found: (M+H)$^+$=329.2.

Example 18a, Step 8: Following the procedure of Example 18a, Step 1, the mixture of tert-butyl (S)-1-((1S,2R,4S)-4-hydroxy-2-methoxycyclohexyl)-2-oxopyrrolidin-3-ylcarbamate and tert-butyl (S)-1-((1R,2S,4R)-4-hydroxy-2-methoxycyclohexyl)-2-oxopyrrolidin-3-ylcarbamate from Example 18a, Step 7 (165 mg) was converted to a mixture of (1S,3R,4S)-4-((S)-3-(tert-butoxycarbonylamino)-2-oxopyrrolidin-1-yl)-3-methoxycyclohexyl methanesulfonate and (1R,3S,4R)-4-((S)-3-(tert-butoxycarbonylamino)-2-oxopyrrolidin-1-yl)-3-methoxycyclohexyl methanesulfonate as a light tan-orange glassy foam (198 mg). MS found: (M+H)$^+$=407.1.

Example 18a, Step 9: Following the procedure of Example 18a, Step 2, the mixture of (1S,3R,4S)-4-((S)-3-(tert-butoxycarbonyl)-2-oxopyrrolidin-1-yl)-3-methoxycyclohexyl methanesulfonate and (1R,3S,4R)-4-((S)-3-(tert-butoxycarbonyl)-2-oxopyrrolidin-1-yl)-3-methoxycyclohexyl methanesulfonate from Example 18a, Step 8 (193 mg) was converted to a mixture of tert-butyl (S)-1-((1S,2R,4R)-4-azido-2-methoxycyclohexyl)-2-oxopyrrolidin-3-ylcarbamate and tert-butyl (S)-1-((1R,2S,4S)-4-azido-2-methoxycyclohexyl)-2-oxopyrrolidin-3-ylcarbamate as a solid (145 mg). MS found: (M+Na)$^+$=376.4.

Example 18a, Step 10: Following the procedure of Example 18a, Step 3, the mixture of tert-butyl (S)-1-((1S,2R,4R)-4-azido-2-methoxycyclohexyl)-2-oxopyrrolidin-3-ylcarbamate and tert-butyl (S)-1-((1R,2S,4S)-4-azido-2-methoxycyclohexyl)-2-oxopyrrolidin-3-ylcarbamate from Example 18a, Step 9 (145 mg) was converted to a mixture of tert-butyl (S)-1-((1S,2R,4R)-4-amino-2-methoxycyclohexyl)-2-oxopyrrolidin-3-ylcarbamate and tert-butyl (S)-1-((1R,2S,4S)-4-amino-2-methoxycyclohexyl)-2-oxopyrrolidin-3-ylcarbamate as a dark brown glass (145 mg) used without further purification. MS found: (M+H)$^+$=328.2.

Example 18a, Step 11: A solution of the mixture of tert-butyl (S)-1-((1S,2R,4R)-4-amino-2-methoxycyclohexyl)-2-oxopyrrolidin-3-ylcarbamate and tert-butyl (S)-1-((1R,2S,4S)-4-amino-2-methoxycyclohexyl)-2-oxopyrrolidin-3-ylcarbamate from Example 18a, Step 10 (145 mg) in 1,2-dichloroethane (2 mL) was treated sequentially with acetone (90 μL), acetic acid (117 μL) and sodium triacetoxyborohydride (348 mg). The mixture was stirred at rt for 5 h, then was treated with 37% aqueous formaldehyde (153 µL) and stirred further at rt. After 17 h, the mixture was treated with saturated aqueous NaHCO₃, stirred for 10 min, and extracted five times with ethyl acetate. The combined organic layers were dried over Na₂SO₄ and concentrated. The residue was dissolved in dichloromethane, filtered through Celite and concentrated to provide a crude mixture of tert-butyl (S)-1-((1S,2R,4R)-4-(isopropyl(methyl)amino)-2-methoxycyclohexyl)-2-oxopyrrolidin-3-ylcarbamate and tert-butyl (S)-1-((1R,2S,4S)-4-(isopropyl(methyl)amino)-2-methoxycyclohexyl)-2-oxopyrrolidin-3-ylcarbamate (67 mg), used without further purification. MS found: $(M+H)^+=384.5$.

Example 18a, Step 12: A solution of the mixture of tert-butyl (S)-1-((1S,2R,4R)-4-(isopropyl(methyl)amino)-2-methoxycyclohexyl)-2-oxopyrrolidin-3-ylcarbamate and tert-butyl (S)-1-((1R,2S,4S)-4-(isopropyl(methyl)amino)-2-methoxycyclohexyl)-2-oxopyrrolidin-3-ylcarbamate from Example 18a, Step 11 (67 mg) in dichloromethane (2 mL) was treated with trifluoroacetic acid (2 mL). After being allowed to stand for 1 h at rt, the mixture was concentrated under vacuum, taken up in toluene and concentrated again under vacuum. The residue was dissolved in water and lyophilized to provide a mixture of the bis-trifluoroacetic acid salt of (S)-3-amino-1-((1S,2R,4R)-4-(isopropyl(methyl)amino)-2-methoxycyclohexyl)pyrrolidin-2-one and the bis-trifluoroacetic acid salt of (S)-3-amino-1-((1R,2S,4S)-4-(isopropyl(methyl)amino)-2-methoxycyclohexyl)pyrrolidin-2-one as a powdery glass (94 mg), used without further purification. MS found: $(M+H)^+=284.3$.

Example 18a, Step 13: A solution of the mixture of the bis-trifluoroacetic acid salt of (S)-3-amino-1-((1S,2R,4R)-4-(isopropyl(methyl)amino)-2-methoxycyclohexyl)pyrrolidin-2-one and the bis-trifluoroacetic acid salt of (S)-3-amino-1-((1R,2S,4S)-4-(isopropyl(methyl)amino)-2-methoxycyclohexyl)pyrrolidin-2-one from example 18a, Step 12 (94 mg), 4-chloro-6-trifluoromethylquinazoline (81 mg), triethylamine (97 µL) and ethanol (1 mL) was heated at reflux for 2.5 h, then was cooled to rt and concentrated under vacuum. The residue was purified by reverse phase HPLC. The material in the first-eluting of the two product peaks was isolated by lyophilization to provide the compound assigned as the bis-trifluoroacetic acid salt of the title structure, (S)-1-((1R,2S,4S)-4-(isopropyl(methyl)amino)-2-methoxycyclohexyl)-3-(6-(trifluoromethyl)quinazolin-4-ylamino)pyrrolidin-2-one, as a white powder (15 mg). MS found: $(M+H)^+=480.4$.

Example 18b

Synthesis of (S)-1-((1S,2R,4R)-4-(isopropyl(methyl)amino)-2-methoxycyclohexyl)-3-(6-(trifluoromethyl)quinazolin-4-ylamino)pyrrolidin-2-one From the reverse phase HPLC purification of Example 18a, Step 13, the material in the second-eluting of the two product peaks was isolated by lyophilization to provide a compound assigned as the bis-trifluoroacetic acid salt of the title structure, as a white powder (9 mg). MS found: $(M+H)^+=480.4$.

TABLE 18-A

The compounds in the following table were made using the methods exemplified above. See Table 1-A for a complete description of the table headings.

| Example | Structure | MS Data |
|---------|-----------|---------|
| 18a | 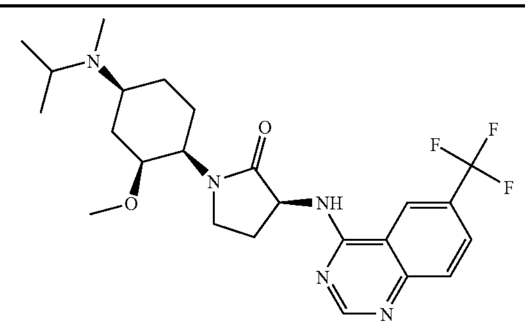 | 480.4 |
| 18b | 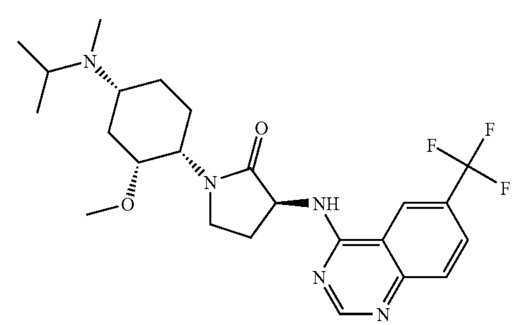 | 480.4 |

TABLE 18-B

The chemical names of the specific examples illustrated in Table 18-A are tabulated below.

| Example | Name |
|---|---|
| 18a | (S)-1-((1R,2S,4S)-4-(isopropyl(methyl)amino)-2-methoxycyclohexyl)-3-(6-(trifluoromethyl)quinazolin-4-ylamino)pyrrolidin-2-one |
| 18b | (S)-1-((1S,2R,4R)-4-(isopropyl(methyl)amino)-2-methoxycyclohexyl)-3-(6-(trifluoromethyl)quinazolin-4-ylamino)pyrrolidin-2-one |

UTILITY

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 30 µM or lower in concentration when measured in a particular assay.

Antagonism of MCP-1 Binding to Human PBMC
(Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5 \times 10^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx
(Sullivan, et al. Methods Mol. Biol., 114, 125-133 (1999))

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8 \times 10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., J. Immunol. Methods, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2-4 \times 10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-induced Human PBMC Chemotaxis
(Bacon et al., *Brit. J. Pharmacol.* 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell derivation and cell culture: A pool of HT1080 cells stably expressing endogenous CC chemokine receptor 5 (CCR5) were developed using the methods outlined by Harrington, Sherf, and Rundlett (see United States patents U.S. Pat. No. 6,361,972 and U.S. Pat. No. 6,410,266). The highest-expressing clones were isolated using repetitive flow cytometry, followed by sub-cloning. These cells were then cultured in 6-well dishes at $3\times10^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation: A cell pellet containing $1\times10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding assay: The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of $[^{125}I]$-MIP-1 beta (Perkin Elmer; material was diluted in Binding buffer such that the addition of 50 microliters/well gives a final concentration of 0.1 nM $[^{125}I]$-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-based Functional assay: HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

The compounds of the present invention are inhibitors of both CCR2 and CCR5 and may be used to treat diseases associated with either chemokine. The compounds of the present invention are considered dual antagonists.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD.) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternativley, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, S excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit. Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

The invention claimed is
1. A compound of formula (I):

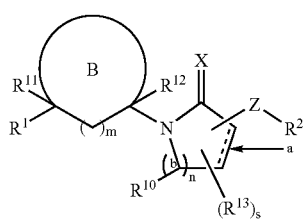

(I)

or a stereoisomer or a pharmaceutically acceptable salt thereof, wherein:
ring B is a cyclohexyl group wherein the cyclohexyl group is substituted with 1-2 $R^5$;
X is selected from O or S;

Z is selected from —$NR^8C(O)$—, —$NR^8C(S)$—, —$NR^8C(O)NH$—, —$NR^8C(S)NH$—, —$NR^8SO_2$—, —$NR^8SO_2NH$—, —$C(O)NR^8$—, —$OC(O)NR^8$—, —$NR^8C(O)O$—, —$CR^{14}$=$CR^{14}$—, —$CR^{15}R^{15}$—, —$CR^{15}R^{15}C(O)$—, —$C(O)CR^{15}R^{15}$—, —$CR^{15}R^{15}C$(=N—$OR^{16}$)—, —O—$CR^{14}R^{14}$—, —$CR^{14}R^{14}$—O—, —O—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$, —$CR^{14}R^{14}$—$S(O)_p$—, and —$S(O)_p$—$NR^9$—;
wherein neither Z nor $R^{13}$ are connected to a carbon atom labeled (b);
bond (a) is a single bond or double bond;
$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isonicotinyl, isoquinolinyl isothiazolyl, isoxazolinyl, isoxazolyl, oxazolyl, phthalazinyl, picolinyl, pyrazinyl, pyrazolyl, pyridazinyl, pyridyl, pyridinyl, pyrimidinyl, pyrrolyl, quinazolinyl, quinolinyl, thiazolyl, thienyl, triazinyl, and tetrazolyl; with the proviso that if $R^1$ is H, then $R^5$ is $(CH_2)_rNR^{5a}R^{5a}$; and with the further proviso that if $R^5$ is H, then $R^1$ is not H or methyl;
$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, pyrrolotriazinyl, quinazolinyl, quinolinyl, thiazolyl, thienyl, and tetrazolyl;
$R^5$, at each occurrence, is independently selected from H, methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl, $(CH_2)_r$phenyl substituted with 0-2 $R^{5e}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl;
$R^{5a}$, at each occurrence, is independently selected from H, methyl, ethyl, propyl, i-propyl, butyl, i-butyl, pentyl, hexyl, cyclopropyl, and cyclobutyl;
$R^{5b}$, at each occurrence, is selected from $C_{1-6}$ alkyl substituted with 0-3 $R^{5e}$, $C_{1-6}$ haloalkyl, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, C(O)OH, $(CH_2)_rC(O)$ $NHSO_2R^{5h}$, $NHSO_2-R^{5h}$, $(CH_2)_r$tetrazolyl, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)OH$, $(CH_2)_rC(O)NHSO_2-R^{5h}$, $NHSO_2R^{5h}$, a $(CH_2)_r$-5-6 membered heterocyclic system containing 1-4 heteroatoms selected from N, O, and S, and $(CH_2)_r$phenyl;

$R^{5f}$, at each occurrence, is selected from H, $C_{1-6}$ alkyl, and $C_{3-6}$ cycloalkyl;

$R^{5h}$, at each occurrence, is selected from $C_{1-5}$ alkyl, $C_{1-5}$ haloalkyl, and $C_{3-6}$ cycloatkyl, and phenyl;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a}R^{6a'}$, $(CH_2)_rOH$, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)OH$, $(CH_2)_rC(O)(CH_2)_rR^{6b}$, $(CH_2)_rC(O)NR^{6a}R^{6a}$, $(CH_2)_rNR^{6f}C(O)R^{6b'}$, $(CH_2)_rNR^{6a}C(O)NR^{6a}R^{6d'}$, $(CH_2)_rNR^{6a}C(S)NR^{6a}R^{6a}$, $(CH_2)_rOC(O)$ $(CH_2)_rR^{6b}$, $(CH_2)_rS(O)_pR^{6b'}$, $(CH_2)_rS(O)_2NR^{6a}R^{6a}$, $(CH_2)_rNR^{6f}S(O)_2(CH_2)_rR^{6b}$, $(CH_2)_rNR^{6f}S(O)_2 NR^{6a}R^{6a}$, $C_{1-6}$ haloalkyl, $(CH_2)_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$, wherein the heterocyclic system is selected from aziridinyl, azetidinyl, pyrrolyl, piperidinyl, and morpholinyl;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6a'}$, at each occurrence, is selected from H, $C_{1-6}$ alkyl and $C_{3-6}$ cycloalkyl;

$R^{6b}$, at each occurrence, is selected from H, methyl, ethyl, propyl, i-propyl, butyl, i-butyl, t-butyl, pentyl, hexyl, cyclopropyl, and phenyl;

$R^{6b'}$, at each occurrence, is selected from H, $C_{1-6}$ alkyl and $C_{3-6}$ cycloalkyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6d'}$, at each occurrence, is selected from H, $CF_3$ and $C_{1-6}$ alkyl and $C_{3-6}$ cycloalkyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, $C(O)NHR^{6h}$, $C(O)$ $OC_{1-5}$ alkyl, $(CH_2)_rOH$, C(O)OH, $(CH_2)_rC(O)$ $NHSO_2-R^{6h}$, $NHSO_2R^{6h}$, $(CH_2)_r$tetrazolyl, $(CH_2)_r$phenyl and a $(CH_2)_r$-5-6 membered heterocyclic system containing 1-4 heteroatoms selected from N, O, and S;

$R^{6f}$, at each occurrence, is selected from H, methyl, ethyl, propyl, i-propyl, butyl, i-butyl, t-butyl, pentyl, hexyl, cyclopropyl, and phenyl;

$R^{6h}$, at each occurrence, is selected from $C_{1-5}$ alkyl, $C_{1-5}$ haloalkyl, and $C_{3-6}$ cycloalkyl, and phenyl;

$R^7$ is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rO(CH_2)_rR^{7d}$, $(CH_2)_rSH$, $(CH_2)_rC(O)$ H, $(CH_2)_rS(CH_2)_rR^{7d}$, $(CH_2)_rC(O)OH$, $(CH_2)_rC(O)$ $(CH_2)_rR^{7b}$, $(CH_2)_rC(O)NR^{7a}R^{7a}$, $(CH_2)_rNR^{7f}C(O)$ $(CH_2)_rR^{7b}$, $(CH_2)_rC(O)O(CH_2)_rR^{7d}$, $(CH_2)_rOC(O)$ $(CH_2)_rR^{7b}$, $(CH_2)_rOC(O)NR^{7a}R^{7a}$, $(CH_2)_rNR^{7a}C(O)$ $NR^{7a}R^{7a}$, $(CH_2)_rNR^{7a}C(O)O(CH_2)_rR^{7d}$, $(CH_2)_rS(O)_p$ $(CH_2)_rR^{7b}$, $(CH_2)_rS(O)_2NR^{7a}R^{7a}$, $(CH_2)_rNR^{7f}S(O)_2$ $(CH_2)_rR^{7b}$, $C_{1-6}$ haloatkyl, adamantyl, $(CH_2)_r$phenyl substituted with 0-3 $R^{7e}$, and a $(CH_2)_r$-5-6 membered heterocyclic system containing 1-4 heteroatoms selected from N, O, and S, substituted with 0-3 $R^{7e}$, wherein the heterocyclic system is selected from thienyl, pyridinyl, benzothiazolyl, and tetrazolyl;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperazinyl, piperidinyl, substituted with 0-1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, C(O)OH, $C(O)NHR^{7h}$, $C(O)OC_{1-5}$ alkyl, $(CH_2)_rSC_{1-5}$ alkyl, $(CH_2)_rNR^{7f}R^{7f}$, $(CH_2)_rC(O)$ $NHSO_2-R^{7h}$, $NHSO_2R^{7h}$, and $(CH_2)_r$phenyl, and $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl;

$R^{7h}$, at each occurrence, is selected from $C_{1-5}$ alkyl, $C_{1-5}$ haloalkyl, and $C_{3-6}$ cycloalkyl, and phenyl;

$R^8$ is selected from H, methyl, ethyl, propyl, i-propyl, and cyclopropyl;

$R^9$ is selected from H, $C_{1-4}$ alkyl, $C_{3-4}$ cycloalkyl, —C(O) H, and —C(O)—$C_{1-4}$alkyl;

$R^{10}$ is H;

$R^{11}$ is selected from H, $C_{1-4}$ alkyl, $(CHR)_qOH$, $(CHR)_qSH$, $(CHR)_qOR^{11d}$, $(CHR)_qS(O)_pR^{11d}$, $(CHR)_qC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, and a $(CH_2)_r$-5-6 membered nonaromatic

251 heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$-$C_{3-6}$ cycloalkyl substituted with 0-2 $R^{11e}$, and a $(CH_2)_r$-5-6 membered nonaromatic heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ cycloalkyl substituted with 0-3 $R^{11e}$, and a $(CH_2)_r$-5-6 membered nonaromatic heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, and a $(CHR)_r$—$C_{3-6}$ carbocyclic residue substituted with 0-5 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$ alkyl substituted with 0-1 $R^{13b}$, —OH, —$NH_2$, F, Cl, Br, I, —$OR^{13a}$, —$N(R^{13a})_2$, and $C_{1-4}$ alkyl substituted with 0-3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$ alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$alkyl, OH, $NH_2$, —O—$C_{1-4}$ alkyl, $NR^{15a}R^{15a}$, $C(O)NR^{15a}R^{15a}$, $NR^{15a}C(O)R^{15b}$, $NR^{15a}C(O)OR^{15d}$, $OC(O)NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is seleced from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

n is 1;

m is selected from 0 and 1;

p, at each occurrence, is independently selected from 0, 1, and 2;

q, at each occurrence, is independently selected from 1, 2, 3, and 4;

r is 0 or 1; and s is 0.

252

2. The compound of claim 1, wherein:

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a'}R^{6a'}$, $(CH_2)_rOH$, $(CH_2)_rOR^{6d}$, $(CH_2)_rSH$, $(CH_2)_rC(O)H$, $(CH_2)_rSR^{6d}$, $(CH_2)_rC(O)OH$, $(CH_2)_rC(O)R^{6b}$, $(CH_2)_rC(O)NR^{6a}R^{6a}$, $(CH_2)_rNR^{6f}C(O)R^{6b'}$, $(CH_2)_rNR^{6a}C(O)NR^{6a'}R^{6d'}$, $(CH_2)_rNR^{6a}C(S)NR^{6a}R^{6a}$, $(CH_2)_rOC(O)R^{6b}$, $(CH_2)_rS(O)_pR^{6b'}$, $(CH_2)_rS(O)_2NR^{6a}R^{6a}$, $(CH_2)_rNR^{6f}S(O)_2R^{6b}$, $(CH_2)_rNR^{6f}S(O)_2NR^{6a}R^{6a}$, $C_{1-6}$ haloalkyl, and $(CHR')_r$phenyl substituted with 0-3 $R^{6e}$; and $R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7f}C(O)R^{7b}$, $NR^{7f}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$,

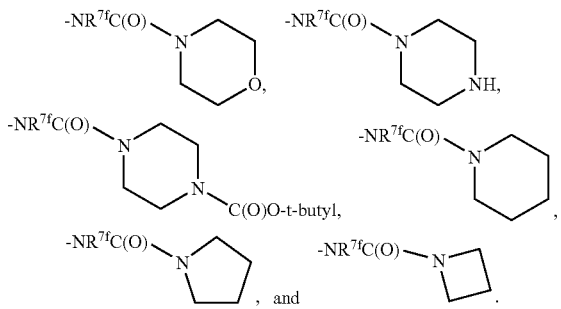

3. A compound of formula (I) ring B is selected from

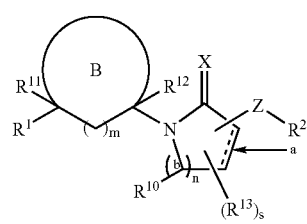

or a stereoisomer or a pharmaceutically acceptable salt thereof, wherein:

ring B is

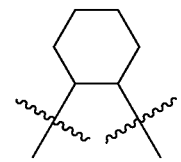

substituted with 0-1 $R^5$;

X is selected from O or S;

Z is selected from —$NR^8C(O)$—, —$NR^9$—, —$C(O)NR^8$—, and —$NHC(O)NH$—;

wherein neither Z nor $R^{13}$ are connected to a carbon atom labeled (b);

bond (a) is a single bond or double bond;

$R^1$ is selected from H, $R^6$, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$; with the proviso that if $R^1$ is H, then $R^5$ is $(CH_2)_rNR^{5a}R^{5a}$; and with the further proviso that if $R^5$ is H, then $R^1$ is not H or methyl;

$R^2$ is phenyl substituted with 0-2 $R^7$;

$R^5$, at each occurrence, is independently selected from H, methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl, $(CH_2)_r$phenyl substituted with 0-2 $R^{5e}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinly;

$R^{5a}$, at each occurrence, is independently selected from H, methyl, ethyl, propyl, i-pronyl, butyl, i-butyl, pentyl, hexyl, cyclopropyl, and cyclobuty;

$R^{5b}$, at each occurrence, is selected from $C_{1-6}$ alkyl substituted with 0-3 $R^{5e}$, $C_{1-6}$ haloalkyl, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyctic residue substituted with 0-2 $R^{5e}$, and a $(CR_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, $C(O)OH$, $(CH_2)_rC(O)NHSO_2$—$R^{5h}$, $NHSO_2R^{5h}$, $(CH_2)_r$teteazolyl, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)OH$, $(CH_2)_rC(O)NHSO_2$—$R^{5h}$, $NHSO_2R^{5h}$, a $(CH_2)_r$-5-6 membered heterocyclic system containing 1-4 heteroatoms selected from N, O, and S, and $(CH_2)_r$phenyl;

$R^{5f}$, at each occurrence, is selected from H, $C_{1-6}$ alkyl; and $C_{3-6}$ cycloalkyl;

$R^{5h}$, at eachoccurrence, is selected from $C_{1-5}$ alkyl, $C_{1-5}$ haloalkyl, and $C_{3-6}$ cycloalkyl, and phenyl;

R, at each occurrence, is indenendently selected from H, methyl, ethyl, nropvl, allyl, propynyl, $(CH_2)_rC_{3-6}$ cycloalkyl, and $(CH_2)_r$phenyl substituted with $R^{5e}$;

$R^6$ is selected from methyl, ethyl, propyl, i-propyl, butyl, F, Cl, Br, I, $NO_2$, CN, $(CH_2)_rO(CH_2)_rR^{6d}$, $C(O)R^{6d}$, $SR^{6d}$, $NR^{6a'}R^{6a'}$, $C(O)NR^{6a'}R^{6d'}$, $NR^{6f}C(O)R^{6b'}$, $OC(O)R^{6b}$, $S(O)_pR^{6b}$, $(CHR')_rS(O)_2NR^{6a'}R^{6a'}$, and $CF_3$;

$R^{6a'}$, at each occurrence, is selected from H, $C_{1-6}$ alkyl and $C_{3-6}$ cycloalkyl;

$R^{6b'}$, is H, methyl, ethyl, propyl, i-propyl or butyl;

$R^{6b'}$, at each occurrence, is selected from H, $C_{1-6}$ alkyl and $C_{3-6}$ cycloalkyl;

$R^{6d}$ is methyl, phenyl, or $CF_3$; and $R^{6d'}$, at each occurrence, is selected from H, $CF_3$ and $C_{1-6}$ alkyl and $C_{3-6}$ cycloalkyl;

$R^{6f}$, at each occurrence, is selected from H, methyl, ethyl, propyl, i-propyl, butyl, i-butyl, t-butyl, phentyl, hexyl, cyclopropyl, and phenyl;

$R^7$ is selected from methyl, ethyl, propyl, i-propyl, butyl, i-butyl, s-butyl, pentyl,hexyl, Cl, Br, I, F, CN, $NO_2$, $NR^{7a}R^{7a}$, $NHC(O)NHR^{7a}$, $NR^{7f}C(O)R^{7b}$, $NR^{7f}C(O)OR^{7d}$, $CF_3$, $CF_2CF_3$, $CHF_2$, $CH_2F$, $OCF_3$, $C(O)R^{7b}$, $C(O)OR^{7d}$, $NR^{7a}C(O)NR^{7a}R^{7a}$, $NHS(O)_2R^{7b}$,

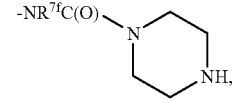
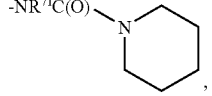
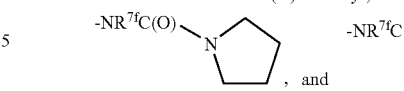
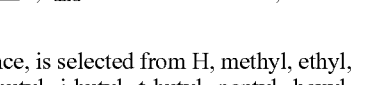
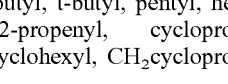

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperizenyl substituted with 0-1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkcyl, Cl, F, Br, I, CN, $NO_2$, $(CF_2)_rCF_3$, $(CH_2)_rOC_{1-5}$ alkyl, $(CH_2)_rOH$, OH, SH, $C(O)OH$, $C(O)NHR^{7h}$, $C(O)OC_{1-5}$ alkyl, $(CH_2)_rSC_{1-5}$ alkyl, $(CH_2)_rNR^{7f}R^{7f}$, $(CH_2)_rC(O)NHSO_2$—$R^{7h}$, $NHSO_2R^{7h}$, and $(CH_2)_r$phenyl, and $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl;

$R^{7h}$, at each occurrence, is selected from $C_{1-5}$ alkyl, $C_{1-5}$ haloalkyl, and $C_{3-6}$ cycloalkyl, and phenyl;

$R^8$ is selected from H, methyl, ethyl, propyl, i-propyl, and cyclopropyl;

$R^9$ is selected from H, $C_{1-4}$ alkyl, $C_{3-4}$ cycloalkyl, —$C(O)$H, and —$C(O)$—$C_{1-4}$ alkyl;

$R^{10}$ is H;

$R^{11}$ is selected from H, $C_{1-4}$ alkyl, $(CHR)_qOH$, $(CHR)_qSH$, $(CHR)_qOR^{11d}$, $(CHR)_qS(O)_pR^{11d}$, $(CHR)_rC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)0R^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_r$ $C_{3-6}$ cycloalkyl, and a $(CH_2)_r$-5-6 membered nonaromatic heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{1-4}$ alkynyl, a $(CH_2)_r$—$C_{3-6}$ cycloalkyl substituted with 0-2$R^{11e}$, and a $(CH_2)_r$-5-6 membered nonaromatic heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ cycloalkyl substituted with 0-3 $R^{11e}$, and a $(CH_2)_r$-5-6membered nonaromatic heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, and a $(CHR)_r$—$C_{3-6}$ carbocyclic residue substituted with 0-5 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl, $R^{13}$, at each occurrence, is independently selected from H, and $C_{1-4}$ alkyl substituted with 0-1 $R^{13b}$, —OH, —$NH_2$, F, Cl, Br, I, —$OR^{13a}$, —$N(R^{13a})_2$, and $C_{1-4}$ alkyl substituted with 0-3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

n is 1;

m is 0;

p, at each occurrence, is indenendently selected from 0, 1, and 2;

q, at each occurrence, is independently selected from 1, 2, 3, and 4;

r is 0 or 1; and s is 0.

4. The compound of claim 1, wherein:

$R^7$, at each occurrence, is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rOR^{7d}$, $(CH_2)_rSH$, $(CH_2)_rC(O)H$, $(CH_2)_rSR^{7d}$, $(CH_2)_rC(O)OH$, $(CH_2)_rC(O)R^{7b}$, $(CH_2)_rC(O)NR^{7a}R^{7a}$, $(CH_2)_rNR^{7f}C(O)R^{7b}$, $(CH_2)_rC(O)OR^{7d}$, $(CH_2)_rOC(O)R^{7b}$, $(CH_2)_rOC(O)NR^{7a}R^{7a}$, $(CH_2)_rNR^{7a}C(O)NR^{7a}R^{7a}$, $(CH_2)_rNR^{7f}C(O)OR^{7d}$, $(CH_2)_rS(O)_pR^{7b}$, $(CH_2)_rS(O)_2NR^{7a}R^{7a}$, $(CH_2)_rNR^{7f}S(O)_2NR^{7b}$, $C_{1-2}$ haloalkyl, $(CH_2)_r$phenyl substituted with 0-3 $R^{7e}$, and a $(CH_2)_r$-5-6 membered heterocyclic system containing 1-4 heteroatoms selected from N, O, and S, substituted with 0-3 $R^{7e}$, wherein the heterocyclic ring is selected from thiophenyl, pyridinyl, benzothiazolyl, and tetrazolyl.

5. The compound of claim 1, wherein the compound is the Compound of formula (Ia)

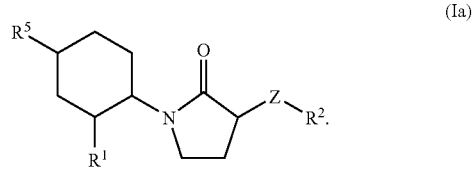

(Ia)

6. A compound of formula (Ia)

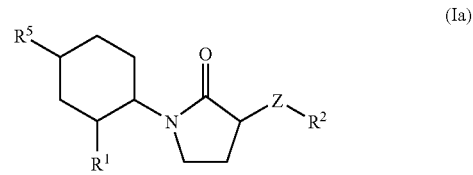

(Ia)

or a stereoisomer or a pharmaceutically acceptable salt thereof, wherein:

Z is selected from —NHC(O)—, —NHC(O)NH—, —NH—;

$R^1$ is selected from $C_{1-6}$ alkyl substituted from 0-1 $R^6$;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl system is selected from from quinazolinyl, triazinyl, pyrimidinyl, picolinyl, isonicotinyl, furanyl, indolyl, pyridinyl, pyrazolyl, pyrazinyl, thiazolyl, thiophenyl, and isoxazolyl;

$R^5$, at each occurrence, is independently selected from methyl, ethyl, propyl, i-propyl, butyl, i-butyl, allyl, propynyl, F, Cl, Br, I, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rC(O)OR^{5b}$, $(CH_2)_rOC(O)R^{5b}$, $(CH_2)_rNR^{5a}S(O)_2R^{5b}$, $C_{1-6}$ haloalkyl and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl;

$R^{5a}$, at each occurrence, is independently selected from H, methyl, ethyl, propyl, i-propyl, butyl, i-butyl, pentyl, hexyl, cycloproyl, and cyclobutyl;

$R^{5b}$, at each occurrence, is selected from $C_{1-6}$ alkyl substituted with 0-3 $R^{5e}$, $C_{1-6}$ haloalkyl, $C_{3-8}$ alkenyl substituted with 0-2 $R^e$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_r$-$C_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, C(O)OH, $(CH_2)_rC(O)NHSO_2$—$R^{5h}$, $NHSO_2R^{5h}$, $(CH_2)_r$tetrazolyl, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)OH$, $(CH_2)_rC(O)NHSO_2$—$R^{5h}$, $NHSO_2R^{5h}$, a $(CH_2)_r$-5-6 membered heterocyclic system containing 1-4 heteroatoms selected from N, O, and S, and $(CH_2)_r$phenyl;

$R^{5f}$, at each occurrence, is selected from H, $C_{1-6}$ alkyl, and $C_{3-6}$ cycloalkyl;

$R^{5h}$, at each occurrence, is selected from $C^{1-5}$ alkyl, $C_{1-5}$ haloalkyl, and $C_{3-6}$ cycloalkyl, and phenyl;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a}R^{6a'}$, $(CH_2)_rOH$, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)(CH_2)_rR^{6b}$, $(CH_2)_rC(O)NR^{6a}R^{6a}$, $(CH_2)_rNR^{6f}C(O)R^{6b'}$, $(CH_2)_rNR^{6a}C(O)NR^{6a'}R^{6d'}$, $(CH_2)_rNR^{6a}C(S)NR^{6a}R^{6a}$, $(CH_2)_rOC(O)(CH_2)_rR^{6b}$, $(CH_2)_rS(O)_pR^{6b'}$, $(CH_2)_rS(O)_2NR^{6a}R^{6a}$, $(CH_2)_rNR^{6f}S(O)_2(CH_2)R^{6b}$, $(CH_2)_rNR^{6f}S(O)_2NR^{6a}R^{6a}$, $C_{1-6}$ haloalkyl, $(CH_2)_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$, wherein the heterocyclic system is selected from aziridinyl, azetidinyl, pyrrolyl, piperidinyl, and morpholinyl;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6a'}$, at each occurrence, is selected from H, $C_{1-6}$ alkyl and $C_{3-6}$ cycloalkyl;

$R^{6b}$, at each occurrence, is selected from H, methyl, ethyl, propyl, i-propyl, butyl, i-butyl, t-butyl, pentyl, hexyl, cyclopropyl, and phenyl;

$R^{6b'}$, at each occurrence, is selected from H, $C_{1-6}$ alkyl and $C_{3-6}$ cycloalkyl;

$R^{6d}$, at each occurrence, is selected from methyl, $CF_3$, ethyl, propyl, i-nropyl, butyl, i-butyl, t-butyl, pentyl, hexyl, cyclopropyl, and phenyl;

$R^{6d'}$, at each occurrence, is selected from H, $CF_3$ and $C_{1-6}$ alkyl and $C_{3-6}$ cycloalkyl;

$R^{6e}$, at each occurrence, is selected from $C_{1-6}$ alkyl, $C_{2-5}$ alkenyl, $C_{2-8}$ alkynyl, $(CH_2)_rC_{3-6}$ cycloalkyl, Cl, F, Br, I, CN, $NO_2$, $(CF_2)_r(CF_3$, $(CH_2)_rOC_{1-5}$ alkyl, OH, SH, $(CH_2)_rSC_{1-5}$ alkyl, $(CH_2)_rNR^{6f}R^{6f}$, $C(O)NHR^{6h}$, $C(O)OC_{1-5}$ alkyl, $(CH_2)_rOH$, $C(O)OH$, $(CH_2)_rC(O)NHSO_2$—$R^{6h}$, $NHSO_2R^{6h}$, $(CH_2)_r$tetrazolyl, $(CH_2)_r$phenyl and a $(CH_2)_r$-5-6 membered heterocyclic system containina 1-4 heteroatoms selected from N, O, and S:

$R^{6f}$, at each occurrence, is selected from H, methyl, ethyl, propyl, i-propyl, butyl, i-butyl, t-butyl, pentyl, hexyl, cyclopropyl, and phenyl;

$R^{6h}$, at each occurrence, is selected from $C_{1-5}$ alkyl, $C_{1-5}$ aloalkyl, and $C_{3-6}$ cycloalkyl, and phenyl;

$R^7$ is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rO(CH_2)_rR^{7d}$, $(CH_2)_rSH$, $(CH_2)_rC(O)$ H, $(CH_2)_rS(CH_2)_rR^{7d}$, $(CH_2)_rC(O)OH$, $(CH_2)_rC(O)(CH_2)_rR^{7b}$, $(CH_2)_rC(O)NR^{7a}R^{7a}$, $(CH_2)_rNR^{7f}C(O)CH_2)_rR^{7b}$, $(CH_2)_rC(O)O(CH_2)_rR^{7d}$, $(CH_2)_rOC(O)CH_2)_rR^{7b}$, $(CH_2)_rOC(O)NR^{7a}R^{7a}$, $(CH_2)_rNR^{7a}C(O)NR^{7a}R^{7a}$, $(CH_2)_rNR^{7a}C(O)O(CH_2)_rR^{7d}$, $(CH_2)_rS(O)_p(CH_2)_rR^{7b}$, $(CH_2)_rS(O)_2NR^{7a}R^{7a}$, $(CH_2)_rNR^{7f}S(O)_2(CH_2)_rR^{7b}$, $C_{1-6}$ haloalkyl, adamantyl, $(CH_2)_r$phenyl substituted with 0-3 $R^{7e}$, and a $(CH_2)_r$-5-6 membered heterocyclic system containing 1-4 heteroatonis selected from N, O, and S, substituted with 0-3 $R^{7e}$, wherein the heterocyclic system is selected from thienyl, pyridinyl, benzothiazolyl, and tetrazolyl;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperizenyl substituted with 0-1 $R^{7e}$, and azetidinyl;

$R^{7d}$, at each occurrence, is selected from methyl, $CF_3$, $CF_2$, $CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_r(CF_3$, $(CH_2)_rOC_{1-5}$ alkyl, $(CH_2)_rOH$, OH, SH, $C(O)OH$, $C(O)NHR^{7h}$, $C(O)OC_{1-5}$ alkyl, $(CH_2)_rC_{1-5}$ alkyl, $(CH_2)_rNR^{7f}R^{7f}$, $(CH_2)_rC(O)NHSO_2$—$R^{7h}$, $NHSO_2R^{7h}$, and $(CH_2)_r$phenyl, and $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl;

$R^{7h}$, at each occurrence, is selected from $C_{1-5}$ alkyl, $C_{1-5}$ haloalkyl, and $C_{3-6}$ cycloalkyl, and phenyl;

p, at each occurrence, is independently selected from 0, 1, and 2; and r is 0 or 1.

7. The compound of claim 1, wherein the compound is of formula (Ia)

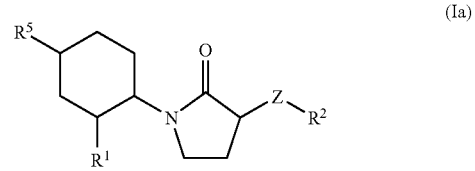

(Ia)

$R^1$ is selected from H, $R^6$ and $C_{1-6}$ alkyl substituted with 0-1 $R^6$; and $R^5$, at each occurrence, is independently selected from F, Cl, Br, I, $(CH_2)_rOH$, $(CH_2)_rOR^{5d}$, $(CH_2)_rNR^{5a}R^{5a}$, and a $(CRR)_r$-5-10 membered heterocyclic system containing 1-4 heteroatoms selected from N, O, and S, substituted with 0-2 $R^{5c}$, wherein the heterocyclic system is selected from pyrrolidinyl, piperidinyl, and morpholinlyl.

8. A pharmaceutical composition, comprising a pharmaceutically acceptable carrier and a therapeutically effective amount of a compound of claim 1.

9. A method for treating disorders comprising administering to a patient in need thereof a therapeutically effective amount of a compound of claim 1, said disorders being selected from asthma, multiple sclerosis, arthersclerosis, and rheumatoid arthritis.

10. A compound of formula (I):

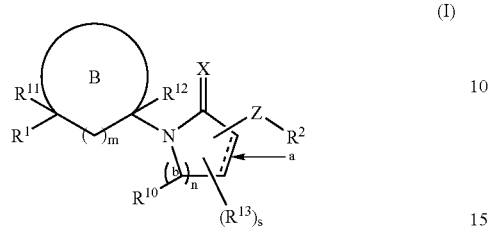

or a stereoisomer or a pharmaceutically acceptable salt thereof, wherein:

ring B is a cyclohexyl group wherein the cyclohexyl group is substituted with 1-2 $R^5$:

X is selected from O or S;

Z is selected from —$NR^8C(O)$—, —$NR^8C(S)$—, —$NR^8C(O)NH$—, —$NR^8C(S)NH$—, —$NR^8SO_2$—, —$NR^8S_2NH$—, —$C(O)NR^8$—, —$OC(O)NR^8$—, —$NR^8C(O)O_{13}$, —$CR^{14}$=$CR^{14}$—, —$CR^{15}R^{15}$—, —$CR^{15}R^{15}C(O)$—, —$C(O)CR^{15}R^{15}$—, —$CR^{15}R^{15}C(=N—OR^{16})$—, —$O$—$CR^{14}R^{14}$—, —$CR^{14}R^{14}$—$O$—, —$O$—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$—, —$CR^{14}R^{14}$—$S(O)_p$—, and —$S(O)_p$—$NR^9$—;

wherein neither Z nor $R^{13}$ are connected to a carbon atom labeled (b);

bond (a) is a single bond or double bond;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isonicotinyl, isoquinolinyl isothiazolyl, isoxazolinyl, isoxazolyl, oxazolyl, phthalazinyl, picolinyl, pyrazinyl, pyrazolyl, pyridazinyl, pyridvl, pyridinyl, pyrimidinyl, pyrrolyl, quinazolinyl, guinolinyl, thiazolyl, thienyl, triazinyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, pyrrolotriazinyl, quinazolinyl, quinolinyl, thiazolvi, thienyl, and tetrazolyl;

$R^5$ is selected from $NR^{5a}R^{5a}$;

$R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl;

$R^6$, at each occurrence, is selected from $C_{1-8}$ alkyl, $C_{2-8}$ alkynyl, $C_{2-8}$ alkynyl, $(CH_2)_rC_{3-6}$ cycloalkyl, Cl, Br, I, F, $NO_2$, CN, $(CH_2)_rNR^{6a}R^{6a'}$, $(CH_2)_rOH$, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)(CH_2)_rR^{6b}$, $(CH_2)_rC(O)NR^{6a}R^{6d}$, $(CH_2)_rNR^{6f}C(O)R^{6b'}$, $(CH_2)_rNR^{6a}C(O)NR^{6a}R^{6d'}$, $(CH_2)_rNR^{6a}C(S)NR^{6a}R^{6a}$, $(CH_2)_rOC(O)(CH_2)_rR^{6b}$, $(CH_2)_rS(O)_pR^{6b}$, $(CH_2)_rS(O)_2NR^{6a}R^{6a}$, $(CH_2)_rNR^{6f}S(O)_2(CH_2)_rR^{6b}$, $(CH_2)_rNR^{6f}S(O)_2NR^{6a}R^{6a}$, $C_{1-6}$ haloalkyl, $(CH_2)_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$, wherein the heterocyclic system is selected from aziridinyl, azetidinyl, pyrrolyl, piperidinyl, and morpholinyl;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6a'}$, at each occurrence, is selected from H, $C_{1-6}$ alkyl and $C_{3-6}$ cycloalkyl;

$R^{6b}$, at each occurrence, is selected from H, methyl, ethyl, propyl, i-propyl, butyl, i-butyl, t-butyl, pentyl, hexyl, cyclonropyl, and phenyl;

$R^{6b'}$, at each occurrence, is selected from H, $C_{1-6}$ alkyl and $C_{3-6}$ cycloalkyl;

$R^{6d}$, at each occurrence, is selected from methyl, $CF_3$, ethyl, propyl, i-propyl, butyl, i-butyl, t-butyl, pentyl, hexyl, cyclonropyl, and phenyl;

$R^{6d}$, at each occurrence, is selected from H, $CF_3$ and $C_{1-6}$ alkyl and $C_{3-6}$ cycloalkyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, $C(O)NHR^{6h}$, $C(O)OC_{1-5}$ alkyl, $(CH_2)_rOH$, $C(O)OH$, $(CH_2)_rC(O)NHSO_2$—$R^{6h}$, $NHSO_2R^{6h}$, $(CH_2)_r$tetrazolyl, $(CH_2)_r$phenyl and a $(CH_2)_r$-5-6 membered heterocyclic system containing 1-4 heteroatoms selected from N, O, and S;

$R^{6f}$, at each occurrence, is selected from H, methyl, ethyl, propyl, i-propyl, butyl, i-butyl, t-butyl, pentyl, hexyl, cyclopropyl, and phenyl;

$R^{6h}$, at each occurrence, is selected from $C_{1-5}$ alkyl, $C_{1-5}$ haloalkyl, and $C_{3-6}$ cycloalkyl, and phenly;

$R^7$ is sefected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rO(CH_2)_rR^{7d}$, $(CH_2)_rSH$, $(CH_2)_rC(O)H$, $(CH_2)_rS(CH_2)_rR^{7d}$, $(CH_2)_rC(O)OH$, $(CH_2)_rC(O)(CH_2)_rR^{7b}$, $(CH_2)_rC(O)NR^{7a}R^{7a}$, $(CH_2)_rNR^{7f}C(O)(CH_2)_rR^{7b}$, $(CH_2)_rC(O)O(CH_2)_rR^{7d}$, $(CH_2)_rOC(O)(CH_2)_rR^{7b}$, $(CH_2)_rOC(O)NR^{7a}R^{7a}$, $(CH_2)_rNR^{7a}C(O)NR^{7a}R^{7a}$, $(CH_2)_rNR^{7a}C(O)O(CH_2)_rR^{7d}$, $(CH_2)_rS(O)_p(CH_2)_rR^{7b}$, $(CH_2)_rS(O)_2NR^{7a}R^{7a}$, $(CH_2)_rNR^{7f}S(O)_2(CH_2)_rR^{7b}$, $C_{1-6}$ haloalkyl, adamantyl, $(CH_2)_r$phenyl substituted with 0-3 $R^{7e}$, and a $(CH_2)_r$-5-6 membered heterocyclic system containing 1-4 heteroatoms selected from N, O, and S, substituted with 0-3 $R^{7e}$, wherein the heterocyclic system is selected from thienyl, pyridinyl, benzothiazolyl, and tetrazolyl;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclonropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopronyl, cyclopentyl, $CH_2$-cyclopentyl, cyclohexyl, $CH_2$-cyclohexyl, $CF_3$, pyrrolidinyl, morpholinyl, piperizenyl substituted with 0-1 $R^{7e}$, and azetidinyl;

$R^{7d}$, at each occurrence, is selected from methyl, $CF_3$, $CF_2CF_3$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$,$(CF_2)_rCF_3$, $(CH_2)_rOC_{1-5}$ alkyl, $(CH_2)_rOH$, OH, SH, C(O)OH, C(O)$NHR^{7h}$, C(O)$OC_{1-5}$ alkyl, $(CH_2)_rSC_{1-5}$ alkyl, $(CH_2)_rNR^{7f}R^{7f}$, $(CH_2)_rC(O)NHSO_2$—$R^{7h}$, $NHSO_2R^{7h}$, and $(CH_2)_r$phenyl, and $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl;

$R^{7h}$, at each occurrence, is selected from $C_{1-5}$ alkyl, $C_{1-5}$ haloalkyl, and $C_{3-6}$ cycloalkyl, and phenyl;

$R^8$ is selected from H, methyl, ethyl, propyl, i-propyl, and cyclopropyl;

$R^9$ is selected from H, $C_{1-4}$ alkyl, $C_{3-4}$ cycloalcyl, —C(O)H, and —C(O)—$C_{1-4}$ alkyl;

$R^{10}$ is H;

$R^{11}$ is selected from H, $C_{1-4}$ alkyl, $(CHR)_qOH$, $(CHR)_qSH$, $(CHR)_qOR^{11d}$, $(CHR)_qS(O)_pR^{11d}$, $(CHR)_qC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, and a $(CH_2)_r$-5-6 membered nonaromatic heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ cycloalkyl substituted with 0-2 $R^{11e}$, and a $(CH_2)_r$-5-6 membered nonaromatic heterocyclic system containing 1-4 heteroatoms selected from N, O, and S, substituted with 0-3 $R^{11e}$;

$R^{11d}$, at each occurrence, is indenendently selected from H, methyl, —$CF_3$, $C_{2-4}$ alkyl, $C_{3-6}$ atkenyl, $C_{3-6}$ alkynyl, a $C_{3-6}$ cycloalkyl substituted with 0-3 $R^{11e}$, and a $(CH_2)_r$-5-6 membered nonaromatic heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC^{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, and a $(CHR)_r$—$C_{3-6}$ carbocyclic residue substituted with 0-5 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$ alkyl substituted with 0-1 $R^{13b}$, —OH, —$NH_2$, F, Cl, Br, I, —$OR^{13a}$, —$N(R^{13a})_2$, and $C_{1-4}$ alkyl substituted with 0-3 $R^{13b}$;

$R^{13a}$ is selected from H, $C_{1-4}$ alkyl and $C_{3-6}$ cycloalkyl;

$R^{13b}$, at each occurrence, is independently selected from —OH, —SR, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$ alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$ akyl, OH, $NH_2$, —O—$C_{1-4}$ alkyl, $NR^{15a}R^{15a}$, C(O)$NR^{15a}R^{15a}$, $NR^{15a}C(O)R^{15b}$, $NR^{15a}C(O)OR^{15d}$, OC(O)$NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently seleced from H, and $C_{1-4}$ alkyl;

$R^{15b}$, at each occurrence, is independently selected from $C_{1-4}$ alkyl, $C_{3-6}$ alkenyl, and $C_{3-6}$ alknyl $R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

n is 1;

m is selected from 0 and 1;

p, at each occurrence, is independently selected from 0, 1, and 2;

q, at each occurrence, is indenendently selected from 1, 2, 3, and 4;

r is 0 or 1; and s is 0.

11. The compound of claim 10, wherein: $R^{11}$ and $R^{12}$ are H.

12. The compound of claim 2, wherein the compound is the compound of formula (Ia)

(Ia)

R⁵, R¹, N, O, Z, R². [structure]

wherein:
$R^1$ is selected from H, $R^6$, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, and $C_{2-6}$ alkynyl substituted with 0-3 $R^6$;

$R^5$ is $NR^{5a}R^{5a}$; and $R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl.

13. The compound of claim 12, wherein Z is —$NR^9$—.

14. The compound of claim 12, wherein Z is selected from —$NR^8C(O)$—.

15. The compound of claim 1 selected from the following:

(S)-1-[(1S,2R,4R)-4-(isopropyl(methyl)amino)-2-propyl-cyclohexyl]-3-(6-(trifluoromethyl)quinazolin-4-ylamino)pyrrolidin-2-one;

N-((S)-1-((1S,2R,4R)-4-(isopropyl(methyl)amino)-2-(methylsulfonylmethyl)cyclohexyl) -2-oxopyrrolidin-3-yl)-3-(trifluoromethyl)benzamide; and N-((S)-1-((1S,2R,4R)-2-(tert-butylsulfonylmethyl)-4-(isopropyl(methyl)amino)cyclohexyl)-2-oxopyrrolidin-3-yl)-3-(frifluoromethyl)benzamide.

16. A pharmaceutical composition, comprising a pharmaceutically acceptable carrier and a therapeutically effective amount of a compound of claim 3.

17. A pharmaceutical composition, comprising a pharmaceutically acceptable carrier and a therapeutically effective amount of a compound of claim 6.

18. A pharmaceutical composition, comprising a pharmaceutically acceptable carrier and a therapeutically effective amount of a compound of claim 10.

19. A method for treating disorders, comprising administering to a patient in need thereof a therapeutically effective amount of a compound of claim 3, said disorders being selected from asthma, multiple sclerosis, artherosclerosis, and rheumatoid arthritis.

20. A method for treating disorders, comprising administering to a patient in need thereof a therapeutically effective amount of a compound of claim 6, said disorders being selected from asthma, multiple sclerosis, artheroscierosis, and rheumatoid arthritis.

21. A method for treating disorders, comprising administering to a patient in need thereof a therapeutically effective amount of a compound of claim 10, said disorders being selected from asthma, multiple sclerosis, artherosclerosis, and rheumatoid arthritis.

* * * * *

UNITED STATES PATENT AND TRADEMARK OFFICE
CERTIFICATE OF CORRECTION

PATENT NO.       : 7,482,335 B2
APPLICATION NO.  : 11/545415
DATED            : January 27, 2009
INVENTOR(S)      : Percy H. Carter et al.

It is certified that error appears in the above-identified patent and that said Letters Patent is hereby corrected as shown below:

In the Claims:

Column 248, line 24, Claim 1, change "isoquinolinyl" to -- isoquinolinyl, --.

Column 248, lines 39 to 40, Claim 1, change "isoquinolinyl" to -- isoquinolinyl, --.

Column 248, line 48, Claim 1, after "$(CH_2)_rNR^{5a}R^{5a}$," insert -- $(CH_2)_rC(O)OH$, --.

Column 248, line 57, Claim 1, change "morpholinlyl" to -- morpholinyl --.

Column 249, lines 5 to 6, Claim 1, change "$(CH_2)rOC(O)NR^{5f}R^{5f}$" to -- $(CH_2)_rOC(O)NR^{5f}R^{5f}$ --.

Column 249, lines 10 to 11, Claim 1, change "$(CH_2)_rC(O)NHSO_2R^{5h}$, $NHSO_2$—$R^{5h}$" to -- $(CH_2)_rC(O)NHSO_2$—$R^{5h}$, $NHSO_2R^{5h}$ --.

Column 249, line 28, Claim 1, change "$C_{3-6}$ cycloatkyl" to -- $C_{3-6}$ cycloalkyl --.

Column 249, line 36, Claim 1, delete "$(CH_2)_rC(O)OH$,".

Column 250, line 19, Claim 1, change "$C_{1-6}$ haloatkyl" to -- $C_{1-6}$ haloalkyl --.

Column 251, line 23, Claim 1, change "0-5 $R^{12}e$" to -- 0-5 $R^{12e}$ --.

Column 251, line 24, Claim 1, change "$R^{12e}$" to -- $R^{12e}$ --.

Column 251, line 32, Claim 1, change "0-1 $R^{13b}$" to -- 0-1 $R^{13b}$ --.

Column 251, line 33, Claim 1, change "—$N(R^{13a})_2$" to -- —$N(R^{13a})_2$ --.

Column 251, line 34, Claim 1, change "0-3 $R^{13b}$" to -- 0-3 $R^{13b}$ --.

Column 251, line 36, Claim 1, change "$R^{13b}$" to -- $R^{13b}$ --.

Column 251, lines 37 to 38, Claim 1, change "—$NR^{13c}R^{13c}$, —$C(O)NR^{13c}R^{13c}$, and —$NHC(O)R^{13c}$" to -- —$NR^{13c}R^{13c}$, —$C(O)NR^{13c}R^{13c}$, and —$NHC(O)R^{13c}$ --.

UNITED STATES PATENT AND TRADEMARK OFFICE
CERTIFICATE OF CORRECTION

PATENT NO. : 7,482,335 B2
APPLICATION NO. : 11/545415
DATED : January 27, 2009
INVENTOR(S) : Percy H. Carter et al.

It is certified that error appears in the above-identified patent and that said Letters Patent is hereby corrected as shown below:

In the Claims:

Column 251, line 39, Claim 1, change "$R^{l3c}$" to -- $R^{13c}$ --.

Column 251, line 52, Claim 1, change "seleced" to -- selected --.

Column 252, line 5, Claim 2, delete "$(CH_2)_rC(O)OH,$".

Column 252, line 10, Claim 2, change "$(CHR')_r phenyl$" to -- $(CH_2)_r phenyl$ --.

Column 252, line 16, Claim 2, change "$NR^{7f}C(O)NR^{7a}R^{7a}$" to -- $NR^{7a}C(O)NR^{7a}R^{7a}$ --.

Column 252, line 32, Claim 3, after "(I)", insert -- : --.

Column 252, line 33, Claim 3, delete "ring B is selected from".

Column 253, line 19, Claim 3, change "morpholinly" to -- morpholinyl --.

Column 253, line 22, Claim 3, change "cyclobuty" to -- cyclobutyl --.

Column 253, line 26, Claim 3, change "carbocyctic" to -- carbocyclic --.

Column 253, line 27, Claim 3, change "$(CR_2)_r$-5-6" to -- $(CH_2)_r$-5-6 --.

Column 253, line 40, Claim 3, change "$(CH_2)_r teteazolyl$" to -- $(CH_2)_r tetrazolyl$ --.

Column 253, line 54, Claim 3, change "$C_{1-6}$ alkyl;" to -- $C_{1-6}$ alkyl, --.

Column 253, line 56, Claim 3, change "eachoccurrence" to -- each occurrence --.

Column 253, line 58, Claim 3, change "indenendently" to -- independently --.

Column 253, line 59, Claim 3, change "nropvl" to -- propyl --.

Column 253, line 67, Claim 3, change "$R^{6b'}$" to -- $R^{6b}$ --.

UNITED STATES PATENT AND TRADEMARK OFFICE
CERTIFICATE OF CORRECTION

PATENT NO. : 7,482,335 B2  
APPLICATION NO. : 11/545415  
DATED : January 27, 2009  
INVENTOR(S) : Percy H. Carter et al.

It is certified that error appears in the above-identified patent and that said Letters Patent is hereby corrected as shown below:

In the Claims:

Column 254, line 7, Claim 3, change "phentyl" to -- pentyl --.

Column 254, line 10, Claim 3, change "pentyl,hexyl" to -- pentyl, hexyl --.

Column 254, line 35, Claim 3, after "i-propyl,", insert -- butyl, --.

Column 254, line 43, Claim 3, change "cycloalkcyl" to -- cycloalkyl --.

Column 254, line 61, Claim 3, change "$(CHR)_rNR^{11a}R^{11a}, (CHR)_rC(O)NR^{11a}R^{11a}$" to -- $(CHR)_rNR^{11a}R^{11a}, (CHR)_rC(O)NR^{11a}R^{11a}$ --.

Column 254, lines 63 to 64, Claim 3, change "$(CHR)_rC(O)0R^{11d}$" to -- $(CHR)_rC(O)OR^{11d}$ --.

Column 255, line 7, Claim 3, change "$C_{1-4}$ alkynyl" to -- $C_{2-4}$ alkynyl --.

Column 255, lines 20 to 21, Claim 3, change "—O—$_{1-6}$ alkyl" to -- —O—$C_{1-6}$ alkyl --.

Column 255, line 38, Claim 3, change "$C_{3-6\ cycloalkyl;}$" to -- $C_{3-6}$ cycloalkyl; --.

Column 255, line 45, Claim 3, change "indenendently" to -- independently --.

Column 255, line 67, Claim 5, change "Compound" to -- compound --.

Column 256, line 26, Claim 6, change "selected from" to -- $R^6$ or --.

Column 256, line 26, Claim 6, change "from" to -- with --.

Column 256, line 30, Claim 6, after "from", delete "from".

Column 256, lines 39 to 40, Claim 6, change "$(CH_2)_rC(O)OR^{5b}$" to -- $(CH_2)_rC(O)OR^{5d}$ --.

Column 256, line 45, Claim 6, change "morpholinlyl" to -- morpholinyl --.

Column 256, line 48, Claim 6, change "cyproyl" to -- cyclopropyl --.

UNITED STATES PATENT AND TRADEMARK OFFICE
CERTIFICATE OF CORRECTION

PATENT NO. : 7,482,335 B2
APPLICATION NO. : 11/545415
DATED : January 27, 2009
INVENTOR(S) : Percy H. Carter et al.

It is certified that error appears in the above-identified patent and that said Letters Patent is hereby corrected as shown below:

In the Claims:

Column 256, line 51, Claim 6, change "0-2 $R^e$" to -- 0-2 $R^{5e}$ --.

Column 256, lines 60 to 61, Claim 6, change "$(CH_2)rOC(O)NR^{5f}R^{5f}$" to -- $(CH_2)_rOC(O)NR^{5f}R^{5f}$ --.

Column 257, line 15, Claim 6, change "$C^{1-5}$ alkyl" to -- $C_{1-5}$ alkyl --.

Column 257, line 31, Claim 6, change "heteroatonis" to -- heteroatoms --.

Column 257, line 46, Claim 6, change "i-nropyl" to -- i-propyl --.

Column 257, line 57, Claim 6, change "containina" to -- containing --.

Column 257, line 58, Claim 6, change "S:" to -- S; --.

Column 257, line 63, Claim 6, change "aloalkyl" to -- haloalkyl --.

Column 258, lines 5 to 6, Claim 6, change "$(CH_{2r}S(O)_p(CH_2)_rR^{7b}$" to -- $(CH_2)_rS(O)_p(CH_2)_rR^{7b}$ --.

Column 258, line 9, Claim 6, change "heteroatonis" to -- heteroatoms --.

Column 258, line 28, Claim 6, change "$(CF_2)_r(CF_3$" to -- $(CF_2)_rCF_3$ --.

Column 258, lines 61 to 62, Claim 7, change "morpholinlyl" to -- morpholinyl --.

Column 258, line 66, Claim 9, change "disorders" to -- disorders, --.

Column 259, line 2, Claim 9, change "arthersclerosis" to -- atherosclerosis --.

Column 259, line 26, Claim 10, change "—$NR^8S_2NH$—" to -- —$NR^8SO_2NH$— --.

Column 259, line 27, Claim 10, change "—$NR^8C(O)O_{13}$ , —$_{CR}{}^{14}=CR^{14}$—" to -- —$NR^8C(O)O$—, —$CR^{14}=CR^{14}$— --.

UNITED STATES PATENT AND TRADEMARK OFFICE
CERTIFICATE OF CORRECTION

| | | |
|---|---|---|
| PATENT NO. | : 7,482,335 B2 | |
| APPLICATION NO. | : 11/545415 | |
| DATED | : January 27, 2009 | |
| INVENTOR(S) | : Percy H. Carter et al. | |

It is certified that error appears in the above-identified patent and that said Letters Patent is hereby corrected as shown below:

In the Claims:

Column 259, line 48, Claim 10, change "isoquinolinyl" to -- isoquinolinyl, --.

Column 259, line 50, Claim 10, change "pyridvl" to -- pyridyl --.

Column 259, lines 51 to 52, Claim 10, change "guinolinyl" to -- quinolinyl --.

Column 259, line 62, Claim 10, change "isoquinolinyl" to -- isoquinolinyl, --.

Column 259, line 65, Claim 10, change "thiazolvi" to -- thiazolyl --.

Column 260, line 27, Claim 10, change "cyclonropyl" to -- cyclopropyl --.

Column 260, line 32, Claim 10, change "cyclonropyl" to -- cyclopropyl --.

Column 260, line 33, Claim 10, change "$R^{6d}$" to -- $R^{6d'}$ --.

Column 260, line 49, Claim 10, change "phenly" to -- phenyl --.

Column 260, line 50, Claim 10, change "sefected" to -- selected --.

Column 261, line 1, Claim 10, change "cyclonropyl" to -- cyclopropyl --.

Column 261, line 6, Claim 10, change "cyclonropyl" to -- cyclopropyl --.

Column 261, line 14, Claim 10, change "$(CH_2)_rOC_{l-5}$ alkyl" to -- $(CH_2)_rOC_{1-5}$ alkyl --.

Column 261, line 27, Claim 10, change "$C_{3-4}$ cycloallcyl" to -- $C_{3-4}$ cycloalkyl --.

Column 261, line 39, Claim 10, change "$R^{1/a}$" to -- $R^{11a}$ --.

Column 261, line 50, Claim 10, change "indenendently" to -- independently --.

Column 261, line 51, Claim 10, change "$C_{3-6}$ atkenyl" to -- $C_{3-6}$ alkenyl --.

UNITED STATES PATENT AND TRADEMARK OFFICE
CERTIFICATE OF CORRECTION

PATENT NO. : 7,482,335 B2
APPLICATION NO. : 11/545415
DATED : January 27, 2009
INVENTOR(S) : Percy H. Carter et al.

It is certified that error appears in the above-identified patent and that said Letters Patent is hereby corrected as shown below:

In the Claims:

Column 262, line 9, Claim 10, change "0-3 $R^{/3b}$" to -- 0-3 $R^{13b}$ --.

Column 262, line 13, Claim 10, change "—NHC(O)$R^{/3c}$" to -- —NHC(O)$R^{13c}$ --.

Column 262, line 21, Claim 10, change "$C_{1-4}$ akyl" to -- $C_{1-4}$ alkyl --.

Column 262, line 27, Claim 10, change "seleced" to -- selected --.

Column 262, line 30, Claim 10, change "$C_{3-6}$ alknyl" to -- $C_{3-6}$ alkynyl; --.

Column 262, line 38, Claim 10, change "indenendently" to -- independently --.

Column 263, lines 7 to 10, Claim 15, change "N-((S)-1-((1S,2R,4R)-2-(tert-butylsulfonylmethyl)-4-(isopropyl(methyl)amino)cyclohexyl)-2-oxopyrrolidin-3-yl)-3-(frifluoromethyl)benzamide" to -- N-((S)-1-((1S,2R,4R)-2-(tert-butylsulfonylmethyl)-4-(isopropyl(methyl)amino)cyclohexyl)-2-oxopyrrolidin-3-yl)-3-(trifluoromethyl)benzamide --.

Column 264, line 4, Claim 19, change "arthersclerosis" to -- atherosclerosis --.

Column 264, line 10, Claim 20, change "artherscierosis" to -- atherosclerosis --.

Column 264, line 16, Claim 21, change "arthersclerosis" to -- atherosclerosis --.

Signed and Sealed this

Eighth Day of December, 2009

David J. Kappos
*Director of the United States Patent and Trademark Office*